United States Patent
Davies et al.

(10) Patent No.: US 6,541,491 B1
(45) Date of Patent: *Apr. 1, 2003

(54) 4-MERCAPTOPYRROLIDINE DERIVATIVES AS FARNESYL TRANSFERASE INHIBITORS

(75) Inventors: David Huw Davies, Macclesfield (GB); Francis Thomas Boyle, Macclesfield (GB); James Michael Wardleworth, Macclesfield (GB); Peter Wedderburn Kenny, Macclesfield (GB); Peter Beverley Scholes, Macclesfield (GB); Zbigniew Stanely Matusiak, Macclesfield (GB)

(73) Assignee: Zeneca Limited, London (GB)

( * ) Notice: Subject to any disclaimer, the term of this patent is extended or adjusted under 35 U.S.C. 154(b) by 42 days.

This patent is subject to a terminal disclaimer.

(21) Appl. No.: 09/725,964

(22) Filed: Nov. 30, 2000

Related U.S. Application Data

(62) Division of application No. 09/011,135, filed as application No. PCT/GB96/01810 on Jul. 30, 1996, now Pat. No. 6,232,338.

(30) Foreign Application Priority Data

Aug. 4, 1995 (GB) .............................. 9515975

(51) Int. Cl.[7] ..................... A61K 31/40; A61P 35/00; C07D 207/12
(52) U.S. Cl. ................. 514/340; 514/423; 514/424; 548/518; 548/541; 548/556
(58) Field of Search ................. 548/518, 541, 548/556; 514/424, 340, 423

(56) References Cited

U.S. PATENT DOCUMENTS 5,478,820 A * 12/1995 Betts et al. ............. 514/210
5,519,015 A * 5/1996 Jung ....................... 514/210

OTHER PUBLICATIONS

09/355,440, Jan. 27, 1998, Boyle et al.
09/011,135, Feb. 3, 1998, Davies et al.

* cited by examiner

Primary Examiner—Fiona T. Powers
(74) Attorney, Agent, or Firm—Finnegan, Henderson, Farabow, Garrett & Dunner, LLP

(57) ABSTRACT

Pharmaceutical compositions comprising an inhibitor of ras farnesylation of formula (I) wherein, $R^1$ is for example H and further values as defined in the specification; $R^2$ is for example H and further values as defined in the specification; $R^3$ is for example H or a substituent having values as defined in the specification; p is 0–3 in which $R^3$ values can be the same or different; L is a linking moiety for example —CO—$NH_2$— and further values as defined in the specification; A is selected from phenyl; naphthyl; a 5–10 membered monocyclic or bicyclic heteroaryl ring containing up to 5 heteroatoms where the heteroatoms are independently selected from O, N and S; or a —S—S-dimer thereof when $R^2$=H; or an enantiomer, diastereoisomer, pharmaceutically acceptable salt, prodrug or solvate thereof together with a pharmaceutically acceptable diluent or carrier. A particular use is cancer therapy.

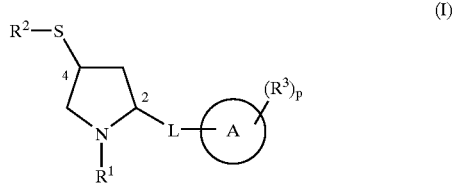

(I)

14 Claims, No Drawings

4-MERCAPTOPYRROLIDINE DERIVATIVES AS FARNESYL TRANSFERASE INHIBITORS

This is a division of application Ser. No. 09/011,135, filed Feb. 3, 1998 now U.S. Pat. No. 6,232,338, which is the National Stage application of International Application No. PCT/GB96/01810 with an International Filing Date of Jul. 30, 1996, which claims priority of UK Patent No. 9515975.2, dated Aug. 4, 1995, all of which are incorporated herein by reference.

This invention relates to compounds that inhibit farnesylation of mutant ras gene products through inhibition of the enzyme farnesyl-protein transferase (FPTase). The invention also relates to methods of manufacturing the compounds, pharmaceutical compositions and methods of treating diseases, especially cancer, which are mediated through farnesylation of ras.

Cancer is believed to involve alteration in expression or function of genes controlling cell growth and differentiation. Whilst not wishing to be bound by theoretical considerations the following text sets out the scientific background to ras in cancer. Ras genes are frequently mutated in tumours. Ras genes encode guanosine triphosphate (GTP) binding proteins which are believed to be involved in signal transduction, proliferation and malignant transformation. H-, K- and N-ras genes have been identified as mutant forms of ras (Barbacid M. Ann. Rev. Biochem. 1987, 56: 779–827). Post translational modification of ras protein is required for biological activity. Farnesylation of ras catalysed by FPTase is believed to be an essential step in ras processing. It occurs by transfer of the farnesyl group of farnesyl pyrophosphate (FPP) to a cysteine at the C-terminal tetrapeptide of ras in a structural motif called the CAAX box. After further post-translational modifications. including proteolytic cleavage at the cysteine residue of the CAAX box and methylation of the cysteine carboxyl, ras is able to attach to the cell membrane for relay of growth signals to the cell interior. In normal cells activated ras is believed to act in conjunction with growth factors to stimulate cell growth. In tumour cells it is believed that mutations in ras cause it to stimulate cell division even in the absence of growth factors (Travis J. Science 1993, 260: 1877–1878), possibly through being permanently in GTP activated form rather than cycled back to GDP inactivated form. Inhibition of farnesylation of mutant ras gene products will stop or reduce activation.

One class of known inhibitors of farnesyl transferase is based on farnesyl pyrophosphate analogues: see for example European patent application EP 534546 from Merck, inhibitors of farnesyl transferase based on mimicry of the CAAX box have been reported. Reiss (1990) in Cell 62, 81–8 disclosed tetrapeptides such as CVIM (Cys-Val-Ile-Met). James (1993) in Science 260, 1937–1942 disclosed benzodiazepine based peptidomimetic compounds. After earliest priority date of the present invention Lerner (1995) in J. Biol. Chem. 270, 26802 and Eisai in International Patent Application WO 95/25086 disclosed further peptidomimetic compounds based on Cys as the first residue. Also after the earliest priority date of the present invention Bristol-Myers Squibb in European Patent Application EP 696593 disclosed for the first time farnesyl transferase inhibitors having a 4-sulfanylpyrrolidine residue in the first position.

According to one aspect of the present invention there is provided a pharmaceutical composition comprising an inhibitor of ras farnesylation of Formula I

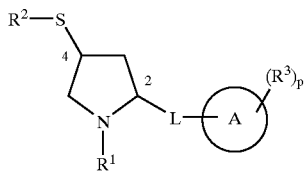

Formula I wherein:

$R^1$ is selected from H; —$C_{1-4}$alkyl; —$C_{1-3}$alkylene-Ph optionally mono or di-substituted on Ph with substituents selected from $C_{1-4}$alkyl, halogen, OH, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, carbamoyl, $C_{1-4}$alkoxycarbonyl, thiol, $C_{1-4}$alkylsulfanyl, $C_{1-4}$alkylsulfinyl, $C_{1-4}$alkylsulfonyl and sulfonamido; —CO—$C_{1-4}$alkyl; —CO—O—$C_{1-4}$alkyl; —CO—O—$C_{2-4}$alkenyl; —CO—O—$(CH_2)_n$Ph optionally substituted on Ph as defined for substitution on Ph in $R^1$=—$C_{1-3}$alkylene-Ph above and n=0–4; —$C_{1-4}$alkylene-$CONR^4R^5$ where $R^4$ & $R^5$ are independently selected from H and $C_{1-4}$alkyl; and —$C_{1-4}$alkylene-$COOR^6$ where $R^6$ is selected from H, $C_{1-4}$alkyl;

$R^2$ is selected from H; —$C_{1-4}$alkyl; —$C_{1-3}$alkylene-Ph optionally substituted on Ph as defined for substitution on Ph in $R^1$=—$C_{1-3}$alkylene-Ph above; —$COC_{1-4}$alkyl; and —$COOC_{1-4}$alkyl;

$R^3$ is selected from H; OH; CN; $CF_3$; $NO_2$; —$C_{1-4}$ alkyl; —$C_{1-4}$alkylene-$R^7$ where $R^7$ is selected from phenyl, naphthyl, a 5–10 membered monocyclic or bicyclic heteroaryl ring containing up to 5 heteroatoms selected from O, N and S and any aryl ring in $R^7$ is optionally substituted as defined for substitution on the Ph group in $R^1$=—$C_{1-3}$alkylene-Ph above; $R^7$; $C_{2-4}$alkenyl; halogen; —$(CH_2)_n COOR^8$ where n=0–3 and $R^8$ represents H, $C_{1-4}$alkyl, or $C_{2-4}$alkenyl; —$CONR^9R^{10}$ where $R^9$ and $R^{10}$ independently represent H. $C_{1-4}$alkyl, $C_{2-4}$alkenyl, —O—$C_{1-4}$alkyl, —O—$C_{2-4}$alkenyl, —$C_{1-3}$alkylenePh optionally substituted as defined for this group for $R^1$ above: —$CON(R^{11})OR^{12}$ where $R^{11}$ and $R^{12}$ independently represent H, $C_{1-4}$alkyl and $C_{2-4}$alkenyl; a group of Formula II, —$CONR^{13}$—$CHR^{14}$—$COOR^{17}$, where $R^{13}$ is H or $C_{1-4}$alkyl. $R^{17}$ is H or $C_{1-6}$alkyl. $R^{14}$ is selected from the side chain of a lipophilic amino acid. carbamoyl$C_{1-4}$alkyl, N-(mono$C_{1-4}$alkyl)carbamoyl$C_{1-4}$alkyl and N-(di$C_{1-4}$alkyl)carbamoyl$C_{1-4}$alkyl, the group of Formula II having L or D confieuration at the chiral alpha carbon in the corresponding free amino acid: a lactone of formula

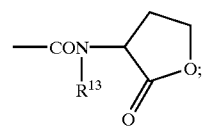

$C_{1-4}$alkyl monosubstituted on carbon with =N—OH; a group of Formula —X—$R^{15}$ where X is selected from O, CO, $CH_2$, S, SO, $SO_2$ and $R^{15}$ is selected from $C_{1-6}$alkyl, phenyl, naphthyl, a 5–10 membered monocyclic or bicyclic heteroaryl ring containing up to 5 heteroatoms selected from O, N and S and any aryl ring in $R^{15}$ is optionally substituted as defined for the Ph group in $R^1$=—$C_{1-3}$alkylene-Ph; p is 0–3, in which $R^3$ values can be the same or different: L is a linking moiety selected from the following groups written from left to right in Formula I: —CO—$NR^{16}$— where $R^{16}$ is selected from H, $C_{1-4}$alkyl, $C_{1-4}$alkylene-Z, —CO—$C_{1-4}$alkylene-Z, —CO—$C_{1-6}$alkyl, —COZ, Z and Z is selected from —O—$C_{1-4}$alkyl, phenyl, naphthyl, a 5–10 membered monocyclic or bicyclic heteroaryl ring containing up to 5 heteroatoms selected from O, N and S and any aryl ring in $R^{16}$ is optionally substituted as defined for the Ph group in $R^1$=—$C_{1-3}$alkylene-Ph; —$CH_2NR^{18}$— where $R^{18}$ represents any value defined for $R^{16}$; —$CH_2S$—; —$CH_2O$—, —$CH_2CHR^{19}$— where $R^{19}$ represents any value defined for $R^{16}$; —$CH=CR^{20}$— where $R^{20}$ represents any value defined for $R^{16}$; —$CH_2NR^{21}$—T— where $R^{21}$ represents any value defined for $R^{16}$, T represents —$(CH_2)_n$— where n is 1–4 and T is optionally monosubstituted with $R^{22}$ where $R^{22}$ represents any value for $R^{16}$ other than H; —$CHNR^2$—$SO_2$— where $R^{23}$ represents any value defined for $R^{16}$; —$CH_2NR^{24}$—CO—T— where $R^{24}$ represents any value defined for $R^{16}$, T represents —$(CH_2)_n$— where n is 0–4 and T is optionally monosubstituted with $R^{29}$ where $R^{29}$ represents any value for $R^{16}$ other than H; —CO—$NR^{25}$—T— where $R^{25}$ represents any value defined for $R^{16}$, T represents —$(CH_2)_n$— where n is 1–4 and T is optionally monosubstituted with $R^{26}$ where $R^{26}$ represents any value for $R^{16}$ other than H, —$CH_2S$—T— where T represents —$(CH_2)_n$— where n is 1–4 and T is optionally monosubstituted with $R^{27}$ where $R^{27}$ represents any value for $R^{16}$ other than H; —$CH_2O$—T— where T represents —$(CH_2)_n$— where n is 1–4 and T is optionally monosubstituted with $R^{28}$ where $R^{28}$ represents any value for $R^{16}$ other than H;

A is selected from phenyl; naphthyl; a 5–10 membered monocyclic or bicyclic heteroaryl ring containing up to 5 heteroatoms where the heteroatoms are independently selected from O, N & S; or a —S—S— dimer thereof when $R^2$=H: or a N-oxide thereof; or an enantiomer, diastereoisomer, pharmaceutically acceptable salt, prodrug or solvate thereof together with a pharmaceutically acceptable diluent or carrier.

Preferably $R^1$ is selected from H; —CO—O—$(CH_2)_n$Ph optionally substituted on Ph as defined for $R^1$=—$C_{1-3}$alkylene-Ph and n=0–4; —CO—O—$C_{2-4}$alkenyl; —CO—$C_{1-4}$alkyl; —$C_{1-4}$alkylene-$CONR^4R^5$ where $R^4$ & $R^5$ are independently selected from H, $C_{1-4}$alkyl.

Preferably $R^2$ is selected from H and —CO—$C_{1-4}$alkyl.

Preferably L is selected from —$CH_2$—$NR^{18}$—; —$CH_2NR^{21}$—T.

Preferably A is selected from phenyl, naphthyl, pyridyl and thienyl.

Preferably combinations of $R^3$ and p are selected from:
i) $R^3$ is selected from a group of Formula II; —$C_{1-4}$alkyl$R^7$; —O—$R^7$ and; $R^7$; and p=1–3 with the proviso that one value of $R^3$ is a group of Formula II;
ii) p=0 with the proviso that A is naphthyl and L is —$CH_2NR^{21}$—T;
iii) p=1 with the proviso that $R^1$=a group of Formula II and A is naphthyl.

In another embodiment of the invention it is preferred that:

$R^1$ is selected from H; —$C_{1-4}$alkyl, —$C_{1-3}$alkylene-Ph optionally mono or di-substituted on Ph with substituents selected from $C_{1-4}$alkyl, halogen, OH, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, thiol, $C_{1-4}$alkylthio, nitro, cyano, carboxy, carbamoyl, $C_{1-4}$alkoxycarbonyl, $C_{1-4}$alkylsulfinyl, $C_{1-4}$alkylsulfonyl, sulfonamido; —CO—$C_{1-4}$alkyl; —CO—O—$C_{1-4}$alkyl; —CO—O—$C_{2-4}$alkenyl; —CO—O—$CH_2$Ph optionally mono- or di-substituted on phenyl with substituents selected from $C_{1-4}$alkyl, halogen, OH, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, thiol, $C_{1-4}$alkylthio, nitro, cyano, carboxy, carbamoyl, $C_{1-4}$alkoxycarbonyl, $C_{1-4}$alkylthiono, $C_{1-4}$alkylsulfonyl, sulfonamido; —$C_{1-4}$ alkylene-$CONR^4R^5$ where $R^4$ & $R^5$ are independently selected from H, $C_{1-4}$alkyl; —$C_{1-4}$alkylene-$COOR^6$ where $R^6$ is selected from H, $C_{1-4}$alkyl;

$R^2$ is selected from H; —$C_{1-4}$alkyl; —$C_{1-3}$alkylene-Ph; —$COC_{1-4}$alkyl; —$COOC_{1-4}$alkyl:

$R^3$ is selected from H; OH; CN; $CF_3$; $NO_2$; —$C_{1-4}$ alkyl, —$C_{1-4}$alkylene-$R^7$ where $R^7$ is selected from phenyl, naphthyl, a 5–10 membered monocyclic or bicyclic heteroaryl ring containing up to 3 heteroatoms selected from O, N and S; $C_{1-4}$alkenyl; halogen; —$(CH_2)_n$$COOR^8$ where n=0–3 and $R^8$ represents H, $C_{1-4}$alkyl, $C_{2-4}$alkenyl: —$CONR^9R^{10}$ where $R^9$ and $R^{10}$ independently represent H, $C_{1-4}$alkyl, $C_{2-4}$alkenyl, —O—$C_{1-4}$alkyl, —O—$C_{2-4}$alkenyl; —$CON(R^{11})OR^{12}$ where $R^{11}$ and $R^{12}$ independently represent H, $C_{1-4}$alkyl and $C_{2-4}$alkenyl; a group of Formula II, —$CONR^{13}$—$CHR^{14}$—$COOR^{17}$, where $R^{13}$ is H or $C_{1-4}$alkyl, $R^{17}$ is H or $C_{1-6}$alkyl, $R^{14}$ is the side chain of a lipophilic amino acid with L or D configuration at the chiral alpha carbon in the corresponding free amino acid; $C_{1-4}$alkyl monosubstituted on carbon with =N—OH; —SO—$C_{1-4}$alkyl; —$SO_2$.$C_{1-4}$alkyl; a group of Formula —X—$R^{15}$ where X is selected from CO, $CH_2$, S, SO, $SO_2$ and $R^{15}$ is selected from $C_{1-6}$alkyl, phenyl, naphthyl, a 5–10 membered monocyclic or bicyclic heteroaryl ring containing up to 3 heteroatoms selected from O, N and S;

p is 0–3 in which $R^3$ values can be the same or different;

L is a linking moiety selected from the following groups written from left to right in Formula I; —CO—$NR^{16}$— where $R^{16}$ is selected from H, $C_{1-4}$alkyl, $C_{1-4}$alkylene-Z and Z is selected from —O—$C_{1-4}$alkyl, phenyl, naphthyl, a 5–10 membered monocyclic or bicyclic heteroaryl ring containing up to 3 heteroatoms selected from O, N and S; —$CH_2NR^{18}$— where $R^{18}$ represents any value defined for $R^{16}$; —$CH_2S$—; —$CH_2O$—; —$CH_2$—$CHR^{19}$— where $R^{19}$ represents any value defined for $R^{16}$; —$CH=CR^{20}$— where $R^{20}$ represents any value defined for $R^{16}$; —$CH_2NR^{21}$—T— where $R^{21}$ represents any value defined for $R^{16}$, T represents —$(CH_2)_n$— where n is 1–4 and T is optionally monosubstituted with $R^{22}$ where $R^{22}$ represents any value for $R^{16}$ other than H, and provided at least one of $R^{21}$ and $R^{22}$ is H; —$CH_2NR^{23}$—$SO_2$— where $R^{23}$ represents any value defined for $R^{16}$; —$CH_2$-$NR^{24}$—CO—T— where $R^{24}$ represents any value defined for $R^{16}$, T represents —$(CH_2)_n$— where n is 0–4 and T is optionally monosubstituted with $R^{29}$ where $R^{29}$ represents any value for $R^{16}$ other than H and provided at least one of $R^{24}$ and $R^{29}$ is H; —CO—$NR^{25}$—T— where $R^{25}$ represents any value defined for $R^{16}$, T represents —$(CH_2)_n$— where n is 1–4 and T is optionally monosubstituted with $R^{26}$ where $R^{26}$ represents any value for $R^{16}$ other than H, and provided at least one of $R^{24}$ and $R^{25}$ is H; —$CH_2S$—T— where T represents —$(CH_2)_n$— where n is 1–4 and T is optionally monosubstituted with $R^{27}$ where $R^{27}$ represents any value for $R^{16}$ other than H; —$CH_2O$—T— where T represents —(CH$_2$)$_n$— where n is 1–4 and T is optionally monosubstituted with R$^{28}$ where R$^{28}$ represents any value for R$^{16}$ other than H;

A is selected from phenyl; naphthyl; a 5–10 membered monocyclic or bicyclic heteroaryl ring containing up to 3 or 5 heteroatoms in the case of monocyclic and bicyclic rings respectively where the heteroatoms are independently selected from O, N & S; or a —S—S— dimer thereof when R$^2$=H.

A preferred pharmaceutical composition is in the form of a tablet.

According to another aspect of the invention there is provided a compound of Formula I, III, IV or V for use as a medicament.

According to another aspect of the invention there is provided a compound of Formula I, III, IV or V for use in preparation of a medicament for treatment of a disease mediated through farnesylation of ras.

Many compounds of Formula I are a feature of this invention and in particular according to another aspect of the invention there is provided a compound of any of the following classes i), ii) or iii):

class i)

Formula III

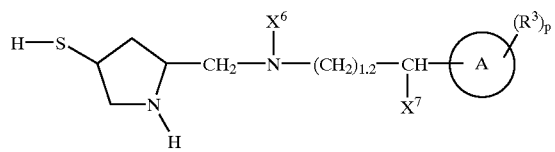

wherein:

X$^1$ is selected from H; C$_{1-6}$alkyl: hydroxyC$_{1-6}$alkyl, C$_{1-6}$alkoxyC$_{1-6}$alkyl C$_{1-6}$alkylcarbonyl: hydroxyC$_{1-6}$alkylcarbonyl: C$_{1-6}$alkoxyC$_{1-6}$alkylcarbonyl;

A is selected from phenyl, naphthyl or a 5–10 membered heterocyclic ring having up to 5 heteroatoms selected from O, N and S.

X$^2$ is selected from H; phenyl: phenylC$_{1-6}$alkyl: a 5–6 membered heteroaryl ring containing up to 3 heteroatoms selected from O, N and S optionally linked to A by C$_{1-6}$alkyl; and X$^2$ is optionally substituted on any ring as defined for phenyl in R$^1$=—C$_{1-3}$alkylene-Ph in claim 1;

X$^3$ is selected from H; C$_{1-6}$alkyl:

X$^4$ is selected from C$_{1-6}$alkylsulfanyl; C$_{1-6}$alkylsulfinyl; C$_{1-6}$alkylsulfonyl; carbamoyl; N-(C$_{1-6}$alkyl)carbamoyl; N-(diC$_{1-6}$alkyl)carbamoyl: and hydroxy or a C$_{1-4}$alkyl ether thereof:

class ii)

Formula IV

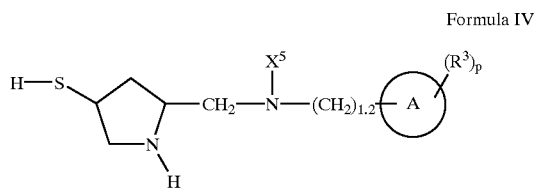

wherein:

X$^5$; is selected from —CO—C$_{1-4}$alkyl-Ph; —CO—C$_{1-6}$alkyl; —CO—C$_{1-6}$alkyl-heteroaryl where heteroaryl is a 5–10 membered heteroaryl ring containing up to 5 heteroatoms selected from O, N and S and Ph or heteroaryl are optionally substituted as defined for Ph in R$^1$=—C$_{1-3}$alkylene-Ph; C$_{1-4}$alkyloxyC$_{1-4}$alkyl;

A is naphthyl or a 10 membered heterocyclic ring having, up to 5 heteroatoms selected from O, N and S;

R$^3$ and p are as defined in claim 1;

class iii)

Formula V

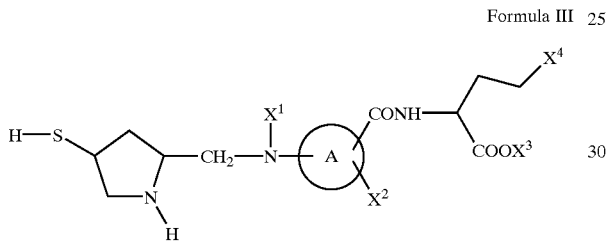

wherein:

X$^6$ has any value defined for X$^5$ in ii) above;

X$^7$ is Ph optionally substituted as defined for Ph in R$^1$=—C$_{1-3}$alkylene-Ph;

A is Ph or naphthyl or a 5–10 membered heterocyclic ring having up to 5 heteroatoms selected from O, N and S;

R$^3$ and p are as defined above:

or a N-oxide, pharmaceutically acceptable salt, prodrug or solvate thereof.

Preferred values for compounds of class i) include,

X$^1$ is selected from H and C$_{1-6}$alkoxyC$_{1-6}$alkyl;

X$^2$ is selected from H; phenyl or phenylC$_{1-6}$alkyl;

X$^4$ is C$_{1-6}$alkylsulfanyl;

A is selected from phenyl or naphthyl;

Other preferred values for X$^4$ are —OMe and the lactone which can be formed when X$^4$ is OH and X$^3$ is H.

Preferred values for compounds of class ii) include p is 0.

Preferred values for compounds of class iii) include,

X$^7$ is Ph;

A is Ph;

p is 0.

In another embodiment of the invention there is provided a compound of Formula I in which: R$^1$ is selected from H or C$_{1-4}$alkyl; R$^2$ is selected from H, C$_{1-4}$alkyl, —COC$_{1-4}$alkyl; —C$_{1-4}$alkylPh; L is selected from the following values as defined herein. CONR$^{16}$, CH$_2$S, CH$_2$O, CH$_2$CHR$^{19}$, CH=CHR$^{20}$, CH$_2$NR$^{24}$COT, CONR$^{25}$T, CH$_2$ST and CH$_2$OT; and values for A, R$^3$ and p are as defined herein, with the proviso that 2-(benzylcarbamoyl)4-sulfanylpyrollidine and 4-(acetylsulfonyl)-2(benzylcarbamoyl)-pyrrolidine are excluded. It is believed that the excluded compounds were disclosed as intermediates for beta-lactam antibiotic synthesis in Japanese patent application 60233076 (Sumitomo Chemical).

According to another aspect of the present invention there is provided any one of the following individual compounds or a pharmaceutically acceptable salt thereof:

(2S)-2-{2-Benzyl-5-[([2S,4S]-4-sulfanylpyrrolidin-2-ylmethyl)-amino]-benzoylamino}-4-methylsulfanylbutyric acid methyl ester;

(2S)-2-{2-Benzyl-5-[([2S,4S]-4-sulfanylpyrrolidin-2-ylmethyl)-amino]-benzoylamino}-4-methylsulfanylbutyric acid;

(2S)-2-({2-phenyl-5-[([2S,4S]-4-sulfanylpyrrolidin-2-ylmethyl)-amino]-phenylcarbonyl}-amino)-4-methylsulfanylbutyric acid methyl ester;

(2S)-2-({2-phenyl-5-[([2S,4S]-4-sulfanylpyrrolidin-2-ylmethyl)-amino]-phenylcarbonyl}-amino)-4-methylsulfanylbutyric acid;

(2S)-2-({3[([2S,4S]-4-sulfanylpyrrolidin-2-ylmethyl)-amino]-naphthalene-1-carbonyl)}-amino)-4-methylsulfanylbutyric acid methyl ester;
(2S)-2-({3-[([2S,4S]-4-sulfanylpyolidin-2-ylmethyl)-amino]-naphthalene-1-carbonyl)}-amino)-4-methylsulfanylbutyric acid;
(2S)-2-({-3-phenyl-5[([2S,4S]-4-sulfanylpyrrolidin-2-ylmethyl)-amino]-phenylcarbonyl}-amino)-4-methylsulfanylbutyric acid methyl ester;
(2S)-2-({-3-phenyl-5[([2S,4S]-4-sulfanylpyrrolidin-2-ylmethyl)-amino]-phenylcarbonyl}-amino)-4-methylsulfanylbutyric acid;
(2S,4S)-2-[{N-(4-methoxybenzyl)-N-(naphthalen-1-ylmethyl)-amino}-methyl]-pyrrolidine-4-thiol;
N-(naphthalen-1-ylmethyl)-N-([2S,4S]-4-sulfanylpyrrolidin-2-ylmethyl)-pentanamide;
N-(naphthalen-1-ylmethyl)-N-([2S,4S]-4-sulfanylpyrrolidin-2-ylmethyl)-2-(pyridin-3-yl)-acetamide;
N-((2S,4S)-4-sulfanyl-pyrrolidin-2-ylmethyl)-3-methyl-N-(2-naphthalen-1-yl-ethyl)butyramide;
N-([2S,4S]-4-sulfanyl-pyrrolidin-2-ylmethyl)-N-(2-naphthalen-1-yl-ethyl)-2-pyridin-3-yl-acetamide;
(2S,4S)-2-{[(3-Methoxypropyl)-(2-naphthalen-1-ylethyl)amino]methyl}-pyrrolidine-4-thiol;
N-([2S,4S]-4-sulfanyl-pyrrolidin-2-ylmethyl)-2-(4-methoxy-phenyl)-N-(2-naphthalen-2-yl-ethyl)-acetamide;
(2S,4S)-2-{[(2-(4-Methoxyphenyl)ethyl)-(2-naphthalen-1-ylethyl)amino]methyl}-pyrrolidine-4-thiol;
N-(2,2-Diphenyl-ethyl)-N-([2S,4S]-4-sulfanyl-pyrrolidin-2-ylmethyl)-3-methyl-butyramide;
N-([2S,4S]-4-sulfanyl-pyrrolidin-2-ylmethyl)-3,3-dimethyl-N-(2-naphthalen-2-yl-ethyl)-butyramide;
N-(2,2-Diphenyl-ethyl)-N-([2S,4S]-4-sulfanyl-pyrrolidin-2-ylmethyl)-3,3-dimethyl-butyramide;
(2S)-2-{3-[([2S,4S]-4-Sulfanyl-pyrrolidin-2-ylmethyl)-(3-methoxy-propyl)-amino]-benzoylamino}-4-methylsulfanyl-butyric acid;
N-([2S,4S]-4-Sulfanyl-pyrrolidin-2-ylmethyl)-3,3-dimethyl-N-(2-naphthalen-1-yl-ethyl)-butyramide:
(2S)-4-Carbamoyl-2-({2-phenyl-5-[([2S,4S]-4-sulfanyl-pyrrolidin-2-ylmethyl)-amino]-phenylcarbonyl}-amino)-butyric acid; and
(2S)-4Carbamnoyl-2-({2-phenyl-5-[([2S,4S]-4-sulfanyl-pyrrolidin-2-ylmethyl)-amino]-phenylcarbonyl}-amino)-butyric acid methyl ester.

According to another aspect of the invention there is provided a pharmaceutical composition comprising a compound as defined in any one Formulas III, IV or V or an individual compound listed above together with a pharmaceutically acceptable diluent or carrier.

According to another aspect of the invention there is provided a process for preparing compounds of classes i), ii) or iii) as defined above which comprises deprotecting a compound of Formula VI

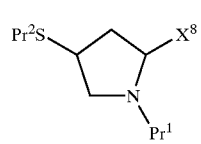

Formula VI wherein $X^8$ represents the right hand side of compound classes i), ii) or iii) as defined above. $Pr^1$ is H or an amino protecting group. $Pr^2$ is H or a thio protecting group and any functional groups in $X^8$ are optionally protected with the proviso that there is at least one protecting group and optionally, if desired, converting the product thus obtained into a pharmaceutically acceptable salt thereof.

In an embodiment of the invention:
Examples of values for $R^1$ include methyl; —$CH_2$-Ph; —$CH_2$-Ph substituted on Ph with nitro, especially 4-nitro; acetyl; BOC; allyloxycarbonyl; —CO—O—$CH_2$-Ph substituted on Ph with nitro, especially 4-nitro; —$CH_2CONH_2$.
Examples of values for $R^2$ include —COMe and —COOtertbutyl.
Examples of values for $R^3$ include Cl; —COOH; —CONH; —SOMe and; —$SO_2$Me.
When $R^3$ represents —$(CH_2)$—$COOR^8$ a suitable value for n is 0.
Examples of lipophilic amino acids which contribute their side chain (denoted $R^{14}$ within the definition of values for $R^3$) include methionine, phenylglycine, phenylalanine. serine, leucine, isoleucine or valine. L configuration in the corresponding free amino acid is preferred. Examples of amino acid side chains are set out below. A preferred value for $R^{14}$ is —$CH_2$—$CH_2$—S—$CH_3$. Further preferred values for $R^{14}$ are —$CH_2$—OMe and —$CH_2$—$CH_2$—OMe.
When $R^{17}$ is H to give a COOH group in Formula II, and $R^{14}$ is —$CH_2$—$CH_2$—OH then a lactone can be formed where $R^{17}$ and $R^{14}$ together form part of a dihydrofuran-2-one heterocyclic ring. The same lactone can be formed for compounds of Formula III where $X^4$ is OH and $X^3$ is H.

| Amino Acid | Side Chain |
|---|---|
| methionine | —$CH_2$—$CH_2$—S—$CH_3$ |
| phenylglycine | Ph |
| phenylalanine | —$CH_2$-Ph |
| serine | —$CH_2$OH or a $C_{1-4}$alkyl (preferably methyl) ether thereof. |
| leucine | —$CH_2$—$CHMe_2$ |
| homoserine | —$CH_2$—$CH_2$—OH or a $C_{1-4}$alkyl (preferably methyl) ether thereof. |

A preferred value for p is 2.
When L is —$CH_2NR^{21}$—T— a suitable value for n is 1. When L is —$CH_2$—$NR^{24}$—CO—T— a suitable value for n is 1. When L is —$CH_2$—$NR^{25}$—T— a suitable value for n is 1. When L is —$CH_2$—S—T— a suitable value for n is 1. When L is —$CH_2$—O—T— a suitable value for n is 1. L is especially —CONH—, —$CH_2$-NH—, —$CH_2NHSO_2$-, —$CH_2NHCO$—.
Examples of values for A when A is heteroaryl are thienyl, pyridyl, quinolyl & quinoxalinyl.
Further preferred values are set out below.
For $R^1$: 4-nitro-benzyloxycarbonyl; allyloxycarbonyl; carbamoylmethyl; acetyl; phenoxycarbonyl; H.
For $R^2$: Acetylsulfanyl; H.
For $R^3$: Methoxycarbonyl; N-methyl-N-methoxy-carbamoyl; nitro; allyloxycarbonyl; N-methyl-allyloxycarbamoyl; ethoxycarbonyl; 3,4-dichloro-benzyl-carbamoyl; hydroxy; carboxy; (2S),4-methylsulfanyl-butyric acid methyl ester-2yl-carbamoyl: (2S),4-methylsulfanyl-butyric acid-2yl-carbamoyl; phenoxy.
For p: 1–2, especially 2; a further preferred value is 0.
For L; —C(O)—NH—; —$CH_2C(O)$—NH—; —$CH_2NH$—C(O)—; —$CH_2$-NH—$SO_2$; especially —C(O)—NH—.
For A: phenyl; pyridyl, thienyl; naphthyl.
For $R^{16}$ & $R^{18-26}$: H, $C_{1-4}$alkyl, especially H.
In another embodiment of the invention preferred values are set out below.

In compounds of Formula III: $X^1$ is H or methoxy$C_{1-4}$ alkyl (especially H); $X^2$ is H, phenyl or benzyl (especially benzyl); $X^3$ is H or $C_{1-4}$alkyl (especially H); $X^4$ is $C_{1-4}$alkylsulfanyl (especially methylsulfanyl); and A is phenyl. When A is a 6-membered aryl or heteroaryl ring then groups —$NX^1$— and the substituent comprising $X^4$ are preferably in meta juxtaposition relative to each other; and $X^2$, if present, is preferably positioned para relative to —$NX^1$—. The chiral carbon to which —$COOX^3$ is attached is preferably in S configuration. The chiral carbons at the 2 and 4 positions of the pyrrolidine ring are preferably in S configuration.

In compounds of Formula IV: $X^5$ is —CO—$C_{1-4}$alkyl (especially —CO—$CH_2$—$CHMe_2$) or —$CH_2$—Ph—O—$C_{1-4}$alkyl (especially —$CH_2$—Ph—OMe); heteroaryl is preferably pyridyl and a preferred aryl or heteroaryl substituent is —O—$C_{1-4}$alkyl (especially methoxy); and A is naphthyl. The chiral carbons at the 2 and 4 positions of the pyrrolidine ring are preferably in S configuration. The attachment point for A relative to —$(CH_2)_{1,2}$— is preferably at the I position of napththalene and the equivalent position for heterocyclic values for A (regardless of ring numbering conventions for heterocycles). A preferred value for —$(CH_2)_{1,2}$— is —$(CH_2)_2$—.

In compounds of Formula V: $X^6$ is —CO—$C_{1-5}$alkyl (more preferably —CO—$CH_2$—$CHMe_2$ or —CO—$CH_2$-t-butyl, especially —CO—$CH_2$—$CHMe_2$) or —$CH_2$—Ph—O—$C_{1-4}$alkyl (especially —$CH_2$—Ph—OMe): heteroaryl is preferably pyridyl and a preferred aryl substitution is —O—$C_{1-4}$alkyl (especially methoxy): and A is phenyl or naphthyl (especially phenyl). The chiral carbons at the 2 and 4 positions of the pyrrolidine ring are preferably in S configuration. A preferred value for —$(CH_2)_{1,2}$— is —$(CH_2)_1$—.

Suitable pairs of values for $R^3$ when p=2 are; —COOMe, —CO.N(Me).OMe: $NO_2$, —CO.N(Me).OMe; —COOMe, allyloxycarbonyl —CO.N(Me).OMe, allyloxycarbonyl; allyloxycarbonyl, —CO.N(Me).O.$CH_2$CH=$CH_2$: OH, COOH; —COOMe, COOMe: Ph, —CO.N-Methionine methyl ester: Ph, —CO.N-Methionine: benzyl, —CO.N-Methionine methyl ester; benzyl, —CO.N-Methionine; benzyl, —CO.N-Methionine isopropyl ester: Ph, —CO.Nα-Glutamine methyl ester: Ph, —CO.Nα-Glutamine.

Suitable values for L=$CHNR^{21}$T include $CH_2$.N($CO.CH_2.CHMe_2$).$CH_2.CH_2$; $CH_2$.N($CH_2CH_2CH_2OMe$).$CH_2.CH_2$; $CH_2$.N($CH_2.pPh.OMe$).$CH_2.CH_2$; $CH_2$.N($CO.CH_2.CHMe_2$).$CH_2$; $CH_2N(CO.CH_2.CH_2.CH_2.Me)$.$CH_2$; $CH_2N(CO.CH_2.CHMe.CH_2Me)$.$CH_2$; $CH_2N(CO.CH_2.CH_2.OMe)CH_2$; $CH_2N(CO.CH_2.$pyridin-3-yl$).CH_2$; $CH_2N(4$-methoxybenzyl$)CH_2$; $CH_2N(CO.CH_2.CHMe_2)CH_2.CH_2.CH(Ph)$; $CH_2N(CO.CH_3)CH_2.CH_2.CH(Ph)$; $CH_2N(CO.CH_2.CHMe_2)CH_2$; $CH_2N(CO.CH_3)CH_2$; $CH_2N(CO.CH_2.CHMe_2)CH_2.CH(Ph)$; $CH_2N(CO.CH_2.CMe_3)CH_2.CH(Ph)$; $CH_2N(CO.CH_2.$pyridin-3-yl$)CH_2.CH(Ph)$; $CH_2N(CO.1$-hydroxy-6-methoxy-pyridin-3-yl$)CH_2.CH(Ph)$; $CH_2N(CO.CH_2CHMe_2)CH_2.CH_2$; $CH_2N(CO.CH_2CMe_3)CH_2.CH_2$; $CH_2N(CO.CH_2$pyridin-3-yl$)CH_2.CH_2$; $CH_2N(CO.4$-methoxybenzyl$)CH_2.CH_2$;

Suitable values for L=—$CH_2NR^{18}$— include $CH_2NH$: $CH_2NMe$; $CH_2N(CO.CH_2.CHMe_2)$ and $CH_2N(CO.CH_2.CH_2.OMe)$.

Various forms of prodrug are well known in the art. For examples of such prodrug derivatives, see:

a) Design of Prodrug, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull. 32, 692 (1984).

Examples of pro-drugs include in vivo hydrolysable esters of a compound of the Formula I. An in vivo hydrolysable ester of a compound of the formula (I) containing Some compounds within the scope of Formula I are known as intermediates in the human or animal body to produce the parent acid. Suitable pharmaceutically-acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Particular substitutions on A for 6 membered rings are in the meta or para positions.

Some compounds within the scope of Formula I are known as intermediates in carbapenem side chain synthesis but it is believed that they have not been previously described in forms suitable as pharmaceutical compositions nor had any pharmaceutical activity associated with them per se. The reader is referred to the following publications in this regard and also in respect of synthetic details for compound preparation: Matsumura. Heterocycles (1995), 41, 147–59: European patent application EP 590885 (Zeneca; Betts et al.); European patent application EP 592167 (Zeneca; Siret); European patent application EP 562855 (Zeneca; Jung et al.); International patent application WO 92/17480 (Imperial Chemical Industries; Betts et al.); European patent application EP 508682 (Imperial Chemical Industries: Betts et al.): European Patent Application EP 280771 (Fujisawa Pharmaceutical, Murata et al.); and International patent application WO 92/17479 (Imperial Chemical Industries: Betts et al.).

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to the other generic terms.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting FTPase. The synthesis of optically active forms may be carried out by standard techniques of organic chemistry well known in the art, for example by synthesis from optically active starting materials or by resolution of a racemic form. Similarly, inhibitory properties against FTPase may be evaluated using the standard laboratory techniques referred to hereinafter.

The term "halogen" refers to fluorine, chlorine, bromine and iodine. The term "carbamoyl" refers to —C(O)$NH_2$. The term "BOC" refers to tert-butyl-O—C(O)—. The ring systems in which both rings of the bicyclic system are aromatic.

Examples of $C_{1-6}$alkyl include methyl, ethyl, propyl, isopropyl, sec-butyl, tert-butyl and pentyl; examples of $C_{1-4}$alkyl include methyl, ethyl, propyl, isopropyl, sec-butyl and tert-butyl; examples of $C_{1-3}$alkyl include methyl, ethyl, propyl and isopropyl; examples of —$C_{1-3}$alkylenePh include benzyl, phenylethyl, phenylpropyl; examples of $C_{1-4}$alkoxy (also called —O—$C_{1-4}$alkyl herein) include methoxy, ethoxy and propoxy; examples of $C_{1-4}$alkanoyl include formyl, acetyl and propionyl; examples of $C_{1-4}$alkanoyloxy include acetyloxy and propionyloxy; examples of $C_{1-4}$alkylamino include methylamino ethylamino, propylamino, isopropylamino, sec-butylamino and tert-butylamino: examples of di-($C_{1-4}$alkyl)amino include di-methylamino, di-ethylamino and N-ethyl-N-methylamino; examples of $C_{1-4}$alkanoylamino include acetamido and propionylamino; examples of $C_{1-4}$alkoxycarbonyl include methoxycarbonyl, ethoxycarbonyl and propoxycarbonyl; examples of $C_{1-4}$alkylsulfanyl include methylsulfanyl, ethylsulfanyl, propylsulfanyl, isopropylsufanyl, sec-butylsulfanyl and tert-butylsulfanyl; examples of $C_{1-4}$alkylsulfinyl include methylsulfinyl, ethylsulfinyl, propylsulfinyl, isopropylsulfinyl, sec-butylsulfinyl and tert-butylsulfinyl: examples of $C_{1-4}$alkylsulfonyl include methylsulfonyl, ethylsulfonyl, propylsulfonyl, isopropylsulfonyl, sec-butylsulfonyl and tert-butylsulfonyl examples of —CO—$C_{1-4}$alkyl include formyl, acetyl, propionyl, butyryl, and valeryl: examples of —CO—O—$C_{1-4}$alkyl include ethyloxycarbonyl; propyloxycarbonyl and tert-butyloxycarbonyl (BOC); examples of —CO—O—$C_{2-4}$alkenyl include allyloxycarbonyl and vinyloxycarbonyl; examples of —CO—O—$(CH_2)_n$Ph where n=0–4 include phenyloxycarbonyl, benzyloxycarbonyl, phenylethyloxycarbonyl and phenylpropyloxycarbonyl; examples of —$C_{1-4}$alkylene-$CONR^4R^5$ include carbamoylmethyl, carbamoylethyl, N-methylcarbamoylethyl, N-methyl-N'-ethylcarbamoylethyl; examples of —$C_{1-4}$alkylene-$COOR^6$ include carboxymethyl, carboxyethyl, carboxypropyl, propionic acid methyl ester, acetic acid ethyl ester; examples of $C_{2-4}$alkenyl include allyl and vinyl; examples of —O—$C_{2-4}$alkenyl include allyloxy and vinyloxy; examples of lipophilic amino acids include valine, leucine, isoleucine, methionine, phenylalanine, serine, threonine and tyrosine; examples of carbamoyl$C_{1-4}$alkyl include carbamoylmethyl, carbamoylethyl and carbamoylpropyl; examples of N-(mono$C_{1-4}$alkyl)carbamoyl$C_{1-4}$alkyl include N-methylcarbamoylmethyl and N-ethyl-carbamoylethyl; examples of N-(di$C_{1-4}$alkyl)carbamoyl-$C_{1-4}$alkyl include N,N-dimethylcarbamoylethyl and N-methyl-N-ethylcarbamoylethyl; examples of $C_{1-4}$alkyl monosubstituted on carbon with =N—OH include butyraldehyde oxime and propionaldehyde oxime: examples of hydroxy$C_{1-6}$ alkyl include hydroxymethyl, hydroxyethyl, hydroxypropyl, 2-hydroxypropyl, 2-(hydroxymethyl)propyl and hydroxypentyl; examples of $C_{1-6}$alkoxy$C_{1-6}$alkyl include methoxyethyl, ethoxyethyl and methoxybutyl; examples of $C_{1-6}$alkylcarbonyl include methylcarbonyl, ethylcarbonyl propylcarbonyl, isopropylcarbonyl, sec-butylcarbonyl, tert-butylcarbonyl and pentylcarbonyl: examples of hydroxy$C_1$alkylcarbonyl include hydroxyacetyl, hydroxypropionyl, hydroxybutyryl, 3-hydroxybutyryl and hydroxypentanoyl; examples of $C_{1-6}$alkoxy$C_{1-6}$alkylcarbonyl include methoxyacetyl, methoxypropionyl, ethoxybutyryl and butoxyacetyl; examples of phenylCtaylky incude benzyl, phenylethyl and phenylpropyl: examples of —CO—$C_{1-4}$alkyl-Ph include phenylacetyl and phenylpropionyl; examples of —CO—$C_{1-4}$ alkyl-heteroaryl include 2-(3-pyridyl)-acetyl and 2-(3-thienyl)-acetyl; examples of N—($C_{1-6}$alkyl)carbamoyl include N-methyl-carbamoyl and N-ethyl-carbamoyl; examples of N-(di$C_{1-6}$alkyl)carbamoyl include N,N-dimethylcarbamoyl and N-methyl-N-ethylcarbamoyl.

Examples of 5–10 membered monocyclic or bicyclic heteroaryl rings containing up to 5 heteroatoms selected from O, N and S include the following. Examples of 5- or 6-membered heteroaryl ring systems include imidazole, triazole, pyrazine, pyrimidine, pyridazine, pyridine, isoxazole, oxazole, isothiazole, thiazole and thiophene. A 9 or 10 membered bicyclic heteroaryl ring system is an aromatic bicyclic ring system comprising a 6-membered ring fused to either a 5 membered ring or another 6 membered ring. Examples of 5/6 and 6/6 bicyclic ring systems include benzofuran, benzimidazole, benzthiophene, benzthiazole, benzisothiazole, benzoxazole, benzisoxazole, pyridoimidazole, pyrimidoimidazole, quinoline, isoquinoline, quinoxaline, quinazoline, phthalazine, cinnoline and naphthyridine.

Preferably monocyclic heteroaryl rings contain up to 3 heteroatoms and bicyclic heteroaryl rings contain up to 5 heteroatoms. Preferred heteroatoms are N and S, especially N. In general, attachment of heterocyclic rings to other groups is via carbon atoms. Suitable values of heterocycles containing only N as the heteroatom are pyrrole, pyridine, indole, quinoline, isoquinoline, imidazole, pyrazine, pyrimidine, purine and pteridine.

Preferably any chiral carbon atoms at the 2 and 4 positions of the pyrrolidine ring in Formulas I and III-V are in S configuration.

Compounds of Formula I and III-V may form salts which are within the ambit of the invention. Pharmaceutically acceptable salts are preferred although other salts may be useful in, for example, isolating or purifying compounds.

When the compound contains a basic moiety it may form pharmaceutically acceptable salts with a variety of inorganic or organic acids, for example hydrochloric, hydrobromic, sulphuric, phosphoric, trifluoroacetic, citric or maleic acid. A suitable pharmaceutically-acceptable salt of the invention when the compound contains and acidic moiety is an alkali metal salt, for example a sodium or potassium salt an alkaline earth metal salt, for example a calcium or magnesium salt an ammonium salt or a salt with an organic base which affords a pharmaceutically-acceptable cation for example a salt with methylamine, dimethylamine, trimethylamine, piperidine, morpholine or tris-(2-hydroxyethyl)amine.

Solvates, for example hydrates, are also within the ambit of the invention and may be prepared by generally known methods.

According to another aspect of the present invention there is provided a compound of Formula I for use as a medicament.

According to another aspect of the present invention there is provided the use of a compound of Formula I in preparation of a medicament for treating ras mediated diseases, especially cancer.

According to another aspect of the present invention there is provided a method of treating ras mediated diseases, especially cancer, by administering an effective amount of a compound of Formula I to a mammal in need of such treatment.

According to a further feature of the invention there is provided a compound of Formula I, or a pharmaceutically-acceptable salt thereof, for use in a method of treatment of the human or animal body by therapy.

The invention also includes a method of treating a disease or medical condition mediated alone or in part by farnesylated ras which comprises administering to a mammal requiring such treatment an effective amount of an active ingredient as defined treatment of the human or animal body by therapy.

The invention also includes a method of treating a disease or medical condition mediated alone or in a part by farnesylated ras which comprises administering to a mammal requiring such treatment an effective amount of an active ingredient in the production of a new medicament for use in a farnesylated ras mediated disease or medical condition.

Specific cancers of interest include:

carcinoma, including that of the bladder, breast, colon, kidney, liver, lung, ovary, pancreas, stomach, cervix, thyroid and skin;

hematopoietic tumors of lymphoid lineage, including acute lymphocytic leukemia, B-cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyosarcoma; and other tumors, including melanoma seminoma, tetratocarcinoma, neuroblastoma and glioma.

The compounds of Formula I are especially useful in treatment of tumors having a high incidence of ras mutation, such as colon, lung, and pancreatic tumors. By the administration of a composition having one (or a combination) of the compounds of this invention, development of tumors in a mammalian host is reduced.

Compounds of Formula I may also be useful in the treatment of diseases other than cancer that may be associated with signal transduction pathways operating through Ras, e.g., neuro-fibromatosis.

Compounds of Formula I may also be useful in the treatment of diseases associated with CAAX-containing proteins other than Ras (e.g., nuclear lamins and transducin) that are also post-translationally modified by the enzyme farnesyl protein transferase.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate. calcium phosphate or kaolin. or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia: dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl g-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1.3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30 $\mu$ or much less, the powder itself comprising either active ingredient alone or diluted with one or more physiologically acceptable carriers such as lactose. The powder for insufflation is then conveniently retained in a capsule containing, for example. 1 to 50mg of active ingredient for use with a turbo-inhaler device. such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch, Chairman of Editorial Board). Pergamon Press 1990.

The amount of active ingredient that is combined with one or more excipients to produce a single dosage form will necessarily vary depending upon the host treated and the particular route of administration. For example, a formulation intended for oral administration to humans will generally contain for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of ras.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

Compounds of this invention may be useful in combination with known anti-cancer and cytotoxic agents. If formulated as a fixed dose such combination products employ the compounds of this invention within the dosage range described herein and the other pharmaceutically active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of activation of ras by farnesylation. Thus, they are useful as pharmacological standards for use in the development of new biological tests and in the search for new pharmacological agents.

According to another aspect of the present invention there is provided individual compounds produced as end products in the Examples set out below and salts thereof.

A compound of the invention, or a salt thereof, may be prepared by any process known to be applicable to the preparation of such compounds or structurally related compounds. Such processes are illustrated by the following representative schemes in which variable groups have any of the meanings defined for Formula I unless stated otherwise. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991. Note abbreviations used have been listed immediately before the Examples below.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (e.g. isopropyl, t-butyl); lower alkoxy lower alkyl groups (e.g. methoxymethyl, ethoxymethyl, isobutoxymethyl; lower aliphatic acyloxy lower alkyl groups, (e.g. acetoxy,methyl, propionyloxymethyl, butyryloxymethyl, pivaloyloxymethyl); lower alkoxycarbonyloxy lower alkyl groups (e.g. 1-methoxycarbonylmethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2–6C)alkenyl groups (e.g. allyl and vinylethyl).

Methods particularly appropriate for the removal of carboxyl protecting groups include for example acid-metal- or enzymically-catalysed hydrolysis.

Examples of hydroxy protecting groups include lower alkenyl groups (e.g. allyl); lower alkanoyl groups (eg. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethyisilyl, t-butyldimethylsilyl, tbutyldiphenylsilyl); aryl lower alkyl groups (e.g. benzyl) groups; and triaryl lower alkyl groups (e.g. triphenylmethyl).

Examples of amino protecting groups include formyl, aralkyl groups (e.g. benzyl and substituted benzyl. e.a. p-methoxybenzyl, nitrobenzyl and 2.4-dimethoxybenzyl, and triphenylmethyl); di-p-anisylmethyl and furylmethyl groups: lower alkoxycarbonyl (e.g. t-butoxycarbonyl): lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl: trialkylsilyl (e.g. trimethylsilyl and t-butyldimethylsilyl): alkylidene (e.g. methylidene): benzylidene and substituted benzylidene groups.

Methods appropriate for removal of hydroxy and amino protecting groups include for example, acid-base, metal- or enzymically-catalysed hydrolysis, or photolytically for groups such as o-nitrobenzyloxycarbonyl, or with fluoride ions for silyl groups.

Examples of protecting groups for amide groups include aralkoxymethyl (e.g benzyloxymethyl and substituted benzyloxymethyl): alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl(e.g. t-butyldimethylsilyoxymethyl, t-butyldiphenyisilyloxymethyl); 4-alkoxyphenyl (e.g. 4-methoxyphenyl); 2,4-di(alkoxy)phenyl (e.g. 2.4-dimethoxyphenyl); 4-alkoxybenzyl (e.g. 4-methoxybenzyl); 2,4-di(alkoxy)benzyl (e.g. 2.4-di(methoxy)benzyl); and alk-1-enyl (e.g. allyl, but-1-enyl and substituted vinyl e.g. 2-phenylyinyl).

Aralkoxymethyl, groups may be introduced onto the amide group by reacting the latter group with the appropriate aralkoxymethyl chloride, and removed by catalytic hydrogenation. Alkoxymethyl, trialkyl/arylsilyl and trialkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

Compounds of Formula I in which L represents —CO—NR$^{16}$— may be prepared by forming an amide bond between compounds 1 and 2 as outlined in Scheme 23 Compounds of Formula I in which L represents —CO—NR$^{25}$—T— may be prepared by an analogous procedure. Suitable coupling conditions include the following.

i) Use of EEDQ at room temperature in an organic solvent (e.g. dichloromethane, methanol).

ii) Use of oxalyl chloride in an organic solvent (e.g. DMF. $CH_2Cl_2$) in the presence of an organic base (e.g. NMM. triethylamine, DMAP) at 0° to room temperature for 0.5–16 h.

iii) Use of EDC/ HOBT in an organic solvent (e.g. DMF. $CH_2Cl_2$).

iv) Use of DCCI/ HOBT in an organic solvent (e.g. DMF. $CH_2Cl_2$) in the presence of an organic base (e.g. triethylamine).

v) Use of mixed anhydride reactions under standard conditions for example isopropylchloroformate in an organic solvent (e.g. DMF. DMA. dichloromethane) in the presence of an organic base (e.g. NMM. DMAP. triethylamine).

vi) Via an active ester under standard conditions e.g. pentafluorophenyl ester in an organic solvent (e.g. dichloromethane) in the presence of an organic base (e.g. triethylamine).

vii) Via an acid chloride under standard conditions e.g. using thionyl chloride and heat for about 150 min followed by an organic base (e.g. triethylamine) in the presence of an organic solvent (e.g. acetonitrile).

Compounds of Formula I in which L represents —$CH_2NR^{18}$—, —$CH_2O$— or —$CH_2S$— may be prepared as outlined in Scheme 24. LG represents a leaving group (e.g. mesyloxy, tosyloxy, halogen) and X represents S.O or NR$^{18}$. Suitable coupling conditions include the following.

i) Use of an inorganic base (e.g. $NaHCO_3$, NaH, $K_2CO_3$, butyllithium) in an organic solvent (e.g. THF, DMF, DMSO) and a temperature of about 70° to 150° ii) Use of an organic base (e.g. triethylam, DMAP) in an organic solvent (e.g. THF, dichloromethane, DMA, DMF) at a temperature range of room temperature –150° iii) Use of an inorganic base (e.g. KOH, NaOH, $K_2CO_{,3}$) in an aqueous (e.g. water) and organic solvents (e.g. dichloromethane) in a 2 phase system, optionally in the presence of a phase transfer catalyst (e.g. tetrabutylammoniumbromide).

Compounds of Formula I in which L represents —CH=CR$^{20}$— may be prepared using a Wittig reaction as outlined in Scheme 25. Suitable reaction conditions include the following.

i) Use of a base (e.g. potassium carbonate, metal hydride, metal alkoxide) in the presence of an organic solvent (e.g. THF, toluene, DMSO) optionally in the presence of an aqueous solvent (2-phase system) and optionally in the presence of a catalyst complexing agent which solubilises alkali metal ions in non-polar solvents such as 1,4,7,10,13 -pentaoxacyclopentadecane ( also called 15-Crown-5) or 1,4,7,10,13,16 -hexaoxacyclooctadecane ( also called 18-Crown-6).

Compounds of Formula I in which L represents —$CH_2$—NR$^{18}$— may be prepared as outlined in Scheme 26 by coupling aldehyde (2) with compound 4. Suitable coupling conditions include the following.

i) Use of a reducing agent (e.g. $NaCNBH_3$, $BH_3$, hydrogen plus catalyst, $LiHBEt_3$— di-isobutyl-aluminiumhydride, lithium aluminium hydride, sodium borohydride) in the presence of a suitable solvent e.g. ethanol & acetic acid.

Aldehyde (2) may be prepared by oxidation of the corresponding alcohol (1) under suitable conditions such as use of an oxidising agent (e.g. TPAP. NMM—O) in the presence of an organic solvent (e.g. acetonitrile, dichloromethane) at room temperature. Other suitable oxidising agents include chromium oxide, pyridinium chlorochromate, pyridinium dichromate, sodium dichromate and sodium hypochlorite.

Aldehyde (2) may also be prepared by reduction of the corresponding ester (1) under standard conditions using for example diisobutyl-aluminium hydride.

Compounds of Formula I in which L represents —$CH_2$—$NR^{21}$—T—. —$CH_2$—O—T— or —$CH_2$—S—T— may be prepared as outlined in Scheme 27 in which LG represents a leaving group (e.g. mesyloxy, tosyloxy, halogen) and X represent O, S or $NR^{21}$. Suitable coupling conditions are as outlined above in relation to Scheme 24. Optionally the positions of LG and XH in compounds 1 & 2 in Scheme 27 can be reversed to give the same end product.

Compounds of Formula I in which L represents —$CH_2$—$NR^{23}$—$SO_2$— may be prepared as outlined in Scheme 28. Compounds 1 & 2 may be coupled under standard conditions such as the following.

i) Use of an organic base (e.g. di-isopropyl-ethylamine, triethylamine, 4-methyl-morpholine) in the presence of an organic solvent (e.g. dichloromethane) at a temperature range of 0°–40° ii) Use of an inorganic base (e.g. potassium carbonate) in the presence of an organic solvent (e.g. DMF) at a temperature range of 0°–150°.

Compounds of Formula I in which L represents —$CH_2$—$NR^{24}$—CO—T— may be prepared as outlined in Scheme 29. Compounds 1 & 2 may be coupled under standard conditions such as described above for L=—CO—$NR^{16}$—.

Compounds of Formula I in which L represents —$CH_2$—$CHR^{19}$—may be prepared as by reduction of compounds of the type set out as compound 3 in Scheme 25 but substituting $R^{19}$ in lieu of $R^{20}$. Reduction is carried out under standard conditions with standard reagents for example using hydrogenation in the presence of a catalyst such as palladium on charcoal at room temperature.

Biological activity was tested as follows. Farnesyl protein transferase (FPT) was partially purified from human placenta by ammonium sulphate fractionation followed by a single Q-Sepharose® (Pharmacia. Inc) anion exchange chromatography essentially as described by Ray and Lopez-Belmonte (Ray K P and Lopez-Belmonte J (1992) Biochemical Society Transations 20 494–497). The substrate for FPT was Kras (CVIM C-terminal sequence). The cDNA for oncogenic val 12 variant of human c-Ki-ras-24B was obtained from the plasmid pSW11-1(ATCC). This was then subcloned into the polylinker of a suitable expression vector e.g. plC 147. The Kras was obtained after expression in the E. coli strain, BL21. The expression and purification of c-KI-ras-24B and the val12 variant in E. coli has also been reported by Lowe et al (Lowe P N et al. J. Biol. Chem. (1991) 266 1672–1678).

Incubations with enzyme contained 300 nM tritiated farnesyl pyrophosphate (DuPont/New England Nuclear), 120 nM ras-CVIM, 50 mM Tris HCl pH 8.0. 5 mM $MgCl_2$, 10 μM $ZnCl_2$, 5 mM dithiotheitol and compounds were added at appropriate concentrations in DMSO (3% final concentration in test and vehicle control). Incubations were for 20 minutes at 37° and were stopped with acid ethanol as described by Pompliano et al. (Pompliano D L et al (1992) 31 3800–3807). Precipitated protein was then collected onto glass fibre filter mats (B) using a Tomtec® cell harvester and tritiated label was measured in a Wallac® 1204 Betaplate scintillation counter.

Although the pharmacological properties of the compounds of the Formula I vary with structural change as expected, in general compounds of the Formula I possess an $IC_{50}$ in the above test in the range, for example, 0.01 to 200 μM. Thus by way of example the compound 5{[(2S,4S)4-acetylsulfanyl-1-(4-nitro-benzyloxycarbonyl)-pyrrolidine-2-carbonyl]-amino}-3(N-methyl-methylcarbamoyl)-benzoic acid allyl ester (see Example 7) has an $IC_{50}$ of approximately 0.5 μM. No physiologically unacceptable toxicity was observed at the effective dose for compounds tested of the present invention.

The invention will now be illustrated in the following non-limiting Examples in which. unless otherwise stated:

(i) evaporations were carried out by rotary evaporation in vacuo and work-up procedures were carried out after removal of residual solids by filtration:

(ii) operations were carried out at room temperature, that is in the range 18–25° C. and under an atmosphere of an inert gas such as argon:

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck. Darmstadt. Germany;

(iv) yields are given for illustration only and are not necessarily the maximum attainable;

(v) the end-products of the Formula I have satisfactory microanalyses and their structures were confirmed by nuclear magnetic resonance (NMR) and mass spectral techniques: chemical shift values were measured on the delta scale; the following abbreviations have been used: s, singlet; d. doublet; t or tr. triplet: m. multiplet: br. broad:

(vi) intermediates were not generally fully characterised and purity was assessed by thin layer chromatographic, infra-red (IR) or NMR analysis:

(vii) melting points are uncorrected and were determined using a Mettler SP62 automatic melting point apparatus or an oil-bath apparatus: melting points for the end-products of the Formula I were determined after crystallisation from a conventional organic solvent such as ethanol, methanol, acetone, ether or hexane, alone or in admixture: and (viii) the following abbreviations have been used:
BOC tert-butoxycarbonyl
DCCI 1,3-dicyclohexylcarbodiimide
DMA N,N-dimethylacetamide
DMAP 4-dimethyl-aminopyridine
DMF N,N-dimethylformamide
DMSO dimethylsulfoxide
EDC 1-(3-dimethylaminopropyl)-3-ethyl-carbodiimide
EEDQ 2-ethoxy-1-ethoxycarbonyl-1,2-dihydroquinoline
HOBT 1-hydroxybenzotriazole
NMM N-methylmorpholine
NMM-O 4-methylmorpholine-N-oxide
TFA trifluoroacetic acid
THF tetrahydrofuran
TMSI trimethylsilyliodide
TPAP tetrapropylammonium perruthenate Note in the Schemes only those hydrogen atoms thought to assist clarity have been illustrated (ie not all hydrogen atoms have been illustrated).

EXAMPLE 1

See Scheme 1

(2S,4S)4-acetylsulfanyl-2[3-nitro-5-(N-methoxy-N-methyl-carbamoyl)-phenylcarbamoyl]-pyrrolidine-1-carboxylic acid 4-nitro-benzyl ester A mixture of 4-acetylsulfanyl-pyrrolidine-1,2-dicarboxylic acid 1-(4-nitrobenzyl) ester (1(c)) (0.2 g) and 3-amino-N-methoxy-N-methyl-5-nitro-benzamide (1(b)) (0.122 g) and EEDQ (0.201 g) in dichloromethane (20 ml) was stirred at ambient temperature for 16 hours. The solution was then stirred with 0.3M hydrochloric acid (20 ml) for ten minutes. The organic phase was separated dried over magnesium sulphate and evaporated under reduced pressure to give a gum. This was purified by chromatography using 1,ethyl acetate/hexane (50:50) 2,ethyl acetate/hexane (75:25) to give the desired product (1) as a colourless gum (0.132 g).

NMR Spectrum (CDCl$_3$) δ2.35 (s, 3H), 2.62 (m, 2H), 3.4 (s. 3H), 3.44 (m, 1H), 3.6 (s, 3H), 4.1 (m, 2H), 4.59 (t, 1H), 5.3 (m, 2H), 7.55 (d, 2H), 8.09 (m, 1H), 8.25(d, 2H), 8.3 (m, 1H), 8.6 (m, 1H), 9.55 (br, s, 1H).

Starting material (1(c)) was synthesised as described in Reference Example 1-4 in European patent no 126587 (Sumitomo).

Starting material (1(b)) was prepared as follows. A mixture of 3-amino-5-nitrobenzoic acid (10 g), pentafluorophenol (10 g) and DCCI (11.3 g) was stirred at ambient temperature for 24 hours. The reaction mixture was filtered and the filtrate poured onto a chromatography column which was then eluted with ethyl acetate/hexane (10:90) to give 3-amino-5-nitrobenzoic acid 2,3,4,5,6-pentafluorophenyl ester (1(a)) as a yellow solid (5.8 g).

NMR Spectrum (CDCl$_3$) δ4.3 (br, s, 2H), 7.7 (tr, 1H), 7.8 (tr, 1H), 8.36 (tr. 1H).

A mixture of (1(a)) (1.0 g), N,O-dimethylhydroxylamine HCl salt (0.84 g) and triethylamine (1.82 ml) in dichloromethane (50 ml) was stirred at ambient temperature for 48 hours. Water(50 ml) was added and the mixture stirred for a further 5 minutes. The organic phase was separated, dried over magnesium sulphate and evaporated under reduced pressure to give a gum. This was purified by chromatography using 1. ethyl acetate/hexane (10:90), 2, ethyl acetate/hexane (50:50) as eluents to give starting material 3-amino-N-methoxy-N-methyl-5-nitro benzamide (1(b)) as a yellow solid (0.55 g).

NMR Spectrum: (CDCl$_3$) δ3.36 (s, 3H), 3.58 (s, 3H), 7.26 (tr, 1H), 7.56 (tr, 1H), 7.90 (tr, 1H).

EXAMPLE 2

See Scheme 2

(2S,4S)4-acetylsulfanyl-2[3-(N-methoxy-N-methylcarbamoyl)-5-nitro-phenylcarbamoyl]-pyrrolidine-1-carboxylic acid allyl ester A mixture of (2S,4S),4-acetylsulfanyl-pyrrolidine-1,2-dicarboxylic acid 1-allyl ester (1(d)) (0.2 g), 1(b) (0.165 g), and EEDQ (0.271 g), in dichloromethane (20 ml) was stirred at ambient temperature for 16 hours. The solution was then stirred with 0. 3M hydrochloric acid for a further 10 minutes. The organic phase was then separated, dried over magnesium sulphate and evaporated under reduced pressure. The product obtained was purified by column chromatography using ethyl acetate/hexane (50:50) as eluent to give the desired product (2) as a colourless gum (0.152 g).

NMR Spectrum (CDCl$_3$) δ2.33 (s, 3H), 2.62(m, 2H), 3.38 (m, 1H), 3.4 (s, 3H), 3.6(s, 3H), 4.05 (m, 2H), 4.59 (tr, 1H), 4.69 (d, 2H), 5.3 (m, 2H), 5.95 (m, 1H) 8.14 (t, 1H), 8.28 (tr, 1H), 8.6 (tr, 1H), 9.7 (br,s, 1H).

Synthesis of starting material (1(d)) is described as "Compound (A)" on page 31 of International Patent Application No. WO 92/17479 (Imperial Chemical Industries). Synthesis of starting material (1(b)) is described in Example 1.

EXAMPLE 3

See Scheme 3

5-{[(2S,4S),4-acetylsulfanyl-1-(4-nitrobenzyloxycarbonyl)-pyrrolidine-2-carbonyl]-amino}-isophthalic acid 1-allyl ester 3-methyl ester DMF (0.07 ml) was added to a stirred solution of oxalyl chloride (0.078 ml) in dichloromethane (20 ml) cooled to −20° C. under an argon atmosphere. After 15 minutes a solution of (1(c)) (0.3 g; see Example 1) in dichloromethane was added followed by a solution of N-methylmorpholine (0.099 ml) in dichloromethane (2 ml). After a further 15 minutes a solution of 5-amino-isophthalic acid allyl ester methyl ester (3(b)) (0.192g) in dichloromethane (5 ml) was added again followed by a solution of N-methylmorpholine (0.099 ml) in dichloromethane (2 ml). The mixture was allowed to warm to ambient temperature and stirred for 16 hours. The reaction mixture was poured onto a flash column and eluted with 1, ethyl acetate/hexane (50:50) and, 2. ethyl acetate/hexane (75:25) to give the desired end product (3) as a colourless gum (0.24 g)

NMR Spectrum (CDCl$_3$) δ2.33 (s, 3H), 2.62 (m, 2H), 3.45 (m, 1H), 3.95 (s, 3H), 4.03 (m, 1H), 4.17 (m, 1H), 4.57 (tr, 1H), 4.85 (m, 2H), 5.32 (m, 2H), 5.36 (m, 2H), 6.05 (m, 1H), 7.51 (m, 2H), 8.20 (m, 2H), 8.32 (m, 2H), 8.34 (s, 1H), 92 (br, s, 1H).

Starting material (3(b)) was synthesised as follows. A mixture of mono-methyl-5-nitroisophthalate (13.8 g), allyl bromide (7.96 g), potassium carbonate (13.94 g) and DMF (160 ml) was stirred at ambient temperature for 4.5 h. The solid was filtered and DMF was evaporated away from the filtrate under reduced pressure. The residue was dissolved in diethyl ether (300 ml) and water (100 ml) and stirred for five minutes. The organic layer was separated and washed with saturated sodium bicarbonate solution (220 ml), brine (200 ml). dried over magnesium sulphate and evaporated under reduced pressure to give 5-nitro-isophthalic acid allyl ester methyl ester (3(a)) as a yellow oil (14.74 g).

NMR spectrum (CDCl$_3$) δ4.0 (s, 3H), 4.9 (m, 2H), 5.4 (m, 2H), 6.1 (m, 1H), 9.0 (m, 3H).

A mixture of (3(a)) (15.46 g), tin (II) chloride dihydrate (65.78 g) and methanol (200 ml) was stirred at reflux for 4 hours. Methanol was evaporated under reduced pressure and the residue redissolved in ethyl acetate (400 ml). Ammonia solution (sp, g, 0.880) was added dropwise until the mixture reached pH 8 and no more precipitate was being formed. The solid was then filtered and the filtrate was washed with water (100 ml), brine( 100 ml), dried over magnesium sulphate and evaporated under reduced pressure to give starting material 3(b) as a yellow solid (13.56 g).

NMR spectrum (CDCl$_3$) δ3.91 (s, 3H) 3.94 (s, 2H), 4.82 (m, 2H), 5.35 (m, 2H), 6.05 (m, 1H), 7.52 (m, 2H), 8.08 (m, 1H).

EXAMPLE 4

See Scheme 4

5-{[(2S,4S),4-acetylsulfanyl-1-(carbamoylmethyl)-pyrrolidine-2-carbonyl]-amino}-isophthalic acid 1-allyl ester 3-methyl ester A mixture of 5-{[(2,4S),4-acetylsulfanyl-pyrrolidine-2-carbonyl]-amino}-isophthalic acid 1-allyl ester 3-methyl ester TFA salt (4(e)) (0.12 g), iodoacetamide (0.085 g), sodium bicarbonate (0.058 g) and DMF (3.0 ml) was stirred at ambient temperature for 16 h. The DMF was evaporated under reduced pressure and the residue purified by chromatography using 1, ethyl acetate/hexane (60:40), 2, ethyl acetate and 3, methanol/ethyl acetate (5:95) as eluents to give the desired product 4 as a yellow solid (0.055 g).

NMR spectrum δ2.19 (2 tr,1H), 2.29 (s, 3H), 2.82 (m, 1H), 3.22 (m, 2H), 3.48 (q, 2H), 3.6 (m, 1H), 3.94 (s, 3H), 4.05 (m, 1H), 4.85 (m, 2H), 5.35 (m, 2H), 6.04 (m, 1H), 6.1 (br, s, 1H) 6.30 (br, s, 1H), 8.43 (m, 1H), 8.55 (m, 1H), 10.46 (br, s, 1H).

Starting material 4(e) was prepared as follows. A mixture of (2S,4.),4-hydroxy-pyrrolidine-1,2-dicarboxylic acid 1-tert-butyl ester (1.0 g), EEDQ (1.6 g), Compound (3(b)) (see Example 3) and dichloromethane (100 ml) was stirred at ambient temperature for 16 hours.

The mixture was poured onto a flash column and eluted with 1, ethyl acetate/hexane (80:20) and. 2. ethyl acetate to give 5-{[(2S,4S),4-hydroxy-1-(tert-butoxycarbonyl)-pyrrolidine-2-carbonyl]-amino}-isophthalic acid 1-allyl ester 3-methyl ester (4(a)) as a colourless gum (0.85 g.).

NMR Spectrum (DMSOd6) δ1.34 (2s, 9H), 1.97 (m, IH), 2.15 (m, 1H), 3.30 (m, 1H), 3.9 (s, 3H), 4.32 (m, 2H), 4.84 (d, 2H), 5.06 (d. 1H), 5.35 (m, 2H) 8.18 (m, 1 H), 8.54 (m, 2H).

A mixture of (4(a)) (0.8 g), methanesulfonyl chloride (0.152 ml), triethylamine (0.256 ml), and dichloromethane (20 ml) was stirred at 5° under an argon atmosphere for 10 minutes and then at ambient temperature for 2 h. Water (20 ml) was then added and the mixture stirred for another 5 minutes. The organic phase was separated, dried over magnesium sulphate and evaporated under reduced pressure. The product was purified by chromatography using 1, ethyl acetate/hexane (30:70) and, 2, ethyl acetate/hexane (80:20) as eluents to give 5-{[(2S,4S), 4-methanesulfanyloxy-1-(tert-butoxycarbonyl)-pyrrolidine-2-carbonyl]-amino}-isophthalic acid 1-allyl ester 3-methyl ester (4(b)) as a clear oil (0.8 g).

NMR spectrum (CDCl₃) δ1.5 (s, 9H), 2.4 (m, 1H), 2.92 (m, 1H), 3.07 (s, 3H), 3.63 (m, 1H), 3.9 (m, 1H), 3.95 (s, 31H) 4.66 (m, 1H), 4.85 (m, 2H), 5.27 (m, 1H), 5.36 (m, 2H), 6.05 (m, 1H), 8.37 (m, 3H), 9.64 (br, s, 1H).

A mixture of 4(b) (0.74 g), potassium thioacetate (0.32 g) and acetone (25 ml) was maintained at reflux for 18 hours. The mixture was then cooled to room temperature and acetone evaporated under reduced pressure. The residue was dissolved in a mixture of ethyl acetate (50 ml), 1.5M hydrochloric acid (25 ml), and ice (25 ml). The organic phase was separated, dried over magnesium sulphate and evaporated under reduced pressure to give a red gum. This was purified by chromatography using 1, ethyl acetate/hexane (30:70) and, 2, ethyl acetate/hexane(70:30) to give 5-{[((2S,4S),4-acetylsulfanyl-1-(tert-butoxycarbonyl)-pyrrolidine-2-carbonyl]-amino}-isophthalic acid 1-allyl ester 3-methyl ester (4(c)) as an orange gum (0.48 g).

NMR spectrum (CDCl₃) δ1.5 (s, 9H), 2.32 (s, 3H), 2.56 (m, 2H) 3.33 (m, 1H), 3.93 (s, 3 H), 4.04 (m, 2H), 4.52 (tr, 1H), 4.85 (m, 2H), 5.35 (m, 2H), 6.05 (m, 1H), 9.63 (br, s, 1H).

A mixture of (4(c)) (3.6 g) and TFA (80 ml) was stirred at ambient temperature for 10 minutes. TFA was evaporated under reduced pressure and the residue dissolved in ethyl acetate (200 ml.) and saturated sodium bicarbonate solution (100 ml). This was then stirred for 10 minutes, the organic phase separated, washed with water (100 ml) and brine (100 ml) and dried over magnesium sulphate. The ethyl acetate was removed under reduced pressure and the residue purified by chromatography using 1, ethyl acetate/hexane (30:70), 2, ethyl acetate/hexane (80:20) as eluents to give 4(f) (the free base which is used in Example 6) as a brown oil (2.3 g). NMR Spectrum (CDCl₃) δ2.05 (m, 1H), 2.30 (s, 3H), 2.42 (br, s, 1H), 2.78 (m, 2H), 3.58 (m, 1H), 3.85 (m, 1H), 3.94 (s, 3H), 3.99 (m, 1H), 4.84 (m, 2H), 5.35 (m, 2H), 6.05 (m, 1H), 8.47 (m, 3H), 9.83 (br, s, 1H).

A mixture of (4(c)) (0.45 g) and TEA (10 ml) was stirred at ambient temperature for 10 minutes. The TFA was evaporated away under reduced pressure and the residue purified by column chromatography using 1 ethyl acetate/hexane (30:70), 2 ethyl acetate/hexane (60:40), 3 ethyl acetate and, 4 methanol/ethyl acetate (10:90) as eluents to give the desired starting material (4(e)) as a brown gum (0.46 g).

NMR Spectrum (CDCl₃) δ2.15 (m, 1H), 2.33 (s, 3H), 2.97 (m, 1H), 3.44 (m, 1H), 3.91 (s, 3H), 3.97 (m, 1H), 4.08 (m, 1H), 4.82 (d, 2H), 4.98 (tr, 1H), 5.35 (m, 2H), 6.03 (m, 1H), 8.12 (m, 2H), 8.26 (m, 1H).

EXAMPLE 5

See Scheme 5

5-{[(2S,4S),4-acetylsulfanyl-1-acetyl-pyrrolidine-2-carbonyl]-amino}-isophthalic acid 1-allyl ester 3-methyl ester A mixture of (4(e)) (0.08 g: see Example 4), triethylamine (0.083 ml), acetic anhydride (0.056 ml) and dichloromethane (5 ml) was maintained at reflux for 16 hours. The mixture was cooled, evaporated under reduced pressure and purified by chromagraphy using 1 ethyl acetate/hexane (70:30), 2 ethyl acetate and, 3 methanol/dichloromethane (5:95) to give the desired product 5 as a colourless gum (0.048 g).

NMR Spectrum (CDCl₃) δ2.18 (s, 3H), 2.35 (s, 3H), 2.48 (m, 1H), 2.77 (m, 1H), 3.42 (m, 1H), 3.95 (s, 3H), 4.1 (m, 2H), 4.85 (m, 3H), 5.35 (m, 2H), 6.06 (m, 1H), 8.40 (m, 3H), 9.88 (br, s, 1H).

Starting material 4(e) was prepared as described in Example 4.

EXAMPLE 6

See Scheme 6

5-{[(2S,4S),4-acetylsulfanyl-1-phenyloxycarbonyl-pyrrolidine-2-carbonyl]-amino}-isophthalic acid 1-allyl ester 3-methyl ester A mixture of (4(f)) (0.07g), phenyl chloroformate (0.026 ml), triethylamine (0.07 ml) and dichloromethane (3 ml) was stirred at ambient temperature for 16 hours. The mixture was then evaporated under reduced pressure to give a gum which was purified by chromatography using 1 dichloromethane 2 ethyl acetate/hexane (30:70) and, 3 ethyl acetate/hexane (60:40) to give the desired product as a colourless gum (0.048 g.).

NMR Spectrum (DMSOd6) δ1.93-2.24 (m, 1H), 2.38 (s, H), 2.70 (m, 1H), 3.63 (m, 1H), 3.91 (d, 3H), 4.18 (m, 2H), 4.60 (m, 1H), 4.87 (tr, 2H), 5.38 (m, 1H), 6.08 (m, 1H) 6.70-7.69 (m, 5H), 8.20-8.53 (m, 3H), 10.61 (d, 1H).

Starting material (4(f)) was prepared as described in Example 4.

EXAMPLE 7

See Scheme 7

5 {[(2S,4S),4-acetylsulfanyl-1-(4-nitro-benzyloxycarbonyl)-pyrrolidine-2-carbonyl]-amino}-3(N-methyl-methoxycarbamoyl)-benzoic acid allyl ester A mixture of (1(c)) (0.02 g: see Example 1), 3-amino-5 (N-methyl-methoxycarbamoyl)-benzoic acid allyl ester (7(d)) (0.16 g.), EEDQ (0.25 g) and dichloromethane (20 ml) was stirred for 16 h at ambient temperature. The mixture was then washed with 0.3M hydrochloric acid (30 ml), the organic phase separated, dried over magnesium sulphate and evaporated to dryness under reduced pressure. The residue was purified by column chromatography using ethyl acetate/hexane (75:25) as eluent to give the desired product 7 as a yellow solid (0.053 g).

NMR Spectrum (CDCl$_3$) δ2.33 (s, 3H), 2.60 (m, 2H), 3.38 (s, 3H), 3.42 (m, 1H), 3.60 (s, 3H), 4.04 (m, 1H), 4.15 (m, 1H), 4.55 (m, 1H), 4.83 (m, 2H), 5.30 (m, 2H), 5.35 (m, 2H), 6.04 (m, 1H), 7.52 (m, 2H), 8.10 (m, 3H), 8.18 (m, 2H), 9.12 (br, s, 1H).

Starting material (1(c)) was prepared as described in Example 1. Starting material 7(d) was prepared as follows. A mixture of potassium carbonate (17.00 g), 5-nitro-isophthalic acid (52.00 g), allyl bromide and dimethylacetamide (400 ml) was stirred at 90° for 4 h. Dimethylacetamide was evaporated away under reduced pressure and the residue was dissolved in ethyl acetate, washed with water (2×300 ml) and then extracted with aqueous saturated sodium bicarbonate solution (3×300 ml). The extracts were combined, acidified to pH 4 with concentrated hydrochloric acid and reextracted with ethyl acetate (2×300 ml). The extracts were combined, washed with water (300 ml), dried over magnesium sulphate and evaporated under reduced pressure to give 5-nitro-isophthalic acid 3-allyl ester (7(a)) as a cream solid (39.48 g).

NMR Spectrum (CDCl$_3$/DMSOd6) δ4.90 (m, 2H), 5.42 (m, 2H), 6.08 (m, 1H). 9.00 (m, 3H).

A solution of 7(a) (10.00 g), N-hydroxysuccinimide (5.04 g) and DCCI (9.03 g) in dichloromethane(400 ml) was stirred at ambient temperature for 3.5 h. The white precipitate which formed was filtered off and the filtrate evaporated under reduced pressure to give a yellow oil. This was purified by flash chromatography eluting with ethyl acetate/hexane (75:25) to give 5-nitro-isophthalic acid 1-(2.5-dioxo-pyrrolidin-1-yl) ester 3-allyl ester (7(b)) as a yellow solid (7.58 g).

NMR Spectrum (CDCl$_3$) δ2.95 (s, 4H), 4.92 (m, 2H), 5.43 (m, 2H), 6.07 (m, 1H), 9.12 (m, 3H).

A mixture of (7(b)) (2.00 g), N,O-dimethylhydroxylamine hydrochloride (0.62 g), triethylamine (0.86 ml) and dichloromethane (60 ml) was stirred at 50 for 30 min and then allowed to warm to ambient temperature and stirred for a further 16 h. The mixture was poured onto a flash column and eluted with ethyl acetate/hexane (40:60) to give 3-(N-methyl-methoxycarbamoyl)-5-nitro benzoic acid allyl ester (7(c)) as a yellow oil.

NMR Spectrum (CDCl$_3$) δ3.43 (s, 3H), 3.58 (s, 3H), 4.90 (m, 2H), 5.40 (m, 2H), 6.07 (m, 1H), 8.71 (m, 1H), 8.76 (m, 1H), 8.95 (m, 1H).

A mixture of (7(c)) (1.11 g), tin(II) chloride dihydrate (4.26 g) and methanol (60 ml) was heated under reflux for 1 hour. The reaction mixture was cooled and the methanol evaporated away under reduced pressure. The residue was redissolved in ethyl acetate (100 ml) and ammonia solution (sp, g, 0.880) was added dropwise until the solution reached pH 8. The precipitate that formed was filtered and washed with ethyl acetate (2×100 ml). The combined fitrate and washings were evaporated under reduced pressure to give the desired starting material 3-amino-5-(-methyl-methoxycarbamoyl)-benzoic acid allyl ester (7(d)) as a white solid (0.610 g).

NMR Spectrum (CDCl$_3$) δ3.35 (s, 3H), 3.59 (s, 3H), 3.90 (br, s, 2H), 4.82 (m, 2H), 4.82 (m, 2H), 6.04 (m, 1H), 7.15 (m, 1H), 7.45 (m, 1), 7.72 (m, 1H).

EXAMPLE 8

See Scheme 8

5 {[(2S,4S),4-acetysulfanyl-1-(4-nitro-benzyloxycarbonyl)-pyrrolidine-2-carbonyl]-amino}-3(N-methyl-allyloxycarbamoyl)benzoic acid allyl ester A mixture of (1(c)) (0.293 g; see Example 1), 3-amino-5(N-methyl-allyloxycarbamoyl)-benzoic acid allyl ester (8(c)) (0.210 g), EEDQ (0.268 g) and dichloromethane (20 ml) was stirred at ambient temperature for 16 hours. The mixture was then washed with 0.3M hydrochloric acid (30 ml), dried over magnesium sulphate and placed straight onto a flash column eluting with ethyl acetate/hexane (75:25). The product obtained was placed onto a flash column eluting with methanol/dichloromethane (2.5:97.5) to give the desired product 8 as a clear gum (0.153 g).

NMR Spectrum (CDCl$_3$) δ2.33 (s, 3H), 2.61 (m, 2H), 3.40 (s, 3H), 3.42 (m, 1H), 4.04 (m, 1H), 4.15 (m, 1H), 4.26 (d, 2H), 4.55 (m, 1H), 4.83 (m, 2H), 5.30 (m, 6H), 5.75 (m, 1H), 6.04 (m, 1H), 7.53 (m, 2H), 8.12 (m, 2H), 8.21 (m, 3H), 9.12 (br, s, 1H).

Starting material (8(c)) was prepared as follows. A mixture of 7(b) (2.00 g; see Example 7), N-methylhydroxylamine hydrochloride (1.06 g) triethylamine (1.72 ml) and dichloromethane (60 ml.) was stirred at 5° for 30 minutes. It was then allowed to warm to ambient temperature and stirred for a further 16 hours. The reaction mixture was then poured directly onto a flash column eluting with ethyl acetate/hexane (50:50) to give 3-(N-methyl-hydroxycarbamoyl)-5-nitro-benzoic acid allyl ester (8(a)) as a cream solid (1.43 g).

NMR Spectrum (CDCl$_3$) δ3.48 (s, 31H), 4.90 (m, 2H), 5.42 (m, 2H), 6.05 (m, 1H), 8.28 (br, s, 1H), 8.55 (m, 1H), 8.63 (m, 1H), 8.96 (m, 1H).

A mixture of (8(a)) (0.60 g), allyl bromide (0.28 g), potassium carbonate (0.59 g) and DMF (20 ml) was stirred for 3 hours at ambient temperature under an argon atmosphere. The dimethyl formamide was then evaporated under reduced pressure and the residue dissolved in ethyl acetate (50 ml) and water (50ml). The organic phase was separated, washed with brine (50 ml), dried over magnesium sulphate and evaporated under reduced pressure to dryness to give 3-(N-methyl-allyloxycarbamoyl)-5-nitro-benzoic acid allyl ester (8(b)) as a yellow oil (0.571 g).

NMR Spectrum 5 3.47 (s, 3H), 4.25 (m, 2H), 4.90 (m, 2H), 5.35 (m, 4H), 5.65 (m, 1H), 6.06 (m, 1H), 8.73 (m, 1H), 8.78 (m, 1H), 8.95 (m, 1H).

A mixture of (8(b)) (0.523 g), tin(II) chloride dihydrate (1.84 g) and ethyl acetate (50 ml) was heated under reflux for 6 hours. The mixture was allowed to cool to ambient temperature and ammonia solution (sp. g. 0.880) was added dropwise until the solution reached pH 8. The white precipitate which had formed was filtered off. washed with ethyl acetate (2×50 ml) and the combined washings and filtrate evaporated to dryness to give the desired starting material (8(c)) as a yellow oil (0.472 g).

NMR Spectrum (CDCl$_3$) δ3.38 (s, 3H), 3.88 (m. 2H), 4.25 (d. 2H), 4.80 (m, 2H), 5.32 (m, 4H), 5.75 (m, 1H), 6.03 (m, 1H), 7.15 (m, 1H), 7.45 (m, 1H), 7.75 (m, 1H).

EXAMPLE 9

See Scheme 9

5-{[(2S,4S),1-(allyloxycarbonyl)-4-sulfanyl-pyrrolidine-2-carbonyl]-amino}-3(N-methyl-allyloxycarbamoyl)-benzoic acid allyl ester An aqueous solution of 0.1M sodium hydroxide (4.41 ml) was added to a solution of 5-{[(2S,4S),4-acetylsulfanyl-1-

(allyloxycarbonyl)-pyrrolidine-2-carbonyl]-amino}-3(N-methyl-allyloxycarbamoyl)-benzoic acid allyl ester (9(a)) in allyl alcohol (15 ml) and the mixture was then stirred at ambient temperature for 1 hour. Hydrochloric acid (1.5M) was then added to bring the solution to pH3 and it was then evaporated to dryness under reduced pressure. The residue was dissolved in ethyl acetate (40 ml) and washed with water (2×40 ml). The organic phase was separated, dried over magnesium sulphate and evaporated to dryness to give a yellow foam. This was purified by chromatography using ethyl acetate/hexane (75:25) as eluent to give the desired product 9 as a yellow gum (0.148 g).

NMR Spectrum (CDCl$_3$)δ1.88 (d, 2H), 2.62 (m, 2H), 3.37 (s, 3H), 3.45 (m, 2H), 3.60 (s, 3H), 4.08 (m, 1H), 4.52 (tr, 1H), 4.65 (m, 2H), 4.83 (m, 2H), 5.35 (m, 4H), 6.00 (m, 2H), 8.10 (m, 1H), 8.15 (m, 1H), 8.21 (m, 1H), 9.15 (br, s, 1H).

Starting material 9(a) was prepared as follows. A mixture of 7(d) (0.568 g; see Example 7), 1(d) (0.645 g,; see Example 20), EEDQ (0.585 g) and dichloromethane (50 ml) was stirred at ambient temperature for 16 hours. The mixture was then washed with 0.3M hydrochloric acid(50 ml). dried over magnesium sulphate and applied to a flash column eluting with ethyl acetate/hexane (75:25). It was further purified with a second column eluting with ethyl acetate/hexane (50:50) to give the desired starting material (9(a)) as a colourless gum (0.401 g).

NMR Spectrum (CDCl$_3$) δ2.33 (s, 3H), 2.60 (m, 2H), 3.37 (s, 31H), 3.40 (m, 1H), 3.61 (s, 3H), 4.02 (m, 1H), 4.13 (m, 1H), 4.58 (tr, 1H), 4.68 (m, 2H), 4.83 (m, 2H), 5.35 (m, 4H), 6.00 (m, 2H), 8.10 (m, 1H), 8.14 (m, 1H), 8.22 (m, 1H), 9.30 (br, s, 1H).

EXAMPLE 10

See Scheme 10

5-[((2S,4S),1-allyloxycarbonyl-4-sulfanyl-pyrrolidin-2-yl-methyl)-carbamoyl]-pyridine-2-carboxylic acid methyl ester To a stirring solution of 5-[((2S,4S),1-allyloxycarbonyl-4-BOCsulfanyl-pyrrolidin-2-yl-methyl)-carbamoyl]-pyridine-2-carboxylic acid methyl ester (10(a)) (991 mg; 2.07 mmole) in dichloromethane. TFA (6 mL; 78 mmole) was added dropwise. The solution was stirred, under argon, for 4 hours. The solvent and excess TFA were removed in vacuo. The residue was azeotroped with toluene (2×10 mL). Keeping exposure to air to a minimum the resultant oil was triturated with diethyl ether (20 mL). The resultant solid was washed with cold diethyl ether (10 mL) and dried under high vacuum yielding the desired product 10 as a cream solid. 654 mg (76%).

[4] has NMR (CDCl$_3$; 250 MHz) 1.70 (m, 1H), 1.75 (d, 1H), 2.63–2.77 (m, 1H), 3.15–3.50 (m, 3H), 3.90–4.00 (m, 1H), 4.05 (s, 3H), 4.07–4.23 (m, 2H), 4.63 (m, 2H), 5.27–5.37 (m, 2H), 5.85–6.03 (m, 1H), 8.22 (d, 1H), 8.35 (dd, 1H), 8.95 (s(br), 1H), 9.20 (s, 1H). MS (FAB) m/z 380 (M+H)$^+$Anal. C$_{17}$H$_{21}$N$_3$O$_5$S. 0.33 C$_2$HF$_3$O$_2$ 417: C, 50.9 (50.8); H, 5.3 (5.1); N, 10.1 (10.1).

Starting material (10(c)) was prepared as follows. Pyridine 2,5-dicarboxylic acid 2-methyl ester (10(a)) (9.0 g; 0.05 mole) was added to stirring thionyl chloride (25 mL) and the mixture refluxed gently for 2.5 hours. The excess thionyl chloride was removed in vacuo and the residual solid azeotroped with toluene (2×25 mL) to give 5-chlorocarbonyl-pyridine-2-carboxylic acid methyl ester (10(b)) which was used crude in the next reaction.

To a stirring solution of compound (15(b)) (Example 15)(220 mg; 0.7 mmole) in acetonitrile (6 mL) was added a solution of (10(b)) (0.7 mmole) in acetonitrile (4 mL). Triethylamine (0.29 mL; 2.1 mmole) was added and the solution stirred for 23 hours. The solvent and excess triethylamine were removed in vacuo and the residue partitioned between chloroform and water. The organic phase was washed with water, aqueous sodium hydrogen carbonate solution and brine, dried over magnesium sulphate and taken to dryness. The residual orange gum was flash chromatographed on kieselgel 9385, eluting initially with iso-hexane then with increasing proportions of ethyl acetate. The desired starting material 10(c) was isolated as a white foam (200 mg; 60%).

NMR (CDCl$_3$; 250 MHz) 1.50 (s, 9H), 1.80 (m, 1H), 2.62–2.75 (m, 1H), 3.30–3.37 (m, 1H), 3.39–3.50 (m, 1H), 3.68–3.80 (m, 1H), 3.83–3.95 (m, 1H), 4.03 (s, 3H), 4.13–4.28 (m, 2H), 4.62 (m, 2H), 5.20–5.37 (m, 2H), 5.87–6.02 (m, 1H), 8.2 (d, 1H), 8.3 (dd, 1H), 8.87 (s, 1H), 9.2 (s, 1H), MS (FAB) m/z 480 (M+H) Anal. C$_{22}$H$_{29}$N$_3$O$_7$S 479 :C, 55.1 (55.1); H, 6.4 (6.1); N, 8.5 (8.8).

EXAMPLE 11

See Scheme 11

(2S,4S)2-{[(5-ethoxycarbonyl-thiophene-2-carbonyl)-amino]-methyl}-4-sulfanyl-pyrrolidine-1-carboxylic acid allyl ester TFA (2 mL: 26 mmole) was added to a stirring solution of (2S,4S)2-{[(5-ethoxycarbonyl-thiophene-2-carbonyl)-amino]-methyl}-4-BOCsulfanyl-pyrollidine-1-carboxylic acid allyl ester (11(b)) (130 mg; 0.26 mmole) in dichloromethane (20 mL). The solution was stirred under argon for 19 hours. The solvent and excess TFA were removed in vacuo and the residue dried under high vacuum to give the desired product 11 as a water-white gum (64%).

NMR (CDCl$_3$; 250 MHz) d 1.38 (t, 3H), 1.55–1.70 (m, 1H), 1.75(d, 1H), 2.60–2.76 (m, 1H), 3.10–3.50 (m, 3H), 3.80–3.95 (m, 1H), 4.05–4.25 (m, 2H), 4.38 (q, 2H), 4.70 (m, 2H), 5.20–5.40 (m, 2H), 5.85–6.05 (m, 1H), 7.47 (d, 1H), 7.73 (d, 1H), 8.52 (s(br), 1H) MS (FAB) m/z 399 (M+H)$^+$ Anal. C$_{17}$H$_{22}$N$_2$O$_5$S$_2$ 0.5 C$_2$HF$_3$O$_2$ 455: C, 47.6 (47.5); H, 5.2 (4.9); N, 6.1 (6.15).

Starting material 11(b) was prepared in an analogous manner to the equivalent step in Example 10 but with addition of 5-chlorocarbonyl-thiophene-2-carboxylic -acid-ethyl-ester (11(a)) to compound (15(b)) (Example 15) with similar chromatographic work up. 11(b) is a tacky water white gum. Yield 60%. Preparation of (11(a)) is described in Journal of the American Pharmaceutical Association (Sci. Ed.) Vol.41 pp 273–276 (1952).

NMR of 11(b): (CDCl$_3$; 250 MHz) d 1.4 (t, 3H), 1.5 (s, 9H), 1.70–1.85 (m, 1H), 2.57–2.73 (m, 1H), 3.26–3.36 (m, 1H), 3.38–3.50 (m, 1H), 3.65–3.87 (m, 2H), 4.10–4.25 (m, 2H), 4.35 (q, 2H), 4.65 (m,2H), 5.20–5.38 (m,2H), 5.85–6.04 (m, 1H), 7.47 (d, 1H), 7.72 (d, 1H), 8.45 (s(br), 1H). MS (FAB) m/z 499 (M+H)$^+$, other m/z 183 Anal. C$_{22}$H$_{30}$N$_2$O$_7$S$_2$ 498 C, 53.4 (53.0); H, 6.3 (6.1); N, 5.5 (5.6)

EXAMPLE 12

See Scheme 12

N-(3,4-dichlorobenzyl)-N'-((2S,4S),4-sulfanyl-pyrrolidin-2-yl-methyl)thiophene-2,5-dicarboxamide To a stirring solution of N-(3,4-dichlorobenzyl)-N'-((2S, 4S),-1-allyloxycarbonyl-4-sulfanyl-pyrrolidin-2-yl-methyl)

thiophene-2,5-dicarboxamide (12(e)) (59 mg: 0.1 mmole) in dichloromethane (10 mL), under argon, was added trimethylsilyliodide (0.35 mL; 0.25 mmole). After 20 hours at ambient temperature the dichloromethane and excess trimethylsilyliodide were removed in vacuo and the residue treated with methanol (3 mL). The insoluble material was treated with further methanol (2×3 mL) and then triturated with diethyl ether to yield a solid which was filtered and dried to give the desired product 12 as a light brown solid (59%).

NMR (DMSO-$d_6$; 250 MHz) $\delta$1.65–1.90 (m, 1H), 2.50–2.62 (m, 1H), 3.20–3.40 (m, 2H), 3.55–3.70 (m, 2H), 3.75–3.90 (m, 2H), 4.45 (d, 2H), 7.32 (m, 1H), 7.58 (m, 2H), 7.73 (d, 1H), 7.78 (d, 1H), 8.68 (br, 1H), 8.88 (t, 1H), 9.22 (t, 1H).

MS (FAB) m/z 444 (M+H)$^+$ other 111. 312 Anal. $C_{18}H_{19}Cl_2N_3O_2S_2$ 1.25 HI 0.5 $C_4H_{10}O$ 640 C, 37.6 (37.5); H, 3.5 (3.9); N, 6.5 (6.6).

Starting material (12(e)) was prepared as follows. To a stirring solution of 3,4-dichlorobenzylamine (0.53 mL; 4.0 mmole) in acetonitrile (10 mL) was added triethylamine (1.67 mL; 12.0 mmole) and a solution of (11(a)) (0.87 g; 4.0 mmole. see Example 11) in acetonitrile (20 mL). The solution was stirred at ambient temperature, under argon, for 22 hours. The solvent and excess triethylamine were removed in vacuo and the residue partitioned between chloroform and water. The organic phase was washed with water and brine, dried over magnesium sulphate and vacuumed to dryness to give 5-(3,4-dichlorobenzyl-carbamoyl)-thiophene-2-carboxylic acid ethyl ester (12(a)) as a cream solid (90%).

NMR (CDCl$_3$; 250 MHz) $\delta$1.40 (t, 3H), 4.38 (q, 2H), 4.57 (d, 2H), 6.47 (t(br), 1H), 7.28 (m, 1H), 7.42 (m, 2H), 7.48 (d, 1H), 7.73 (d, 1H) MS (CI) m/z 358 (M+H)$^+$ Anal. $C_{15}H_{13}Cl_2NO_3S$ 358: C, 50.4 (50.3); H, 3.8 (3.7); N, 3.9 (3.9).

Aqueous 1M sodium hydroxide (16.3 mL; 16.3 mmole) was added to a stirring solution of (12(a)) (1.17 g; 3.3 mmole) in ethanol (70 mL). The reaction mixture was stirred at ambient temperature for 19 hours, reduced to a small volume, diluted with water and adjusted to pH 2 by addition of 2M hydrochloric acid. The filtered solid was washed with water and dried in vacuo to give 5-(3,4-dichlorobenzyl-carbamoyl)-thiophene-2-carboxylic acid (12(b)) as a white solid (83%).

NMR (DMSO d6; 200 MHz) d 4.43 (d, 2H), 7.3 (dd, 1H), 7.58 (m, 2H), 7.68 (d, 1H), 7.78 (d, 1H), 9.28 (t, 1H) MS (CI) m/z 330 (M+H)$^+$ Anal. $C_{13}H_9Cl_2NO_3S$ 330 C, 47.3 (47.3); H, 2.7 (2.7); N, 4.2 (4.2).

A stirring solution of (12(b)) (495 mg; 1.5 mmole) in dichloromethane (25 mL) was cooled in an ice bath and DMF (1 drop) and oxalyl chloride (0.175 mL: 2.0 mmole) added dropwise. The solution was stirred at ambient temperature under argon for 4 hours. The dichloromethane and excess oxalyl chloride were removed in vacuo. The residue was azeotroped with toluene (2×15 mL) to give 5-(3,4-dichlorobenzyl-carbamoyl)-thiophene-2-carbonyl-chloride (12(c)) which was used crude in the next step.

Triethylamine (0.83 mL: 4.5 mmole) and a solution of compound (15(b)) (Example 15) (316 mg; 1.0 mmole) in acetonitrile (10 mL) were added to a stirring mixture of (12(c)) (1.5 mmole) in acetonitrile (15 mL) and stirred at ambient temperature under argon for 19 hours. The acetonitrile and excess triethylamine were removed in vacuo and the residue partitioned between chloroform and water. The organic phase was washed with water and brine, dried over magnesium sulphate and vacuumed to dryness to give N-(3,4-dichlorobenzyl)-N'-((2S,4S),-1-allyloxycarbonyl-4-BOCsulfanyl-pyrrolidin-2-yl-methyl)thiophene-2,5-dicarboxamide (12(d)) as a tacky brown solid (95%).

NMR (CDCl$_3$; 200 MHz) $\delta$1.5 (s, 9H), 1.65–1.85 (m, 1H), 2.47–2.73 (m, 1H), 3.25–3.50 (m, 2H), 3.65–3.85 (m, 2H), 4.10–4.23 (m, 2H), 4.57 (d, 2H), 4.64 (m, 2H), 5.20–5.40 (m, 2H), 5.85–6.05 (m, 1H), 6.45 (t, 1H), 7.20 (dd, 1H), 7.40 (m, 2H), 7.46 (d, 1H), 7.53 (d, 1H), 8.47 (br, 1H) MS (FAB) m/z 628 (M+H )$^+$ Anal. $C_{27}H_{31}Cl_2N_3O_6S$ .$H_2O$ 646 C, 50.2 (50.2); H, 4.9 (5.1); N, 6.5 (6.5).

TFA (5 mL: 65 mmole) was added to a stirred solution of (12(d)) (600 mg; 0.93 mmole) in dichloromethane (25 mL). The solution was stirred at ambient temperature under argon for 4 hours. solvent and excess TFA were removed in vacuo and the residue azeotroped with toluene to give the desired starting material (12(e)).

NMR (CDCl$_3$; 250 MHz) $\delta$1.55–1.75 (m, 1H), 1.75 (d, 1H), 2.50–2.72 (m, 1H), 3.12–3.43 (m, 1H), 3.65–3.90 (m, 2H), 4.03–4.20 (m, 2H), 4.54 (d, 2H), 4.63 (m, 2H), 5.17–5.37 (m, 2H), 5.85–6.03 (m, 1H 0, 6.63 (br, 1H), 7.10–7.55 (m, 5H), 8.5 (br, 2H), MS (FAB) m/z 528 (M+H)$^+$ Anal. $C_{22}H_{23}Cl_2N_3O_4S_2$ 0.33 $C_4H_{10}O$ 0.3 $C_2HF_3O_2$ 586.5 C, 49.0 (49.0); H, 4.5 (4.6); N, 7.2 (7.2).

EXAMPLE 13

See Scheme 13

5-[N-(3,4-dichlorobenzyl)carbamoyl]-N-((2S,4S)-4-sulfanylpyrrolidin-2-yl-methyl)pyridine-2-carboxamide 5-[N-(3,4-dichlorobenzyl)carbamoyl]-N-((2S,4S)-1-allyloxycarbonyl-4-sulfanylpyrrolidin-2-yl-methyl) pyridine-2-carboxamide (13(e)) was treated with trimethyl-silyliodide in similar manner to compound (12(e)) in Example 12. The desired product 13 was obtained as a medium brown solid (26%).

NMR (DMSO-d6; 200 MHz) $\delta$1.70–1.82 (m, 1H), 3.15–3.40 (m, 2H), 3.55–3.90 (m, ?H), 4.52 (d, 2H) 7.35 (dd, 1H) 7.60 (m, 2H), 8.18 (d 1H), 8.47 (dd, 1H), 8.75 (br. 1H), 9.10 (d, 1H), 9.28 (t+?,2H), 9.42 (t, 1H), MS (FAB) m/z 439 (M+H)$^+$, Anal. $C_{19}H_{20}Cl_2N_4O_2S$. 1.5 HI.0.33 $C_4H_{10}O$ 655.7 C, 37.4 (37.2); H, 3.4 (3.7); N, 8.1 (8.5).

Starting material (13(e)) was prepared as follows. 5-chlorocarbonyl-pyridine-2-carboxylic acid methyl ester was reacted with 3,4-dichlorobenzylamine analogously with preparation of compound (12(a)) in Example 12 to obtain 5(3,4-dichlorobenzylcarbamoyl)-pyridine-2-carboxylic acid methyl-ester (13(a)) as a cream solid (61%).

NMR (CDCl$_3$; 250 MHz), d 4.05 (s, 3H), 4.62 (d, 2H), 6.80 (t(br). 1H), 7.22 (dd, 1H), 7.43 (m, 2H), 8.20 (d, 1H), 8.30 (m, 1H), 9.08 (d, 1H), MS (CI) m/z 339 (M+H)$^{30}$ Anal. $C_{15}H_{12}Cl_2N_2O_3$ 339 C, 53.2 (53.1); H, 3.5 (3.6); N, 8.1 (8.3).

Compound (13(a)) was treated in an analogous manner to compound (12(a)) in Example 12 to obtain 5(3,4-dichlorobenzylcarbamoyl)-pyridine-2-carboxylic acid (13 (b)) as an off-white solid (82%).

NMR (DMSO-$d_6$; 200 MHz) $\delta$4.50 (d, 2H), 7.33 (dd, 1H), 7.58 (m, 2H), 8.13 (d, 1H), 8.37 (dd, 1H), 9.12 (d, 1H), 9.40 (t, 1H) MS (CI) m/z 325 (M+H)$^+$ Anal. $C_{14}H_{10}Cl_2N_2O_3$. $H_2O$ 343 C, 48.9 (48.9); H, 3.5 (3.5); N, 8.0 (8.2).

Compound (13(b)) was treated in an analogous manner to compound (12(b)) in Example 12 to give 5(3,4- dichlorobenzylcarbamoyl)pyridine-2-carbonylchloride (13 (c)) which was used crude in the next reaction.

Compound (13(c)) was reacted with compound (15(b)) (Example 15) in a similar manner to compound (12(c)) in Example 12 to give 5-[N-(3,4-dichlorobenzyl)carbamoyl]-N-((2S,4S )-1-allyloxycarbonyl-4-BOCsulfanylpyrrolidin-2-yl-methyl)pyridine-2-carboxamide as a light brown solid (13(d)) (81%).

NMR (CDCl$_3$; 250 MHz) δ1.50 (s, 9H), 1.73–1.90 (m, 1H), 2.50–2.65 (m, 1H), 3.20–3.30 (m, 1H), 3.62–3.80 (m, 2H), 4.10–4.27 (m, 2H), 4.65 (d?, 4H), 5.18–5.38 (m, 2H), 5.83–6.05 (m, 1H), 6.80 (t(br), 1H), 7.20–7.28 (m, 2H), 7.40–7.48 (m, 2H), 8.23 (s, 2H), 8.75 (br, 1H), 8.98 (d?, 1H). MS (FAB) m/z 623 (M+H)$^+$ Anal. C$_{28}$H$_{32}$Cl$_2$N$_4$O$_6$S 623 C, 53.8 (53.9); H, 5.1 (5.2); N, 8.9 (9.0) mp 136–137.5° C.

Compound (13(d)) was treated in a similar manner to compound (12(d)) in Example 12 to give the desired starting material (13(e)) as a light brown solid (64%).

NMR (CDCl$_3$; 250 MHz) δ1.70 (d, 1H), 1.80–2.00 (m, 1H), 2.52–2.65 (m, 1H), 3.05–3.25 (m, 2H), 3.60–3.85 (m, 2H), 4.05–4.20 (m, 2H), 4.60 (d?, 4H), 5.18–5.33 (m, 2H), 5.85–6.03 (m, 1H), 6.80 (br, 1H), 7.20 (dd, 1H), 7.40–7.47 (m, 2H), 8.23 (s, 2H), 8.78 (br, 1H), 9.0 (s, 1H), MS (FAB) m/z 523 (M+H)$^+$ Anal. C$_{23}$H$_{24}$Cl$_2$N$_4$O$_4$S. 0.1 C$_2$HF$_3$O$_2$ 534.4 C, 52.4 (52.1); H, 4.6 (4.5); n, 10.3 (10.5); mp 101–105° C.

EXAMPLE 14

See Scheme 14

1-hydroxy-4-[((2S,4S) 4-sulfanyl-pyrrolidin-2yl-methyl)-amino-sulfonyl]naphthalene-2-carboxylic-acid To a stirring solution of 1-hydroxy-4-[((2S,4S),1-allyloxycarbonyl-4-sulfanyl-pyrrolidin-2yl-methyl)-aminosulfonyl]-naphthalene-2-carboxylic-acid (14(c)) (47.5 mg; 0.1 mmole) in dichloromethane (10 mL) was added TMSI (0.56 mL; 0.4 mmole). The solvent and excess TMSI were removed in vacuo after 6 hours. Methanol (5 mL) was added to the residue and then removed in vacuo from the solution. The residue was triturated with diethyl ether, filtered and dried in vacuo to obtain the desired product 14 as a brown solid (74%).

NMR (DMSO-d6: 250 MHz) δ1.45–1.62 (m, 1H), 2.25–2.45 (m, 1H), 2.90–3.25 (m, 3H), 3.45–3.70 (m, 2H), 7.72 (m 1H), 7.85 (m, 1H), 8.12 (m, 1H), 8.38–8.60 (m, 2H), 9.15 (br, 1H) MS (FAB) m/z 383 (M+H)$^+$ Anal. C$_{16}$H$_{18}$N$_2$O$_5$S$_2$. 1.25 HI.0.5 C$_4$H$_{10}$O 579 C, 37.0 (37.3); H, 4.1 (4.2), N, 4.8 (4.8).

Starting material (14(c)) was prepared as follows. Compound (15(b)) (Example 15) and 1-hydroxy-4-chlorosulfonyl-naphthalene-2-carboxylic acid (14(a)) were coupled in a similar manner to the equivalent step in Example 15 to give 1-hydroxy-4-[((2S,4S),1-allyloxycarbonyl-4-BOCsulfonyl-pyrrolidin-2yl-methyl)-aminosulfonyl]-naphthalene-2-carboxylic-acid (14(b)) as a light brown solid (80%).

NMR (CDCl$_3$; 250 MHz) δ1.45 (s, 9H), 1.50–1.75 (m, 1H), 2.28–2.42 (m, 1H), 2.96–3.10 (m, 2H), 3.48–3.60 (m, 1H), 3.80–3.90 (m, 1H), 3.95–4.05 (m, 1H), 4.47 (m, 2H), 4.53–4.63 (m, 1H), 7.55 (m, 1H), 7.67 (m, 1H), 8.50 (m, 2H), 8.70 (m, 1H) MS (FAB) M+Na$^+$589, other 317.261 Anal. C$_{25}$H$_{30}$N$_2$O$_9$S$_2$.H$_2$O.0.8 C$_3$H$_{15}$N 664.8 C, 53.7(53.8); H, 6.7 (6.6); N, 5.9 (5.9).

2M Aqueous sodium hydroxide (5 mL 10.0 mmole) was added to a stirring solution of (14(b)) (333 mg; 0.5 mmole) in methanol (5 mL). The solution was evaporated to dryness after 42 hours and the residue dissolved in water (10 mL). The solution was adjusted to pH 2 with 2M hydrochloric acid and the solid was filtered, washed with water and dried in vacuo to give the desired starting material (14(c)) as a white solid (72%).

NMR (CDCl$_3$; 200 MHz) δ1.48–1.70 (m, 2H), 2.38–2.52 (m, 1H), 2.85–3.40 (m, ?H),3.90–4.05 (m, 2H), 4.40–4.60 (m, 3H), 5.10–5.35 (m, 3H), 5.70–5.95 (m, 2H), 6.20–6.45 (br, 1H), 7.57–7.90 (m, 3H), 8.43–8.70 (m, 4H) MS (FAB) m/z 467 (M+H)$^+$ Anal. C$_{20}$H$_{22}$N$_2$O$_7$S$_2$. 0.5 H$_2$O 475 C, 50.6 (50.5), H, 4.8 (4.8), N, 6.0 (5.9).

EXAMPLE 15

See Scheme 15

(2S)-2-{3-[([2S,4S]-4-sulfanyl-pyrrolidin-2-yl-methyl)-sulfamoyl]-benzoylamino}4-methylsulfanyl-butyric acid methyl ester TFA (2.0 mL) was added to a stirred solution of (2S)-2-{(3-[([2S ,4S]-4-BOCsulfanyl-pyrrolidin-2-yl-methyl)-sulfamoyl]-benzoylamino}-4-methylsulfanyl-butyric acid methyl ester (15(d)) (101 mg, 0.18 mmol) in CH$_2$Cl$_2$ (2.0 mL) at room temperature under argon. After 1 h the reaction mixture was concentrated to a dryness, azeotroped with toluene (3×10 mL) and dried to yield the desired product 15 as a colourless gum: 101.8 mg (99%).

$^1$H NMR (CDCl$_3$, 250 MH$^z$) δ1.6–1.8 (1H, m); 2.0 (1H, d, SH); 2.1–2.4 (5H, m): 2.52.65 (3H, m); 3.15–3.4 (3H, m) 3.45–3.65 (1H, m); 3.7–3.85 (4H, m) 3.9–4.1 (1H, m); 4.85–5.0 (1H, m); 7.55–7.7 (2H, m) 7.8 (1H, s); 8.0 (1H, d); 8.1 (1H, d); 8.3 (1H, s); 9.0–9.4 (1H, s); 10.0–10.4 (1H, s). MS (ESP+) m/z 462 (M+H)$^+$.

Starting material (15(d)) was prepared as follows. Triethylamine (3.0 mL, 21.5 mmol) was added to a stirred suspension of L-methionine methyl ester. HCl(4.37 g, 21.8 mmol) in CH$_2$Cl$_2$ (50 mL). The resulting mixture was left to stir for 30 min at room temperature then filtered. The filtrates were then added to a stirred solution of 3-chlorosulphonyl-benzoyl chloride (5.23 g, 21.9 mmol) and triethylamine (7.6 mL, 54.7 mmol) in CH$_2$Cl$_2$ (50 mL) at 0° under argon. The reaction mixture was allowed to warm to room temperature and quenched with ice-water(100 mL). The organics were the dried over MgSO$_4$, filtered and concentrated to a viscous brown gum. This was then purified by flash chromatography on 9385 SiO$_2$, eluting with 50% EtOAc/i-Hexane to give (2S)-2-(3-chlorosulfonyl-benzoylamino)-4-methylsulfonyl-butyric acid methyl ester 15(a)) as a viscous orange oil: 2.88 g (36%).

$^1$H NMR (CDCl$_3$, 250 MHZ) δ2.1–2.2 (5H, m); 2.65 (2H, t); 3.83 (3H, s); 4.95 (1H, m); 7.23 (1H, d); 7.74 (1H,t); 8.2 (2H,m); 8.47 (1H,m). MS (CI) m/z 366 (M+H)$^+$, 332.300.

A solution of 15(a) (1.53 g. 4.18 mmol) in CH$_2$Cl$_2$ (20 mL) was added to a stirred solution of (2S,4S)-2-aminomethyl-4-BOCsulfanyl-pyrollidine-1-carboxylic acid allyl ester (15(b)) (prepared as described in International Patent Application WO 92/17480. see pages 39–41) (1.32 g. 4.18 mmol) and ($^i$Pr)$_2$NEt (1.5 mL. 9.0 mmol) in CH$_2$Cl$_2$ (30 mL) at 0° C. under argon. The resulting solution was allowed to warm to room temperature and stirred for 18 hours. The reaction mixture was then washed with water (100 mL), dried over MgSO$_4$, filtered and concentrated to a viscous white gum. This was then purified by flash chromatography on 9385 SiO$_2$. eluting with a gradient of 35–50% EtOAc/i-Hexane to give (2S,4S)-4-BOCsulfanyl- 2-{[3-([1S]-1-methoxycarbonyl-3-methylsulfanyl-propylcarbamoyl)-benzenesulfonylamino]- methyl}-pyrrolidine-1-carboxylic acid allyl ester (15(c)) as a colourless foam: 2.19 g (81.3%).

1H NMR (CDCl$_3$,200 MH$_z$) δ1.5 (9H, s): 1.65–1.9 (1H, s): 2.05–2.35 (5H, m): 2.4–2.7 (3H, m); 3.3–3.4 (3H, m): 3.55–3.75 (1H, m); 3.8 (3H, s): 3.9–4.2 (2H, m); 4.55 (2H, d); 4.98 (1H, m); 5.15–5.35 (2H, m): 5.8–6.0 (1H, m): 6.5 (1H, s); 7.4 (1H, s); 7.55 (1H, t); 7.9–8.05 (2H, m); 8.25 (1H, m).MS (FAB) n/z 646 (M+H)$^+$, 590,568,546,230. Anal. Calcd for C$_{27}$H$_{39}$N$_3$O$_9$S$_3$.0.3CH$_2$Cl$_2$ :C, 48.8: H, 5.95; N, 6.26. Found C, 48.9; H, 6.2 N, 6.0.

Tri-nButyl tin hydride (565 mL, 2.1 mmol) was added to a stirred solution of (15(c)) (1.18 g, 1.8 mmol) and (PPh)$_3$PdCl$_2$ (13 mg. 0.018 mmol) in a mixture of water (0.5 mL) and CH$_2$Cl$_2$ (100 mL). The reaction mixture was left to stir for 10 minutes. dried over MgSO$_4$, filtered and concentrated to a brown oil. This was then purified by flash chromatography on 9385 SiO$_2$, elutins with a gradient of 0–10% EtOAc/i-Hexane to give the desired starting material 15(d) as a white foam: 751 mg (73%).

$^1$H NMR (CDCl$_3$+CD$_3$COOD,250 MH$^z$) δ1.5 (9H, s); 1.85–1.97 (1H, m); 2.1–2.35 (5H, m); 2.45–2.7 (3H, m); 3.1–3.4 (3H, m): 3.65–4.25 (6H, m); 4.9–5.0 (1H, m); 7.63 (1H, t); 7.97–8.05 (1H, m); 8.1–8.17 (1H, m) 8.35–8.42 (1H, m). MS (ESP+) m/z 562 (M+H)$^+$, 462. Anal. Calcd for C$_{23}$H$_{35}$N$_3$O$_7$S$_3$: C, 49.2: H, 6.28; N, 7.48. Found C, 49.4; H, 6.3: N, 7.2.

EXAMPLE 16

See Scheme 16

(2S),2-{3-[([2S,4S]-4-sulfanyl-pyrrolidin-2-yl-methyl)-sulfamoyl]-benzoylamino}-4-methylsulfanyl-butyric acid 2N NaOH(2.0 mL, 4.0 mmol) was added to a stirred solution of compound (15(d)) (prepared in Example 15) (200 mg, 0.36 mmol) in MeOH at room temperature under argon. After 18 h the reaction mixture was concentrated to remove the MeOH, The resulting residues were dissolved in H$_2$O (2.0 mL) and acidified to pH3 with 2N HCl. The resulting solution was purified by reverse phase HPLC (Dynamax C18.8μ prepcolumn), eluting with a gradient of 0–40% MeOH/H$_2$O. Product fractions were concentrated and azeotroped with toluene (3×25 mL) to give a colourless glass which was then triturated with Et$_2$O (25 mL), filtered and dried to yield the desired product 16 as a white powder: 85.2 mg (54%).

$^1$H NMR (DMSO-D$_6$+CD$_3$COOD,250 MH$^z$) δ1.45–1.65 (1H, m); 2.0–2.2 (5H, m); 2.3–2.7 (3H+DMSO, m); 2.95–3.2 (3H, m); 3.35–4.2 (3H, m); 4.54–4.65 (1H, m); 7.65–7.8 (1H, m); 7.9–8.05 (1H, m); 8.1–8.25 (1H, m); 8.3–8.4 (1H, m). MS (FAB) m/z 448 (M+H)$^+$. Anal. Calcd for C$_{17}$H$_{25}$N$_3$O$_5$S$_3$: C, 45.6: H, 5.63; N, 9.39. Found C, 45.5: H, 5.8; N, 9.1.

EXAMPLE 17

See Scheme 17

N-(3,4-dichlorophenyl)-3-[([2S,4S],4-sulfanyl-pyrrolidin-2-yl-methyl)-sulfamoyl]-benzamide N-(3,4-dichlorobenzyl)-3-[([2S,4S],4-BOCsulfanyl-pyrrolidin-2-yl-methyl)-sulfamoyl]-benzamide (17(c)) was deprotected with TFA (analogously to compound (15(d)) in Example 15) to give the desired product 17 in 97% yield after trituration with Et$_2$O.

$^1$H NMR (CDCl$_3$,200 MH$_z$) δ1.5–1.8 (1H, m); 1.8–2.2 (2H+H$_2$O,m.SH.NH); 2.5–2.7 (1H,m): 3.1–3.35 (3H, m); 3.4–4.1 (3H, m); 4.55 (2H, d); 7.15 (1H, dd); 7.2 (1H, s): 7.32 (1H, d); 7.4 (1H, d); 7.65 (1H+PPh$_3$PO, m); 7.9 (1H, m); 8.2 (1H, m): 8.35 (1H, m); 8.5–9.3 (1H, s, NH); 10.3–10.7 (1H, s, NH). MS (ESP+) m/z 474 (M+H)$^+$279 (Ph$_3$PO)

Starting material (17(c)) was prepared as follows. 3,4-Dichlorobenzylamine was coupled with 3-Chlorosulphonylbenzoyl chloride (analogously as for compound (15(a)) in Example 15) to give 3-(3,4-dichloro-benzylcarbamoyl)-benzene-sulfonyl-chloride (17(a)) in 28% yield.

$^1$H NMR (CDCl$_3$,250 MH$_z$) δ4.6 (2H d); 6.6 (1H, s, NH); 7.2 (1H, dd). 7.4–7.5 (2H, m); 7.75 (1H, t): 8.15–8.25 (2H, m): 8.4 (1H, m) MS (FAB) m/z 378 (M+H)$^+$.380.

Compound 15(b) (Example 15) was coupled with (17(a)) analogously as for the equivalent step in Example 15 to give N-(3,4-dichlorobenzyl)-3-[([2S,4S],4-BOCsulfanyl-pyrrolidin-2-yl-methyl)-sulfamoyl]-benzamide (17(b)) in 72.5% yield.

1H NMR (CDCl$_3$,20 OMH$_z$) δ1.5 (9H, s); 1.6–1.9 (1H+H$_2$O, m); 2.4–2.6 (1H, m); 3.1–3.3 (3H, m); 3.6–3.7 (1H, m); 3.8–4.1 (2H, m); 4.4 (2H, d); 4.6 (2H, d); 5.1–5.3 (2H, m); 5.7–5.95 (1H, m); 6.08 (1H, s, NH); 7.2 (1H, dd); 7.35–7.7 (4H, m); 7.95 (1H, d); 8.15 (1H, d); 8.25–8.35 (1H, s, NH). MS (FAB) m/z 658 (M+H)$^+$ Anal. Calcd for C$_{28}$H$_{33}$N$_3$Cl$_2$O$_7$S$_2$: C, 51.1; H, 5.05; N, 6.38. Found C, 50.8; H,5.2; N,6.2.

Compound (17(b)) was deprotected. analogously as for the equivalent step in Example 15. to give the desired starting material (17(c)) in 70% yield.

$^1$H NMR (CDCl$_3$, 250 MH$_z$) δ1.15–1.45 (1H, m); 1.5 (9H, s); 2.25–2.4 (1H, m): 2.6–2.9 (4H, m): 3.02 (1H, dd): 3.25–3.4 (2H, m); 3.45–3.6 (1H, m); 4.6 (2H, m); 7.05 (1H, m); 7.2 (1H, dd); 7.4 (1H, d); 7.45 (1H, d); 7.6 (1H, t): 7.95 (1H, d); 8.1 (1H, d); 8.25 (1H, s). MS (ESP+) m/z 574 (M+H)$^+$.574,279 (PPh$_3$O)

EXAMPLE 18

See Scheme 18

N-(3,4-dichlorobenzyl)-N'-([2S,4S],4-sulfanyl-pyrrolidin-2yl-methyl)-isophthalamide N-(3,4-dichlorobenzyl)-N'-([2S,4S],4-BOCsulfanyl-pyrrolidin-2yl-methyl)-isophthalamide (18(e)) was deprotected with TFA (analogously to the equivalent step in Example 15) to give the desired product 18 in 100% yield after trituration with Et$_2$O.

$^1$H NMR (CDCl$_3$+CD$_3$COOD, 250 MH$_z$) δ1.75–1.9 (1H, m); 2.6–2.75 (1H, m); 3.2–3.35 (1H, m); 3.45–3.65 (1H, m); 3.7–3.95 (3H, m): 4.05–4.15 (1H, m); 4.6 (2H, s), 7.2 (1H, dd); 7.4 (1H, d): 7.55 (1H, t); 7.95–8.05 (1H, m): 8.1–8.2 (1H, m): 8.4 (1H, m). MS (ESP+) m/z 438 (M+H)$^+$.

Starting material (18(e)) was prepared as follows. A suspension of isophthalic acid monomethyl ester (18(a)), (2.65 g, 14.7 mmol) in CH$_2$Cl$_2$ (100 mL) and DMF (10 drops) was treated with oxalyl chloride (2.6 ml, 29.8 mmol) at 0° under argon. The reaction mixture was allowed to warm to room temperature over 18 h. The resulting solution was concentrated and azeotroped with toluene to give a crystalline yellow solid. This was then redissolved in CH$_2$Cl$_2$ (100 mL) and added dropwise to a stirred solution of 3,4-dichlorobenzylamine (2.6 g. 14.7 mmol) and Et$_3$N (5 mL, 35.9 mmol) in CH$_2$Cl$_2$ (100 mL) at 0° under argon. The resulting solution was allowed to warm to room temperature over 4 hours. washed with 1N HCl(50 mL), saturated NaHCO$_3$ (aq) (50 mL), dried over MgSO$_4$, filtered and concentrated to an orange oil. This was then purified by flash chromatography on 9385 SiO$_2$ eluting on a gradient of 25–50% EtOAc/i-Hexane to yield 3-(3,4-dichlorobenzyl-carbamoyl)-benzoic acid methyl ester (18(b)) as a pale yellow oil: 3.99 g (80%).

$^1$H NMR (CDCl$_3$,200 MHz) δ3.9 (3H, s); 4.6 (2H, d); 6.6–6.8 (1H, t, NH); 7.18 (1H, dd); 7.38–7.45 (2H, m); 7.54 (1H,t): 8.0–8.1 (1H, m); 8.13–8.23 (1H, m); 8.35–8.42 (1H, m). MS (Cl) m/z 338 (M+H)$^+$.

A stirred solution of (18(b)) (3.85 g, 11.4 mmol) in MeOH (100 mL) at room temperature under argon was treated with 2N NaOH (12 mL, 24 mmol). The reaction mixture was allowed to stir at room temperature for 4 h. concentrated to 1/5 volume and acidified to pH4 with 2N HCl. The resulting precipitate was then collected by filtration. washed with water (2×25 mL) and dried under high vacuum to yield 3-(3,4-dichlorobenzyl-carbamoyl)-benzoic acid (18(c)) as a white powder: 2.9 g (79%).

1H NMR (DMSO-D$_6$, 200 MHz) δ4.49 (2H, d); 7.32 (1H, dd); 7.5–7.7 (3H, m): 8.0–8.2 (2H, m); 8.42–8.53 (1H, m); 9.27 (1H, t, NH), 13.0–13.4 (1H, s, COOH). MS (ESP+) m/z 324 (M+H)$^+$. 159. Anal. Calcd for C$_{15}$H$_{11}$NO$_3$Cl$_2$,0.4H$_2$O C, 54.4: H, 3.59: N, 4.23 Found C, 54.0: H, 3.2: N, 4.2

1-(3-Dimethylaminopropyl)-3-ethyl carbodiimide.HCl (655 mg, 3.4 mmol) and 1-Hydroxybenztriazole (463 mg, 3.4 mmol) were added portionwise to a stirred solution of (18(c)) (1.0 g, 3.1 mmol) in DMF (20 mL) at 0° under argon. After 30 mins a solution of compound (15(b)) (Example 15) (1.13 g, 3.57 mmol) in DMF (20 mL) was added dropwise. followed by N-methyl morpholine (375 ml, 3.4 mmol). The mixture was then allowed to warm to room temperature over 4 hours. The resulting reaction mixture was concentrated to 1/5 volume and diluted with EtOAc(100 mL). This solution was then washed successively with 1N citric acid (100 mL). saturated NaHCO$_3$(aq) (100 mL), water (100 mL) and brine (100 mL), dried over MgSO$_4$, filtered and concentrated to a white foam. This was then purified by flash chromatography on 9385 SiO$_2$, eluting on a gradient of 50–75% EtOAc/i-Hexane to yield (2S,4S),4-BOCsulfanyl-2-{[3-(3,4-dichlorobenzylcarbamoyl)-benzoylamino]-methyl}-pyrrolidine-1-carboxylic acid allyl ester (18(d)) as a white foam: 1.57 g (82%).

$^1$H NMR (CDCl$_3$, 250 MHz) δ1.5 (9H, s); 1.6–1.9 (1H, m); 2.55–2.75 (1H, m): 3.2–3.6 (2H,m); 3.65–3.9 (2H, m); 4.1–4.25 (2H, m); 4.5–4.65 (4H, m); 5.15–5.35 (2H, m); 5.38–6.0 (1H, m); 6.87 (1H, t, NH); 7.2 (1H, dd); 7.4 (1H, d); 7.45 (1H, d); 7.55 (1H, t); 7.95 (1H, d); 8.07 (1H, d); 8.25 (1H, s); 8.35–8.6 (1H, s, NH). MS (ESP+) m/z 622 (M+H)$^+$, 566,522. Anal. Calcd for C$_{29}$H$_{33}$N$_3$Cl$_2$O$_6$S : C, 55.9: H, 5.34: N, 6.75 Found C, 56.1 H, 5.6; N, 6.6

Compound (18(d)) was deprotected (analogously as for the equivalent step in Example 15) to give the desired starting material (18(e)) in 67% yield.

$^1$H NMR (CDCl$_3$,200 MHz) δ1.2–1.6(10H, m): 2.25–2.55 (2H, m1H+1NH); 2.9 (1H,q); 3.3–3.75 (5H, m); 4.6 (2H, d): 6.9–7.05 (1H, m, NH); 7.05–7.15 (1H, m, NH); 7.2 (1H, dd); 7.4 (1H, d): 7.45 (1H, d): 7.52 (1H, t); 7.9–8.05 (2H, m): 8.23 (1H, m). MS (ESP+) m/z 538 (M+H)$^+$. 438.

EXAMPLE 19

See Scheme 19

(2S,4S),4-sulfanyl-2-[(3-methoxycarbonyl-benzoylamino)-methyl]-pyrrolidin-1-carboxylic acid allyl ester (2S,4S),4-BOCsulfanyl-2-[(3-methoxycarbonyl-benzoylamino)-methyl]-pyrrolidin-1-carboxylic acid allyl ester (19(a)), (300 mg, 0.63 mmol) was dissolved in TFA (5 mL) at room temperature under argon. The reaction mixture was concentrated and azeotroped with toluene (3×20 mL) to yield the desired product (19) as a colourless viscous gum: 250 mg (105%).

$^1$H NMR (CDCl$_3$, 200 MHz) δ1.6–1.85 (2H, m, CH+SH): 2.55–2.85 (2H, m); 3.1–3.6 (3H, m); 3.92 (3H, bs); 4.04–4.4 (2H, m); 4.65 (2H, d); 5.15–5.4 (2H, m); 5.8–6.1 (1H, m) 7.53 (1H, t); 8.0–8.1 (1H, m): 8.1–8.25 (1H, m); 8.3–8.7 (2H, m, Aromatic-H+NH). MS (FAB) m/z 379 (M+H)$^+$, 163.

Starting material (19(a)) was prepared as follows. A suspension of isophthalic acid monomethyl ester (compound 18(a). Example 18). (2.5 g. 13.89 mmol) in CH$_2$Cl$_2$ (50 mL) and DMF (10 drops) was treated with oxalyl chloride (1.35 mL, 15.5 mmol) at 0° under argon. The reaction mixture was allowed to warm to room temperature over 18 h. The resulting solution was concentrated and azeotroped with toluene to give a crystalline yellow solid. This was then redissolved in CH$_2$Cl$_2$ (50 mL) and added dropwise to a stirred solution of (2S,4S)-2-aminomethyl-4-BOCsulfanyl-pyrollidine-1-carboxylic acid allyl ester (compound 15(b). Example 15) (2.0 g, 6.3 mmol) and ($^i$Pr)$_2$NEt (2.2 mL. 12.66 mmol) in CH$_2$Cl$_2$ (50 mL) at 0° under argon. The reaction mixture was allowed to warm to room temperature and stirred for 18 hours. then washed with water (2×50 mL). dried over MgSO$_4$, filtered and concentrated to a dark brown oil. This was then purified by flash chromatography on 9385 SiO$_2$ eluting with a gradient of 25–50%EtOAc/i-Hexane to yield the desired starting material (19(a)) as a pale yellow, viscous oil: 1.81 g (60%).

$^1$H NMR (CDCl$_3$, 200 MH$^Z$) δ1.5 (9H, s); 1.65–1.9 (1H, m); 2.55–2.8 (1H, m): 3.3 (1H, q); 3.4–3.65 (1H, m); 3.65–3.9 (2H, m) 3.95 (3H, s); 4.05–4.35 (2H, m) 4.64–4.7 (2H,m); 5.15–5.4 (2H, m); 5.8–6.1 (1H, m); 7.52 (1H, t): 8.02 (1H, dd); 8.15(1H, dd) 8.25–8.5 (1H, bs, NH): 8.55 (1H, bs). MS (FAB) m/z 479 (M+H)$^+$, 423,163. Anal. Calcd for C$_{23}$H$_{30}$N$_2$O$_7$S : C, 57.7: H, 6.32 N, 5.85. Found C, 57.5; H, 6.4; N, 5.7.

EXAMPLE 20

See Scheme 20

N-([2S,4S],4-sulfanyl-pyrrolidin-2yl-methyl)-3-phenoxy-benzamide

3-Phenoxybenzoic acid was coupled with (2S,4S)-2-aminomethyl-4-BOCsulfanyl-pyrollidine-1-carboxylic acid allyl ester (compound (15(b)), Example 15). followed by selective deprotection of the N-allyloxycarbonyl group and removal of the BOC group (analogously to the equivalent steps in Example 15) to give the desired product 20.

NMR CDCl$_3$δ1.8 (1H, m), 2.72 (1H, m), 3.01–3.31 (1H, bd), 3.69–3.97 (4H, m), 4.3 (1H, bs). 6.92–7.17 (4.5H, m, aromatics), 7.23–7.45 (5.5H, m, aromatics), 7.56 (1H, m), 7.68 (1H, t): 8.02–8.29 (1H, 2t), 9.02–9.29 (1H, 2bs). +ether. Analysis requires for C$_{18}$H$_{20}$N$_2$O$_2$S, H1 C=47.33, H=4.6, N=6.13; Found C=47.8, H=4.5, N=6.1

EXAMPLE 21

See Scheme 21

5-{([2S,4S],1-allyloxycarbonyl-4-sulfanyl-pyrrolidin-2yl-methyl)-carbamoyl}-isophthalic acid dimethyl ester Benzene-1,3,5-tricarboxylic acid dimethyl ester was coupled to (2S,4S)-2-aminomethyl4-BOCsulfanylpyrollidine-1-carboxylic acid allyl ester (compound (15(b)), Example 15). followed by removal of the BOC group (analogously to the equivalent steps in Example 15) to give the desired product 21.

NMR $CDCl_3\delta1.67$ (1H, m), 1.75 (1H, d), 2.66–2.89 (3H, m), 3.21 (1H, q), 3.27–3.37 (1H, m), 3.5 (1H, m), 3.9 (2H, bs), 3.97 (6H, s), 4.08–4.27 (2H, m), 4.68 (2H, d), 5.2–5.4 (2H, m), 5.88–6.06 (1H, m), 8.68 (2H, bs), 8.8 (1H, d). Analysis requires for $C_{20}H_{24}N_2O_7S$ C=55.0 H=5.54 N=6.42; Found C=54.9 H=5.6 N=5.75

EXAMPLE 22

See Scheme 22

(2S)-2-{3-[([2S,4S]-4-sulfanyl-pyrrolidin-2-yl-methyl)-amino]-benzoyl-amino}4-methylsulfanyl-butyric acid methyl ester (2S)-2-{3-[([2S,4S]-4-BOCsulfanyl-pyrrolidin-2-yl-methyl)-amino]-benzoylamino}-4-methylsulfanyl-butyric acid methyl ester (22 g) was deprotected (analogously as for the equivalent step in Example 15) to yield the desired end product (22).

$^1$H NMR ($CDCl_3+CD_3COOD$) $\delta1.7$–1.9 (1H,m); 2.0–2.4 (6H+$CH_3COOH$,M); 2.5–2.8 (3h,M); 3.23 (1h,Q); 3.45–3.7 (2H,m); 3.7–3.9(4H,m); 3.95–4.15 (1H,m); 4.8–4.95 (1H, m); 6.8 (1H,d); 7.0 5–7.18(2H,m); 7.23 (1H,t). MS (ESP) m/z 398 $(M+H)^+235$. Anal.Calcd for $C_{18}H_{27}N_3O_3S_2$1.25TFA:C,45.6;H,5.27;N,7.78 Found C,45.2:H,5.3:N,7.4

Staring material 22 g was prepared as follows.

i) Preparation of (2S,4S),4-BOCsulfanyl-2-formyl-pyrrolidine-1-carboxylic acid allyl ester (22b)

TPAP (5.5 mg,0.0156 mmol) was added to a stirred mixture of (2S,4S),4-BOCsulfanyl-2-hydroxymethyl-pyrrolidine-1-carboxylic acid allyl ester (22a)(100 mg,0.31 mmol) and NMM-O (56 mg,0.478 mmol) in $CH_2Cl_2$(2.0 mL) and $CH_3CN$ (100 µL) containing dried powdered 4A° molecular sieve(200 mg). The reaction mixture was left to stir for 1 h then concentrated to dryness. This was then purified by flash chromatography on $SiO_2$ (Varian Mega Bond Elut Column) eluting with 50% EtOAc/i-Hexane to give compound 22b as a colourless gum: 66.3 mg(66.7%).

$^1$H NMR ($CDCl_3$,250 $MH_Z$) $\delta1.4$–1.6 (9H,m), 2.0–2.25 (1H,m): 2.45–2.75 (1H,m): 3.45–3.6 (1H,m): 3.75–3.9 (1H, m); 3.94–4.1 (1H,m): 4.1–4.35(1H,m); 4.5–4.7 (2H,m); 5.15–5.4 (2H, m); 5.75–6.05 (1H,m): 9.4 (1H,s,CHO). MS (Cl) m/z 316 $(M+H)^+$,260.216.

ii) Preparation of (2S),2-[(3-amino-benzoyl)-amino]-4-methylsulfanyl-butyric acid methyl ester (22e)

3-Nitro-benzoic acid (22c)(2.0 g,11.9 mmol) was coupled with L-methionine methyl ester hydrochloride (2.6 g,13 mmol) according to the method used to synthesise compound 18a. to give (2S),2-[(3-nitro-benzoyl)-amino]-4-methylsulfanyl-butyric acid methyl ester (22d) as a white solid:3.15 g(93.4%)

$^1$H NMR ($CDCl_3$,200 $MH_Z$) $\Delta2.05$–2.45 (5H,m); 2.63 (2H,t); 3.82 (3H,s); 4.96 (1H,m); 7.2 (1H,d,NH); 7.65,1H,t); 8.18 (1H,m); 8.39 (1H,m); 8.65 (1H,m). MS (ESP) m/z 313 $(M+H)^+$,265,253. Anal. Calcd for $C_{13}H_{16}N_2O_5S$:C,50.0:H, 5.16:N,8.97 Found C,50.3:H,5.1 ;N,8.9

A stirred solution of 22d (500 mg, 1.62 mmol) in MeOH (10 mL) was treated portionwise with decolourising charcoal (50 mg). and iron III chloride hexahydrate (7 mg,0.026 mmol). N,N-Dimethyl hydrazine (1.5 mL, 19.8 mmol) was then added dropwise and the resulting suspension was heated to reflux for a total of 18 h. The reaction mixture was then concentrated to dryness and the residues purified by flash chromatography on $SiO_2$ (Varian Mega Bond Elut Column) elutine with 50%EtOAc/i-Hexane. Product fractions were then concentrated to yield a colourless oil which crystallised on standing. This was then triturated with $Et_2O$ to give 22e as a white powder which was collected by filtration and dried:367 mg (81.2%)

$^1$H NMR ($CDCl_3$,250 $MH_Z$) $\delta2.0$–2.4 (5H,m): 2.5–2.65 (2H,m); 3.8 (3H,s): 4.9 (1H,m): 6.75–6.95 (2H,m,ArH+ CONH); 7.05–7.3 (3H,m). MS (ESP) m/z 283 $(M+H)^+$.251, 235,223. Anal. Calcd for $Cl_{13}H_{18}N_2O_3S$:C,55.3:H,6.43:N, 9.92 Found C,55.5:H,6.6:N,9.8 iii) Preparation of 22 g

A solution containing 22e (50 mg, 0.17 mmol) and 22b (54 mg,0.17 mmol) in EtOH(2.5 mL) was treated with powdered 4A° molecular sieves (100 mg) and the resulting suspension was stirred at room temperature for 1 h. Acetic acid (10 µL) and sodium cyanoborohydride(17 mg,0.27 mmol) were then added and the reaction mixture was left to stir for 18 h at room temperature. The reaction mixture was then partitioned between EtOAc(50 mL) and saturated $NaHCO_3$(aq)(50 mL). The aqueous phase was then washed with EtOAc(50 mL) and the combined organics dried over $MgSO_4$, filtered and concentrated to a colourless gum. This was then purified by flash chromatography on $SiO_2$ (Varian Mega Bond Elut Column) eluting a gradient of 25–40% EtOAc/i-Hexane to give (2S)-2-{3-[([2S,4S]-1-allyloxycarbonyl-4-BOCsulfanyl-pyrrolidin-2-yl-methyl)-amino]-benzoyl-amino }-4-methylsulfanyl-butyric acid methyl ester (22f) as a colourless gum:60.1 mg(60.3%).

1H NMR ($CDCl_3$,200 $MH_Z$) $\delta1.45$ (9H,s,$^t$Bu); 1.7–1.9 (1H,m); 2.0–2.4 (5H,m); 2.45–2.7 (3H,m): 3.1–3.35 (2H,m); 3.4–3.6 (1H,m), 3.6–3.85 (4H,m), 4.04–4.3 (2H,m); 4.6 (2H,m): 4.8–4.95 (1H, m); 5.15–5.4 (2H,m); 5.8–6.1 (1H, m); 6.75 (1H,d); 6.5–7.3 (5H,m). MS (ESP) m/z 582 $(M+H)^+$,482.

Compound 22f was deprotected (analogously as for the equivalent step in Example 15) to give the desired starting material 22 g in 64% yield.

$^1$H NMR ($CDCl_3+D_2O$) $\delta1.15$–1.95 (10H, m); 1.95–2.15 (4H,m,SMe+H); 7.15–2.35(1H.m); 2.35–2.5(1H.m); 2.55 (2H.t); 2.75–2.95(1H.m); 2.95–3.15(1H.m); 3.15–3.55(3H, m); 3.55–3.7(1H.m); 3.78(3H.s.COMe); 4.9(1H.m); 6.73 (1H,m); 6.98–7.13(2H.m); 7.2(1H,t). MS (ESP) m/z 498 $(M+H)^+$0.398. Anal.Calcd for $C_{23}H_{35}N_3O_5S_2O$0.35$CH_2Cl_2$: C,53.2;H,6.82;N,7.97; Found C,53.5:H,7.1;N,7.5

EXAMPLE 23

See Scheme 30

Preparation of N-((2S,4S)4-sulfanyl-pyrrolidin-2-ylmethyl)-3-methyl-N-(2-naphthalen-1-yl-ethyl) butyramide (compound 9)

(2S,4S)-2-{[(3-Methoxypropyl)-(2-naphthalen-1-ylethyl)amino]methyl}-pyrrolidine-4-thiol (compound 10) and;
(2S,4S)-2-{[(2-(4-Methoxyphenyl)methyl)-(2-naphthalen-1-ylethyl)amino]methyl}-pyrrolidine-4-thiol (compound 11).

Preparation of Compound 9

A solution of starting material N-((2S,4S)-4-BOCsulfanyl-pyrrolidin-2-ylmethyl)-3-methyl-N-(2-naphthalen-1-yl-ethyl)butyramide (6) (770 mg) in trifluoroacetic acid (40 ml) was stirred at ambient temperature for 10 minutes. The trifluoroacetic acid was evaporated under reduced pressure and the residue redissolved in diethyl ether (90 ml). Ethereal HCl(1M, 10 ml) was added and the resulting suspension centrifuged. The diethyl ether was decanted off and more ether(90 ml) added to the residue. This mixture was stirred for five minutes and then recentrifuged. The washing/centrifuging procedure was repeated once more and the resulting white solid dried under reduced pressure to give compound (9), (600 mg)

NMR, data in DMSOd6 d 0.6(2d, 6H), 0.95(d, 1H), 1.7(m, 3H), 2.15(m, 1H), 1.9(m, 1H), 3.0 to 3.85(m, 10h), 7.3 to 8.4(m, 7H), 8.9(br.s, 1H), 9.5(br.s, 1H).

| Micro Analysis: | % Theory | C64.9. | H7.7. | N6.9 |
| --- | --- | --- | --- | --- |
| (1.00 HCl) | % Found | C64.7. | H7.9. | N6.8 |

Starting material (6) was prepared as follows.

(2S,4S)-2-Formyl-4-BOCsulfanyl-pyrrolidine-1-carboxylic acid allyl ester (1) (1.84 g) in dichloromethane (20 ml) was added dropwise over 10 minutes to a mixture of 2-naphthalen-1-ylethylamine (1.0 g), sodium triacetoxyborohydride(1.36 g) and 4A powdered molecular sieve (3.0 g) in dichloromethane (130 ml) cooled to −20° C. and stirred under an argon atmosphere. After the addition was complete the reaction was allowed to warm to ambient temperature and stirred for a further 18 hours. The molecular sieves were filtered off and the fitrate stirred with saturated aqueous sodium bicarbonate solution(100 ml) for 5 minutes. The mixture was separated, the organic phase dried over magnesium sulphate and applied to a silica flash column which was then eluted with 1.Ethyl acetate/Hexane(50:50), 2. Ethyl acetatelHexane(80/20), 3.Ethyl acetate to give (2S, 4S)4-BOCsulfanyl-2[(2-naphthalen-1-ylethylamino)-methyl]pyrrolidine-1-carboxylic acid allyl ester (2) (2.2 g) as a colourless gum.

NMR data in CDCl₃, d 1.5(s, 9H), 1.85(m, 1H), 2.5(m. 1H), 2.8(m. 1H), 3.0(m. 3H), 3.2(m, 3h), 3.7(m, 1H), 4.05(m, 2H), 4.55(d, 2H). 5.25(m. 2H), 5.9(m. 1H), 7.43(m, 4H), 7.7(d, 1H), 7.83(m, 1H), 8.05(m, 1H).

A mixture of compound (2)(1.2 g), isovaleryl chloride (0.61 g) and triethylamine(0.77 g) in dichloromethane(75 ml) was stirred for 1 hour at ambient temperature. The reaction mixture was then applied to a silica flash colomn which was eluted with ethyl acetate/hexane(20:80) to give compound(3) as a colourless gum (1.3 g).

Tributyltin hydride(6.46 g) was added dropwise over 5 minutes to a stirred mixture of compound(3 )(1.23 g) and bis(triphenylphosphine)palladium(0) chloride(20 mg) in dichloromethane(75 ml). This mixture was stirred at ambient temperature for 30 minutes and then applied to a silica flash column which was eluted with 1.Ethyl acetatelHexane (50:50). 2.Ethyl acetate. 3.Ethyl acetate/Methanol(95:5). The product obtained was recolumned on an Isolute® C18 (10 g) column eluting with methanol/water(80:20) to give starting material compound (6) as a white solid (769 mg), m.pt. 86°.

NMR data (CDCl₃) d 0.9(2d, 6H). 1.3(m, 1H), 1.5(s, 9H), 1.8–2.5(m, 6H), 2.9(m, 1H), 3.05–3.9(m, 9H), 7.25–8.35(m, 7H).

Preparation of Compound(10)

A solution of starting material (2S,4S)-2-{[(3-methoxypropyl)-(2-naphthalen-1-ylethyl)amino]methyl}-pyrrolidine-4-BOCthiol (compound 7) (78 mg) in trifluoroacetic acid(5 ml) was stirred at ambient temperature for 30 minutes. The trifluoroacetic acid was removed under reduced pressure and the residue treated with diethyl ether(5 ml). The ether was decanted off and the residue dried under reduced pressure for 24 hours to give the desired end product as a colourless gum (compound 10)(70 mg).

NMR data (CDCl₃) d 1.95(m, 4H), 2.05(m, 1H), 3.16–3.62(m. 10H), 3.29(s. 3H), 3.7(m, 1H), 4.15(m, 2H), 7.3–7.65(m, 4H), 7.68((d, 1H), 7.88(d, 1H), 7.98(d, 1H), 11.2(br.s, 2H).

| Micro Analysis: | % Theory | C48.2. | H5.13, | N4.32 |
| --- | --- | --- | --- | --- |
| (2.5 TFA. 0.25 H₂O) | % Found | C48.5. | H5.20, | N4.40 |

Starting material (compound 7) was prepared as follows.

A solution of 4-methoxy-butyraldehyde(140 mg) in dichloromethane(10 ml) was added dropwise to a mixture of compound (2)(250 mg), sodium triacetoxyborohydride(338 mg) and 4A molecular sieves(1.0 g) in dichloromethane(30 ml) stirred under an argon atmosphere at −20°. After the addition was completed (5 minutes) the reaction mixture was allowed to warm to ambient temperature and stirred for 18 hours. The molecular sieves were filtered off and the filtrate washed with saturated sodium bicarbonate solution (20 ml), then brine and dried over magnesium sulphate. The solution was then applied to a silica column and eluted with ethyl acetate/hexane(50:50) to give a clear gum, compound (4)(260 mg).

Compound(7) was synthesised from compound(4) analogously to the preparation of compound(6)

NMR data (CDCl₃) d 1.35(m, 1H), 1.48(s, 9H), 1.74(m, 2H), 2.31(m, 1H), 2.42–3.1(m, 7H), 3.15–3.5(m, 9H), 3.65 (m, 1H), 7.28–8.1(m, 7H).

Preparation of Compound(11)

Compound(11) was synthesised from starting material (2S,4S)-2-{[(2-(4-methoxyphenyl)methyl)-(2-naphthalen-1-ylethyl)amino]methyl}-pyrrolidine-4-BOCthiol (compound 8) by the method described for the equivalent step in preparation of compound(10).

NMR data (CDCl₃) d 1.9(m, 1H), 2.05(m, 1H), 2.3(m, 1H), 3.1–3.8(m. 8H), 3.82(s, 3H), 4.25(m, 3H), 6.96(d, 2H), 7.42(m, 6H), 7.83(m, 3H).

| Micro Analysis: | % Theory | C55.7. | H5.77. | N4.06 |
| --- | --- | --- | --- | --- |
| (2 TFA. 0.75 diethyl ether) | % Found | C56.0. | H5.40. | N4.50 |

The starting material for compound(11) was prepared as follows:

A mixture of compound(2) (200 mg), p-methoxybenzyl chloride(133 mg), saturated aqueous sodium bicarbonate(5 ml) and dichloromethane(20 ml) was stirred at ambient temperature for 24 hours. The layers were separated and the organic layer dried, applied to a silica flash column which was then eluted with ethyl acetate/hexane(80:20) to give (2S,4S)-1-allyloxycarbonyl-2-{[(2-(4-methoxyphenyl) methyl)-(2-naphthalen-1-ylethyl)amino]methyl}-pyrrolidine-4-BOCthiol compound(5) as a colourless gum (140 mg).

NMR data (CDCl₃) d 1.45(s, 9H), 2.0(m, 1H), 2.35(m, 1H), 2.53–4.15(m, 10H), 3.8(s, 3H), 4.6(m, 4H), 5.25(m, 2H), 5.9(m, 1H). 6.85(m,3H), 7.3(m, 6H), 7.75(m, 2H).

The desired starting material (compound(8)) was synthesised from compound(5) by the same procedure used to prepare compound(6) from compound (3). Mass Spec. (ESP+) m/e 507.0

EXAMPLE 24

See Scheme 31

Preparation of a) 3-Methyl-N-(naphthalen-1-ylmethyl)-N-([2S,4S]4-sulfanylpyrrolidin-2-ylmethyl)-butanamide (compound 23):

b) N-(naphthalen-1-ylmethyl)-N-([2S,4S]-4-sulfanylpyrrolidin-2-ylmethyl)-pentanamide (compound 24);
c) N-(naphthalen-1-ylmethyl)-1-([2S,4S]-4-sulfanylpyrrolidin-2-ylmethyl)-2-(pyridin-3-yl)-acetamide (compound 27);
d) 3-Methyl-N-(naphthalen-1-ylmethyl)-N-([2S,4S]-4-sulfanylpyrrolidin-2-ylmethyl)-pentanamide (compound 25);
e) 3-Methoxy-N-(naphthalen-1-ylmethyl)-N-([2S,4S]-4-sulfanylpyrrolidin-2-ylmethyl)-propanamide (compound 26) and;
f) (2S,4S)-2-[{N-(4-methoxybenzyl)-N-(naphthalen-1-ylmethyl)-amino}-methyl]-pyrrolidine4-thiol (compound 54).

a) Preparation of Compound 23

A solution of starting material 3-methyl-N-(naphthalen-1-ylmethyl)-N-([2S,4S]4-BOCsulfanyl-pyrrolidin-2-ylmethyl)-butanamide (compound(18)) (187 mg) in trifluoroacetic acid (10 ml) was stirred at ambient temperature for 5 minutes. The trifluoroacetic acid was evaporated under reduced pressure and the resulting residue was redissolved in ethyl acetate (5 ml). A solution of hydrogen chloride (2ml/1.0M) was added to the solution followed by diethylether (5 ml). The mixture was centrifuged, the solvent decanted off and the residue was washed with more diethylether (2×15 ml) and dried to give the hydrochloride salt of compound(23) as an off-white solid (43 mg).

N.M.R. data (DMSO-d6) δ0.83 (m,6H), 0.95(d,1H), 1.68 (m,1H), 2.10(m,3H), 2.42(m,1H), 3.10(m,1H), 3.28–3.90 (m,5H), 5.20(m,2H), 7.08(d,1H), 7.57(m,3H), 7.87(d,1H), 8.00(m,2H), 9.10–9.80(2br.s,2H)

| Micro Analysis: | Theory % | C62.7. | H7.52. | N6.97 |
|---|---|---|---|---|
| (1 HCl, 0.5 H₂O) | Found % | C62.4. | H7.6. | N6.7 |

The starting material compounds(18) was prepared as follows.

A solution of (2S,4S)-2-formyl-4-BOCsulfanyl-pyrrolidine-1-carboxylic acid allyl ester (compound (1)) (3.11 grm.) in dichloromethane(60 ml.) was added dropwise to a stirred mixture of of 1-naphthalenemethylamine (1.71 g), 4A molecular sieves(12 grms) and sodium triacetoxyborohydride(2.3 grms) in dichloromethane (200 ml) under an argon atmosphere at −20°. The mixture was stirred for a further 30 minutes at −20° C. and then allowed to warm to ambient temperature and stirred for a further 16 hours. The mixture was filtered and washed with aqueous sodium bicarbonate solution (2×200 ml),the organic phase further washed with water (200 ml), separated, dried over magnesium sulphate and purified by column chromatography, using ethyl acetate/hexane (30:70) as eluent to give (2S ,4S)-2-{[naphthalen-1-ylmethyl]-amino)-methyl}-BOCsulfanyl-pyrrolidine-1-carboxylic acid allyl ester (compound(12)) as a pale yellow oil (2.09 g).

N.M.R. data (CDCl₃) δ1.50(s,9H), 1.55(m,1H), 1.90(m, 1H), 2.50(m,1H), 2.90(m,1H), 3.05(m,1H), 3.20(m,1H), 3.68(m,1H), 4.08(m,2H), 4.23(s,2H), 4.55(d,2H), 5.20(m, 2H), 5.90(m,1H), 7.47(m,4H), 7.77(m,1H), 7.86(m,1H), 8.13(m,1H).

A mixture of compound(12) (507 mg), triethylamine(0.3 ml) and isovaleryl chloride(0.271 ml) in dichloromethane (30 ml) was stirred at ambient temperature for 1.5 hours and then applied directly to a silica flash column. This was eluted with ethyl acetate/hexane (25:75) and ethylacetate/hexane (35:65) to give 3-Methyl-N-(naphthalen-1-ylmethyl)-N-([2S,4S]-1-allyloxycarbonyl-4-BOCsulfanylpyrrolidin-2-ylmethyl)-butanamide (compound(13)) as a gum (475 mg).

N.M.R. data (DMSO-d6. 373° .K) δ0.90(m,6H), 1.45(s, 9H), 1.78(m,1H), 2.18(m,3H), 2.50(m, 1H), 3.15(q, 1H), 3.45(m,1H), 3.70(m,2H), 4.03(q,1H), 4.20(m, 1H), 4.45(m, 2H), 5.10(m,4H), 5.80(m,1H), 7.20(d,1H), 7.50(m,3H), 7.80 (d,1H), 7.92(m.1H), 8.00(m, 1H).

Tributyltin hydride(2.22 ml) was added dropwise to a mixture of compound(13) (446 mg), bis-triphenylphosphine palladium chloride(5.8 mg) in dichloromethane (10 ml). The mixture was stirred at ambient temperature under an arson atmosphere for 70 minutes and then applied directly to a flash column which was eluted with (1)Ethyl acetate/hexane (50:50) and (2) Ethyl acetate. The product obtained was recolumned on an Isolute® C18 (10 g) column, eluting with methanol/water (1) (70:30), (2)(75:25) and (3)(80:20) to give the desired starting material (compound(18)) as a gum (197 mg).

N.M.R. data (DMSO-d6,373° .K) 67 0.90(m,6H), 1.45 (m,5H), 1.60(m,1H), 1.68(m,2H), 2.12(m,2H), 2.25(d,2H), 2.40(m,1H), 2.60–3.85(m,8H), 5.14(s,2H), 7.20(d,1H), 7.50 (m,3H), 7.83(m,1H), 7.93(m,1H), 8.03(m,1H).

b) Preparation of Compound 24

Compound(24) was synthesised by the same procedure used for compound(23) but substituting appropriate compounds as indicated in Scheme 31.

Compound 24:

N.M.R. data (DMSO-d6) δ0.85(m,3H), 1.15–1.75(m,5H), 2.28(t,2H), 3.10(m,1H), 3.33–3.95(m,6H), 5.18(m,2H), 7.20 (2d,1H), 7.55(m,3H), 7.85(d,1H), 8.00(m,2H), 8.95–9.90 (2br.s,2H)

| Micro Analysis: | % Theory | C62.7, | H7.52, | N6.97 |
|---|---|---|---|---|
| (1 HCl, 0.5 H₂O) | % Found | C62.5, | H7.80, | N6.8 |

Compound(14): p N.M.R. data (CDCl₃) δ0.90(m,3H), 1.12–2.10(m,6H), 1.48(s,9H), 2.26(m,1H), 2.50(m,1H), 3.00–5.70(m,12H), 5.87(m,1H), 7.07–8.06(m,7H).

Compound(19):

N.M.R. data (DMSO-d6.373° .K) δ0.84(m,3H), 1.30(m, 3H), 1.45(s,9H), 1.55(m,2H), 2.34(m,3H), 2.80(m,2H), 3.45 (m,5H), 5.10(m,2H), 7.25(d,3H), 7.50(m,3H), 7.80(d,1H), 7.90(m,1H), 8.03(m,1H).

c) Preparation of Compound(27)

Compound(27) was synthesised, in the same manner as the equivalent step for compound(23), from starting material N-(naphthalen-1-ylmethyl)-N-([2S,4S]-4-BOCsulfanylpyrrolidin-2-ylmethyl)-2-(pyridin-3-yl)-acetamide (compound(22)).

Compound(27):

N.M.R. data (DMSO-d6) δ1.70(m,1H), 2.50(m,1H),3.14 (m,1H), 3.28–5.10(m,7H), 5.35(m,2H), 7.20–9.00(m,11H), 9.20(br.s,1H), 10.05–10.50(2br.s,1H)

| Micro Analysis: | % Theory | C55.10. | H6.60. | N7.97 |
|---|---|---|---|---|
| (2 HCl.2.25 H₂O. 0.3 diethyl ether) | % Found | C54.80. | H6.10. | N7.60 |

Starting material (compound(22)) was synthesised as follows.

A mixture of compound(12)(345 mg), 4-dimethylamino-pyridine(305 mg), 3-pyridylacetic acid hydrochloride(262 mg) and 1-(3-dimethylaminopropyl)-3-ethylcarbodiimide hydrochloride(348 mg) in dichloromethane (30 ml) was stirred at ambient temperature, under an argon atmosphere, for 16 hours. The mixture was then purified by silica flash column chromatography, eluting with ethyl acetate/hexane (75:25) and then ethyl acetate to give N-(naphthalen-1-ylmethyl)-N-([2S,4S]-1-allyloxycarbonyl-4-BOCsulfanylpyrrolidin-2-ylmethyl)-2-(pyridin-3-yl)-acetamide (compound(17)) as a colourless gum (394 mg).

Compound(17):
N.M.R. data (DMSO-d6. 373° .K) δ1.46(s,9H), 1.75(m, 1H), 2.50(m,1H), 3.17(q,1H), 3.50(m,1H), 3.75(m,4H), 4.04 (m,1H), 4.27(m,1H), 4.45(m,2H), 5.15(m,4H), 5.83(m,1H), 7.25(m,2H), 7.43(t,1H), 7.52(m,2H), 7.58(m,1), 7.82(d,1H), 7.95(m,2H), 8.40(d,2H).

Using the procedure previously described for the equivalent step in synthesis of compound 23, the desired starting a material (compound(22)) was synthesised from compound (17).

Compound(22)
N.M.R. data (DMSO-d6. 373° .K) δ1.45(s,9H), 2.38(m, 1H), 2.55–4.00(m,10H), 5.20(m,2H), 7.25(m,2H), 7.50(m, 4H), 7.90(m,3 H), 8.40(m,2H).

d) Preparation of Compound(25)

Compound(25) was synthesised using compounds 12, 15 and 20 as intermediates, in the same manner as the equivalent steps for synthesis of compound (27) (see Scheme 31).

Compound(25):
N.M.R. data (DMSO-d6) δ0.80(m,6H), 0.95–4.80(m, 14H), 5.18(m,2H), 7.08(d,1H), 7.55(m,3H), 7.95(m,3H), 8.90–10.15(2br.d,2H).

| Micro Analysis: | % Theory | C59.1, | H7.30, | N6.27 |
|---|---|---|---|---|
| (2 HCl. 0.2 H$_2$O) | % Found | C59.1, | H6.90, | N5.9 |

Compound(15):
N.M.R. data (DMSO-d6. 373° .K) δ0.85(m,6H), 1.15(m, 1H), 1.35(m,1H), 1.45(s,9H), 1.75(m,1H), 1.90(m,1H), 2.17 (m,1H), 2.30(m,1H), 2.50(m,1H), 3.15(q,1H), 3.45(m,1H), 3.70(m,2H), 4.03(q,1H), 4.20(m,1H), 4.44(d,2H), 5.10(m, 4H), 5.80(m,1H), 7.20(d,1H), 7.50(m,3H), 7.80(d,1H), 7.90 (m,1H), 8.00(m,1H).

Compound(20):
N.M.R. data (DMSO-d6. 373° .K) δ0.85(m,6H), 1.25(m, 3H), 1.45(s,9H), 1.93(m,1H), 2.27(m,3H), 3.40(m,6H), 5.13 (m,2H), 7.25(d,1H), 7.50(m,3H), 7.80(d,1H), 7.90(m,1H), 8.04(m,1H).

e) Preparation of Compound(26)

Compound(26) was synthesised using compounds 12, 16 and 21 as intermediates in the same manner as the equivalent steps for synthesis of compound(27) (see Scheme 31).

Compound(26):
N.M.R. data (DMSO-d6) δ1.70(m,1H), 2.40–4.15(m, 14H), 5.20(m,2H), 7.20(2d,1H), 7.55(m,3H), 7.85(m,1H), 8.00(m,2H), 9.05–10.25(2br.d,2H).

| Micro Analysis: | % Theory | C59.5. | H6.99. | N6.93. |
|---|---|---|---|---|
| (2 HCl. 0.2 H$_2$O) | % Found | C59.3. | H7.30. | N6.70 |

Compound(16):
N.M.R. data (DMSO-d6. 373° .K) δ1.45(s,9hH), 1.78(m, 1H), 2.40–3.80(m,12H), 4.00(m,1H), 4.20(m,1H), 4.45(m, 2H), 5.10(m,4H), 5.80(m,1H), 7.20(d,1H), 7.45(t,1H), 7.50 (m,2H), 7.80(d,1H), 7.90(m,1H), 8.00(m,1H).

Compound(21):
N.M.R. data (DMSO-d6, 373° .K) δ1.30(m,1H), 1.48(s, 9H), 2.30(m,1H), 2.56–3.70(m,14H), 5.15(m,2H), 7.30(d, 1H), 7.47(t,1H), 7.53(m,2H), 7.83(d,1H), 7.94(m,1H), 8.05 (m,1H).

f) Preparation of Compound(54)

A mixture of starting material (2S,4S)-2-[{N-(4-methoxybenzyl)-N-(naphthalen-1-ylmethyl)-amino}-methyl]-pyrrolidine-4-BOCthiol (compound(53))(100 mg) and trifluoroacetic acid(5 ml) was stirred at ambient temperature for 1 hour. The trifluoroacetic acid was removed under reduced pressure and the residue coevaporated with diethylether to give compound(54) as a colourless gum (83 mg) NMR data (CDCl$_3$) d 1.5(m. 1H). 1.75(br.d. 1H). 1.95(m. 1H). 2.6(t. 1H). 3.05(m. 1H). 3.2(d. 1H). 3.35(m. 2H). 3.85(s. 3H). 4.2(s. 2H). 4.6(2d. 2H). 6.95(d. 2H). 7.4(d. 2H). 7.6(m. 4H). 7.9(m. 3H).

| Micro Analysis: | % Theory | C52.0. | H5.40. | N3.90 |
|---|---|---|---|---|
| (2.5 TFA. 0.4 diethyl ether) | % Found | C52.0. | H4.92. | N3.96. |

The starting material was prepared as follows.

A mixture of compound(12)(240 mg), dimethylformamide(20 ml), anhydrous potassium carbonate (80 mg) and p-methoxybenzylchloride(0.143 ml) was stirred at 70° under an argon atmosphere for 4 hours. The solvent was removed under reduced pressure and the residue purified by column chromatography eluting with ethyl acetate/hexane(20:80) to give a colourless gum (2S,4S)-1-allyloxycarbonyl-2-[{N-(4-methoxybenzyl)-N-(naphthalen-1-ylmethyl)-amino}-methyl]-pyrrolidine-4-BOCthiol (compound(52)) (213 mg). NMR data (CDCl$_3$) d 1.45(s. 9H), 2.15(m. 1H), 2.5(m. 1H), 2.8(m, 1H), 3.05(m. 1H). 3.5(m. 2H), 3.8(br.s. 7H), 3.9(m. 1H), 4.2(m, 1H). 4.6(s. 2H). 5.25(m. 2H), 5.9(m, 1H), 6.85(d. 2H). 7.2(d, 2H). 7.4(m. 4H), 7.8(2d. 2H), 8.1(d. 1H).

Tributyltin hydride(0.77 ml) was added to a mixture of compound(52) and bis(triphenyl phosphine) palladium (O) chloride(2 mg) in dichloromethane(10 ml). The solution was stirred at ambient temperature for 30 minutes. A second portion of tributyltin hydride(0.335 ml) and bis (triphenylphosphine) palladium (0) chloride(2 mg) were added and the stirring was continued for a further 30 minutes. The mixture was applied directly to a silica flash column which was eluted with ethyl acetate/hexane(25:75), (50:50) and finally ethyl acetate. The product obtained was further purified by reverse phase HPLC on a C18 column eluting with water/methanol/TFA(20:80:0.2) to give the desired starting material (compound(53)) as a colourless gum. (168 mg.)

NMR data (CDCl$_3$) d 1.45(s, 9H). 155(m. 1H), 2.0(m. 1H), 2.5(m. 1H), 3.1(d. 1H) 3.4(m. 3H), 3.6(t. 1H). 3.8(s, 31H), 4.1(2d, 2H), 4.4(d, 1H). 4.6(d. 1H). 6.95(d. 2H).m 7.4(d. 2H). 7.5(m. 414). 7.9(m. 3H).

| Micro Analysis: | % Theory | C54.4. | H5.40. | N3.70 |
|---|---|---|---|---|
| (2 TFA) | % Found | C55.0. | H5.31. | N3.89 |

EXAMPLE 25

See Scheme 32

Preparation of a) (2S,4S)-2[((N-methylnaphthalen-1-ylamino)-methyl]-4-sulfanylpyrrolidine (compound 36) and:

b) N-(naphthalen-1-yl)-N-((2S,4S)-4-sulfanylpyrrolidin-2-yl-methyl)-3-methylbutanamide (compound 37).

Preparation of Compound 36

A mixture of starting material (2S,4S)-2[(N-methylnaphthalen-1-ylamino)-methyl]-4-BOCsulfanylpyrrolidine (compound (34)) (110 mg) and trifluoroacetic acid (5 ml) was stirred at ambient temperature for 1 hour. The trifluoroacetic acid was removed under reduced pressure and the residue dried under high vacuum to give compound(36) as a colourless gum(110 mg).

N.M.R. data (CDCl$_3$) δ1.7 (m. 1H), 1.9 (d. 1H), 2.6 (m, 1H), 2.95 (s.3H), 3.1 (2d.1H), 3.5 (m. 1H), 3.65 (m. 3H), 4.05 (m. 1H), 7.0 (br. s. 1H), 7.4 (t. 1H), 7.55 (m. 3H), 7.7 (d. 1H), 7.85 (m. 1H), 8.2 (m. 1H).

| Micro Analysis: | % Found | C 45.5. | H 4.2. | N 5.0 |
|---|---|---|---|---|
| (2.0 TFA. 1.0 H$_2$O) | % Theory | C 46.3. | H 4.67. | N 5.4 |

The starting material for compound(36) was prepared as follows:

A mixture of (2S,4S)-2-formyl4-BOCsulfanyl-pyrrolidine-1-carboxylic acid allyl ester (compound(1)) (711 mg), ethanol(25 ml), 1-naphthylamine(333 mg) and 3A molecular sieves(4.5 g.) was stirred under an argon atmosphere at ambient temperature for 6 hours. Acetic acid (0.4 ml) was added followed by sodium cyanoborohydride(1 70 mg). The mixture was then stirred for a further 20 hours when the sieves were removed by filtration. The filtrate was concentrated under reduced pressure and the residue applied to a silica column and eluted with ethyl acetate/hexane (20:80) to give (2S,4S)-1-allyloxycarbonyl-2[(naphthalen-1-ylamino )-methyl]-4-BOCsulfanylpyrrolidine (compound (31)) as a clear oil (560 mg).

N.M.R. data (CDCl$_3$) δ1.5 (s.9H), 1.85 (m.1H), 2.7 (m.1H), 3.35 (m.2H), 3.5 (m.1H), 3.8 (m.1H), 4.2 (m.1H), 4.5 (m.1H). 4.65 (d.2H). 5.3 (2d.2H), 5.95 (m.1H), 6.55 (m.1H), 7.2 (d.1H), 7.3 (t.1H), 7.4 (m.2H), 7.75 (m.1H), 7.9 (m.1H).

A mixture of (compound(31))(218 mg), dimethylformamide(40 ml), iodomethane(0.6 ml.) and anhydrous potassium carbonated 150 mg) was stirred at 80° for 20 hours. The solvent was removed under reduced pressure and the residue taken up in ethyl acetate(30 ml.) and washed with water(20 ml). The organic phase was dried over magnesium sulphate, filtered and concentrated under reduced pressure to give (2S,4S)-1-allyloxycarbonyl-2[(N-methylnaphthalen-1-ylamino)-methyl]-4-BOCsulfanylpyrrolidine (compound (32)) as a yellow gum (183 mg).

N.M.R. data (CDCl$_3$) δ1.45 (s,9H), 2.0 (m.1H), 2.4 (m.1H), 2.85 (s.3H), 3.0 (2d.1H), 3.25 (m.1H), 3.7 (2d.1H), 3.8 (m.2H), 4.1 (m.2H), 4.6 (d.2H), 5.3 (9m.2h), 5.95 (m.1H), 7.45 (m.5H), 7.8 (m.1H), 8.25 (m.1H).

To a solution of compound(32)(178 mg) in dichloromethane(10 ml) was added tri-n-butyl tin hydride (0.2 ml.) followed by bis(triphenyl phosphine) palladium chloride (2 mg) and the mixture then stirred at ambient temperature. After 10 min and 20 min a second and third portion of tri-n-butyl tin hydride (0.2 ml.) and bis(triphenyl phosphine) palladium chloride (2 mg) were added and stirring continued for a further 90 min. The reaction solution was applied direct to a silica column and eluted with ethyl acetate/hexane(25:75). (50:50) and ethyl acetate. The product was further purified on a reverse phase HPLC. C18 column which was eluted with water/methanol/ trifluoroacetic acid(20:80:0.2) to give as a colourless gum the desired starting material (compound(34))(160 mg).

N.M.R. data (CDCl$_3$) δ1.45 (s.9H), 2.2 (s.1H), 2.39 (m.1H), 2.85 (s.3H), 2.9 (2d.1H), 3.1 (2d.1H), 3.25 (m.2H), 3.4 (m.1H), 3.6 (m.1H), 7.15 (d,1H), 7.45 (m.4H), 7.8 (m.1H), 8.35 (m.1H).

| Micro Analysis: | % Found | C 50.8. | H 5.20. | N 4.6 |
|---|---|---|---|---|
| (2.0 TFA. 0.5 H$_2$O) | % Theory | C 49.3. | H 5.13. | N 4.6 | b) Preparation of Compound (37)

A mixture of starting material (compound(35))(187 mg) and trifluoroacetic acid(5 ml.) was stirred at ambient temperature for 1 hour. The trifluoroacetic acid was removed under reduced pressure and the residue dried under high vacuum to give a colourless gum. compound (37)(200 mg.).

N.M.R. data (CDCl$_3$) δ0.8 (m.6H). 1.6–2.2 (m.5H), 2.6 (m.1H), 3.2–5.0 (m,6H), 7.6 (m.5H), 8.0 (m.2H).

| Micro Analysis: | % Found | C 48.4. | H 4.80. | N 4.5 |
|---|---|---|---|---|
| (2.0 TFA. 1.0 H$_2$O) | % Theory | C 49.0. | H 5.14. | N 4.76 |

The starting material was prepared as follows.

Isovaleryl chloride(0.164 ml.) was added dropwise over 10 minutes to a stirred solution of compound(3 1)(297 mg.), dichloromethane(50 ml) and triethylamine(0.136 ml.). The solution was stirred at ambient temperature for 24 hours. The solvent was removed under reduced pressure and the residue applied directly to a silica column and eluted with ethyl acetate/hexane(25/75) to give a white foam, N-(naphthalen-1-yl)-N-((2S,4S)-1-allyloxycarbonyl-4-BOCsulfanylpyrrolidin-2-yl-methyl)-3-methylbutanamide, (compound(33))(329 mg).

N.M.R. data (CDCl$_3$) δ0.75 (m.6H), 1.5 (s,9H), 1.65–2.7 (m.5H), 3.15–6.0 (m.9H), 7.25 (m.1H), 7.5 (m,3H), 7.7 (m.1H) 7.9 (m,2H).

To a solution of compound(33 )(296 mg.) in dichloromethane(10 ml) was added tri-n-butyl tin hydride (0.3 ml.) followed by bis(triphenyl phosphine) palladium chloride(2 mg.). The solution was stirred at ambient temperature. After 10 min and 20min a second and third portion of tri-n-butyl tin hydride(0.3 ml.) and bis(triphenyl phosphine) palladium chloride(2 mg) were added and the stirring continued for a further 30 minutes. The reaction solution was applied directly to a silica column which was then eluted with ethyl acetate/hexane(25:75), (50:50) and ethyl acetate. The product was further purified on a reverse phase HPLC. C18 column eluting with water/methanol/ trifluoroacetic acid(20:80:0.2) to give the desired starting material. (compound (35))(216 mg.).

N.M.R. data (CDCl$_3$) δ0.8 (m.6H), 1.49 (s.9H), 1.1–2.2 (m.6H), 2.9–5.6 (m.6H), 7.4–8.0 (m.7H).

| Micro Analysis: | % Found | C 57.0. | H 6.20. | N 4.80 |
|---|---|---|---|---|
| (1.0 TFA. 0.75 H$_2$O) | % Theory | C 56.9. | H 6.45. | N 4.91 |

EXAMPLE 26

See Scheme 33

Preparation of a) 3-Methyl-N-(3,3-diphenylpropyl)-N-([2S,4S]-4-sulfanylpyrrolidin-2-ylmethyl)-butanamide (compound 43) and;

b) N-(3,3-diphenylpropyl)-N-([2S,4S]-4-sulfanylpyrrolidin-2-ylmethyl)-butanamide (compound 44)

Compounds (43) and (44) were synthesised using the procedure described in Example 23 using appropriate starting materials and intermediates as set out in Scheme 33.

Preparation of Compound (43)

Compound (43):

NMR data (DMSOd6 at 373° K.) d 0.9(d. 6H), 1.7(m. 1H), 2.1(m, 1H), 2.33(m 2H), 2.45(m. 1H), 2.9–4.00(m. 9H), 4.2–4.95(m, 2H), 7.3–8.1(m, 10H), 9.65(v.br.s 2H)

| Micro Analysis: | % Theory | C64.8. | H7.7. | N5.9 |
| 1.00 HCl. 1 H$_2$O | % Found | C64.5. | H7.9. | N6.0 |

The starting material 3-Methyl-N-(3-diphenylpropyl)-N-([2S,4S]-4-BOCsulfanylpyrrolidin-2-ylmethyl)-butanamide (compound 41) was synthesised from compound (1) and 3.3-diphenylpropylamine using a similar procedure to that outlined in Example 23.

Compound (38):

NMR data (CDCl$_3$) d 1.5(s, 9H), 1.8(m. 1H), 2.19(m. 2H), 2.42(m. 1H), 2.55(m. 2H), 2.7(m. 1H), 2.82(m. 1H), 3.19(m, 1H), 3.67(m. 1H), 4.0(m. 3H), 4.55(d. 2H), 5.2(2d. 2H), 5.9(m. 1H), 7.2(m, 10H).

Compound (39):

NMR data (CDCl$_3$) d 0.75–1.0(m. 6H), 1.22(m. 1H), 1.5(s. 9H), 1.78–2.02(m. 2H), 2.3(m. 4H), 3.2(m, 3H), 3.4–4.2(m, 6H), 4.52(m. 2H), 5.21(m. 2H), 5.9(m. 1H), 7.2(m 10H).

Compound (41):

NMR data (CDCl$_3$) d 0.75–1.00(m, 6H), 1.25(m. 1H), 1.5(s. 9H), 1.85–2.4(m, 6H), 2.83(m. 1H), 3.05–3.47(m, 6H), 3.6(m. 1H), 3.87(2t, 1H), 7.25(m, 10H)

b) Preparation of Compound (44)

Characterisation data is set out below:

Compound (44):

NMR data (DMSOd6 at 373° K.) d 1.65(m, 1H), 1.85(s, 3H), 2.32(q, 2H), 2.45(m, 1H), 2.69–4.3(m, 9H), 7.2(m, 10H), 9.37(v.br.s, 2H).

| Micro Analysis: | % Theory | C 63.3, | H 7.3. | N. 6.6 |
| 1.00 HCl, 0.75 H$_2$O | % Found | C63.1, | H 7.3. | N. 6.7 |

Compound (40):

NMR data (CDCl$_3$) d 1.5(s. 9H), 1.82(s, 3H), 1.6–2.5(m. 4H), 3.2(m. 3H), 3.32–4.25(m. 6H), 4.54(m, 2H), 5.23(m. 2H), 5.9(m. 1H), 7.23(m. 10H).

Compound (42):

NMR data (CDCl$_3$) d 1.48(s. 9H), 1.8(m. 1H), 1.87(s. 2H), 2.07(s. 1H), 2.33(m. 3H), 2.83(m. 1H), 28(m. 6H), 3.6(m. 1H), 3.85(m. 1H), 7.25(m. 10H).

EXAMPLE 27

See Scheme 34

Preparation of a) 3-Methyl-N-(naphthalen-2-ylmethyl)-N-([2S,4S]-4-sulfanylpyrrolidin-2-ylmethyl)-butanamide (compound 50) and;

b) N-(naphthalen-2-ylmethyl)-N-([2S 4S]-4-sulfanylpyrrolidin-2-ylmethyl)-acetamide (compound 51)

Compounds (50) and (51) were synthesised using the procedure described in Example 23 using appropriate starting materials and intermediates as set out in Scheme 34.

a) Preparation of Compound (50).

Compound 50

NMR data (DMSOd6) d 0.75–1.1(m. 6H), 1.63(m. 1H), 2.1(m. 1H), 2.48(m. 1H), 2.83(m, 3H), 3.0–4.95(m. 8H). 7.17(m. 7H).

| Micro Analysis: | % Theory | C64.2. | H7.44. | N7.13. |
| (1.0 HCl) | % Found | C64.0. | H7.40. | N7.10. |

Starting material 3-Methyl-N-(naphthalen-2-ylmethyl)-N-([2S,4S]-4-BOCsulfanylpyrrolidin-2-ylmethyl)-butanamide (compound (48)) was synthesised from compound (1) and 2-naphthylmethylamine.

Compound (45):

NMR data (CDCl$_3$) d 1.48(s, 9H), 1.92(m, 1H), 2.5(m. 1H), 2.82(m. 1H), 2.96(m. 1H), 3.2(2d. 1H), 3.7(m. 1H), 3.96(s. 2H), 4.08(m, 2H), 4.54(m, 2H), 5.2(m. 2H), 5.9(m, 1H), 7.42(m, 3h), 7.8(m, 4H).

Compound (46):

NMR data (CDCl$_3$) d 0.96(2d. 6H), 1.48(s. 9H), 1.9(m. 1H), 2.13–2.6(m. 4H), 3.3(m. 1H), 3.72(m. 2H), 4.15(m. 2H), 4.5(m. 2H), 4.76(m. 1H), 5.2(m. 2H), 5.9(m. 1H), 7.48(m. 3H), 7.73(m. 4H).

Compound (48):

NMR data (CDCl$_3$) d 0.98(2d. 6H), 1.3(m. 1H), 1.48(s. 9H), 2.3(m. 4H), 2.9(m. 1H), 3.1–3.7(m. 5H), 4.85(m. 2H), 7.15–7.9(m, 7H).

b) Preparation of Compound (51)

Characterisation data is set out below.

Compound 51:

NMR data (DMSOd6 at 373° K.) d 1.7(m, 1H), 2.14(s. 3H), 2.47(m. 1H), 2.8–4.00(m, 6H), 4.8(m. 2H), 7.32–8.1 (m. 7H).

| Micro Analysis: | % Theory | C64.2. | H7.44. | N7.13. |
| (1.00 HCl) | % Found | C64.0. | H7.40. | N7.10. |

Compound (47):

NMR data (CDCl$_3$) d 1.5(s, 9H), 1.9(m. 1H), 2.12(s, 2H), 2.29(s. 1H), 2.5(m. 1H), 3.18–5(m. 10H), 5.2(m. 2H), 5.95 (m. 1H), 7.2–7.89(m, 7H).

Compound (49):

NMR data (CDCl$_3$) d 1.3(m. 1H), 1.47(s, 9H), 2.15(s. 2H), 2.3(s. 1H), 2.35(m, 1H), 2.88(m. 1H), 3.1–3.7(m, 5H), 4.85(m. 2H), 7.4–7.9(m. 7H).

EXAMPLE 28

See Scheme 35

(2S)-2-({4-[([2S,4S]-4-sulfanylpyrrolidin-2-ylmethyl)-amino]-naphthalene-2-carbonyl}-amino)-4-methylsulfanylbutyric acid methyl ester (compound 30)

Starting material (2S)-2-({4-[([2S,4S]-4-BOCsulfanylpyrrolidin-2-ylmethyl)-amino ]-naphthalene-2-carbonyl}-amino)-4-methylsulfanylbutyric acid methyl ester 30e (72.1 mg.0.132 mmol) was deprotected (analogously as for the equivalent step in Example 15) to give the title compound 30.76mg (97.8%).

$^1$H NMR (CDCl$_3$×CD$_3$COOD.200 MHz) d1.75–2.0(1 H.m); 2.0–2.5(5H+DMSO.m); 2.55–3.0(3H.m);3.15–3.4 (1H.m); 3.5–3.7(1H.m); 3.7–3.9(6H.m); 4.2–4.4(1H.m); 4.9–5.05(1 H.m); 7.0–8.1(6H.m.ArH).

MS (ESP$^+$) m/z 448 (M+H)$^+$. Anal.Calcd for $C_{22}H_{29}N_3S_2O_3$ 1.25 TFA: C,49.9;H, 5.17;N,7.12 Found: C,49.6;H,5.3;N,6.7

Starting material 30e was prepared as follows.

Compound 30a

2-Napthoic acid was nitrated with conc $HNO_3$ (Tetrahedron 49,17.3655.1993) to give a mixture of nitro-acids 30a containing the required 4-Nitro-2-Napthoic acid. MS (ESP$^+$) m/z 216 (M–H).

Compound 30b

Oxalyl chloride (6.0 mL, 68.7 mmol) was added dropwise to a stirred solution of the nitro acid mixture.30a(7.3 g.33.6 mmol) in a mixture of DMF(1.0 mL) and $CH_2Cl_2$ (100 mL) at 0° C. under argon. The solution was allowed to warm to RT stirred 18hrs. evaporated to dryness and azeotroped with toluene(2×25 mL).The resulting residues were redissolved in $CH_2Cl_1$ (100 mL) and cooled to 0° C. under argon. $Et_3N$ (7.0mL.50 mmol) was then added, followed by L-Methionine methylester hydrochloride (7.4 g,37 mmol), portionwise, such that the internal temperature did not rise above 10° C. The reaction mixture was left to warm to room temperature and stirred for 18 hr washed with water(100 mL), dried over $MgSO_4$, filtered and concentrated to a viscous brown gum. This was then purified by flash chromatography on $SiO_2$(Merck 9385).eluting with 25%EtOAc/i-Hexane. Appropriate fractions were combined and evaporated to give 30b as a viscous orange gum,490 mg(4%).

$^1$HNMR (CDCl$_3$,200 MHz) d2.1–2.5(5H.m); 2.55–2.75 (2H.m); 3.85(3H.s); 4.9–5.1(1H.m);7.32(1H,d); 7.6–8.0 (2H.m); 8.05(1H,dd); 8.5–8.7(3H.m).

MS (ESP$^+$) m/z 363 (M+H)$^+$.

Compound 30c 30b (450 mg. 1.24 mmol) was reduced (analogously as for the equivalent step in Example 22) to give the corresponding aniline.30c as a yellow gum.310 mg (75.3%)

$^1$H NMR (CDCl$_3$,250 MHz) d2.0–2.45(5H.m): 2.5–2.75 (2H.m): 3.83(3H.s): 4.3(2H.bs.NH$_2$); 4.9–5.05(1H.m), 7.0 (1H.d.NHCO); 7.2(1H.d):7.45–7.65(2H.m); 7.72(1H.s); 7.8–8.0(2H.m). MS (ESP$^{30}$) m/z 333 (M+H)$^+$.271.170.

Compound 30d 30c (300 mg,0.9 mmol) was coupled with the aldehyde 22b(428 mg,1.36 mmol) under the conditions employed to synthesise 22 g using MeOH as solvent and in the presence of 3A° molecular sieves as drying agent to give 30d as yellow gum.460mg (76.5%) MS (ESP$^+$) m/z 632 (M+H)$^+$ Compound 30e 30d (450 mg,0.7 mmol) was deprotected (analogously as for the equivalent step in Example 15) to give the desired starting material 30 e.220 mg (56.4%)

$^1$H NMR (CDCl$_3$,200 MHz) d1.4–1.9(10H+H$_2$0,m); 2.0–2.75(9H.m); 2.95(1H.q.); 3.1–3.35(1H.m); 3.35–3.55 (2H.m); 3.55–3.8(2H.m); 3.82(3H.s.CO$_2$Me); 4.98(1H.m); 5.15(1H.bs.NH); 6.9–7.1(2H.m.ArH+NHCO); 7.4–7.6 (2H.m); 7.61(1H.d); 7.8–8.0(2H.m). MS (ESP$^+$) m/z 548 (M+H)$^+$, 448.

EXAMPLE 29

See Scheme 36

Preparation of a) (2S)-2-({3-[([2S,4S]-4-sulfanylpyrrolidin-2-ylmethyl)-amino]-naphthalene-1-carbonyl}-amino)-4-methylsulfanylbutyric acid methyl ester (compound 31)

b) (2S)-2-({3-[([2S,4S]-4-sulfanylpyrrolidin-2-ylmethyl)-amino]-naphthalene 1-carbonyl}-amino)-4-methylsulfanylbutyric acid (compound 31f)

a) Preparation of Compound 31

31e (55 mg,0.1mmol)was deprotected (analogously as for the equivalent step in Example 15) then treated with Et$_2$O.HCl to give the title compound.31 as a white solid. (37 mg,64.8%)

$^1$H NMR (DMSO-D$_6$+CD$_3$CO$_2$D.250 MHz) d1.05(1H,t. (CH$_2$CH$_2$)$_2$O);1.6–1.8(1H,m); 1.9–2.15(4H,m);2.3–2.7 (4H+DMSO.m);3.04–4.0(9H+(CH$_3$C H$_2$)$_2$O);4.55–4.7(1H,m); 6.95(1H,s);7.1(1H,s);7.15(1H,t); 7.32(1H,t);7.62(1H,d);7.92(1H,d)MS (ESP$^+$) m/z 448 (M+H)$^+$. Anal.Calcd for $C_{22}H_{29}N_3S_2O_3$.2.7HCl 0.3Et$_2$ O C,49.0;H,6.15;N,7.39 Found C,49.1;H,6.1;N,7.2

Compound 31a

3-Nitro-1-napthoic acid 31a was synthesised from 3-nitro-1.8-napthalic anhydride according to the method of G. J. Leuck et al (Journal of the American Chemical Society 51,1831.1929).

Compound 31b

3-Nitro-1-Napthoic acid 31a (5.0 g,23.04 mmol) was coupled with L-Methionine methylester hydrochloride (analogously as for the equivalent step in Example 22) to give 31b as a white cyystalline solid.2.53 g(30.3%)

$^1$H NMR (CDCl$_3$,200 MHz) d2.0–2.5(5H,m);2.55–2.75 (2H,m);3.85(3H,s);5.05(1H,m); 6.9(1H,d,N H);7.6–7.85(2H,m);8.0–8.15(1H,m);8.3–8.5(2H,m);8.83 (1H,m) MS (ESP$^+$) m/z 363 (M+H)$^+$

Compound 31c 31b (2.3 g,6.35 mmol) was reduced (analogously as for the equivalent step in Example 22) to give the corresponding aniline 31c as a yellow gum.1.75 g(83%)

$^1$H NMR (CDCl$_3$,250 MHz) d2.05–2.2(4H,m);2.25–2.45 (1H,m);2.63(2H,m); 3.83(3H,s);5.03(1H,m);6.66(1H,d); 7.05(1H,m);7.15(1H,m);7.28(1H,m);7.39(1H,m); 7.6(1H, m);8.15(1H,m) MS (ESP$^+$) m/z 333 (M+H)$^+$,170.

Compound 31d 31c (1.7 g,5.12 mmol) was coupled with the aldehyde 22b(1.76 g,5.59 mmol). (analogously as for the equivalent step in Example 30) to give 31d as an off-white foam.2.95 g(91.3%).

$^1$H NMR (CDCl$_3$+CD$_3$COOD,250 MHz) d1.5(9H,s),1.9 (1H,m); 2.0–2.25(4H+CH$_3$COOH,m);2.25–2.44(1H,m); 2.55–2.75(3H,m);3.25–3.53(2H,m); 3.55–3.7(1H,m)-3.7–3.95(4H,m)4.1–4.25(1H,m);4.25–4.4(1H,m);4.55–4.8 (2H,m); 5.03(1H,m);5.15–5.45(2H,m);5.96(1H,m);6.9–7.5 (4H+CHCl$_3$,m);7.66(1H,m); 8.1(1H,m) MS (ESP$^+$) m/z 632 (M+H)$^+$.

Compound 31e 31d (2.0 g,3.17 mmol) was deprotected (analogously as for the equivalent step in Example 15) to give the desired starting material 31e as a pale yellow foam, 1.62 g(93.4%).

$^1$H NMR (CDCl$_3$,300 MHz) d2.4–2.6(10H,m);1.85(4H, bs);2.0–2.2(4H,m); 2.35(1H,m);2.5(1H,m);2.65(2H,t);2.9 (1H,m);3.1(1H,m);3.3 (1H,m);3.4(1H,m); 3.55(1H,m,)3.65 (1H,m);3.8(3H,s);5.02(1H,m);6.65(1H,d);6.9(1H,m);7.1 (1H,m); 7.2–7.3(1H+C HCl$_3$,m)7.4(1H,m);7.62(1H,m);8.1(1H,m) MS (ESP+) m/z 548 (M+H)$^+$,448.

b) Compound 31f 31e (180 mg,0.33 mmol) was hydrolysed (analogously as for Example 16) then purified by reverse phase HPLC (Dynamax® 60A,C$_{18}$,8 m prep column), eluting with 50%MeOH/H$_2$O (0.1% TFA) to give product 31f as a white foam,126 mg(65.9%).

$^1$H NMR (DMSO-D$_6$+CD$_3$COOD, 300 MHz) d1.5–1.8 (1H,m);1.9–2.1(5H,m); 2.4–2.7(3H+DMSO,m);3.0–3.1

(1H,m);3.4–3.7(4H,m);3.75–3.9(1H,m);4.57(1H,m); 6.9 (1H,m);7.07(1H,m);7.17(1H,m);7.35(1H,m);7.63(1H,m); 7.95(1H,m) MS (ESP+) m/z 434 (M+H)$^+$,285. Anal.Calcd for $C_{21}H_{27}N_3S_2O_3$,13TFA C,48.7;H,4.9;N,7.22 Found C,48.6;H,4.9;N,7.1

EXAMPLE 30

See Scheme 37

Preparation of a) (2S)-2-({-3-phenyl-5[([2S,4S]-4-sulfanylpyrrolidin-2-ylmethyl)-amino]-phenylcarbonyl}-amino)-4-methylsulfanylbutyric acid methyl ester (compound 32) and;
b) (2S)-2-({-3-phenyl-5[([2S,4S]-4-sulfanylpyrrolidin-2-ylmethyl)-amino]-phenylcarbonyl}-amino)-4-methylsulfanylbutyric acid (compound 32f)

a) Preparation of Compound 32

Starting material compound 32e (55 mg,0.096 mmol) was deprotected (analogously as for the equivalent step in Example 15) to give the title compound 32 as a white foam (56 mg).

$^1$H NMR (CDCl$_3$,250 MHz) d1.6–1.85(1H,m);1.9–2.4 (6H+C$\underline{H}_3$C$_5$H$_6$);2.45–2.7(3H,m); 3.1–3.25(1H,m);3.35–4.1 (11H+H$_2$O.m);4.75–4.95(1H,m);6.8(1H,m);6.9–7.05(1H, m); 7.1–7.55(6H+CH$_3$C$_6$$\underline{H}_5$+C$\underline{H}$Cl$_3$,m.) MS (ESP+) m/z 474 (M+H)$^+$. Anal.Calcd for $C_{24}H_{31}N_3O_3S_2$, 2TFA.0.75toluene C,51.8;H,5.1;N,5.45 Found C,51.6;H, 5.2;N,5.1

Starting Material 32e was Prepared as Follows.

Compound 32a

Saturated NaHCO$_3$(aq) (90 mL) was added to a stirred solution of methyl-3-bromo-5-nitro-benzoate (4.0 g,15.38 mmol) (Mindl and Vecera, Coll.Czech.Chem.Comm. 38,3496,1973.) and phenyl boronic acid (2.0 g,16.38 mmol) in dimethoxyethane (180 mL) Tetrakis(triphenylphosphine) palladium(0), (444 mg,0.38 mmol) was added and the mixture heated at reflux for 1 hr. The resulting black solution was allowed to cool to RT then quenched with saturated NaHCO$_3$(aq)(400 mL). The aqueous was extracted with EtOAc(200 mL).then acidified to pH3 with 2N HCl. The resulting suspension was filtered, washed with water and azeotroped with toluene (3×25 mL) to give 32a as an off-white solid which was triturated with i-Hexane filtered and dried, 2.6 g(69.5%).

$^1$H NMR (DMSO-D$_6$,300 MHz) d7.5(3H,m),7.8(2H,m) 8.4–8.7(3H,m) MS (ESP$^+$) m/z 242 (M–H)$^+$. Anal. Calcd for $C_{13}H_9NO_4$; C,64.2;H,3.73.N,5.76 Found C,64.0;H,3.7;N, 5.6

Compound 32b 32a (3.1 g,12.76 mmol)was coupled with L-Methionine methylester hydrochloride (analogously as for the equivalent step in Example 22) to give 32b,4.9 g(99%).

$^1$H NMR (CDCl$_3$,200 MHz) d2.1–2.45(5H,m);2.65(2H,t) 3.83(3H,s);4.99(1H,m); 7.2–7.35(1H+C$\underline{H}$Cl$_3$,m.);7.4–7.6(3H,m).7.6–7.7(2H,m);8.38(1H,m);8.58(2H,m) MS (ESP+) m/z 389 (M+H)$^+$. Anal. Calcd for $C_{19}H_{20}N_2O_5S$ C,58.8;H,5.19;N,7.21 Found C,58.8;H,5.1;N,7.2

Compound 32c

32b(3.0 g,7.73 mmol) was reduced (analogously as for the equivalent step in Example 30) to give the corresponding aniline 32c.2.43 g(87.8%).

$^1$H NMR (CDCl$_3$,250 MHz) d2.0–2.2(4H,m);2.2–2.4(1H, m);2.6(2H,m);3.8(3H,s); 3.9(2H,bs,N$\underline{H}_2$);4.93(1H,m);6.93(1H,d,N$\underline{H}$CO);7.03(1H,m);7.12(1H,m); 7.3–7.5(4H,m);7.5–7.65 (2H,m) MS (ESP+) m/z 359 (M+H)$^+$.

Compound 32d 32c (1.0 g,2.8 mmol) was coupled with the aldehyde 22b (880 mg,2.8 mmol) (analogously as for the equivalent step in Example 30) to give 32d .1.51 g(82.3%)

$^1$H NMR (CDCl$_3$+CD$_3$COOD.250 MHz) d1.5(9H,s); 1.8–2.0(1H,m); 2.0–2.4(5H+C$\underline{H}_3$ COOH,m);2.5–2.75(3H, m);3.2–3.45(2H,m);3.5–3.7(1H,m); 3.7–3.9(4H,m);4.0–4.4 (2H,m)4.5–4.75(2H,m);4.9–5.05(1H,m);5.1–5.45(2H,m); 5.8–6.1(1H,m);7.03(1H,m); 7.1–7.5(5H+C$\underline{H}$Cl$_3$,m)7.55–7.7(2H,m) MS (ESP+) m/z 658 (M+H)$^+$. Anal.Calcd for $C_{33}H_{43}N_3O_7S_2$.0.1H$_2$O C,59.9;H,6.61;N, 6.35 Found C,59.7;H,6.8;N,6.2

Compound 32e 32d (1.1 g,1.67 mmol) was deprotected (analogously as for the equivalent step in Example 15) to give the desired starting material 32e.800 mg(83.4%).

$^1$H NMR (CDCl$_3$,250 MHz) d1.25(1.5H,t.C$\underline{H}_3$CH$_2$COCH$_3$);1.4–1.6(10H,m); 1.9(2H,bs.N$\underline{H}$+H$_2$O);2.0–2.22(4H+CH$_3$CH$_2$CO$_2$CH$_3$);2.23–2.55(2H,m); 2.51–2.65(2H,m);2.9(1H,m);3.12(1H,m);3.2–3.75(4H,m); 3.8(3H,m); 4.13(1.3H,q,CH$_3$C$\underline{H}$CO$_2$CH$_3$);4.45(1H,bs,N$\underline{H}$);4.95(1H,m); 6.85–7.0(2H,m,Ar$\underline{H}$+N$\underline{H}$CO);7.07(1H,m);7.2–7.5(4H+CHCl3,m);7.5–7.65(2H,m) MS (ESP+) m/z 574 (M+H)$^+$,474. Anal.Calcd for $C_{29}H_{39}N_3O_5S_2$.0.5EtOAc C,60.3;H,7.02;N,6.8 Found C,59.9;H,7.1;N,6.6 b) Preparation of Compound 32f

Starting material 32e (140 mg,0.244 mmol) was hydrolysed (analogously as for the equivalent step in Example 31) to give the desired product 32f as a white foam, 96.3 mg (64.9%).

$^1$H NMR (DMSO-D$_6$+CD$_3$COOD.250 MHz) d 1.5–1.8 (1H,m);1.9–2.2(5H,m); 3.05(1H,q);3.15–3.6(7H,m); 3.65–3.9(1H,m);4.45–4.65(1H,m);6.95–7.05(1H,m); 7.05–7.2(1H,m);7.25–7.5(4H,m);7.55–7.7(2H,m). MS (ESP+)m/z 450 (M+H)$^+$,279. Anal.Calcd for $C_{23}H_{29}N_3S_2O_3$1.3TFA C,50.6;H,5.02;N,6.91 Found C,50.6;H,5.1;N,7.2

The starting material was prepared as described in a) immediately above.

EXAMPLE 31

See Scheme 38

Preparation of a) (2S)-2-({2-phenyl-5-[([2S,4S]-4-sulfanylpyrrolidin-2-ylmethyl)-amino]-phenylcarbonyl}-amino)4-methylsulfanylbutyric acid methyl ester (compound 33) and;
b) (2S)-2-({2-phenyl-5-[([2S.4S]-4-sulfanylpyrrolidin-2-ylmethyl)-amino]-phenylcarbonyl}-amino)-4-methylsulfanylbutyric acid (compound 33f)

a) Preparation of Compound 33

Starting material 33e (53.4 mg,0.093 mmol) was deprotected (analogously as for the equivalent step in Example 31) to give the title compound 33 as a white solid.43.2 mg(87%).

$^1$H NMR (DMSO-D$_6$+CD$_3$COOD.300 MHz) d1.5–1.9 (3H+C$\underline{H}_3$COOH,m);1.95(3H,s); 2.0–2.3(2H,m);2.4–2.65 (1H+DMSO,m);3.0–3.15(1H,m);3.3–3.9(8H,m); 4.25–4.4 (1H,m);6.7(1H,m);6.78(1H,m);7.1–7.4(6H,m). MS (CI$^+$) m/z 474 (M+H)$^+$. Anal.Calcd for $C_{24}H_{31}N_3S_2O_3$1.75TFA C,53.6;H,6.14;N,7.82 Found C,53.6;H,6.3;N,7.7

The starting material was prepared as follows.

Compound 33a

2-Bromo-5-nitrobenzoic acid (12.28 g,0.05 mmol) was coupled with benzene boronic acid (6.7 g,0.055 mmol), (analogously as for the equivalent step in Example32) to give 33a as a white solid.10.95 g(90.3%).

$^1$H NMR (DMSO-D$_6$,300 MHz) d7.3–7.5(5H,m);7.65 (1H,m);8.35(1H,m);8.45(1H,m). MS (ESP−) m/z 242 (M−H)$^-$,198.

Compound 33b 33a (3.58 g,14.7 mmol)was coupled with L-Methionine methyl ester hydrochloride (3.25.16.2 mmol),(analogously as for the equivalent step in Example32) to give 33b as a pale yellow solid.3.02 g(52.6%)

$^1$H NMR (CDCl$_3$,300 MHz) d1.7–2.2(7H,m);3.7(3H,s); 4.7(1H,m);6.05(1H,m,NH); 7.35–7.6(6H,m)8.33(1H,m); 8.55(1H,m) MS (ESP+) m/z 389 (M+H)$^+$.

Compound 33c

33b(1.0 g,2.6 mmol) was reduced (analogously as for the equivalent step in Example 30) to give the corresponding aniline 33c.725 mg(78.6%).

$^1$H NMR (CDCl$_3$,300 MHz) d1.6–1.8(1H,m);1.8–2.15 (6H,m);3.6(3H,s); 3.7–3.9(2H,bs.NH$_2$);4.6–4.7(1H,m);5.85(1H,d,NHCO);6.79(1H,m);7.0(1H,m); 7.15(1H,d);7.2–7.45(5H+CH+Cl$_3$,m) MS (ESP+) m/z 359.(M+H)$^+$, 196.

Compound 33d 33c (710 mg,1.98 mmol) was coupled with the aldehyde 22b (625 mg,1.98 mmol) (analogously as for the equivalent step in Example 30) to give 33d.1.1 g(84.4%).

$^1$H NMR (CDCl$_3$+CD$_3$COOD.250MHz) d1.5(9H,s); 1.6–2.2(8H+CH$_3$COOH,m); 2.5–2.75(1H,m),3.2–3.4(2H, m);3.45–3.9(5H,m);4.05–4.35(2H,m);4.54–4.8(3H,m); 5.15–5.45(2H,m);5.8–6.1(1H,m);6.75–6.9(1H,m)l;6.9–7.05 (1H,m);7.1–7.23(1H,m); 7.25–7.45(5H+CHCl$_3$,m) MS (ESP+) m/z 658 (M+H)$^+$. Anal.Calcd for C$_{33}$H$_{43}$N$_3$S$_2$O$_7$ C,60.3;H,6.59;N,6.39 Found C,60.0;H,6.9;N,6.2

Compound 33e 33d (1.0 g,1.52 mmol) was deprotected (analogously as for the equivalent step in example 15) to give the desired starting material 33e.658 mg(75.4%).

$^1$H NMR (CDCl$_3$+CD$_3$COOD.250 MHz) d1.5(9H,s); 1.6–2.2(8H+CH$_3$COOH,m); 2.55–2.75(1H,m);3.25–3.4 (1H,m);3.5–3.75(5H,m);3.75–4.2(3H,m); 4.55–4.75(1H,m); 6.7–6.85(1H,m);6.85–6.97(1H,m);7.1–7.25(1H,m); 7.25–7.48(5H+CHCl$_3$,m). MS (ESP+) m/z 574 (M+H)$^+$, 474. Anal.Calcd for C$_{29}$H$_{39}$N$_3$O$_5$S$_2$ C,60.7;H,6.85;N,7.32 Found C,60.7;H,7.20;N,7.30 b) Preparation of Compound 33f

Starting material 33e (100 mg,0.174 mmol) was hydrolysed (analogously as for the equivalent step in Example 31) to give 33f as a white foam.64.6 mg(59.8%).

$^1$H NMR (DMSO-D$_6$+CD$_3$COOD.300 MHz) d1.5–2.0 (6H+CH$_3$COOH,m); 2.0–2.3(2H,m);2.3–2.7(1H+DMSO); 3.0–3.1(1H,m);3.2–3.9(5H,m);4.2–4.35(1H,m); 6.6–6.9 (2H,m);7.1–7.4(6H,m). MS (ESP+) m/z 460 (M+H)$^+$,311. Anal Calcd for C$_{23}$H$_{29}$N$_3$O$_3$S$_2$1.4TFA C,50.0;H,4.95;N, 6.79 Found C,49.9;H,5.1;N,6.7

Starting material 33e was prepared as described in a) immediately above.

EXAMPLE 32

See Scheme 39

Preparation of a) (2S)-2-{2-Benzyl-5-[(4-sulfanylpyrrolidin-2-ylmethyl)-amino]-benzoylamino}-4-methylsulfanylbutyric acid methyl ester (compound 34) and;
b) (2S)-2-{2-Benzyl-5-[(4-sulfanylpyrrolidin-2-ylmethyl)-amino]-benzoylamino}-4-methylsulfanylbutyric acid (compound 34h)

a) Preparation of Compound 34

Starting material 34 g (500 mg,0.85 mmol) was deprotected (analogously as for the equivalent step in Example 31) to give the title compound 34 as a white solid. 454 mg (89.3%).

$^1$H NMR (DMSO-D$_6$+CD$_3$COOD.300 MHz) d1.5–1.7 (1H,m);1.85–2.1(5H,m); 2.35–2.6(3H+DMSO,m);2.9–3.1 (1H,m);3.1–3.8(8H,m);3.9(2H,q);4.4–4.6(1H,m); 6.5–6.7 (>1H,m);6.9–7.0(1H,m);7.0–7.3(6H,m). MS (ESP+) m/z 488 (M+H)$^{30}$ ,325. Anal.Calcd for C$_{25}$H$_{33}$N$_3$S$_2$O$_3$, 3HCl C,50.3;H,6.08;N,7.04 Found C,50.4;H,6.3;N,7.3

Starting material 34 g was prepared as follows.

Compound 34a

A solution of 2-bromo-5-nitrobenzoic acid (9.0 g,36.6 mmol) in MeOH (200 mL) was treated with SO$_2$Cl$_2$(2.0 mL) and the resulting solution heated at reflux for 18 hrs. The reaction mixture was then evaporated pre-absorbed on SiO$_2$ (Merck.9385) and chromatographed. eluting with 10% EtOAc/i-Hexane. Appropriate fractions were combined and evaporated to give 34a as a crystalline white solid.8.38 g(88.%)

$^1$H NMR (CDCl$_3$,300 MHz) d4.0(3H,s,CO$_2$CH$_3$);7.85(1H,m);8.18(1H,m);8.63(1H,m).

Compound 34b

A solution of benzyl bromide (2.0 mL. 17.3 mmol) in THF(10 mL) was added dropwise at 0° C. to a stirred suspension of zinc dust(1.7 g,26 mmol) in THF(10 mL) which had been activated according to the method described by Knochel (J.O.C. 53,2392.1988). The mixture was left to warm to RT and stir for 3 hrs.An aliquot (6.5 mmol) of the supernatent containing the benzyl zinc reagent was then added to a stirred solution of 34a (1.0 g,3.85 mmol) and Pd(PPh$_3$)$_2$Cl$_2$ (27 mg,0.0385 mmol) in THF(10 mL) at RT under argo After 1 hr a second aliquot (6.5 mmol) of the benzyl zinc reagent was added. The resulting black reaction mixture was quenched with 2N HCl (250 mL) and extracted with EtOAc (2×100 mL).The combined organics were washed with water (50 mL) and brine (50 mL).filtered through phase separating paper and evaporated to an orange gum. This was chromatographed on SiO$_2$ (Merck.9385) eluting with 10%EtOAc/i-Hexane to give 34b as a yellow oil, 590 mg(56.6%).

$^1$H NMR (CDCl$_3$,300 MHz) d3.9(3H,s,CO2CH$_3$);4.48(2H,s,CH$_2$Ph);7.0–7.5(6H,m); 8.23(1H,m);8.75 (1H,m). MS (ESP$^-$) m/z 270 (M−H)$^-$,210.

Compound 34c

2N NaOH (2.0 mL,4 mmol) was added to a solution of 34b (560 mg,2.06 mmol) in MeOH (10 mL) at RT. After 2 hrs the RM was evaporated to remove the MeOH and then partitioned between Et$_2$O (20 mL) and 2N NaOH (20 mL).The aqueous was acidified to pH2/3 with 2N HCl and extracted with EtOAc(3×20 mL).The combined organics were washed with water (20 mL) and brine (20 mL) filtered through phase separating paper and evaporated to yield 34c as a white solid.453 mg(85.3%).

$^1$H NMR (DMSO-D$_6$,300 MHz) d4.45(2H,s,CH$_2$Ph);7.0–7.4(5H,m); 7.55(1H,m);8.3(1H,m);8.53(1H,m). MS (ESP$^-$) m/z 256 (M–H)$^-$,212.

Compound 34d 34c (630 mg,2.45 mmol) was coupled with L-Methionine methyl ester hydrochloride (540 mg,2.7 mmol). (analogously as for the equivalent step in Example 32) to give 34d as a pale yellow solid. 900 mg (91.3%).

$^1$H NMR (DMSO-D$_6$,250 MHz) d1.9–2.25(5H,m); 2.5–2.75(2H+DMSO,m); 3.74(3H,s,CO2CH3);4.28(2H,q,CH$_2$Ph);4.55–4.75(1H,m);7.15–7.5(5H,m) 7.6(1H,m); 8.2–8.35(2H,m);9.13(1H,d,NHCO). MS (ESP+) m/z 403 (M+H)$^+$.

Compound 34e

SnCl$_2$2H$_2$O (2.5 g,11.08 mmol) was added to a stirred solution of 34d (900 mg,2.24 mmol) in EtOAc(50 mL) and the resulting mixture heated at reflux for 18 hrs. The RM was cooled to RT and treated with 0.88S0 SG NH$_3$(aq) dropwise to pH8. The resulting heavy white precipitate was removed by filtration through celite(545). The filtrates were then evaporated and purified by chromatography (Mega Bond Elut,SiO$_2$),eluting with CH$_2$Cl$_2$ and then 50%EtOAc/i-Hexane to give the corresponding aniline 34e,595 mg(71.4%).

$^1$H NMR (CDCl$_3$,300 MHz) d1.75–2.2(5H,m);2.25–2.45 (2H,m); 3.6–3.8(5H,m,CO2CH$_3$+NH$_2$);4.08(2H,q,CH$_2$Ph); 4.65–4.85(1H,m);6.24(1H,d,NHCO);6.7(1H,m); 6.78(1H, m);7.0(1H,m); 7.05–7.3(5H+CHCl$_3$,m). MS (ESP+) m/z 373 (M+H)$^+$,210.

Compound 34f 34e (570 mg,1.53 mmol) was coupled with the aldehyde 22b (580 mg,1.84 mmol) (analogously as for the equivalent step in Example 30) to give 34f as a crude pale green foam(1.54 g). MS (ESP+) m/z 672 (M+H)$^-$.

Compound 34g 34f (1.5 g,2.24 mmol) was deprotected (analogously as for the equivalent step in Example 15) to give the desired starting material 34 g as a pale brown glass,550 mg (41.9%).

$^1$H NMR (CDCl$_3$,300 MHz) d1.3–1.65(10H,m);1.7–2.2 (5H+H$_2$O,m);2.25–2.6(3H,m); 2.8–3.9(9H,m);3.9–4.25(2H, m);4.6–4.9(1H,m);6.3(1H,d,NHCO);6.55–6.8(2H,m); 6.9–7.4(5H+CHCl$_3$,m). MS (ESP+) m/z 588 (M+H)$^+$,488.

b) Preparation of Compound 34h

Starting material 34 g (52 mg,0.087 mmol) was hydrolysed (analogously as for the equivalent step in Example 16), then purified by reverse phase HPLC (Dynamax® 60A.C$_{18}$,8 m prep column),eluting with 50%MeOH/H$_2$O (0.1%TFA) to give 34h as a colourless glass,38.2 mg(56.6%).

$^1$H NMR (DMSO-D$_6$+CD$_3$COOD,300 MHz) d1.5–1.7 (1H,m); 1.8–2.1(5H+CH$_3$COOH,m);2.3–2.6 (3H+DMSO, m);2.9–3.1(1H,m);3.2–4.1 (7H,m);4.3–4.5(1H,m);6.5–6.7 (2H,m);6.9–7.0(1H,m); 7.05–7.25(5H,m). MS (ESP+) 474 (M+H)$^+$. Anal.Calcd for C$_{24}$H$_{31}$N$_3$S$_2$O$_3$1.4TFA C,50.8;H, 5.16;N,6.14 Found C,51.0;H,5.3;H,6.7

The starting material was prepared as described in a) immediately above.

EXAMPLE 33

See Scheme 40

Preparation of a) (2S)2-{2-Benzyl-4-[([2S,4S]4-sulfanylpyrrolidin-2-ylmethyl)-amino]-benzoylamino}4-methylsulfanylbutyric acid methyl ester (compound 35) and;

b) (2S)2-{2-Benzyl-4-[([2S,4S]4-sulfanylpyrrolidin-2-ylmethyl)-amino]-benzoylamino}4-methylsulfanylbutyric acid (compound 35 g)

a) Preparation of Compound 35

The title compound 35 was synthesised from methyl-2-bromo-4-nitro-benzoate using the same methodology as described in Example 32 but using Pd$_2$(dba)$_3$ as a source of catalytic palladium in the benzylation reaction.

$^1$H NMR (DMSO-D$_6$+CD$_3$COOD, 300 MH$_z$) d1.5–1.7 (1H,m):1.8–2.1(5H,m); 2.3–2.6(3H+DMSO,m):2.9–3.1(1 H, m)3.2–3.8(8H,m);4.05(2H,m);4.4–4.6(1H,m); 6.4–6.6 (2H,m);7.0–7.35(6H,m)

MS (ESP+) m/z 488(M+H)$^+$, 325. Anal Calcd for C$_{25}$H$_{33}$N$_3$S$_2$O$_3$, 2HCl: C,53.6;H,6.29;N,7.5 Found: C,53.5;H,6.5;N,7.3 b) Preparation of Compound 35 g

Compound 35 (100 mg, 0.18 mmol; see a) above) was hydrolysed (analogously as for the equivalent step in Example 32) to give 35 g, as a white solid, 85.8 mg(67.3%).

$^1$H NMR (DMSO-D$_6$+CD$_3$COOD, 300 MH$_z$) d1.5–1.7 (1H,m);1.8–2.1(5H,m); 2.3–2.6(3H+DMSO,m);2.9–3.9 (6H,m);3.95–4.2(2H,m);4.3–4.6(1H,m);6.4–6.5(2H,m); 7.0–7.3(6H,m)

MS (ESP+) m/z 474(M+H)$^+$, 325. Anal Calcd for C$_{24}$H$_{31}$N$_3$S$_2$O$_3$, 1.3TFA C,51.4;H,5.24;N,6.76 Found: C,51.2;H,5.4;N,6.7

EXAMPLE 34

See Scheme 41

(2S)2-{2-Benzyl-5-[([2S,4S]4-sulfanylpyrrolidin-2-ylmethyl)-amino]-benzoylamino}4-methylsulfanylbutyric acid isopropyl ester (compound 36)

The nitro compound 36b was reduced to the corresponding aniline, coupled with the thioproline aldehyde 22b using IPA as solvent and deprotected exactly analogously as for Example 32 to give the title compound 36.

$^1$H NMR (DMSO-D$_6$+CD$_3$COOD, 300 MH$_z$) d1.0–1.3 (6H,m);1.5–1.7(1H,m); 1.8–2.1(5H,m);2.3–2.6(3H+ DMSO,m);2.9–4.1(8H,m);4.8–5.0(1H,m); 6.5–6.7(2H,m); 6.8–7.3(6H,m);

MS (ESP+) m/z 516(M+H)$^+$, 325. Anal Calcd for C$_{27}$H$_{37}$N$_3$S$_2$O$_3$, 2HCl: C,55.1;H,6.68;N,7.14 Found: C,54.9;H,7.0;N,7.1

Compound 36a

A solution of 34d (25.24 g, 62.78 mmol) in MeOH (500 mL) was treated with 2N NaOH (35 mL, 70 mmol). The resulting solution was then evaporated to dryness and the solids partitioned between Et$_2$O (200 mL) and water (500 mL). The aqueous was then acidified to pH2 with 2N HCl and extracted with EtOAc(2×250 mL). The combined organics were washed with water(2×100 mL), brine(100 mL), filtered through phase separating paper and evaporated to give 36a as a white solid, 23.57 g(96.8%).

$^1$H NMR (DMSO-D$_6$, 300 MH$_z$) d1.8–2.2(5H,m);2.3–2.6 (2H+DMSO,m); 4.1–4.3(2H,m);4.4–4.6(1H,m);7.1–7.3 (5H,m);7.4–7.6(1H,m);8.1–8.3(2H,m); 8.9–9.0(1H,m, NHCO)

MS (ESP−) m/z 387(M−H)$^-$.

Compound 36b

Sulphuryl chloride (5.0 mL,62 mmol) was added to a stirred suspension of 36a(19.2 g, 50 mmol) in IPA(500 mL). The resulting mixture was then heated at reflux for 18 hrs. The reaction mixture was then evaporated to ⅕ volume and partitioned between EtOAc (1 L) and saturated NaHCO$_3$ (aq) (500 mL). The organics were then washed with water (200 mL), brine (200 mL), filtered through phase separating paper and evaporated to give 36b as a white solid, 21.25 g(100%)

$^1$H NMR (DMSO-D$_6$, 300 MH$_z$) d1.0–1.3(6Hm); 1.8–2.2 (5H,m); 2.3–2.6(2H+DMSO,m)4.1–4.3(2H,m);4.4–4.6(1H, m);4.8–5.0(1H,m);7.1–7.3(5H,m); 7.4–7.6(1H,m);8.1–8.3 (2H,m);9.0(1H,m,NHCO)

MS (ESP+) m/z 431(M+H)$^+$.

EXAMPLE 35

See Scheme 42

(2S)2-{2-Benzyl-5-[N-([2S,4S]4-sulfanylpyrrolidin-2-ylmethyl)-N-(3-methoxypropionyl)-amino]-benzoylamino}-4-methylsulfanylbutyric acid isopropyl ester (compound 37)

Starting material 37b was deprotected using the same methodology for the equivalent step described in Example 32 to give the title compound 37.

$^1$H NMR (DMSO-D$_6$CD$_3$COOD,300 MH$_z$) d1.0–1.3(6H, m); 1.5–1.7(1H,m); 1.8–2.1 (5H,m);2.2–2.6(5H+DMSO,m) :2.9–3.95(10H,m);4.0–4.2(3H,m); 4.4–4.6(1H,m);4.8–5.0 (1H,m);7.0–7.5(8H,m)

MS (ESP+) m/z 602 (M+H)$^+$.

| Anal Calcd for C$_{31}$H$_{43}$N$_3$S$_2$O$_5$.1.5 HCl | C,56.7;H,6.83;N,6.4 |
| Found | C,56.7;H,7.0;N,6.0 |

The starting material was prepared as follows.

EEDQ (530 mg, 2.15 mmol) was added to a stirred solution of 36d (1.5 g, 2.15 mmol; see Example 34) and 3-methoxy propionic acid (220 mL, 2.36 mmol) in CH$_2$Cl$_2$ (15 mL). The mixture was left to stir 18 hrs at RT then evaporated. The residues were then partitioned between 1N citric acid(aq) (200 mL) and EtOAc (100 mL). The organics were washed with saturated NaHCO$_3$ (aq) (50 mL), water (50 mL) and brine(5 mL), filtered through phase separating paper and evaporated to give a pale yellow gum. This was then purified by flash chromatography on SiO$_2$ (Merck 9385) eluting a gradient of 0–50% EtOAc/i-Hexane. Appropriate fractions were filtered and evaporated to give starting material 37b as a colourless gum, 1.14 g(67.7%).

MS (ESP+) m/z 786 (M+H)$^+$.

EXAMPLE 36

See Scheme 43

Preparation of a) N-([2S,4S]-4-sulfanyl-pyrrolidin-2-ylmethyl)-3,3-dimethyl-N-(2-naphthalen-1-yl-ethyl)-butyramide (compound 56) and;
a) N-([2S,4S]-4-sulfanyl-pyrrolidin-2-ylmethyl)-N-(2-naphthalen-1-yl-ethyl)-2-pyridin-3-yl-acetamide (compound 57)

a) Preparation of compound 56

The method described in Example 23 for the synthesis of compound (6) was used to prepare compound (56) as set out in Scheme 43.

NMR data in CDCl$_3$δ0.91(s, 9H), 1.5(m, 1H), 1.75(m, 1H), 1.82(d,1H), 1.91(d, 1H), 2.52(m, 1H), 2.92(m, 1H), 3.33(m, 3H), 3.72(m, 4H), 4.15(m, 1H), 7.26(d,1H), 7.41(t, 1H), 7.56(m, 2H), 7.8(d, 1H), 7.9(2d, 2H), 9.08(br,s, 1H).

| Micro Analysis: | % Theory | C64.2, | H7.97, | N6.5 |
| (1.00 HCl. 0.5 H$_2$O) | % Found | C64.4, | H7.90, | N6.3 |

Starting material compound (54) was synthesised analogously with Example 23 using the appropriate intermediates:
Compound (52).

NMR data in CDCl$_3$ δ1.00(2s, 9H), 1.46(d, 9H), 1.95(m, 2H), 2.4(m, 2H), 3.3(m, 4H), 3.7(m, 3H), 4.00(m, 3H), 4.57(d, 2H), 5.22(2d, 2H), 5.90(m, 1H), 7.24–8.4(m, 7H).

Compound (54).

NMR data in CDCl$_3$ δ1.00(2s, 9H), 1.35(m, 1H), 1.49(s, 9H), 1.89(br.s,1H), 1.95(d, 1H). 2.3(m, 1H), 2.32(d, 1H), 2.88(2q, 1H), 3.1–3.9(m, 9H), 7.25–8.31(m, 7H).

b) Preparation of Compound 57

The method described in Example 24 for the synthesis of compound (27) was used in a similar manner to prepare compound (57).

NMR data in CDCl$_3$ δ1.2(m, 1H), 2.00(m, 1H), 2.6(m, 2H), 3.15–4.40(m, 10H), 7.28–8.70(m, 11H), 9.4(br.s, 1H).

| Micro Analysis: | % Theory | C56.0, | H6.20. | N8.17 |
| (2 HCl. 2 H$_2$O) | % Found | C56.4, | H6.46. | N7.70 |

Starting material compound(55) was synthesised analogously with Example 24 using appropriate intermediates:
Compound (53).

NMR data in CDCl$_3$ δ1.48(s, 9H), 1.84(m, 1H), 2.42(m, 1H), 2.87–3.45(m, 5H), 3.63–4.26(m, 7H), 4.55(d, 2H), 5.22(2d, 2H), 5.9(m, 1H), 7.1–8.7(m, 1.1H).

Compound (55).

NMR data in CDCl$_3$ δ1.34(m, 1H), 1.5(s, 9H), 1.95(m, 1H), 2.32(m, 2H), 2.72–4.00(m, 10H), 7.1–8.6(m, 11H).

EXAMPLE 37

See Scheme 44

Preparation of a) N-(2,2-Diphenyl-ethyl)-N-([2S,4S]-4-sulfanyl-pyrrolidin-2-ylmethyl)-3-methyl-butyramide (compound 67);

b) N-(2,2-Diphenyl-ethyl)-N-([2S,4S]-4-sulfanyl-pyrrolidin-2-ylmethyl)-3,3-dimethyl-butyramide (compound 68);
c) N-(2,2-Diphenyl-ethyl)-N-([2S,4S]-4-sulfanyl-pyrrolidin-2-ylmethyl)-2-pyridin-3-yl-acetamide (compound 69) and:
d) N-(2,2-Diphenyl-ethyl)-1-oxy-N-([2S,4S]-4-sulfanyl-pyrrolidin-2-ylmethyl)-6-methoxy-nicotinamide (compound 70).

a) Preparation of Compound 67

The method described in Example 23 for the synthesis of compound (6) was used in an analogous manner to prepare compound (67) using appropriate intermediates—see Scheme 44.

NMR data in DMSO-d6 δ0.75(m, 6H), 1.55(m,1H), 1.87 (m, 2H), 2.05–2.45(m, 1H), 3.05(m, 1H), 3.25–3.70(m, 6H), 4.05(m, 2H), 4.20–4.55(m,1H), 7.30(m,10H), 8.80–9.80 (2br.s, 2H)

| Micro Analysis: | % Theory | C63.9. | H7.82. | N6.21 |
|---|---|---|---|---|
| (1.00 HCl.1.00 H₂O) | % Found | C64.1. | H7.70. | N6.00 |

Compound (58).
NMR data in CDCl₃ δ1.50(s, 9H), 1.77(m, 1H), 2.40(m, 1H), 2.75(m, 1H), 3.00(m, 1H). 3.14(q, 1H), 3.24(d, 2H), 3.67(m, 1H), 3.93(m, 1H), 4.10(m, 2H), 4.54(d, 2H), 5.25 (m, 2H), 5.90(m, 1H), 7.25(m,10H)

Compound (59).
NMR data in CDCl₃ δ0.85(m, 6H), 1.48(m, 9H), 1.80(m, 2H), 2.1(m, 2H), 2.40(m, 1H), 2.80–4.35(m, 9H), 4.55(m, 2H), 5.25(m, 2H), 5.90(m, 1H), 7.25(m,10H)

Compound (63).
NMR data in CDCl₃ δ0.85(2d, 6H), 1.24(m, 1H), 1.48(s, 9H), 1.68(m,1H), 1.81(d, 1H), 1.95–2.35(m, 3H), 2.75–3.65 (m, 6H), 3.90–4.55(m, 3H), 7.25(m, 10H)

b) Preparation of Compound 68

Similarly compound (68) was synthesised from compound (60) as set out in Scheme 44.

Compound (68)
NMR data in DMSO-d6 δ0.85(m, 9H), 1.55(m, 1H), 1.74–2.27(m, 2H), 2.37(m, 1H), 3.05(m, 1H), 3.45(m, 6H), 4.05(m, 2H), 4.18–4.55(m, 1H), 7.28(m, 10H), 8.90–9.90 (m, 2H)

| Micro Analysis: | % Theory | C64.6. | H8.02. | N6.02 |
|---|---|---|---|---|
| (1.0 HCl.1.0 H₂O) | % Found | C64.8. | H8.30. | N5.70 |

Compound (60).
NMR data in CDCl₃ δ0.93(m, 9H), 1.50(s, 9H), 1.82(m, 2H), 2.35(m, 3H), 2.90–4.35(m, 8H), 4.55(m, 2H), 5.25(m, 2H), 5.90(m, 1H), 7.25(m, 10H).

Compound (64).
NMR data in CDCl₃) δ0.93(s, 9H), 1.24(m, 1H), 1.48(s, 9H), 1.80(q, 1H), 2.23(d, 1H), 2.30(m, 1H), 2.75–3.70(m, 6H), 3.90–4.60(m, 3H), 7.25(m, 10H).

c) Preparation of Compound 69

Compound (69) was synthesised from compound (61) (see Scheme 44) analogously with the procedure described in Example 24 for the preparation of compound (27).

Compound (69).
NMR data in CDCl₃ δ1.95(m, 1H), 2.40(m, 1H), 2.60(m, 1H), 3.15–4.50(m, 11H), 7.28(m, 10H), 7.67(m, 1H), 8.05 (m, 1H), 8.50(m, 1H), 8.71(m, 1H), 9.10–10.20(br.d, 2H).

| Micro Analysis: | % Theory | C55.1. | H5.51. | N7.01 |
|---|---|---|---|---|
| (2.0 HCl.0.75 TFA.0.5 H₂O) | % Found | C55.0. | H5.60. | N6.90 |

Compound (61).
NMR data in CDCl₃ δ1.47(s, 9H), 1.80(m, 1H), 2.30–4.65 (m, 14H), 5.23(m, 2H), 5.90(m, 1H), 7.25(m, 12H), 8.10–8.55(m, 2H).

Compound (65).
NMR data in CDCl₃ δ1.25(m, 1H), 1.48(s, 9H), 2.30(m, 1H), 2.70–4.55(m, 12H), 7.30(m, 12H), 8.28(2d, 1H), 8.45 (m, 1H).

d) Preparation of Compound 70

Similarly compound (70) was synthesised from compound (62) using appropriate intermediates.

NMR data in CDCl₃ δ1.67(m, 1H), 2.15(d, 1H), 2.47(m, 1H), 3.16(br.s, 1H), 3.50(m, 2H), 3.85–4.40(m, 8H), 5.22 (br.s, 1H), 6.56(d, 1H), 7.00–7.35(m, 11H), 7.90(s, 1H), 8.85–10.75(2br.s, 2H)

| Micro Analysis | % Theory | C57.2. | H5.91, | N7.70 |
|---|---|---|---|---|
| (2.0 HCl.0.5 H₂O) | % Found | C57.5. | H5.60, | N7.30 |

Compound (62).
NMR data in CDCl₃ δ1.50(s, 9H), 1.60(m, 1H), 2.47(m, 1H), 3.00–4.50(m, 12H), 4.58(d, 2H), 5.25(m, 2H), 5.90(m, 1H), 6.53(d,1H), 6.95(m, 1H), 7.25(m, 11H).

Compound (66).
NMR data in CDCl₃ δ1.20(m, 1H), 1.45(s, 9H), 2.30(m, 1H), 2.66(m, 1H), 3.00–3.45(m, 4H), 3.55(m, 1H), 3.95–4.25(m, 5H), 4.47(m, 1H), 6.55(d,1H), 7.25(m, 11H), 7.65(m, 1H).

EXAMPLE 38

See Scheme 45

Preparation of
a) N-([2S,4S]-4-sulfanyl-pyrrolidin-2-ylmethyl)-3-methyl-N-(2-naphthalen-2-yl-ethyl)-butyramide (compound 80);
b) N-([2S,4S]-4-sulfanyl-pyrrolidin-2-ylmethyl)-3,3-dimethyl-N-(2-naphthalen-2-yl-ethyl)-butyramide (compound 81);
c) N-([2S,4S]-4-sulfanyl-pyrrolidin-2-ylmethyl)-N-(2-naphthalen-2-yl-ethyl)-2-pyridin-3-yl-acetamide (compound 82) and;
d) N-([2S,4S]-4-sulfanyl-pyrrolidin-2-ylmethyl)-2-(4-methoxy-phenyl)-N-(2-naphthalen-2-yl-ethyl)-acetamide (compound 83).

a) Preparation of Compound 80

The method described in Example 23 for the synthesis of compound (6) was used to prepare compound (80).

NMR data in DMSO-d6 δ0.75(m, 6H), 0.87(d, 1H), 1.65(m, 1H), 1.92(m, 1H), 2.02(d, 1H), 3.03(m, 3H), 3.20–3.80(m, 9H), 7.48(m, 3H), 7.75(d, 1H), 7.85(m, 3H), 8.90–9.90(br.d, 1H)

| Micro Analysis: | % Theory | C64.9, | H7.68, | N6.88 |
|---|---|---|---|---|
| (1.00 HCl) | % Found | C64.9, | H7.50, | N6.80 |

Starting material compound (76) was synthesised analogously with Example 23 using appropiate intermediates—see Scheme 45.

Compound (71).
NMR data in CDCl$_3$ δ1.50(s, 9H), 1.85(m, 1H), 2.50(m, 1H), 2.80(m, 1H), 3.00(m, 5H), 3.20(m, 1H), 3.65(m, 1H), 4.00(m, 1H), 4.10(m, 1H), 4.53(d, 2H), 5.20(m, 2H), 5.90(m, 1H), 7.32(m, 1H), 7.42(m, 2H), 7.63(s, 1H), 7.80(m, 3H).

Compound (72).
NMR data in CDCl$_3$ δ0.90(m, 7H), 1.00–2.60(m, 14H), 3.00(m, 2H), 3.10–4.20(m, 7H), 4.60(m, 2H), 5.25(m, 2H), 5.90(m, 1H), 7.30–7.50(m, 3H), 7.60(m, 1H), 7.80(m, 3H).

Compound (76).
NMR data in CDCl$_3$ δ0.90(m, 6H), 1.10–2.50(m, 15H), 2.80–3.80(m, 9H), 7.26–7.50(m, 3H), 7.60(m, 1H), 7.80(m, 3H)

b) Preparation of Compound 81
Compound (81) was synthesised from compound (73) as set out in Scheme 45 in a similar manner to preparation of compound 80 (see above).
NMR data in DMSO-d6 δ1.08(d, 9H), 1.80(m, 1H), 2.15(m, 2H), 2.65(m, 1H), 3.00–4.00(m, 10H), 7.63(m, 3H), 7.90(s, 1H), 8.03(m, 3H), 9.50(br.d, 2H).

| Micro Analysis: | % Theory | C64.9. | H7.93. | N6.58 |
|---|---|---|---|---|
| (1.0 HCl, 0.25 H$_2$O) | % Found | C64.8. | H8.10. | N6.50 |

Compound (73).
NMR data in CDCl$_3$ δ1.00(m, 9H), 1.47(s, 9H), 1.80–2.55(m, 4H), 3.00(m, 2H), 3.10–4.20(m, 8H), 4.60(d, 2H), 5.25(m, 2H), 5.90(m, 1H), 7.30–7.85(m, 7H)

Compound (77).
NMR data in DMSO-d6(100° C.) δ0.95(m, 9H), 1.35–1.75(m, 9H), 2.15(s, 2H), 2.40(m, 1H), 2.60–3.90(m, 12H), 7.40(m, 3H), 7.70(m, 1H), 7.80(m, 3H).

c) Preparation of Compound 82
Compound (82) was synthesised from compound (74) as set out in Scheme 45 by a similar procedure to that described in Example 24 for the preparation of compound (27).

Compound (82).
NMR data in DMSO-d6 δ1.65(m, 1H), 2.90–4.15(m, 14H), 7.35–8.90(m, 11H), 9.50(br.d, 2H).

| Micro Analysis: | % Theory | C51.9. | H5.19. | N6.99 |
|---|---|---|---|---|
| (2.0 HCl, 1.0 TFA.0.5 H$_2$O) | % Found | C52.2. | H5.40. | N.7.00 |

Compound (74).
NMR data in DMSO-d6 (100° C.) δ1.45–1.75(m, 10H), 2.85–3.85(m, 11H), 4.03(m, 1H, 4.20(m, 1H), 4.45–4.65(m, 2H) 5.20(m, 2H), 5.90(m, 1H), 7.23(m, 1H), 7.45(m, 4H), 7.67(s, 1H), 7.80(m, 3H), 8.35(m, 2H).

Compound (78)
NMR data in DMSO-d6 (100° C.) δ1.30–1.75(m, 9H), 2.40(m, 1H), 2.55–3.90(m, 14H), 7.10–8.45(m, 11H).

d) Preparation of Compound 83
Similarly compound (83) was synthesised from compound (75) using appropriate intermediates as set out in Scheme 45.

Compound (85).
NMR data in DMSO-d6 δ1.65(m, 1H), 2.95(m, 2H), 3.08(m, 1H), 3.25–4.00(m, 13H), 6.80(m, 2H), 7.06(2d, 2H), 7.47(m, 3H), 7.68(d, 1H), 7.85(m, 3H), 9.35(br.d, 2H).

| Micro Analysis: | % Theory | C62.7, | H6.57, | N5.62 |
|---|---|---|---|---|
| (1.5 HCl.0.5 H$_2$O) | % Found | C62.4, | H6.50, | N5.40 |

Compound (75).
NMR data in DMSO-d6 (100° C.) δ1.45(s, 9H), 1.75(m, 1H), 2.75–3.85(m, 14H), 4.00(m, 1H), 4.14(m, 1H), 4.45–4.65(m, 2H), 5.20(m, 2H), 5.90(m, 1H), 6.80(m, 2H), 7.05(m, 2H), 7.33(m, 1H), 7.45(m, 2H), 7.63(s, 1H), 7.80(m, 3H).

Compound (79).
NMR data in DMSO-d6 (100° C.) δ6 1.30–1.75(m, 9H), 2.35(m, 1H), 2.60–3.90(m, 17H), 6.78(m, 2H), 7.05(m, 2H), 7.40(m, 3H), 7.65(m, 1H), 7.80(m, 3H).

EXAMPLE 39

See scheme 46

Preparation of a) (2S)-2-({2-phenyl-4-[((2S,4S)-4-sulfanyl-pyrrolidin-2-ylmethyl)-amino]-phenylcarbonyl}-amino)-4-methylsulfanyl-butyric acid methyl ester (compound 38) and;

b) (2S)-2-({2-phenyl-4-[((2S,4S)-4-sulfanyl-pyrrolidin-2-ylmethyl)-amino]-phenylcarbonyl}-amino)-4-methylsulfanyl-butyric acid (compound 38f).

a) Preparation of Compound 38
Methyl-2-bromo4-nitro-benzoate was coupled with phenyl boronic acid (analogously as for the equivalent step in Example 30) then coupled and deprotected using the same methodology as previously described for Example 32 to give the title compound 38.
$^1$H NMR (DMSO-D$_6$, 250 MHz) δ1.35–1.75(3H,m); 1.8 (3H,s); 1.9–2.2(2H,m); 2.25–2.5(2H+DMSO,m); 2.75–3.9 (10H,m); 4.0–4.25(1H,m)5.0–5.9(5H,bs,H$_2$O); 6.3–6.6(2H, m); 7.0–7.3(7H,m)7.95(1H,m); 9.2–9.8(2H,bd).
MS (ESP+) m/z 474 (M+H)$^+$, 311,196.

| Anal.Calcd for C$_{24}$H$_{31}$N$_3$O$_3$S$_2$.2HCl.1.5H$_2$O | C,50.3;H,6.3;N,7.3 |
|---|---|
| Found | C,50.4;H,6.1;N,7.3 | b) Preparation of Compound 38f
Compound 38 was hydrolysed to the corresponding acid (analogously as for the equivalent step in Example 33) to give 38f.
$^1$H NMR (DMSO-D$_6$+CD$_3$COOD, 300 MHz) δ1.5–1.9 (3H+CD3COOD,m); 1.95(3H,s); 2.05–2.35(2H,m); 2.4–2.6 (2H+DMSO,m); 3.0–3.1 (1H,m); 3.2–3.9(4H,m); 4.2–4.3 (1H,m); 6.5–6.7(2H,m);7.2–7.4(6H,m).
MS (ESP+) m/z 460 (M+H)$^+$, 311.

| Anal.Calcd for C$_{23}$H$_{29}$N$_3$O$_3$S$_2$.1.35TFA | C,50.3;H,4.99;N,6.85 |
|---|---|
| Found | C,50.2;H,5.1;N,6.8 |

EXAMPLE 40

Pharmaceutical Compositions

The following illustrate representative pharmaceutical dosage forms of the invention as defined herein (the active ingredient being termed "Compound X"). for therapeutic or prophylactic use in humans:

|  |  | mg/tablet |
|---|---|---|
| (a) | Tablet 1 |  |
|  | Compound X | 100 |
|  | Lactose Ph.Eur | 182.75 |
|  | Croscarmellose sodium | 12.0 |
|  | Maize starch paste (5% w/v paste) | 2.25 |
|  | Magnesium stearate | 3.0 |
| (b) | Tablet II |  |
|  | Compound X | 50 |
|  | Lactose Ph.Eur | 223.75 |
|  | Croscarmellose sodium | 6.0 |
|  | Maize starch | 15.0 |
|  | Polyvinylpyrrolidone (5% w/v paste) | 2.25 |
|  | Magnesium stearate | 3.0 |
| (c) | Tablet III |  |
|  | Compound X | 1.0 |
|  | Lactose Ph.Eur | 93.25 |
|  | Croscarmellose sodium | 4.0 |
|  | Maize starch paste (5% w/v paste) | 0.75 |
|  | Magnesium stearate | 1.0 |
| (d) | Capsule | mg/capsule |
|  | Compound X | 10 |
|  | Lactose Ph.Eur | 488.5 |
|  | Magnesium | 1.5 |
| (e) | Injection I | (50 mg/ml) |
|  | Compound X | 5.0% w/v |
|  | 1M Sodium hydroxide solution | 15.0% v/v |
|  | 0.1M Hydrochloric acid (to adjust pH to 7.6) |  |
|  | Polyethylene glycol 400 | 4.5% w/v |
|  | Water for injection to 100% |  |
| (f) | Injection II | (10 mg/ml) |
|  | Compound X | 1.0% w/v |
|  | Sodium phosphate BP | 3.6% w/v |
|  | 0.1M Sodium hydroxide solution | 15.0% v/v |
|  | Water for injection to 100% |  |
| (g) | Injection III | (1 mg/ml, buffered to pH 6) |
|  | Compound X | 0.1% w/v |
|  | Sodium phosphate BP | 2.26% w/v |
|  | Citric acid | 0.38% w/v |
|  | Polyethylene glycol 400 | 3.5% w/v |
|  | Water for injection to 100% |  |
| (h) | Aerosol I | mg/ml |
|  | Compound X | 10.0 |
|  | Sorbitan trioleate | 13.5 |
|  | Trichlorofluoromethane | 910.0 |
|  | Dichlorodifluoromethane | 490.0 |
| (i) | Aerosol II |  |
|  | Compound X | 0.2 |
|  | Sorbitan trioleate | 0.27 |
|  | Trichlorofluoromethane | 70.0 |
|  | Dichlorodifluoromethane | 280.0 |
|  | Dichlorotetrafluoroethane | 1094.0 |
| (j) | Aerosol III |  |
|  | Compound X | 2.5 |
|  | Sorbitan trioleate | 3.38 |
|  | Trichlorofluoromethane | 67.5 |
|  | Dichlorodifluoromethane | 1086.0 |
|  | Dichlorotetrafluoroethane | 191.6 |
| (k) | Aerosol IV |  |
|  | Compound X | 2.5 |
|  | Soya lecithin | 2.7 |
|  | Trichlorofluoromethane | 67.5 |
|  | Dichlorodifluoromethane | 1086.0 |
|  | Dichlorotetrafluoroethane | 191.6 |
| (l) | Ointment | ml |
|  | Compound X | 40 mg |
|  | Ethanol | 300 μl |
|  | Water | 300 μl |
|  | 1-Dodecylazacycloheptan-2-one | 50 μl |
|  | Propylene glycol | to 1 ml |

Note The above formulations may be obtained by conventional procedures well known in the pharmaceutical art. The tablets (a)–(c) may be enteric coated by conventional means. for example to provide a coating of cellulose acetate phthalate. The aerosol formulations (h)–(k) may be used in conjunction with standard. metered dose aerosol dispensers. and the suspending agents sorbitan trioleate and soya lecithin may be replaced by an alternative suspending agent such as sorbitan monooleate. sorbitan sesquioleate. polysorbate 80. polyglycerol oleate or oleic acid.

EXAMPLE 41

See Scheme 47

Preparation of a) (2S)-4-Carbamoyl-2-({2-phenyl-5-[([2S,4S]-4-sulfanyl-pyrrolidin-2-ylmethyl)-amino]-phenylcarbonyl}-amino)-butyric acid (compound 39e); and b) (2S)-4-Carbamoyl-2-({2-phenyl-5-[([2S,4S]-4-sulfanyl-pyrrolidin-2-ylmethyl)-amino]-phenylcarbonyl}-amino)-butyric acid methyl ester (compound 39)

a) Preparation of Compound 39

Compound 39a 32a (1.5 g,6.2 mmol) was coupled with L-Glutamine methyl ester (analogously as for the equivalent step in Example 30) to give compound 39a as a white solid, 1.2 g(50.5%) MS (ESP)+m/z 386 (M+H)$^+$.

Compound 39

39a was reduced, coupled with the aldehyde (22b) and selectively deprotected using the same methodology as previously described for Example 32 to give the title compound 39. MS (ESP+) m/z 471 (M+H)$^+$.

| Anal.Calcd for $C_{24}H_{30}N_4O_4S,3HCl,0.25H_2O$ | C,49.3;H,5.8;N.9.6 |
|---|---|
| Found | C,49.2;H,5.9;N,9.2 | b) Preparation of Compound 39e 39 was hydrolysed (analogously as for the equivalent step in Example 32) to give the title compound 39e. MS (ESP−) m/z 455 (M−H)$^−$.

| Anal.Calcd for $C_{23}H_{28}N_4O_4S,2TFA$ | C,47.4;H,4.4;N,8.2 |
|---|---|
| Found | C,47.0;H,4.5;N,7.9 |

Scheme 1
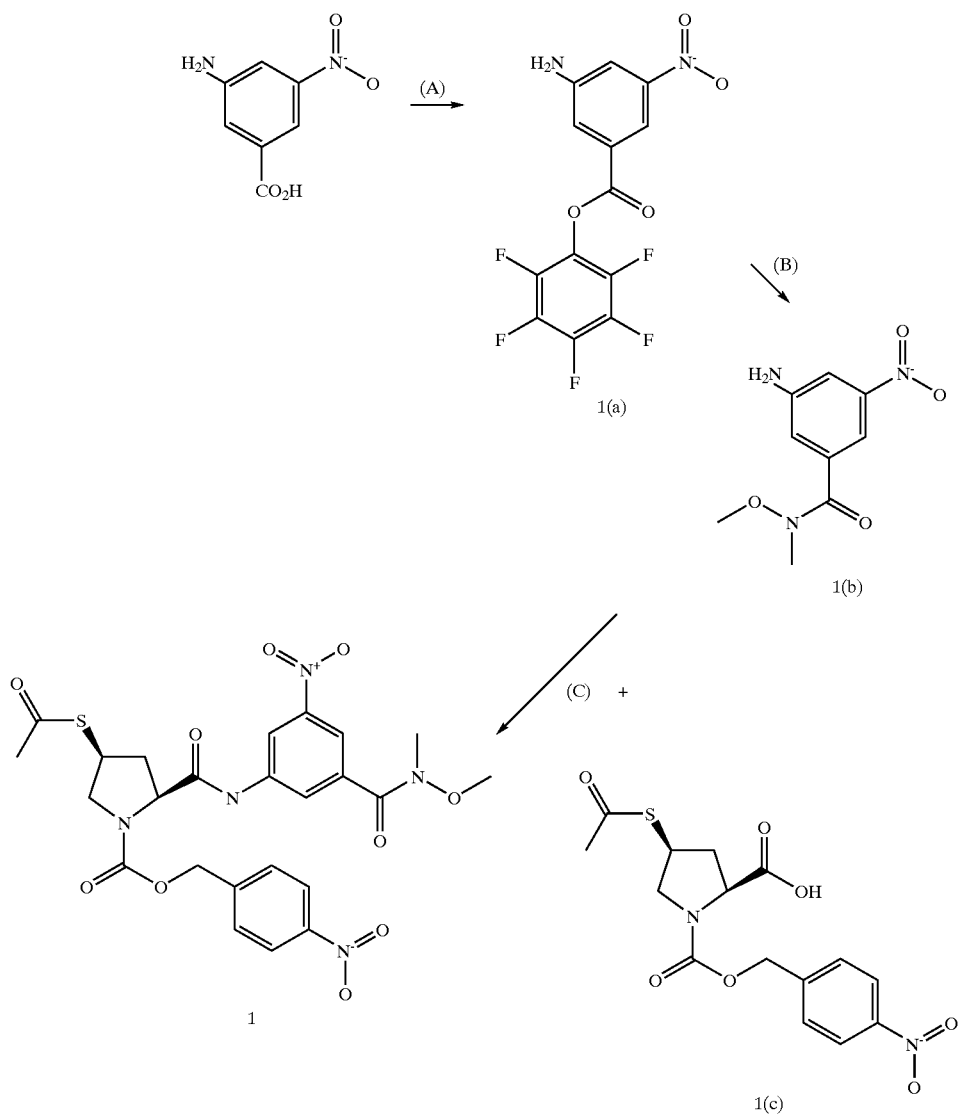
(A) Pentafluoro-phenol/DCCl/CH$_2$Cl$_2$
(B) N, O-Dimethylhydroxylamine/Triethylamine/CH$_2$Cl$_2$
(C) EEDQ/CH$_2$Cl$_2$
Scheme 2
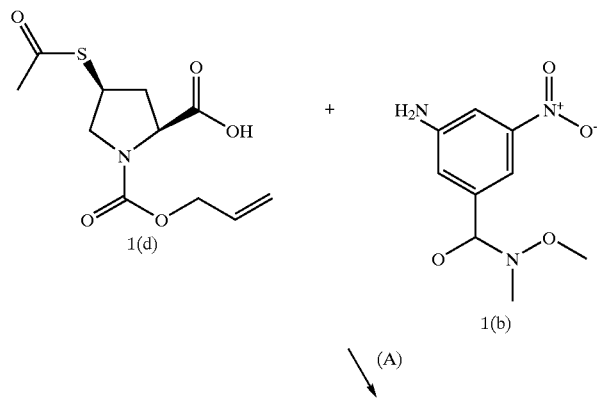

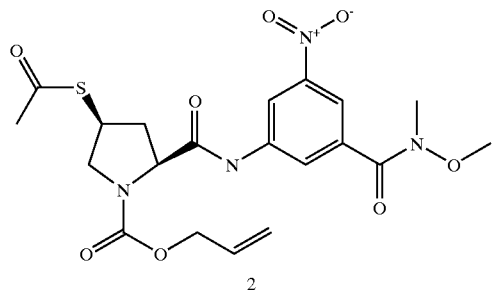
2
(A) EEDQ/CH$_2$Cl$_2$
Scheme 3
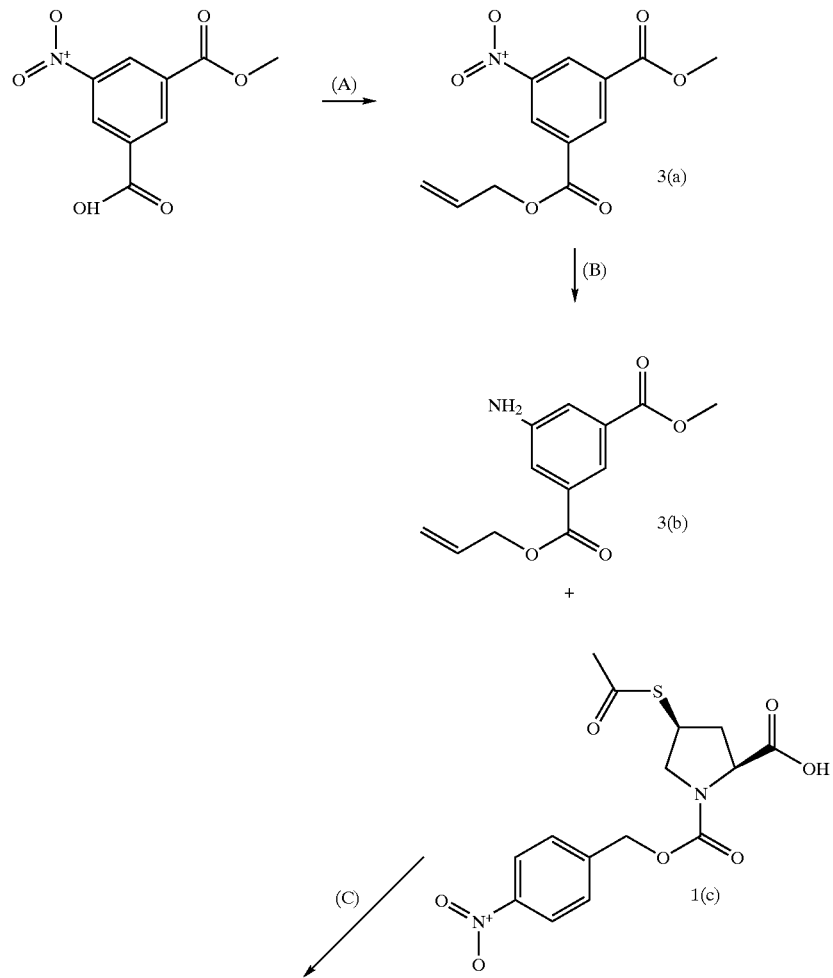

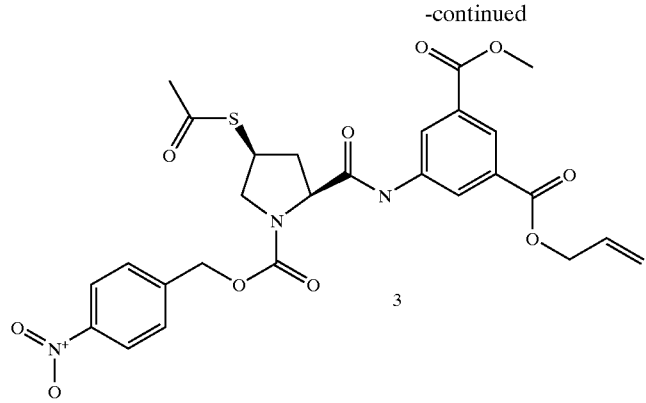
(A) Alyl bromide/K$_2$CO$_3$/DMFl
(B) Tin(II)chloride dihydrate/MeOH/Reflux
(C) EEDQ/CH$_2$Cl$_2$
Scheme 4
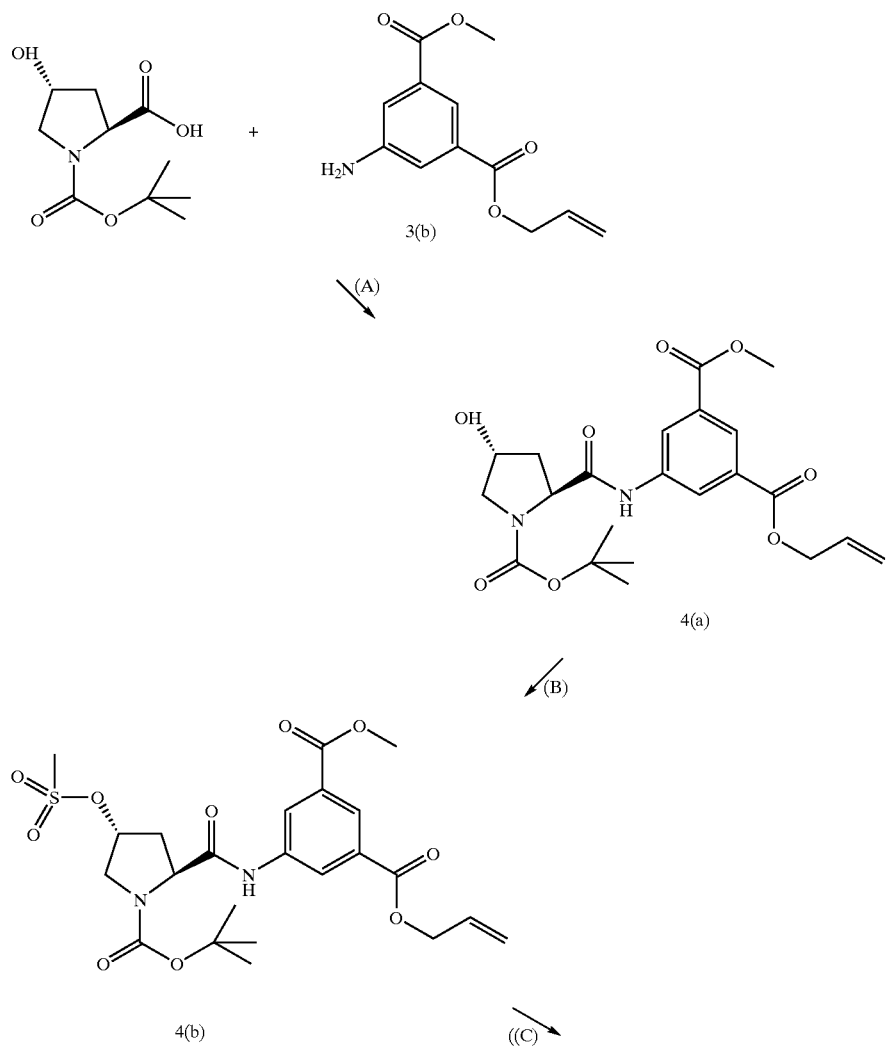

-continued
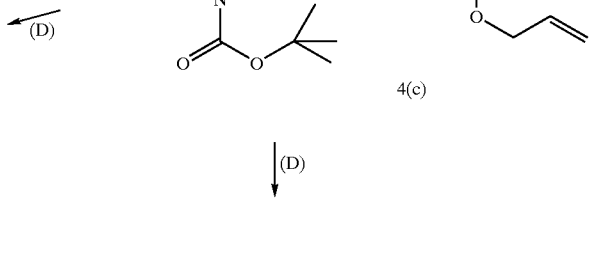
4(c)
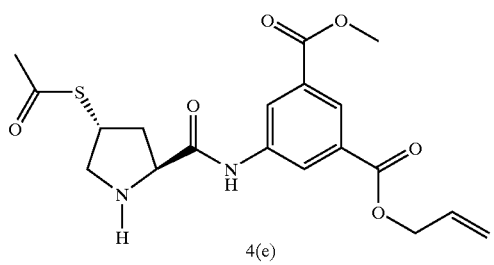
4(e)
(T.F.A Salt)
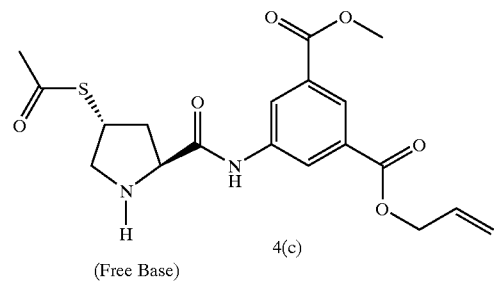
4(c)
(Free Base)
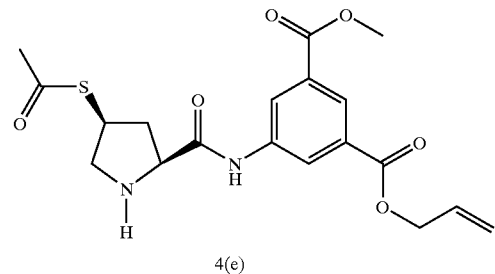
4(e)
(T.F.A salt)
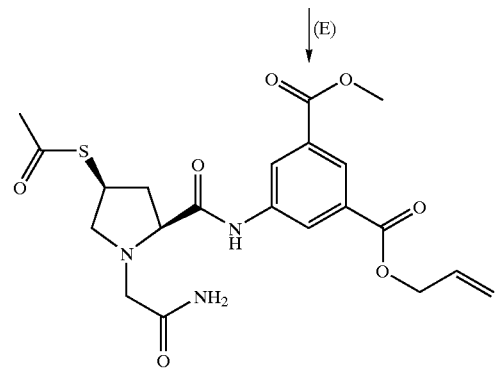
4
(A) EEDQ/CH$_2$Cl$_2$
(B) Methanesulphonyl chloride/triethylamine/CH$_2$Cl$_2$
(C) Potassium thioacetate/acetone
(D) T.F.A
(E) Iodoacetamide/Sodium Bicarbonate/DMF Scheme 5
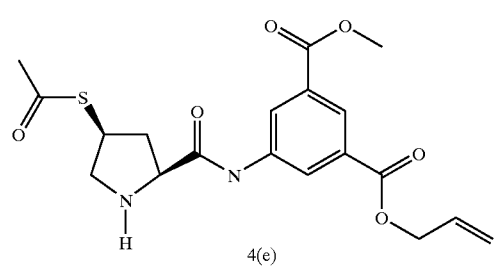
4(e)
TFA salt
(A)
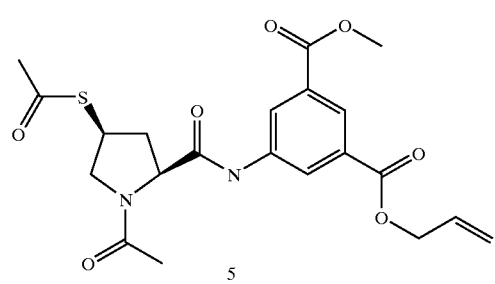
5
(A) Acetic anhydride/triethylamine/CH₂Cl₂
Scheme 6
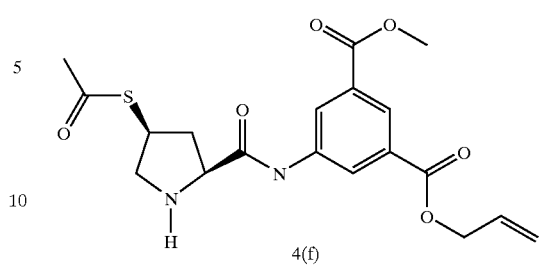
4(f)
(Free Base)
(A)
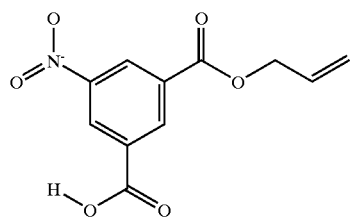
6
(A) Phenyl chloroformate/triethylamine/CH₂Cl₂
Scheme 7
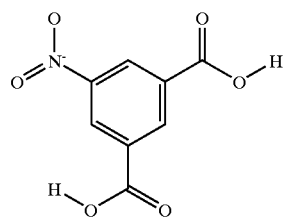
(A)
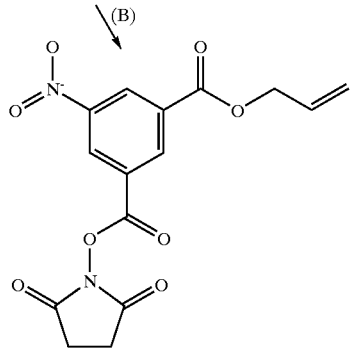
7(a)
(B)
7(b)
(C)
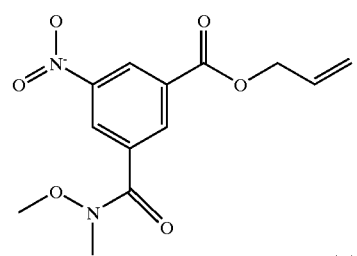
7(c)
(D)

-continued
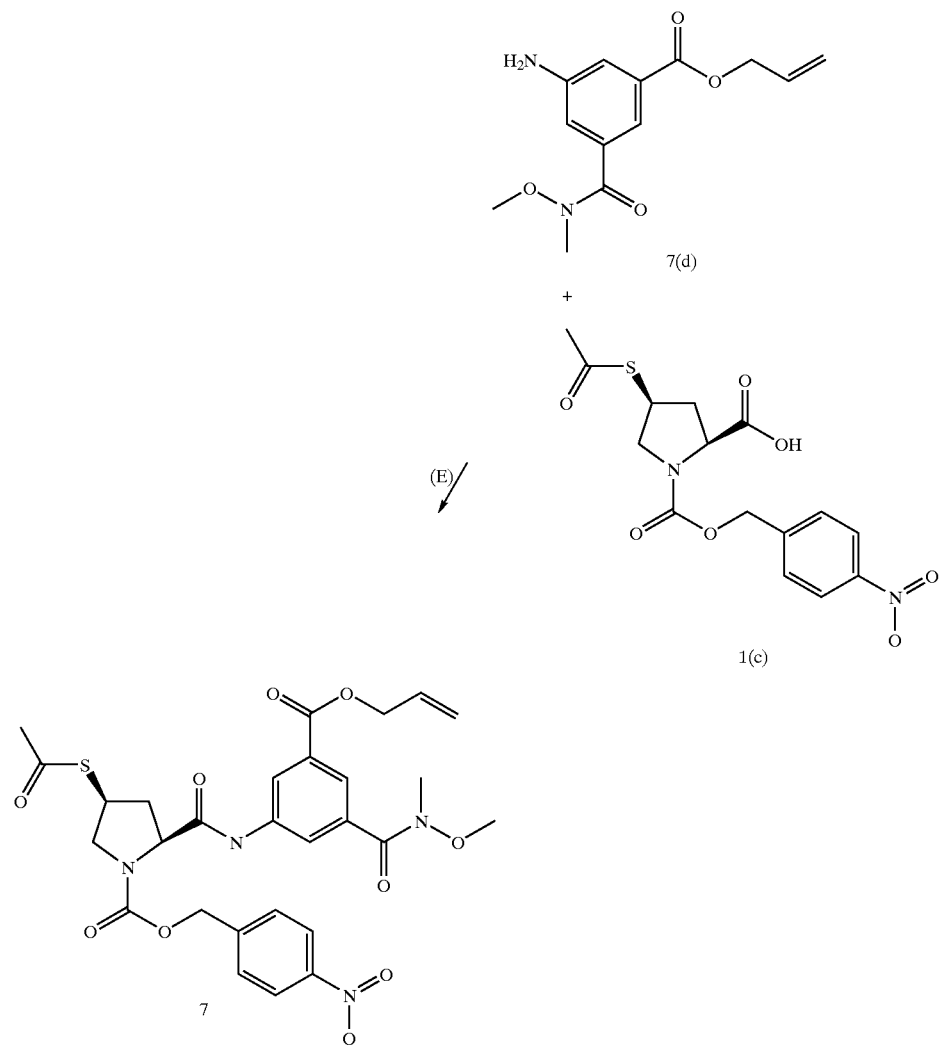
(A) Allyl bromide/potassium carbonate/DMA/90deg./4hrs
(B) DCCl/N-Hydroxysuccinimide/CH₂Cl₂/R.T./3.5hrs.
(C) N,O-Dimethylhydroxylamine HCl/Triethylamine/5deg./16hrs
(D) Tin(II)Chloride/Methanol/Reflux/1hr
(E) EEDQ/CH₂Cl₂/R.T./16hrs.
Scheme 8
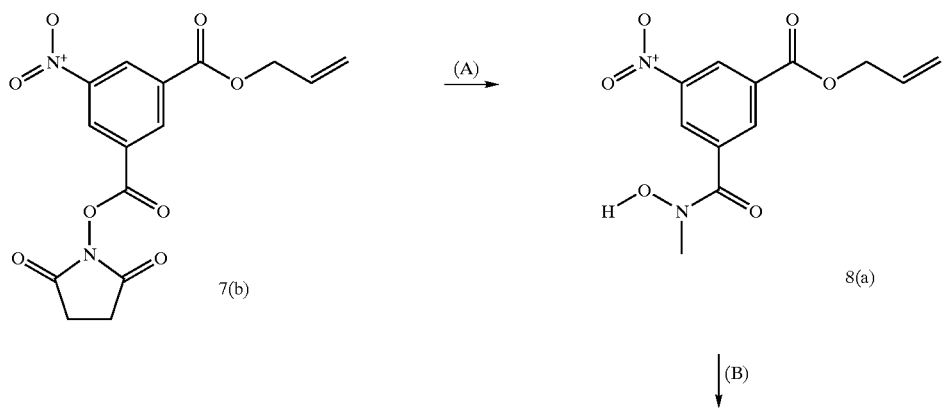

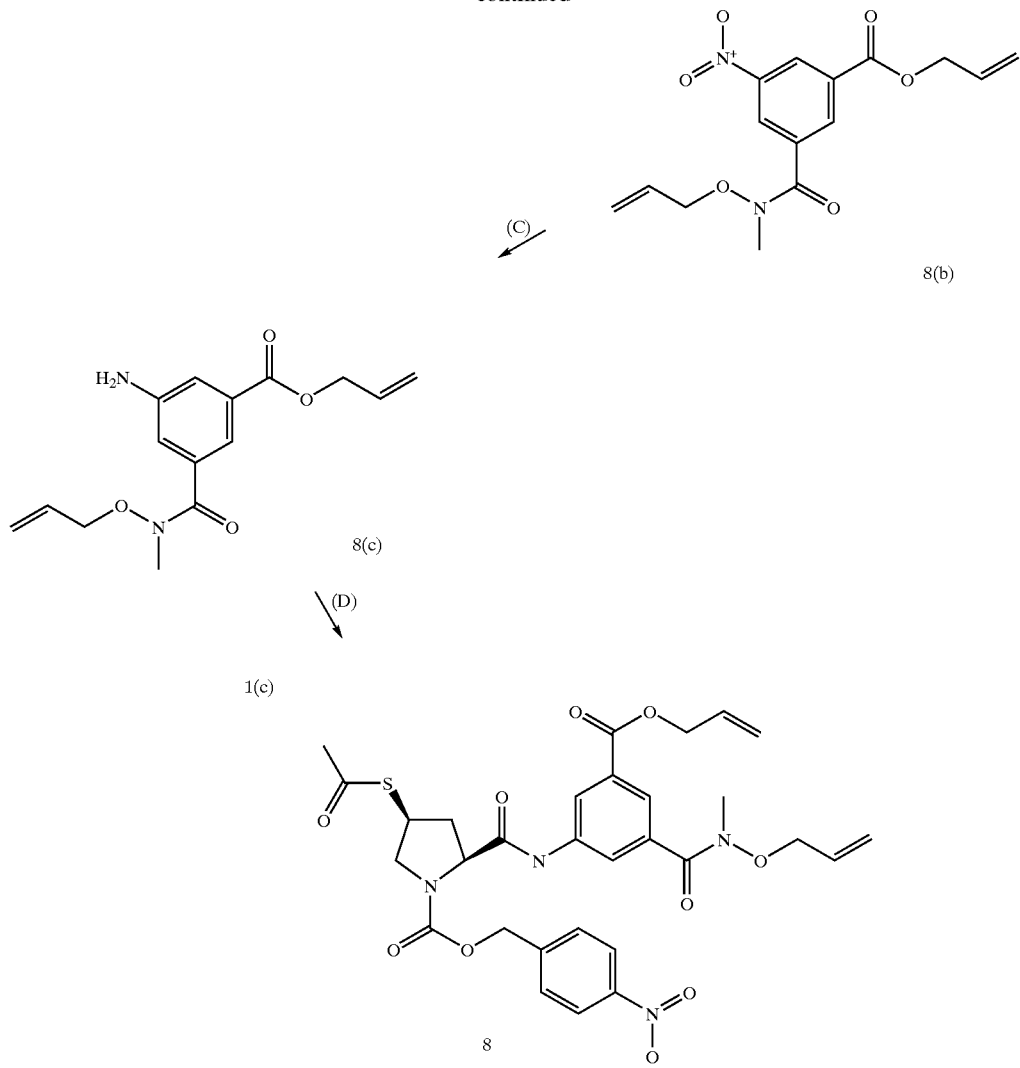
8(b)
8(c)
1(c)
8
(A) N-Methylhydroxylamine HCl./Triethylamine/CH$_2$Cl$_2$/5deg./16hrs.
(B) Allyl bromide/Potassium carbonate/R.t/DMF/3hrs.
(C) Tin (II) chloride/Ethyl acetate/70 Deg.
Scheme 9
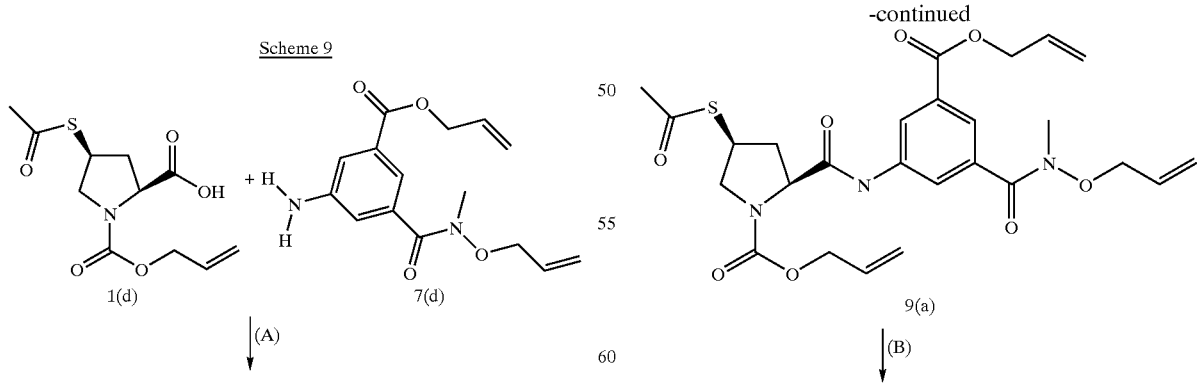
1(d)   7(d)   9(a)

-continued
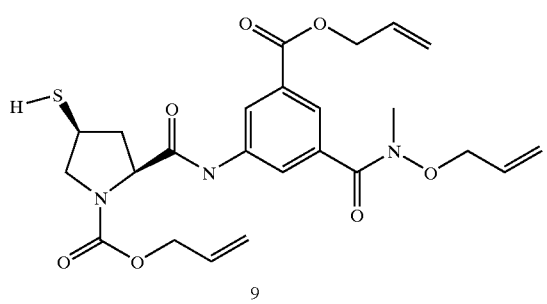
9
(A) EEDQ/CH$_2$Cl$_2$
(B) 0.1 M Sodium hydroxide/Allyl alcohol/R.t.
SCHEME 10
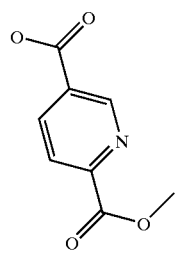  10(a)
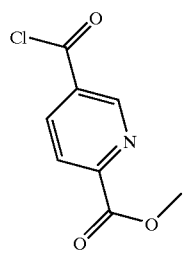  10(b)
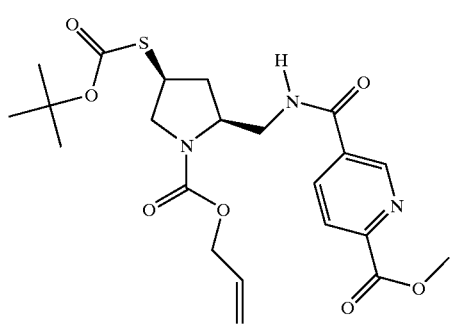  10(c)
SCHEME 11
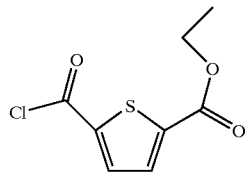  11(a)
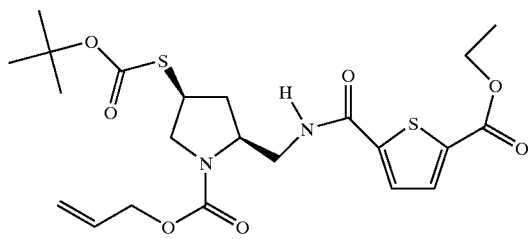  11(b)
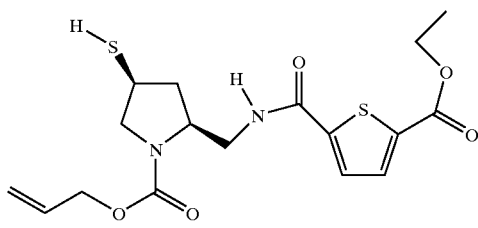  11
SCHEME 12
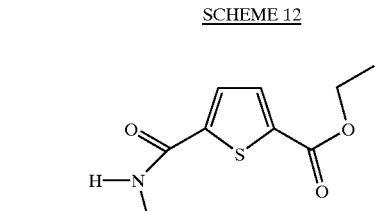  12(a)
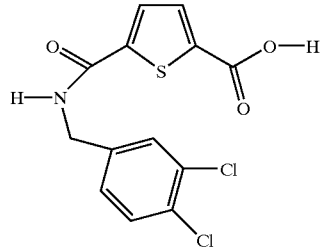  12(b)
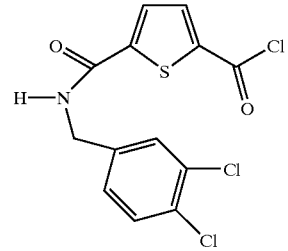  12(c)

12(d)
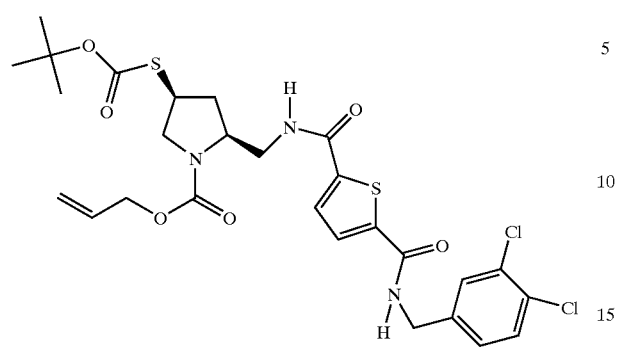
13(b)
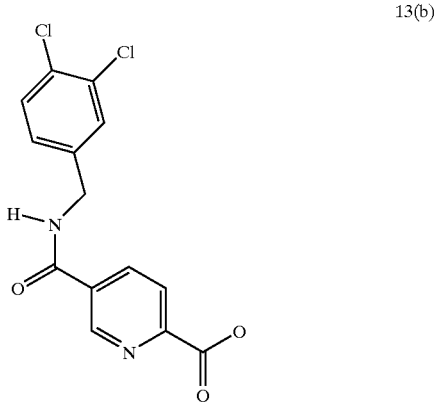
12(e)
13(c)
12
SCHEME 13
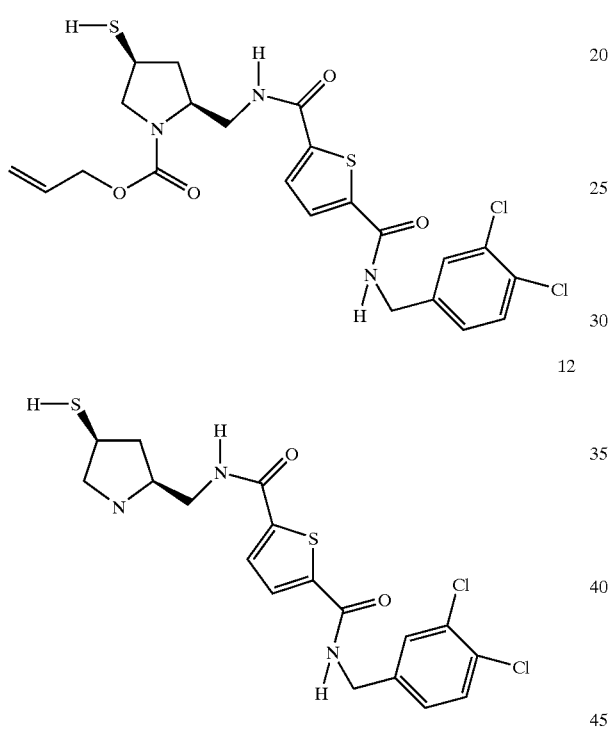
13(a)
13(d)
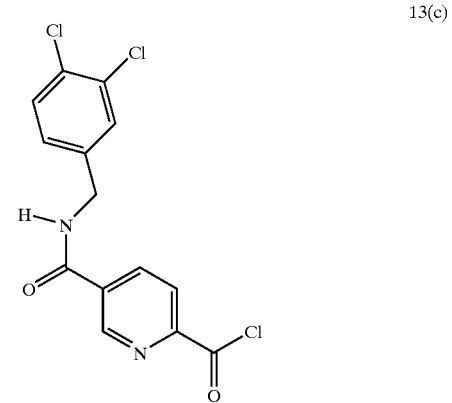
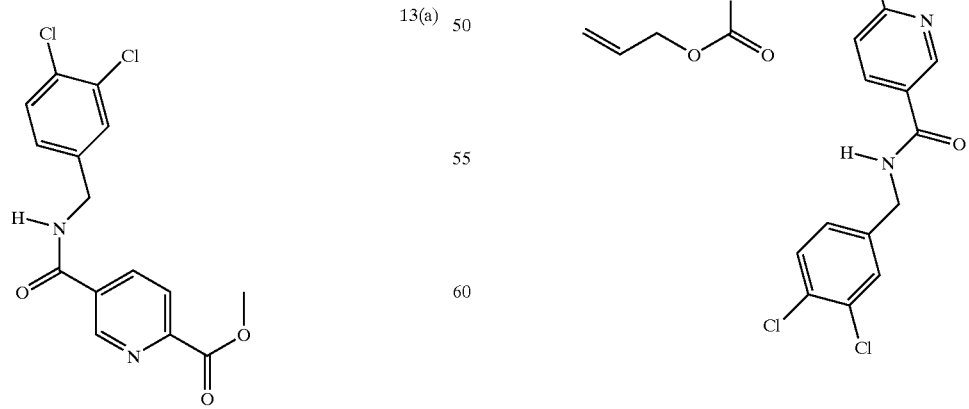

83
-continued
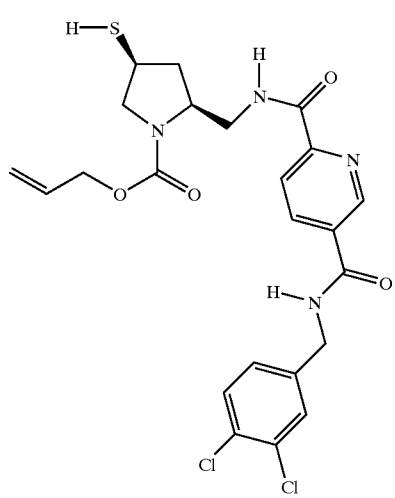
13(e)
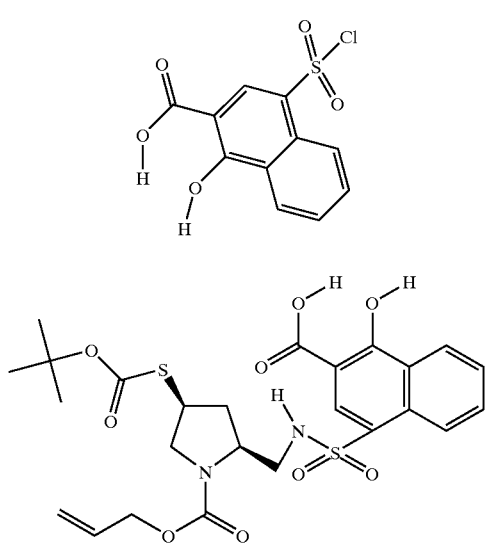
13
SCHEME 14
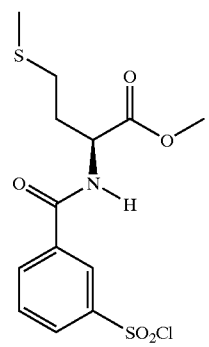
14(a)
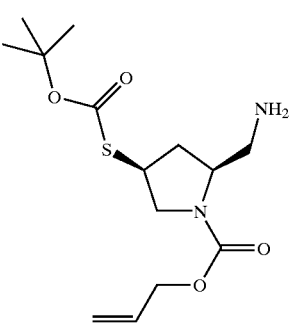
14(b)
84
-continued
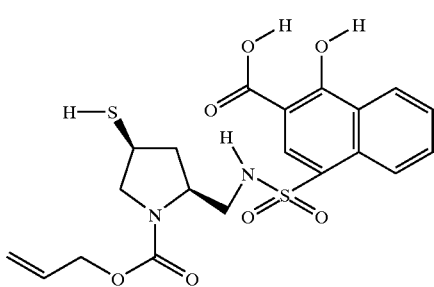
14(c)
14
SCHEME 15
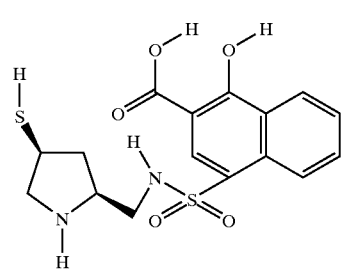
15(a)
15(b)

15(c)
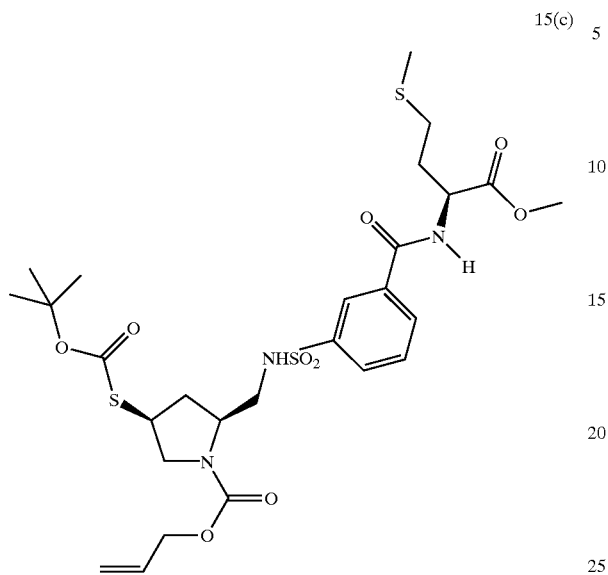
SCHEME 16
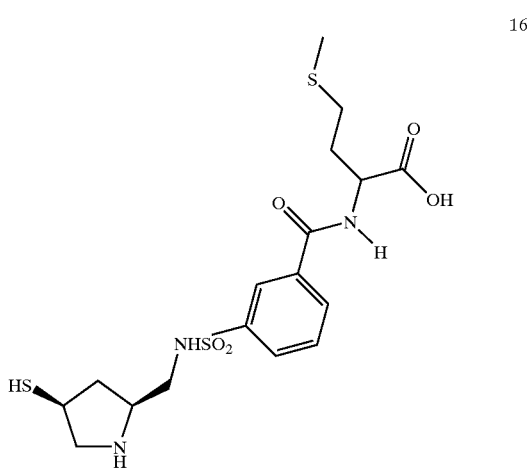
15(d)
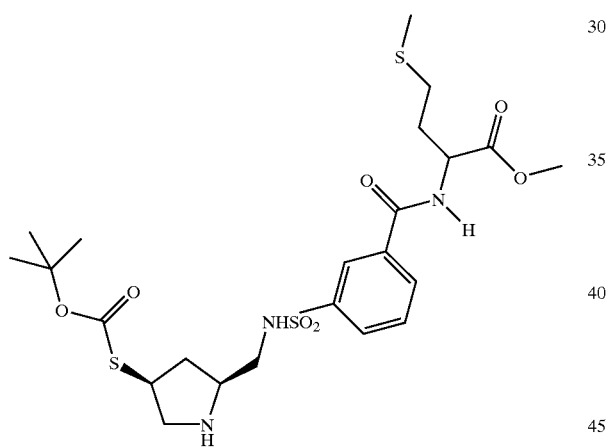
SCHEME 17
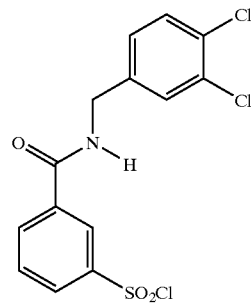
17(a)
15
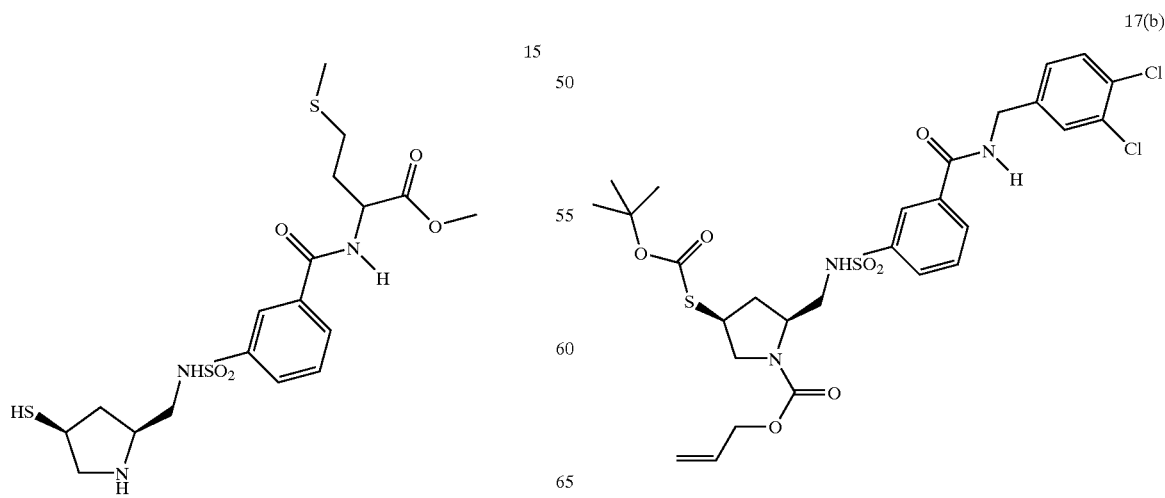
17(b)

17(c)
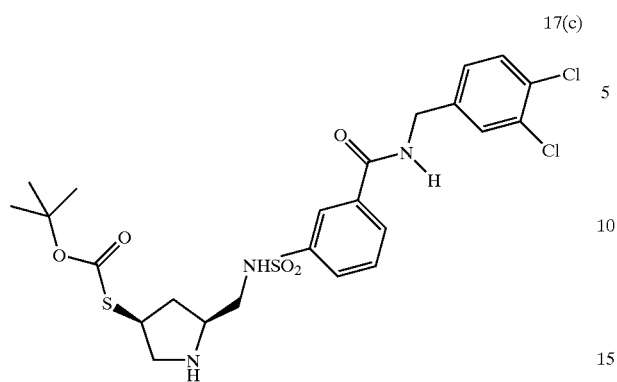
17
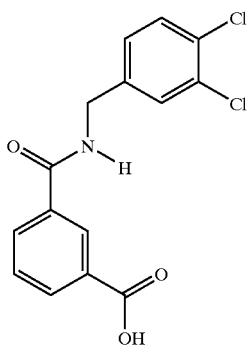
SCHEME 18
18(a)
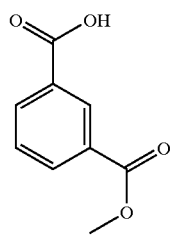
18(b)
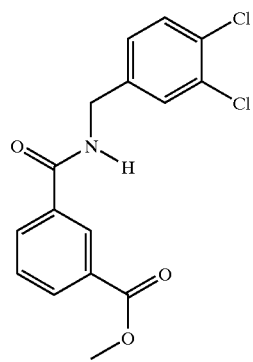
18(c)
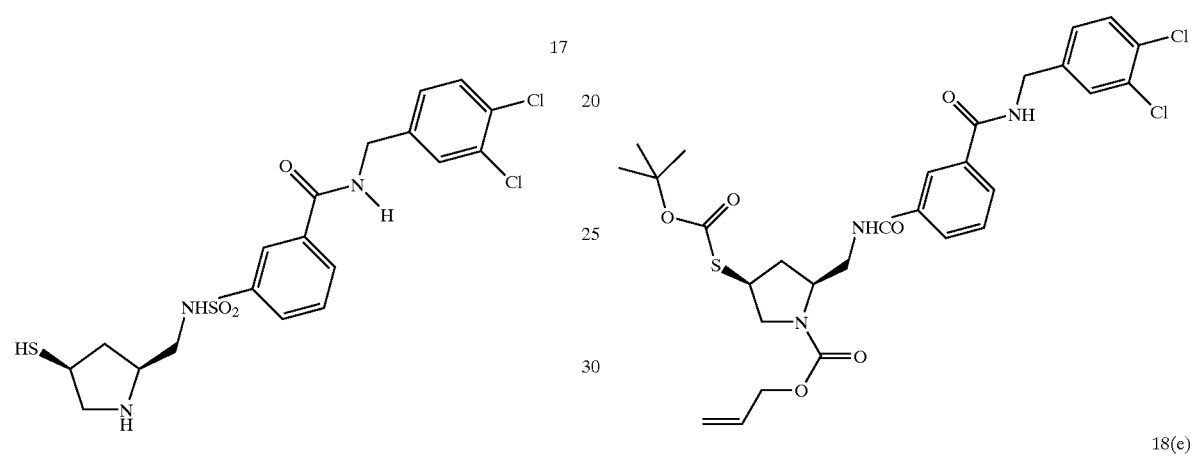
18(d)
18(e)
18
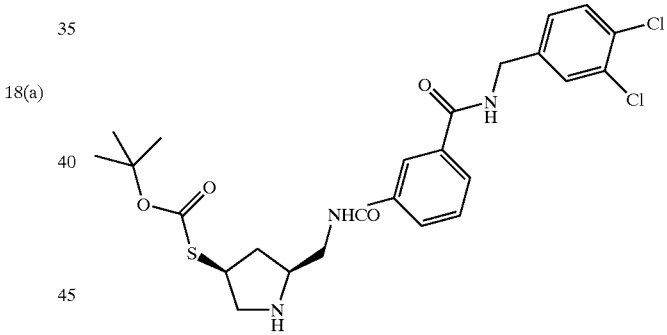
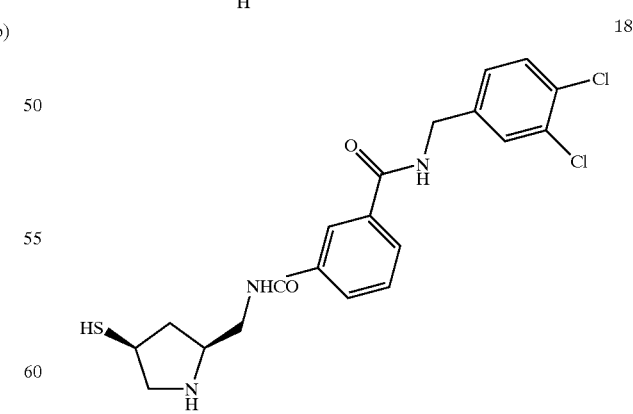

SCHEME 19
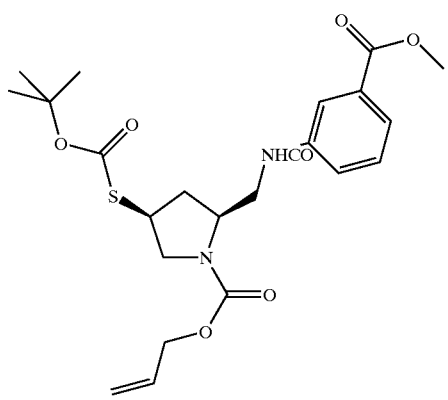
19(a)
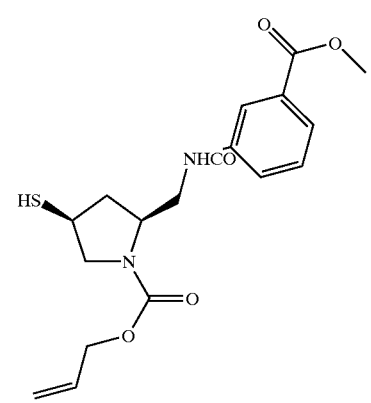
19
SCHEME 20
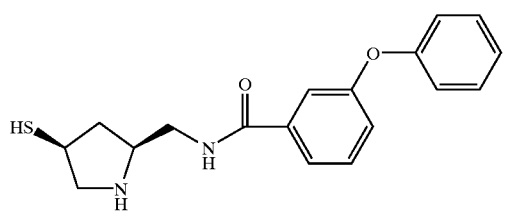
20
SCHEME 21
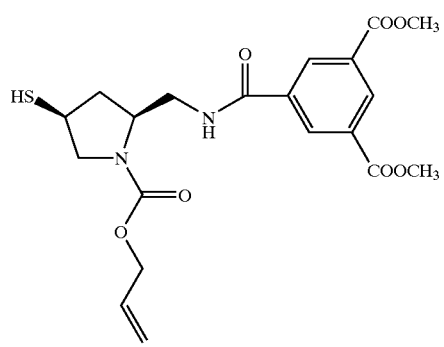
21
SCHEME 22
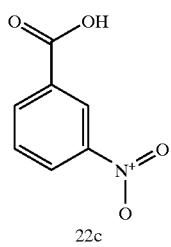
22c
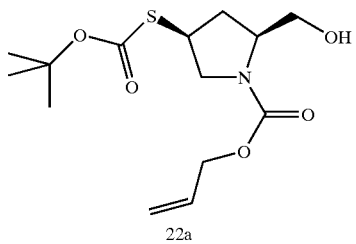
22a
↓ (ii)
↓ (i)
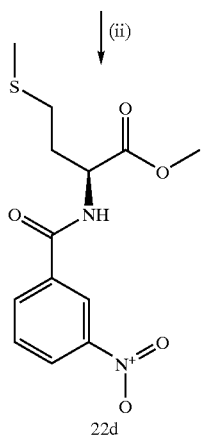
22d
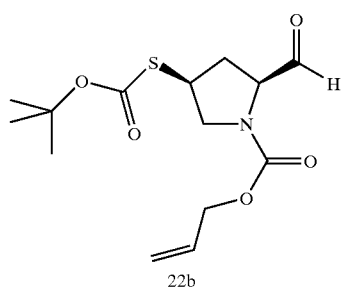
22b 91 92
-continued
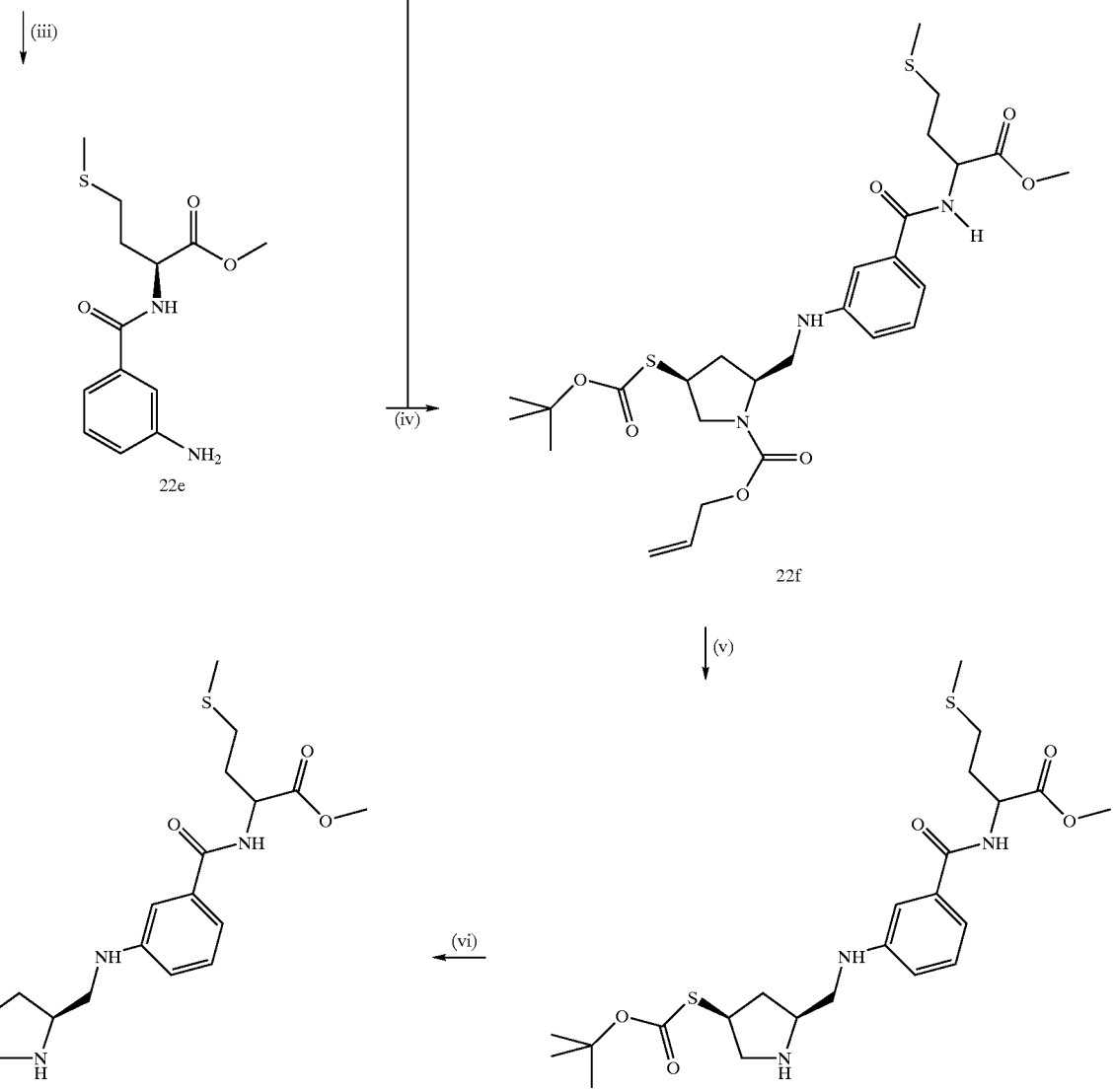
(i) TPAP, NMM-O/CH₃CN, CH₂Cl₂, RT, Ar.
(ii) Me₂N(CH₂)₃N=C=NEtHCl, HOBT/DMF, 0° C.
 L-Methionine methyl ester, HCl, NMM/DMF, 0° C.-RT, 2 hrs
(iii) Me₂NNH₂, FeCl₃·6H20/MeOH,Δ Reflux, 18 hrs
(iv) NaCNBH₃, AcOH/EtOH, RT, 18 hrs
(v) Pd Cl₂,(PPh₃)₂, n-Bu₃SnH/CH₂Cl₂, H₂O, RT
(vi) TFA/CH₂Cl₂, RT
SCHEME 23
-continued
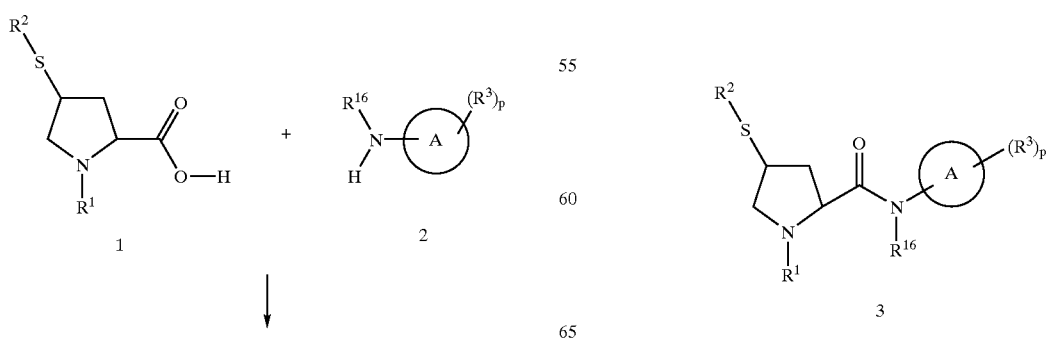

SCHEME 24
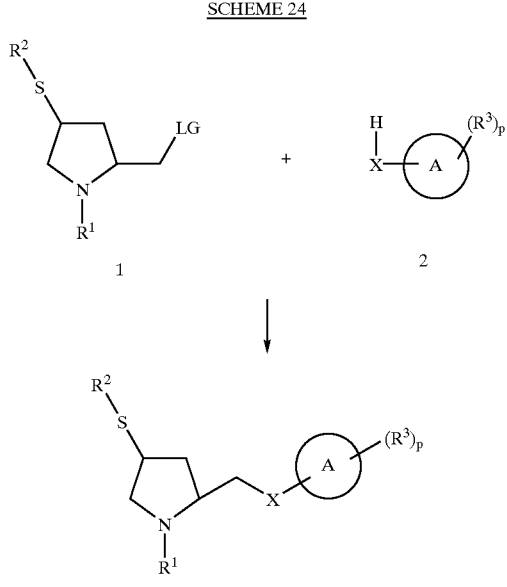
Scheme 26
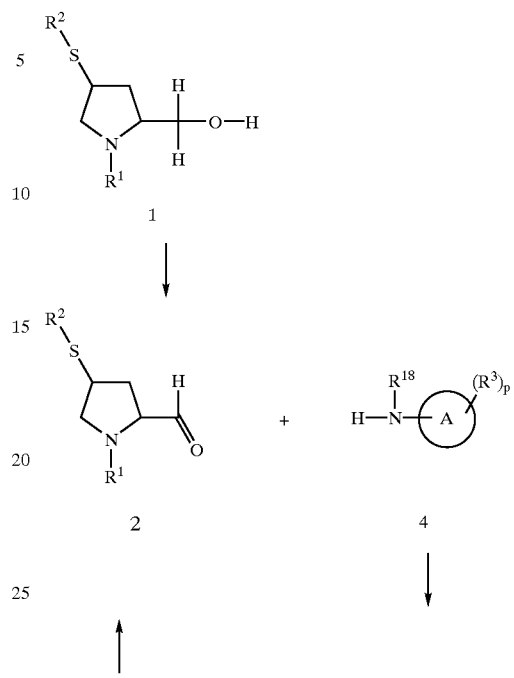
Scheme 25
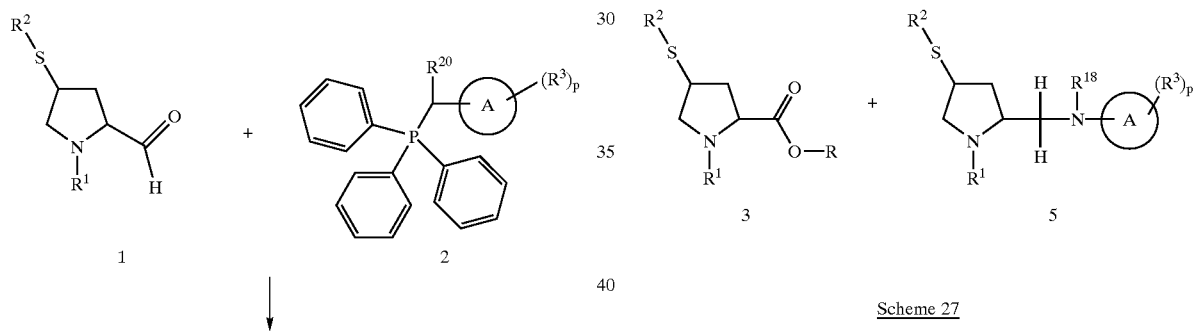
Scheme 27
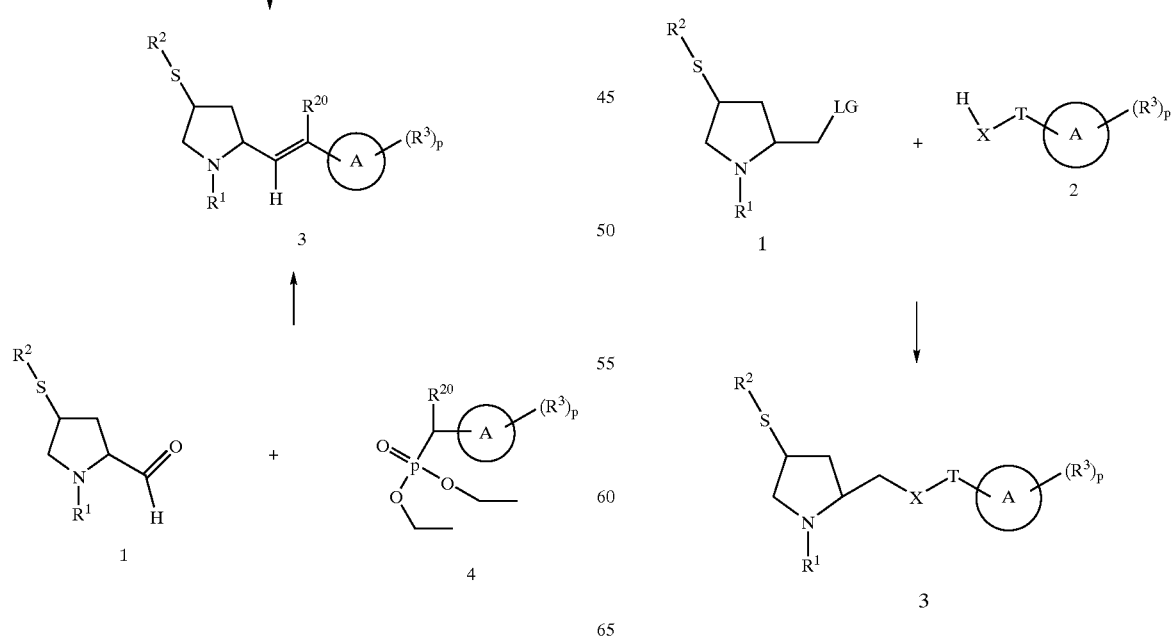

Scheme 28
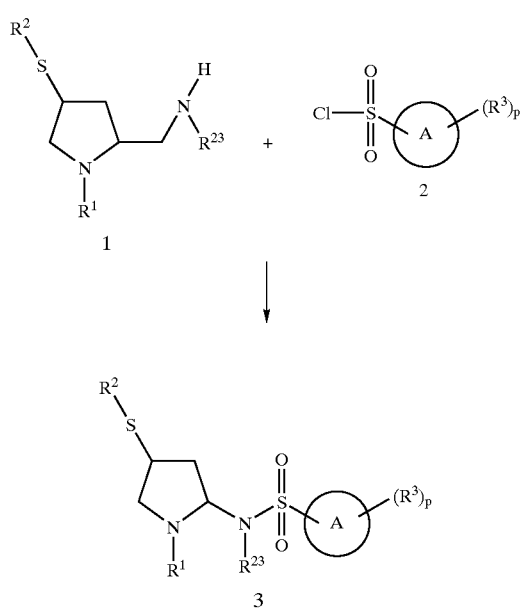
Scheme 29
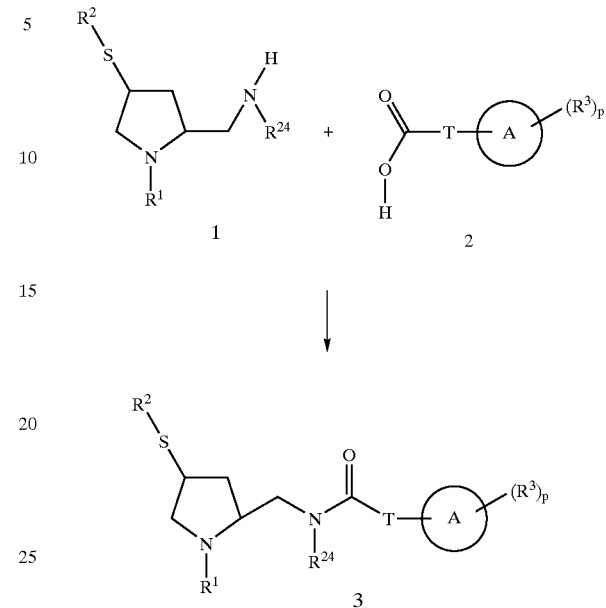
Scheme 30
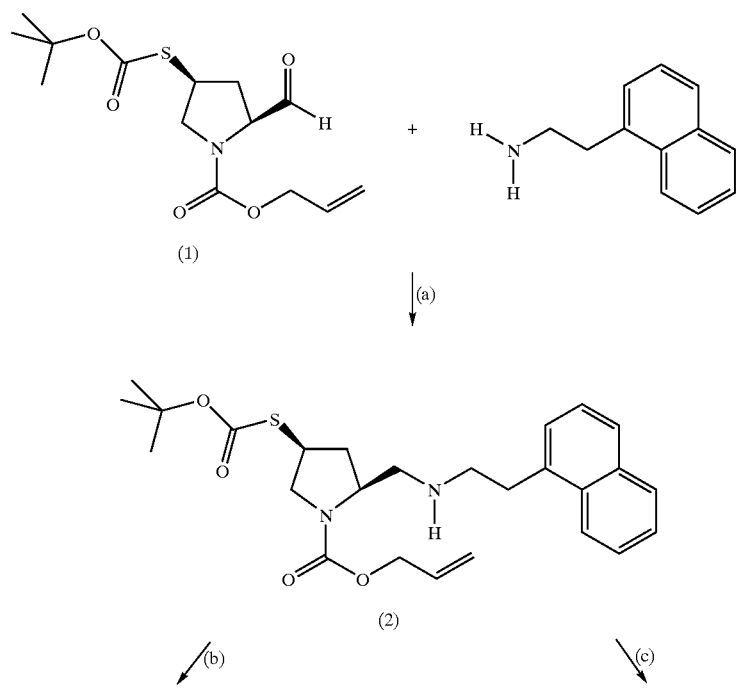

-continued

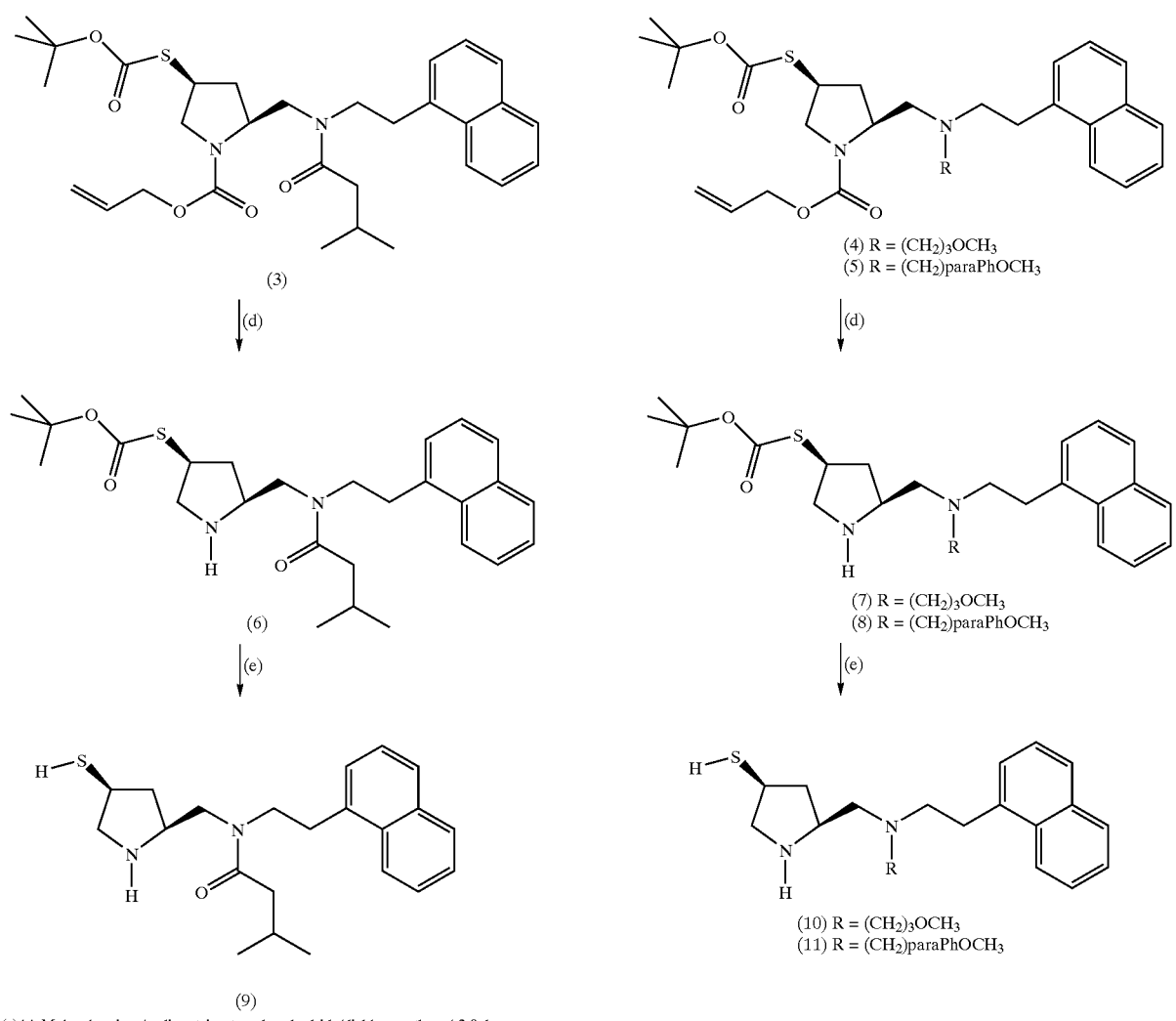

(a) 4A Molecular sieve/sodium triacetoxy borohydride/dichloromethane/-2 0 deg.
(b) Isovaleryl chloride/triethylamine/dichloromethane/R.T.
(c) R = (CH₂)₃OCH₃. 4A Molecular sieve/sodium triacetoxy borohydride/dichlorormethane
(c) R = CH₂paraPhOCH₃. paraMethoxybenzyl chloride/sodium bicarbonate/H₂O/dichlorormethane
(d) Tributyltin hydride/bis(triphenylphosphine)palladium(0) chlorid e/dichloromethane
(e) Trifluroacetic acid/R.T..

Scheme 31

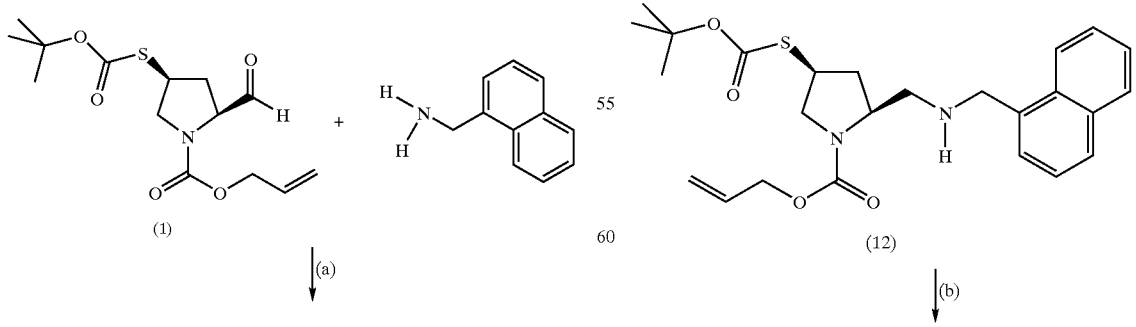

Scheme 32

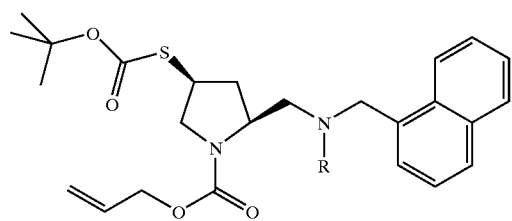

(13) R = COCH₂CH(Me)₂
(14) R = CO(CH₂)₃Me
(15) R = COCH₂CH(Me)CH₂Me
(16) R = CO(CH₂)₂OMe
(17) R = COCH₂-pyridin-3-yl
(52) R = CH₂-4-methoxyPh ↓(c)

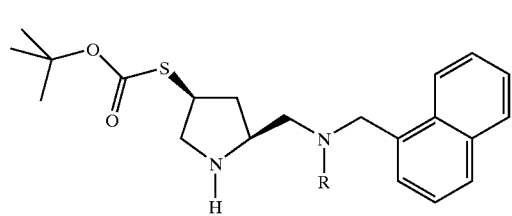

(18) R = COCH₂CH(Me)₂
(19) R = CO(CH₂)₃Me
(20) R = COCH₂CH(Me)CH₂Me
(21) R = CO(CH₂)₂OMe
(22) R = COCH₂-pyridin-3-yl
(53) R = CH₂-4-methoxyPh ↓(d)

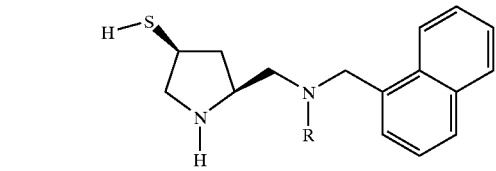

(23) R = COCH₂CH(Me)₂
(24) R = CO(CH₂)₃Me
(25) R = COCH₂CH(Me)CH₂Me
(26) R = CO(CH₂)₂OMe
(27) R = COCH₂-pyridin-3-yl
(54) R = CH₂-4-methoxyPh (a) 4A Molecular sieve/sodium triacetoxy borohydride/dichloromethane/ −20 deg.
(b) R = 13. Isovaleryl chloride/triethylamine/dichloromethane/R.T.
  R = 14. Valeryl chloride/triethylamine/dichloromethane/R.T.
  R = 15. 3-Methylvaleric acid/EDC/4-Dimethylamino-pyridine/ dichloromethane
  R = 16. 3-Methoxypropionic acid/EDC/4-Dimethylamino-pyridine/ dichloromethane
  R = 17. 3-Pyridylacetic acid HCl/EDC/4-Dimethylamino-pyridine/ dichloromethane
  R = 52. p-Methoxybenzyl chloride/potassium carbonate/ DMF/70 degs.
(c) Tributyltin hydride/bis(triphenylphosphine)palladium(0) chlorid e/ dichloromethane.
(d) Trifluoroacetic acid/R.T.

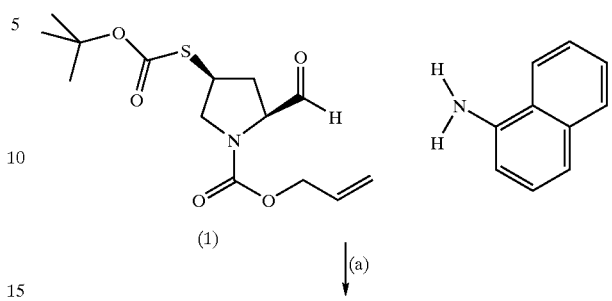

(1)

↓(a)

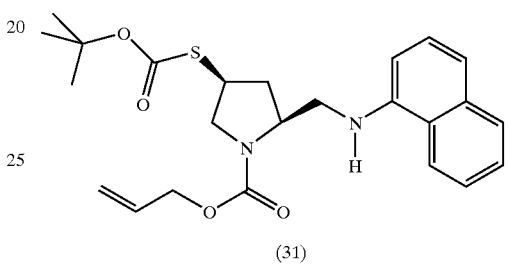

(31)

↓(b)

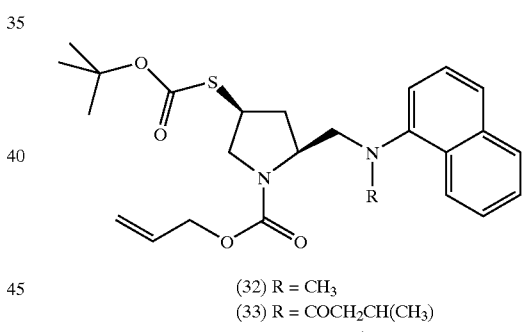

(32) R = CH₃
(33) R = COCH₂CH(CH₃)

↓(c)

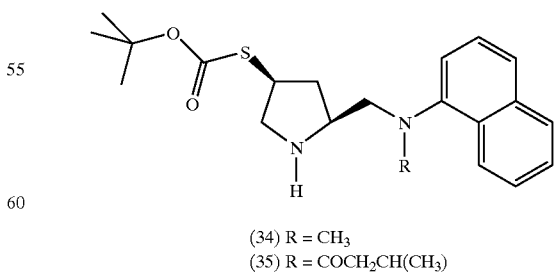

(34) R = CH₃
(35) R = COCH₂CH(CH₃)

↓(d)

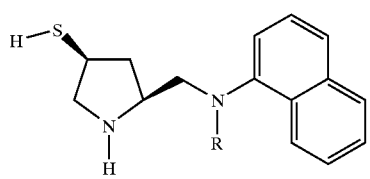

(36) R = CH₂
(37) R = COCH₂CH(CH₃)

(a) 3A Molecular sieve/acetic acid/ethanol/sodium cyanoboro hydride/R.T.
(b) R = CH₃, Methyl iodide/dimethyl formamide/potassium carbonate/80 deg.
R = COCH₂CH(CH₃)₂, Isovaleryl chloride/triethylamine/dichloromethane/R.T.
(c) Tributyltin hydride/bis(triphenylphosphine)palladium(0) chlorid e/dichloromethane
(d) Trifluoroacetic acid/R.T.

Scheme 33

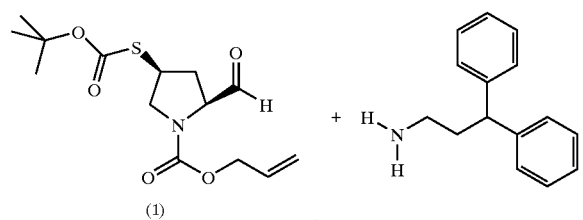

(1)

↓(a)

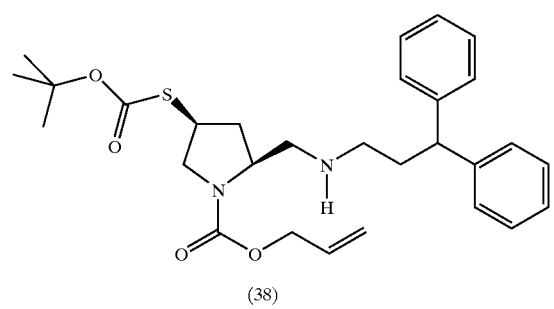

(38)

↓(b)

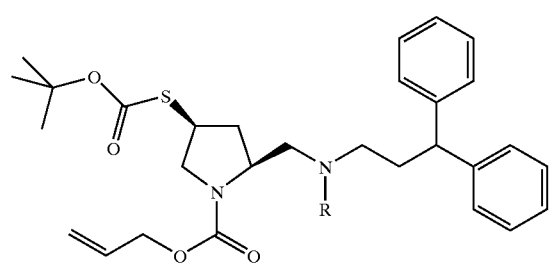

(39) R = COCH₂CH(CH₃)₂
(40) R = COCH₃

↓(c)

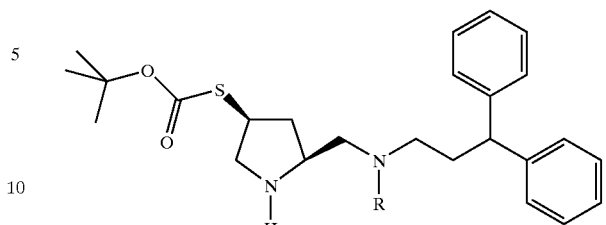

(41) R = COCH₂CH(CH₃)
(42) R = COCH₃

↓(d)

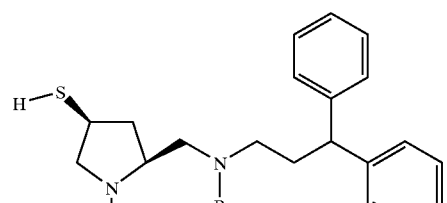

(43) R = COCH₂CH(CH₃)
(44) R = COCH₃

(a) 4A Molecular sieve/sodium triacetoxy borohydride/dichloromethane/-2 0 deg.
(b) R = COCH₂CH(CH₃)₂, Isovaleryl chloride/triethylamine/dichloromethane/R.T.
R = COCH₃, Acetyl chloride/dichloromethane/triethylamine/R.T.
(c) Tributyltin hydride/bis(triphenylphosphine)palladium(0) chlorid e/dichloromethane Scheme 34

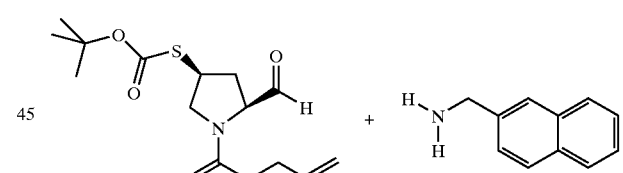

(1)

↓(a)

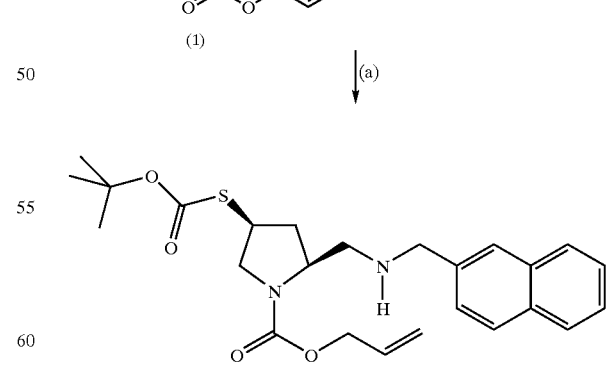

(45)

↓(b)

103
-continued

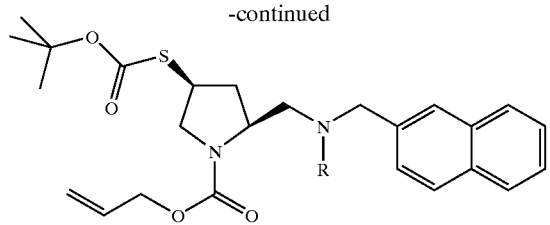

(46) R = COCH$_2$CH(CH$_3$)$_2$
(47) R = COCH$_3$

|(c)

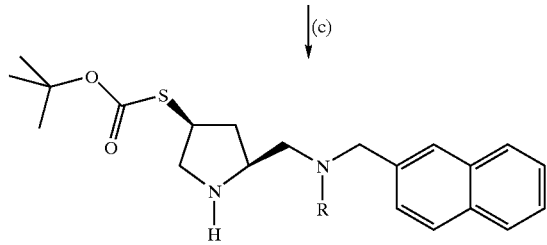

(48) R = COCH$_2$CH(CH$_3$)$_2$
(49) R = COCH$_3$

|(d)

104
-continued

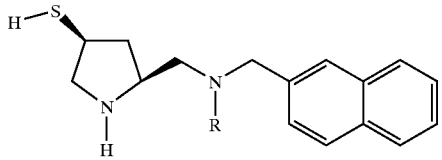

(50) R = COCH$_2$CH(CH$_3$)$_2$
(51) R = COCH$_3$ (a) 4A Molecular sieve/sodium triacetoxy borohydride/dichloromethane/−2 0 deg.
(b) R = COCH$_2$CH(CH$_3$)$_2$, Isovaleryl chloride/triethylamine/dichloromethane/R.T.
     R = COCH$_3$, Acetyl chloride/dichloromethane/triethylamine/R.T.
(c) Tributyltin hydride/bis(triphenylphosphine)palladium(0) chloride/dichloromethane
(d) Trifluoroacetic acid/R.T.

Scheme 35

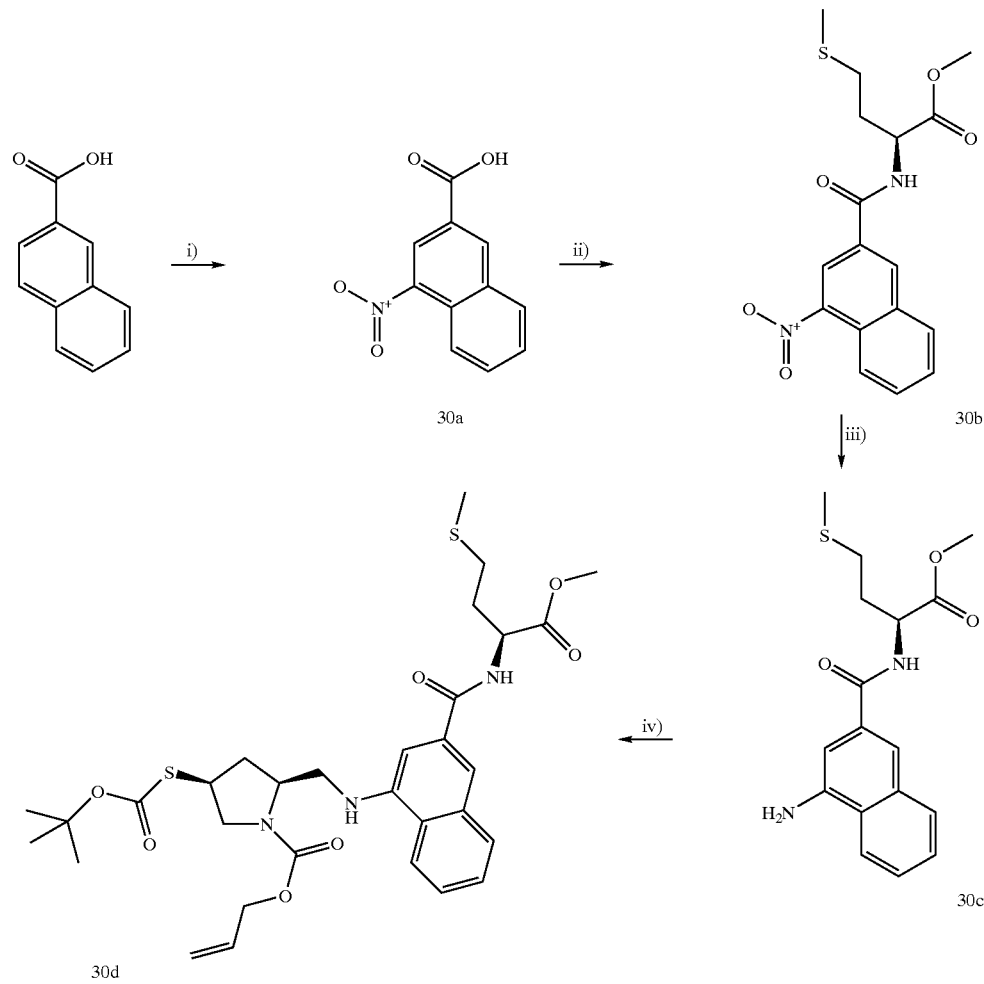

-continued
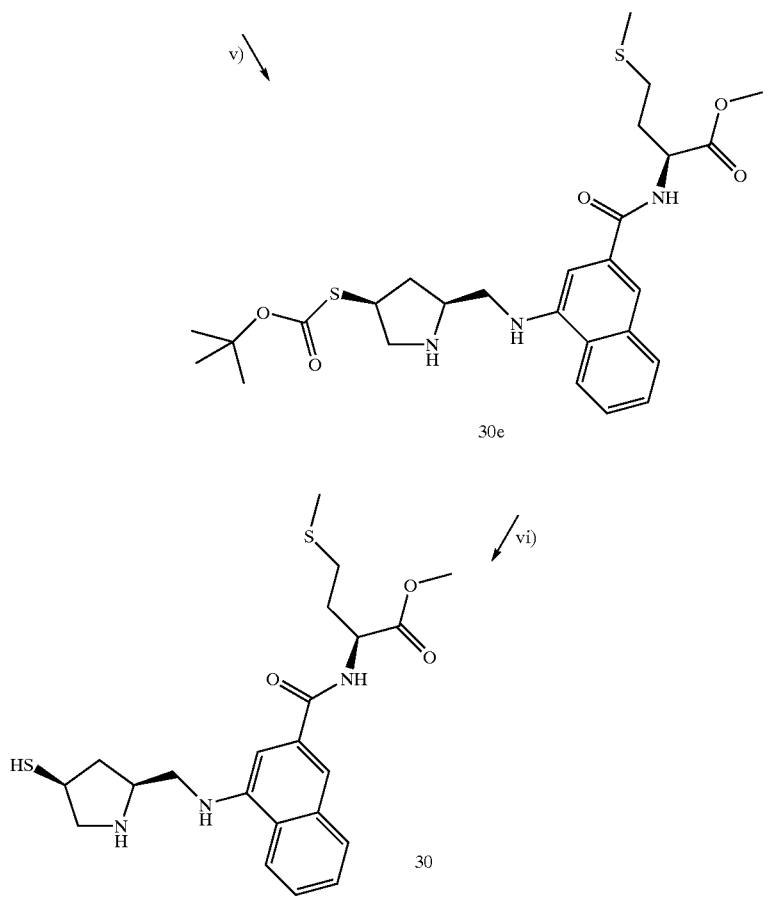
i) HNO₃, 50° C.
ii) (COCl)₂, DMF/CH₂Cl₂ Et₃N, L-Methionine methyl esterhydrochloride
iii) Me₂NNH₂, FeCl₃·6H₂O/MeOH Δ Reflux
iv) 22b/MeOH, 3A° sieves AcOH, NaCNBH₃
v) PdCl₂(PPh₃)₂, ⁿBu₃SnH/CH₂Cl₂, H₂O
vi) TFA
SCHEME 36
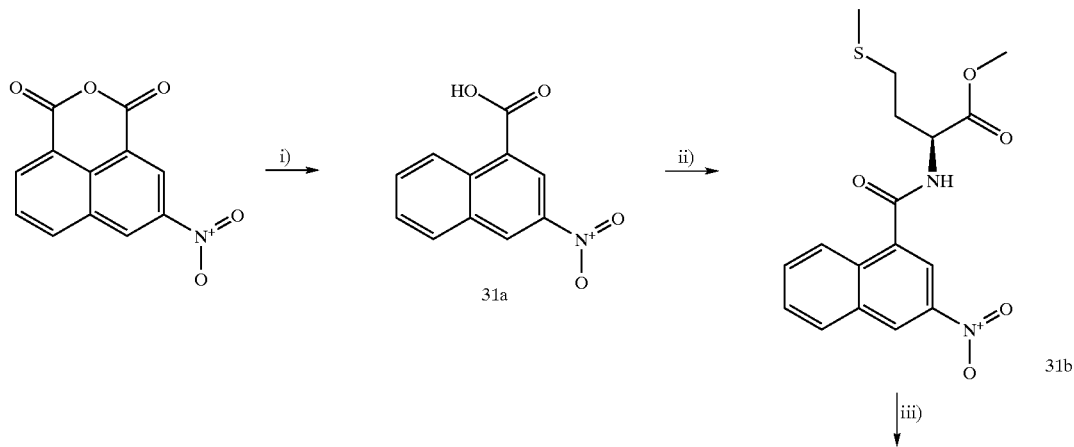

-continued
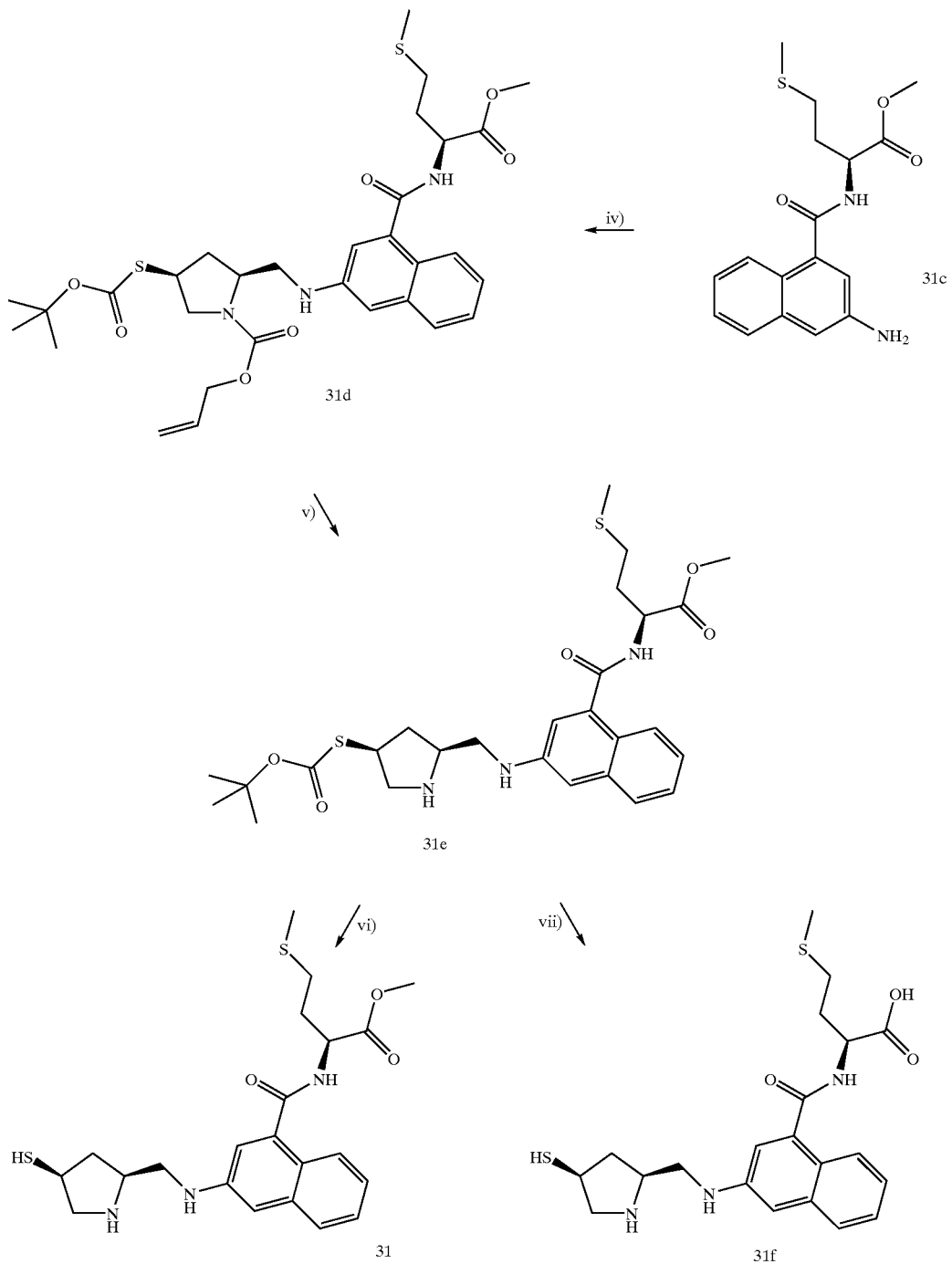
i) G. J. Leuck et al JACS 51, 1831, 1929
ii) EDC, HOBT/DMF 0° C. NMM, L-Methionine methyl ester hydrochloride 0° C.RT
iii) Me$_2$NNH$_2$, FeCl$_3$·6H$_2$O/MeOH Δ Reflux
iv) 22b/MeOH, 3A° sieves AcOH, NaCNBH$_3$
v) PdCl$_2$(PPh$_3$)$_2$, $^n$Bu$_3$SnH/CH$_2$Cl$_2$, H$_2$O
vi) TFA
vii) 2N NaOH/MeOH

SCHEME 37
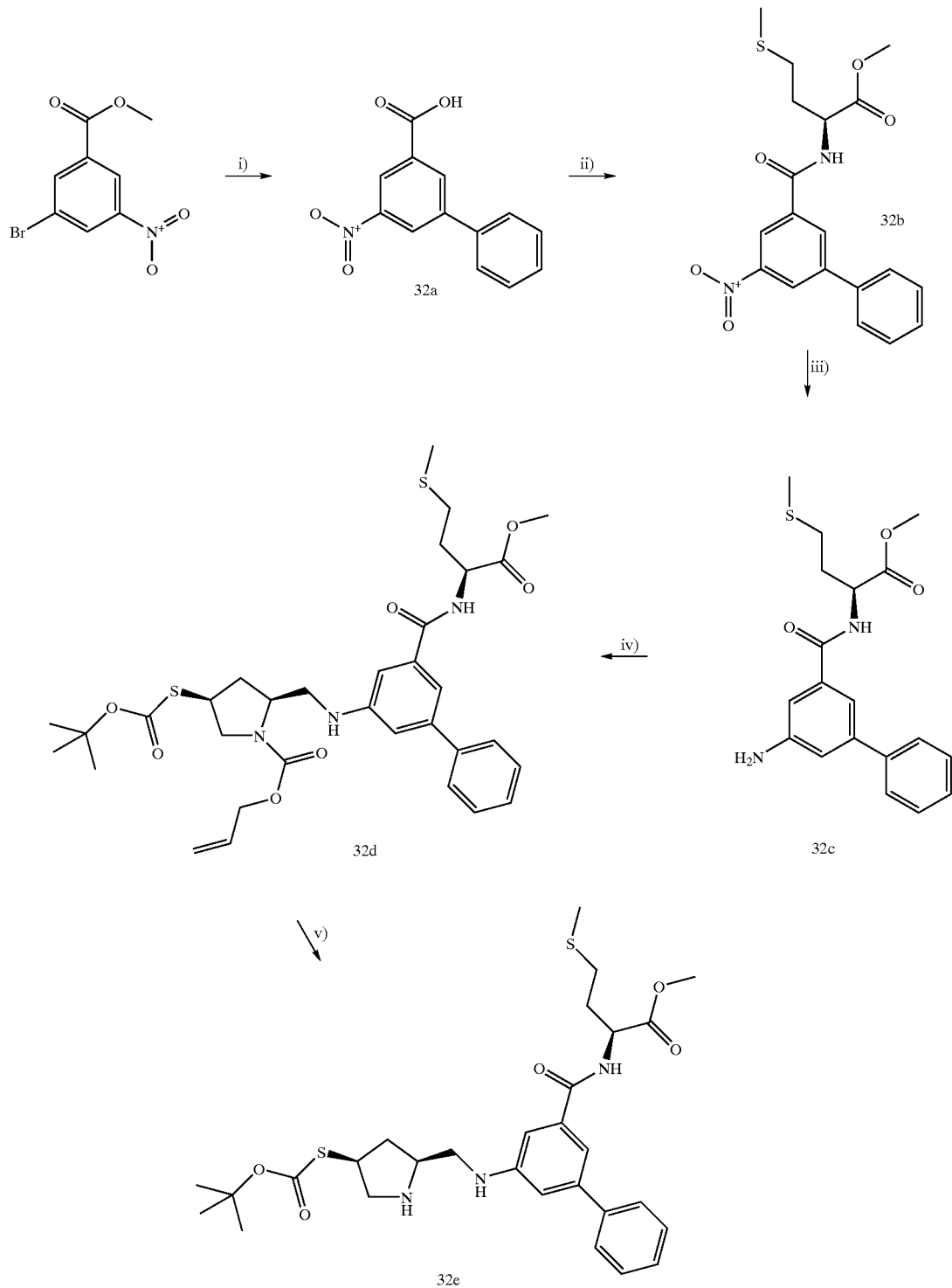

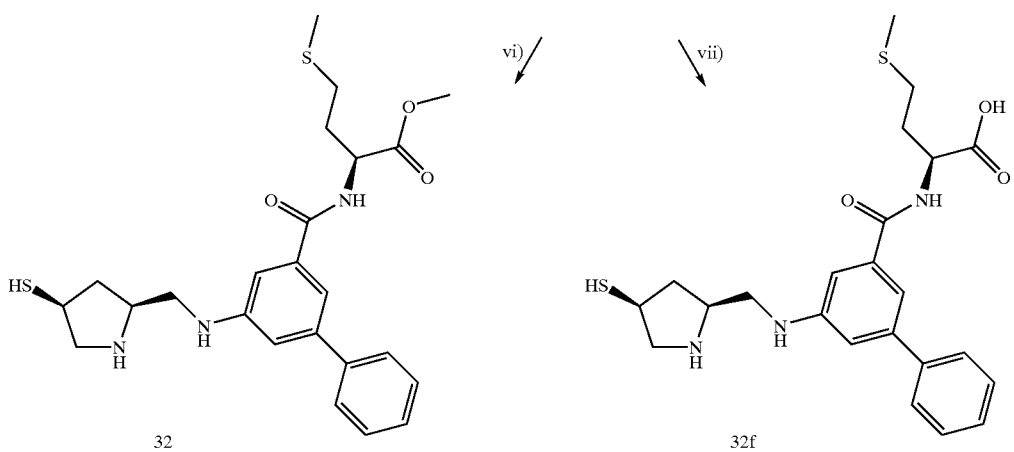
i) PhB(OH)$_2$, (PPh$_3$)$_4$ Pd°/DME, NaHCO$_3$(aq) Δ Reflux
ii) EDC, HOBT/DMF 0° C. NMM, L-Methionine methyl ester hydrochloride 0° C.-RT
iii) Me$_2$NNH$_2$, FeCl$_3$·6H$_2$O/MeOH Δ Reflux
iv) 22b/MeOH, 3A° sieves AcOH, NaCNBH$_3$
v) PdCl$_2$(PPh$_3$)$_2$, $^n$Bu$_3$SnH/CH$_2$Cl$_2$, H$_2$O
vi) TFA
vii) 2N NaOH/MeOH
SCHEME 38
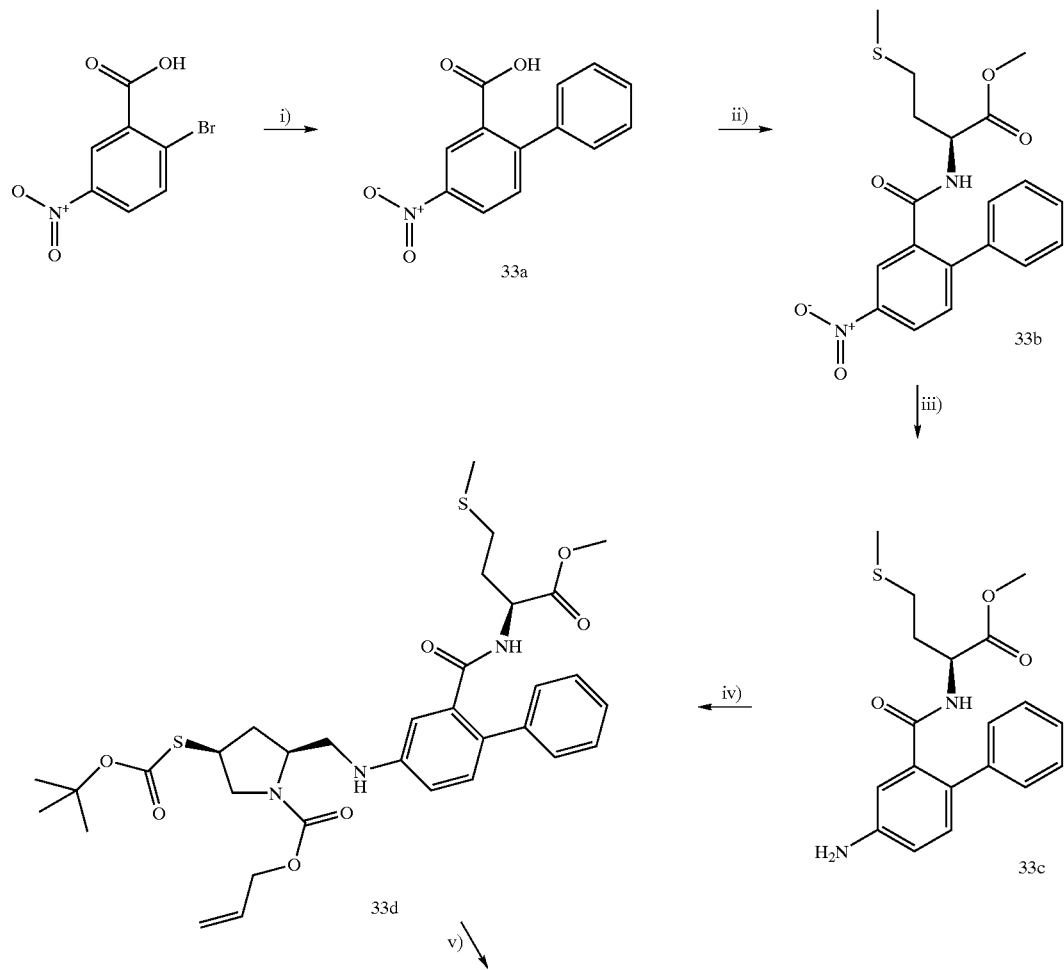

-continued
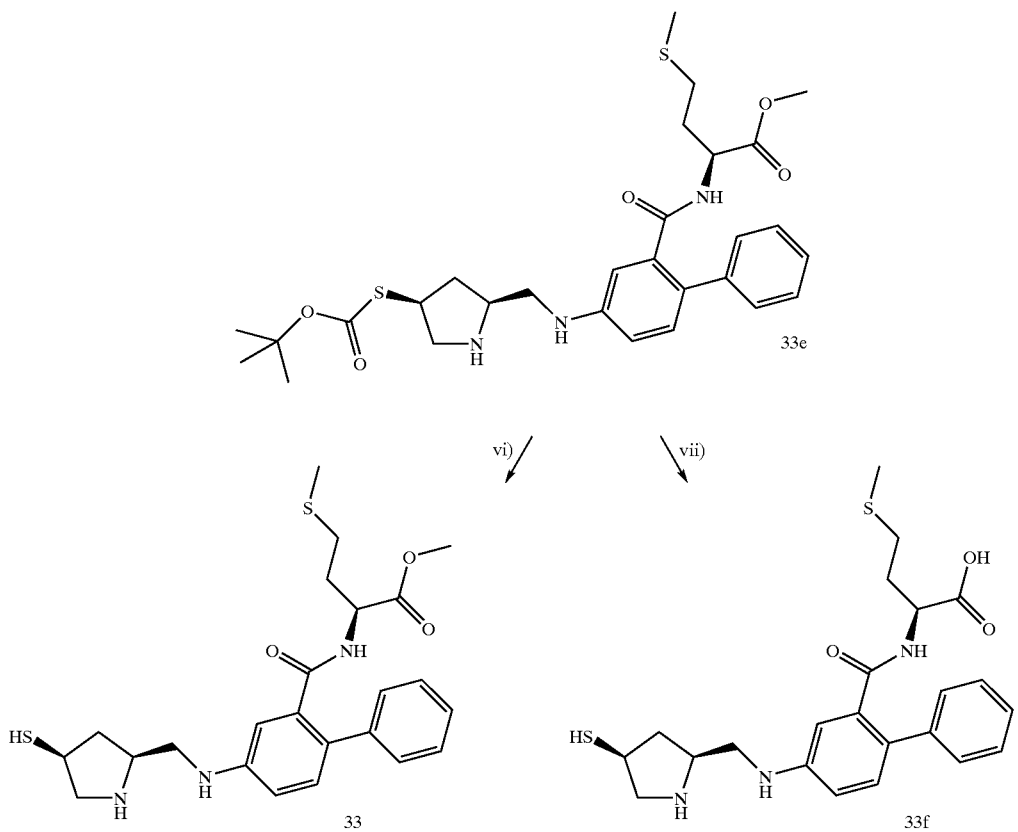
i) PhB(OH)$_2$, (PPh$_3$)$_4$ Pd°/DME, NaHCO$_3$(aq) Δ Reflux
ii) EDC, HOBT/DMF 0° C. NMM, L-Methionine methyl ester hydrochloride 0° C.-RT
iii) Me$_2$NNH$_2$, FeCl$_3$•6H$_2$O/MeOH Δ Reflux
iv) 22b/MeOH, 3A° sieves AcOH, NaCNBH$_3$
v) PdCl$_2$(PPh$_3$)$_2$, $^n$Bu$_3$SnH/CH$_2$Cl$_2$•H$_2$O
vi) TFA
vii) 2N NaOH/MeOH
SCHEME 39
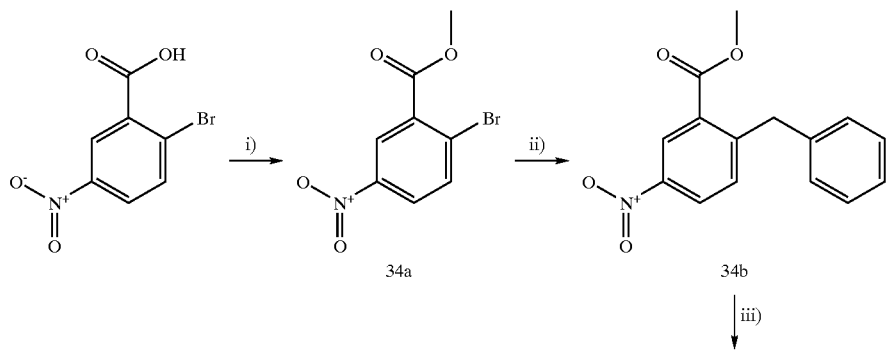

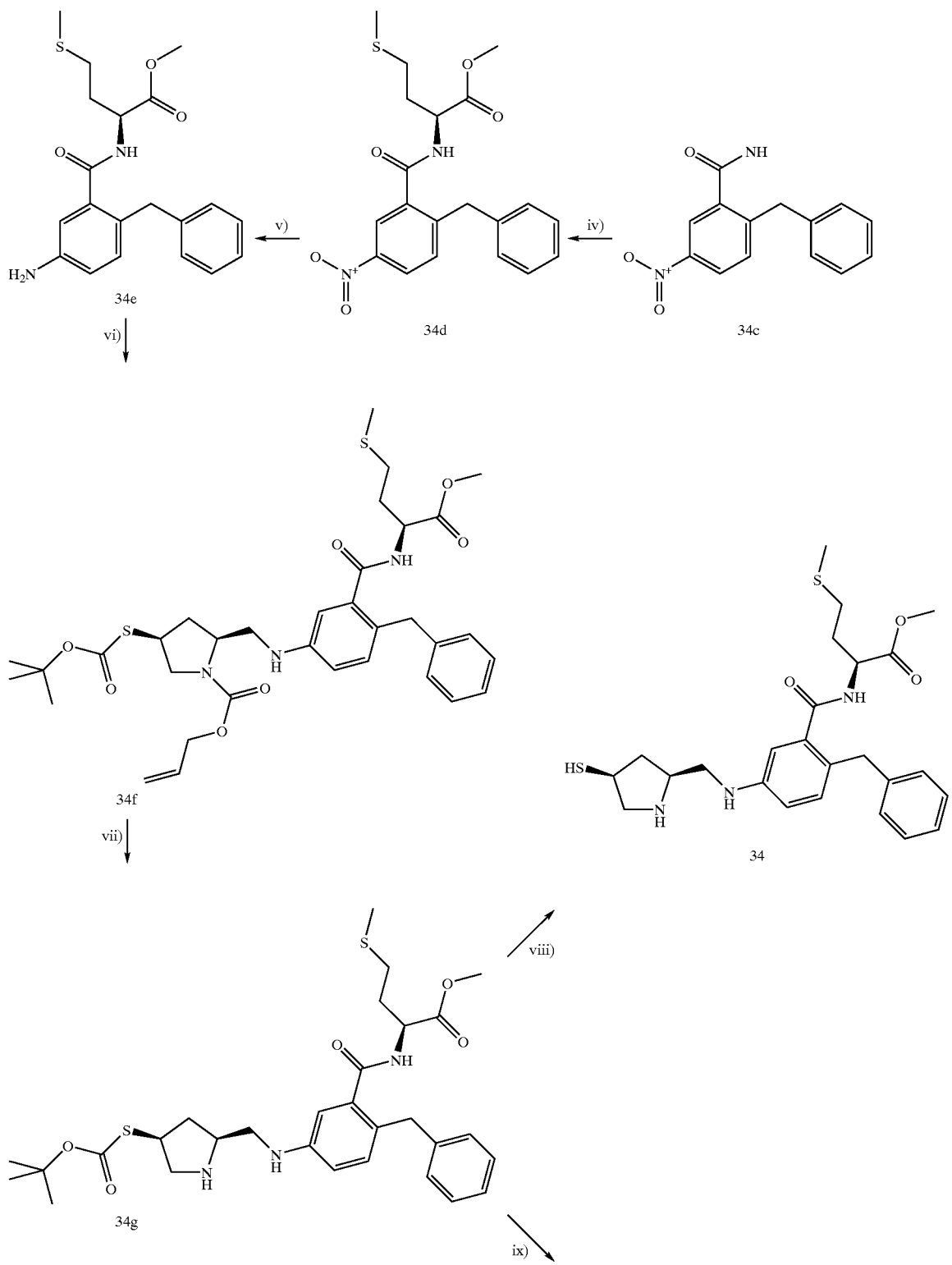

-continued
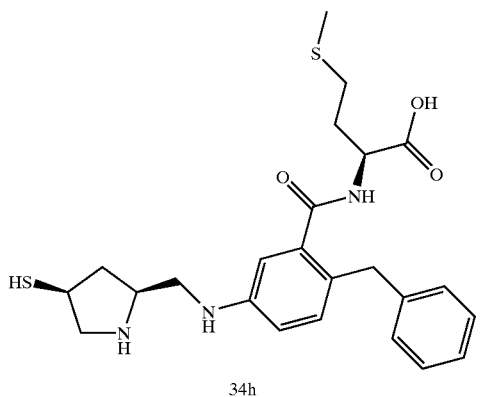
34h
i) SO$_2$Cl$_2$/MeOH Δ Reflux
ii) BzZnBr, PdCl$_2$(PPh$_3$)$_2$/THF
iii) 2N NaOH/MeOH
iv) EDC, HOBT/DMF 0° C.
    NMM,L-Methionine methyl ester hydrochloride 0° C.-RT
v) SnCl$_2$•2H$_2$O/EtOAc Δ Reflux
vi) 22b/MeOH•3A° sieves
    AcOH•NaCNBH$_3$
vii) PdCl$_2$(PPh$_3$)$_2$, $^n$Bu$_3$SnH/CH$_2$Cl$_2$•H$_2$O
viii) TFA
ix) 2N NaOH/MeOH
SCHEME 40
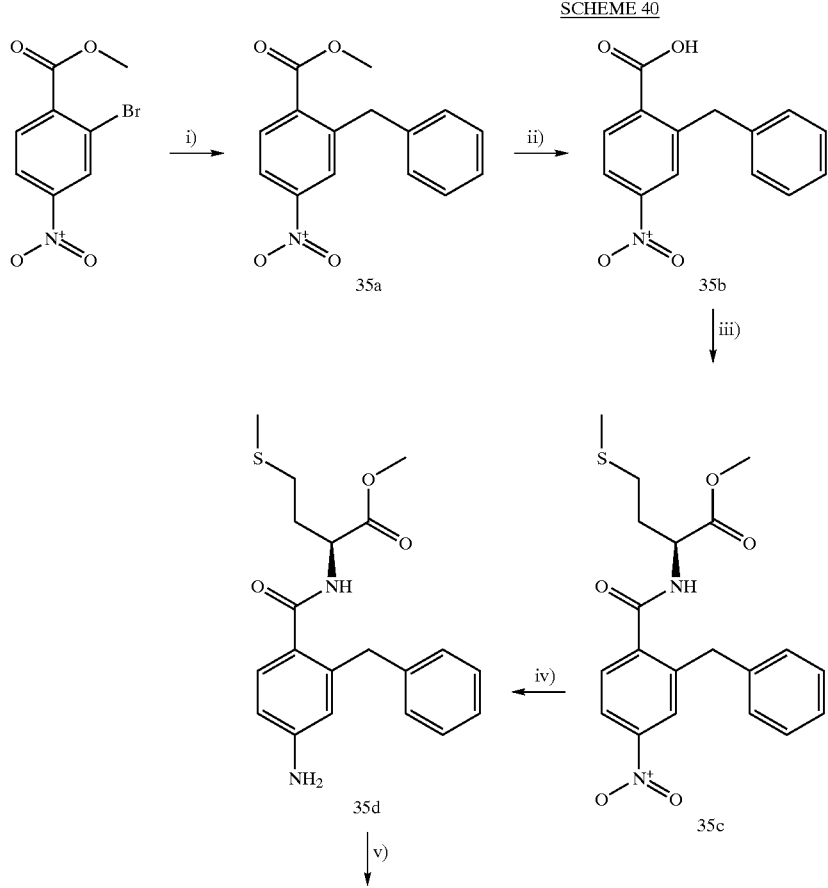

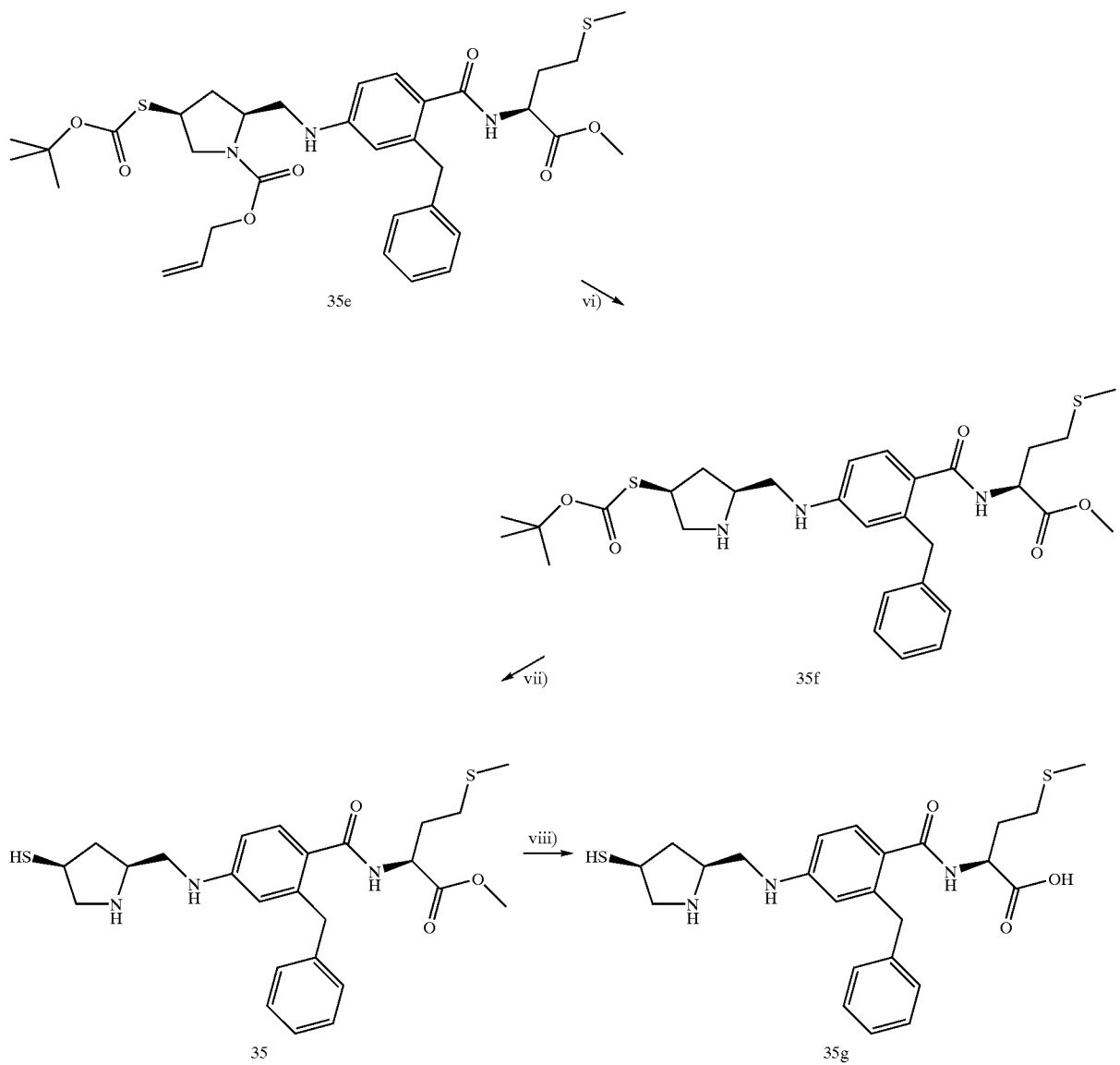
i) BzZnBr, Pd₂(dba)₃/THF
ii) 2N NaOH/MeOH
iii) EDC, HOBT/DMF 0° C.
   NMM•L-Methionine methyl ester hydrochloride 0° C.-RT
iv) SnCl₂•2H₂O/EtOAc Δ Reflux
v) 22b/MeOH•3A°sieves
   AcOH•NaCNBH₃
vi) PdCl₂(PPh₃)₂, ⁿBu₃SnH/CH₂Cl₂, H₂O
vii) TFA
viii) 2N NaOH/MeOH SCHEME 41
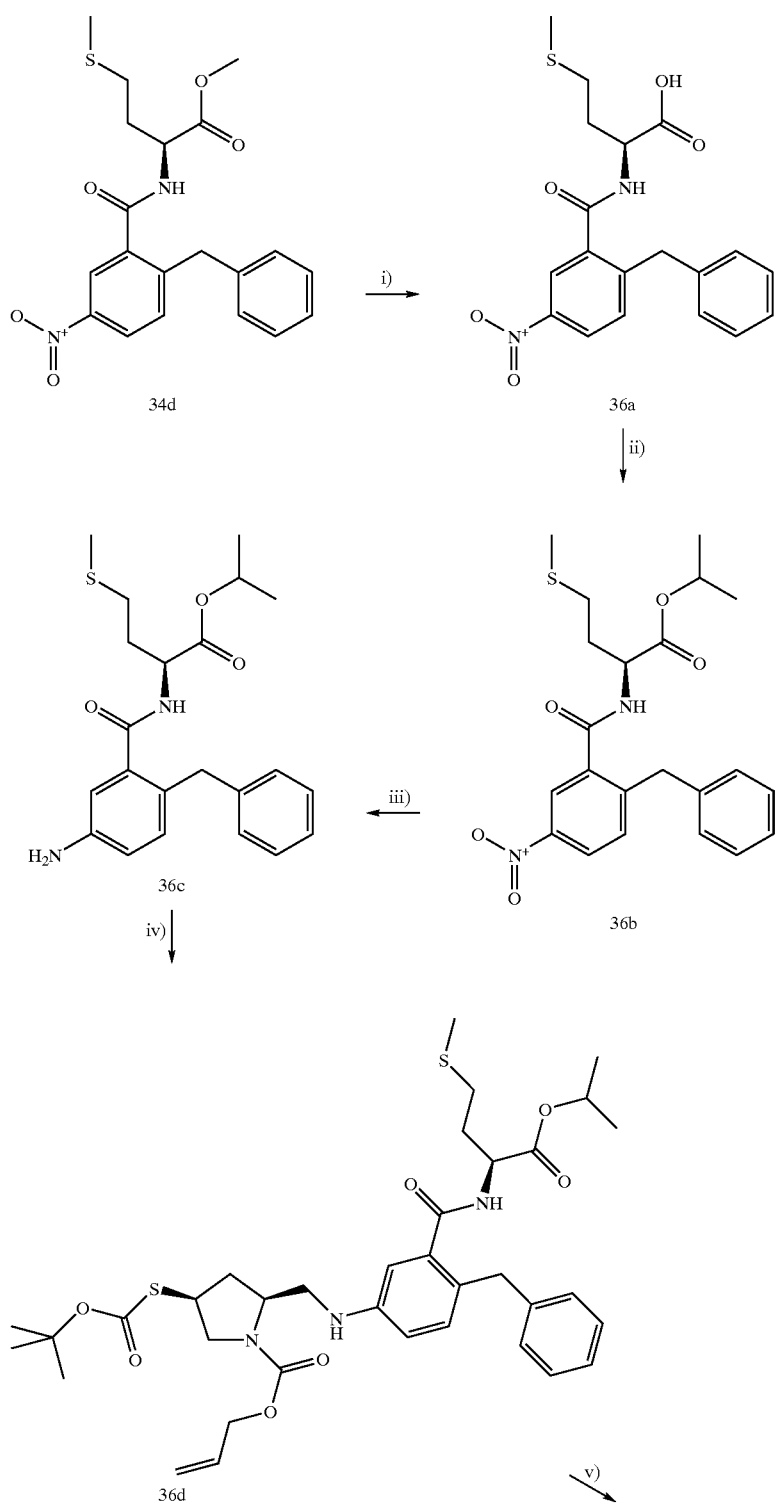

-continued
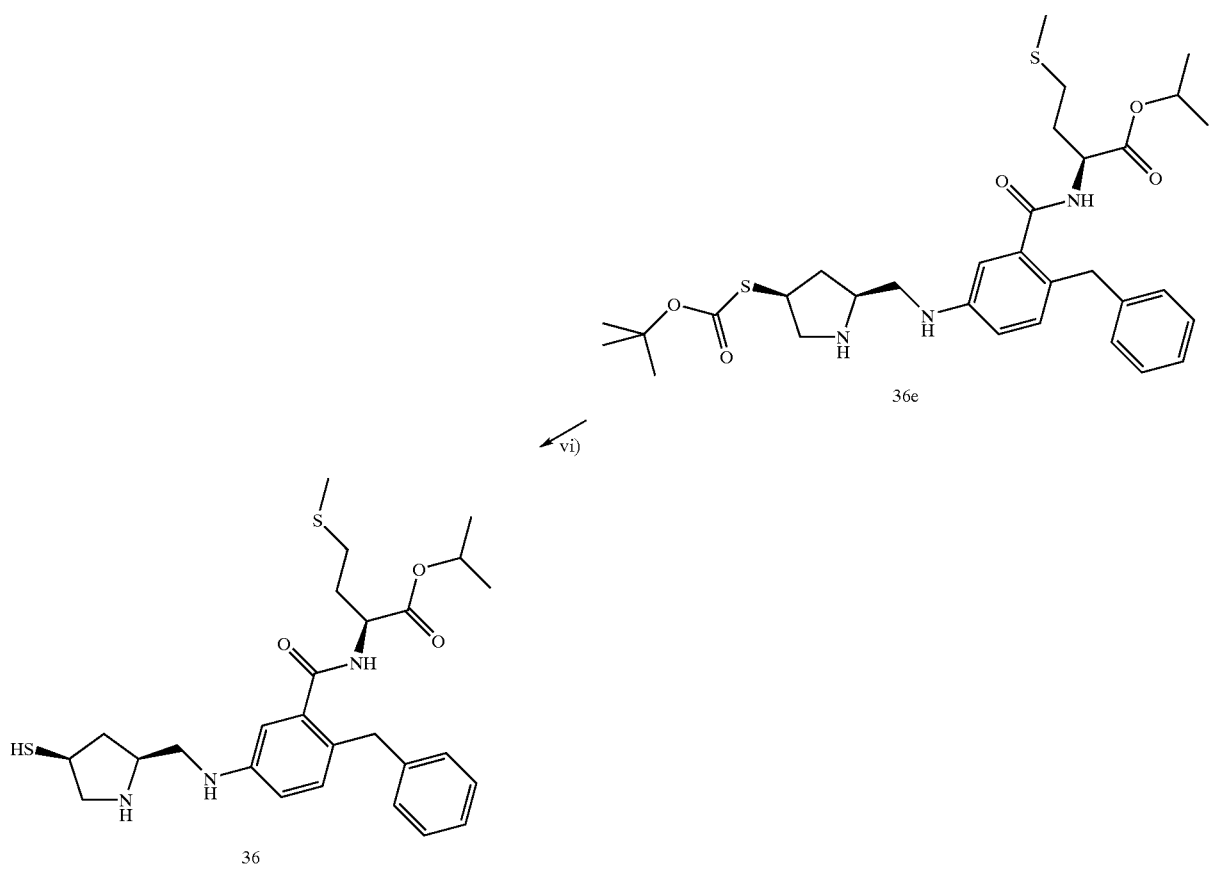
36e
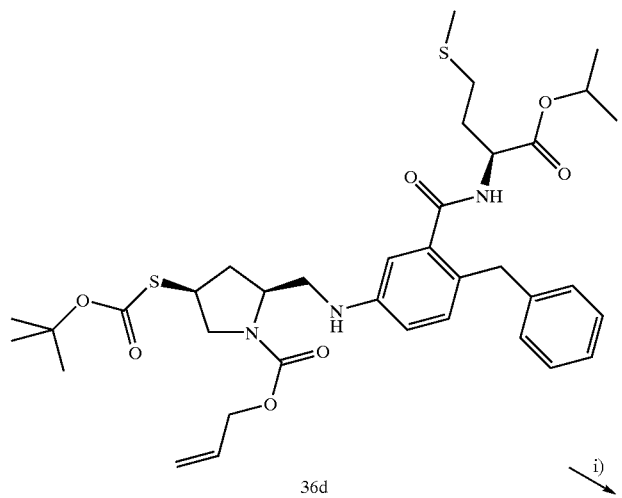
36
i) 2N NaOH/MeOH
ii) SO₂Cl₂/IPA Δ Reflux
iii) SnCl₂·2H₂O/EtOAc Δ Reflux
iv) 22b/IPA·3A° sieves
    AcOH·NaCNBH₃
v) PdCl₂(PPh₃)₂, ⁿBu₃SnH/CH₂Cl₂,H₂O
vi) TFA
SCHEME 42
36d
i)

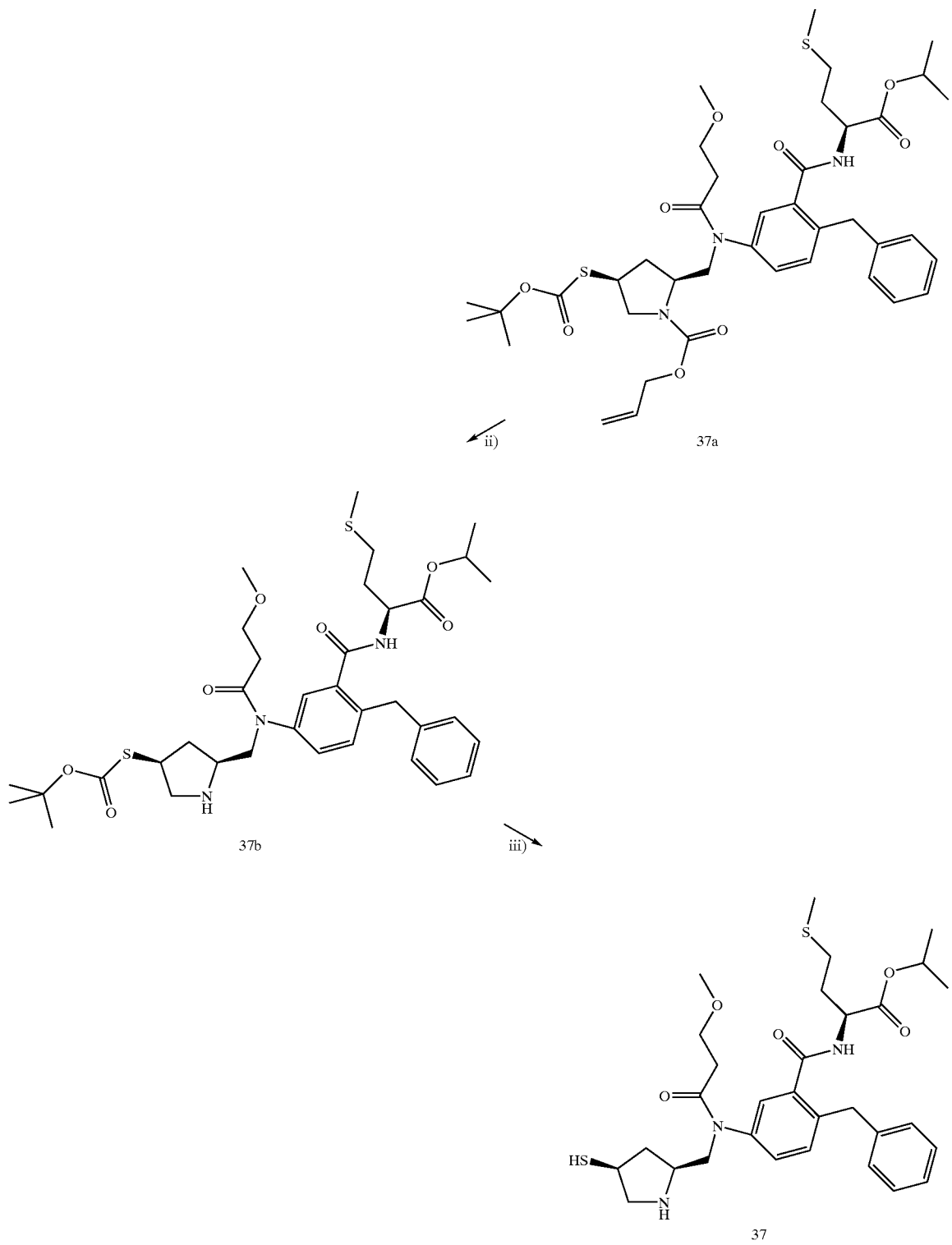
i) CH₃O(CH₂)₂CO₂H•EEDQ/CH₂Cl₂
ii) PdCl₂(PPh₃)₂, ⁿBu₃SnH/CH₂Cl₂•H₂O
iii) TFA Scheme 43
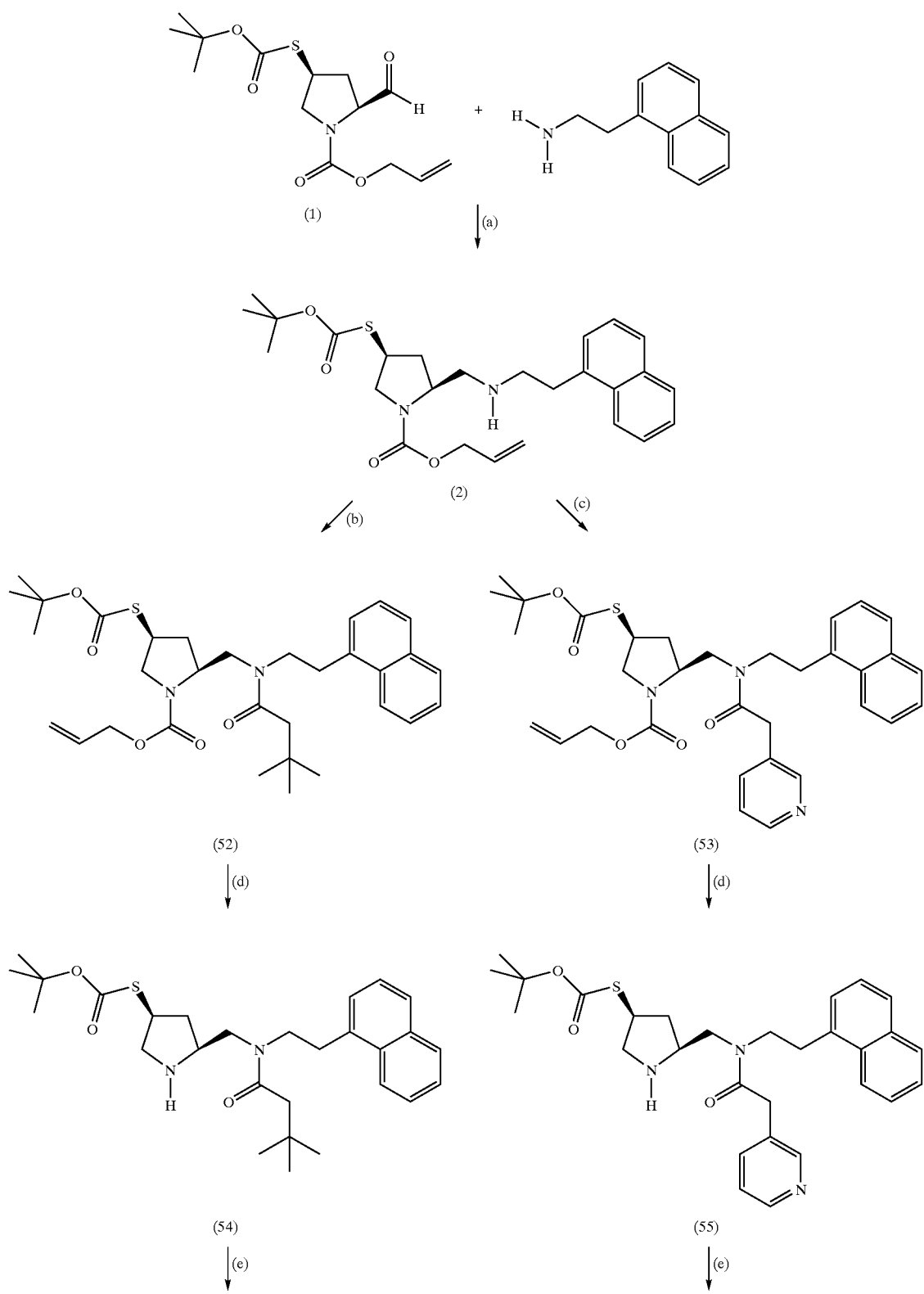

-continued

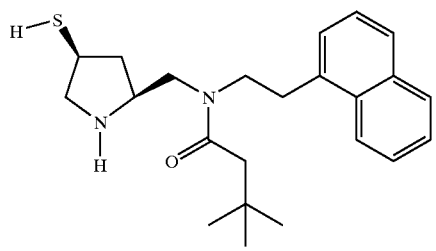

(56)

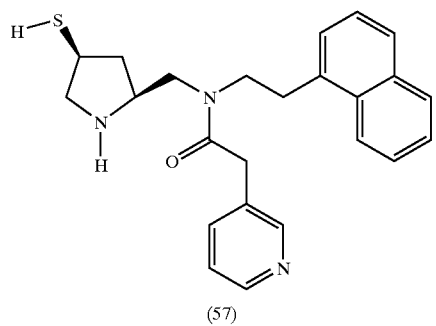

(57)

(a) 4A Molecular sieve/sodium triacetoxy borohydride/dichloromethane/- 20 deg.
(b) Tert.butylacetyl chloride/triethylamine/dichloromethane/R.T.
(c) 3-Pyridylacetic acid/EDC/HOBT/N-methylmorpholine/dichloromethane/0 deg-R.T.
(d) Tributyltin hydride/bis(triphenylphosphine)palladium(0) chloride/dichloromethane
(e) Trifluoroacetic acid/R.T.

Scheme 44

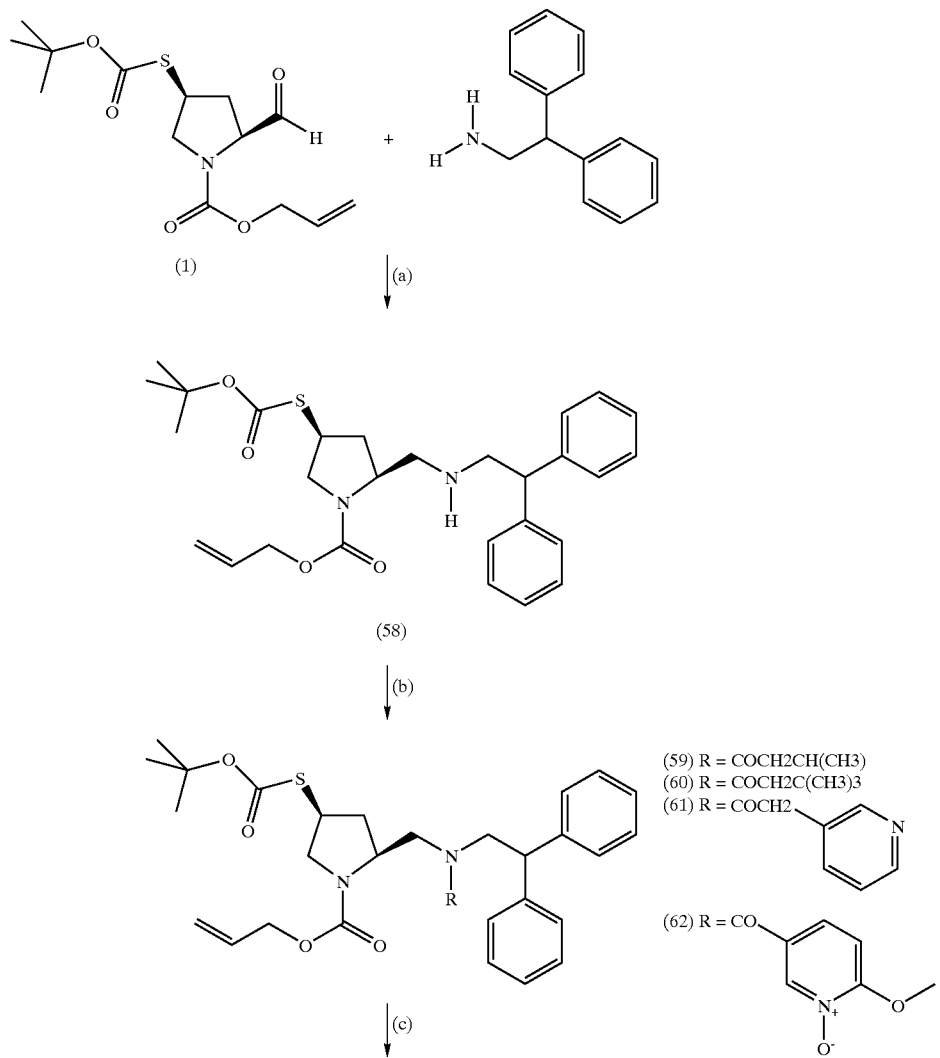

(59) R = COCH2CH(CH3)
(60) R = COCH2C(CH3)3
(61) R = COCH2-(3-pyridyl)

(62) R = CO-(6-methoxy-pyridin-N-oxide-3-yl)

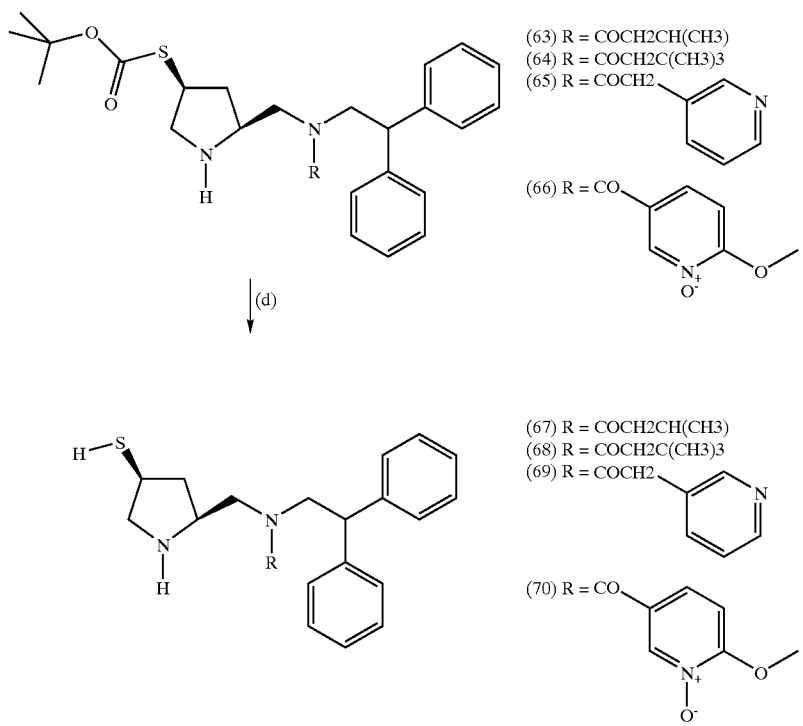

(63) R = COCH2CH(CH3)
(64) R = COCH2C(CH3)3
(65) R = COCH2-[3-pyridyl]
(66) R = CO-[6-methoxy-pyridine N-oxide-3-yl]

(67) R = COCH2CH(CH3)
(68) R = COCH2C(CH3)3
(69) R = COCH2-[3-pyridyl]
(70) R = CO-[6-methoxy-pyridine N-oxide-3-yl]

(a) 4A Molecular sieve/sodium triacetoxy borohydride/dichloromethane/- 20 deg.
(b) R = COCH2CH(CH3)2. isovaleryl chloride/triethylamine/dichloromet hane/R.T.
   R = COCH2C(CH3)3. Tert.butylacetyl chloride/dichloromethane/trie thylamine/R.T.
   R = COCH2-[3-pyridyl]  3-Pyridylacetic acid/EDC/HOBT/N-methylmorpholine/dichloromethane.

R = COCH2-[6-methoxy-pyridine N-oxide-3-yl]  6-Methoxy-1-oxo-nicotinic acid/EDC/HOBT/N-methylmorpholine/dichlorometha ne.

(c) Tributylin hydride/bis(triphenylphosphine)palladium(0) chlorid e/dichloromethane
(d) Trifluoroacetic acid/R.T.

Scheme 45

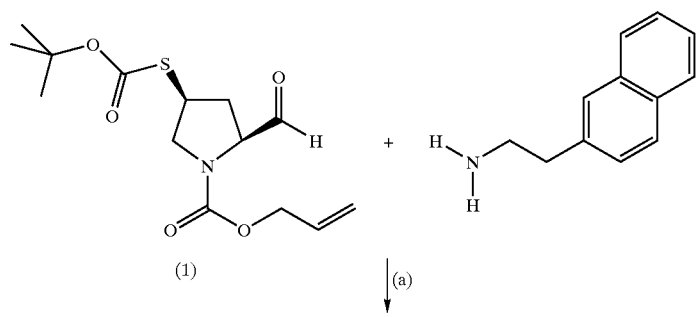

(1)  (a)

-continued

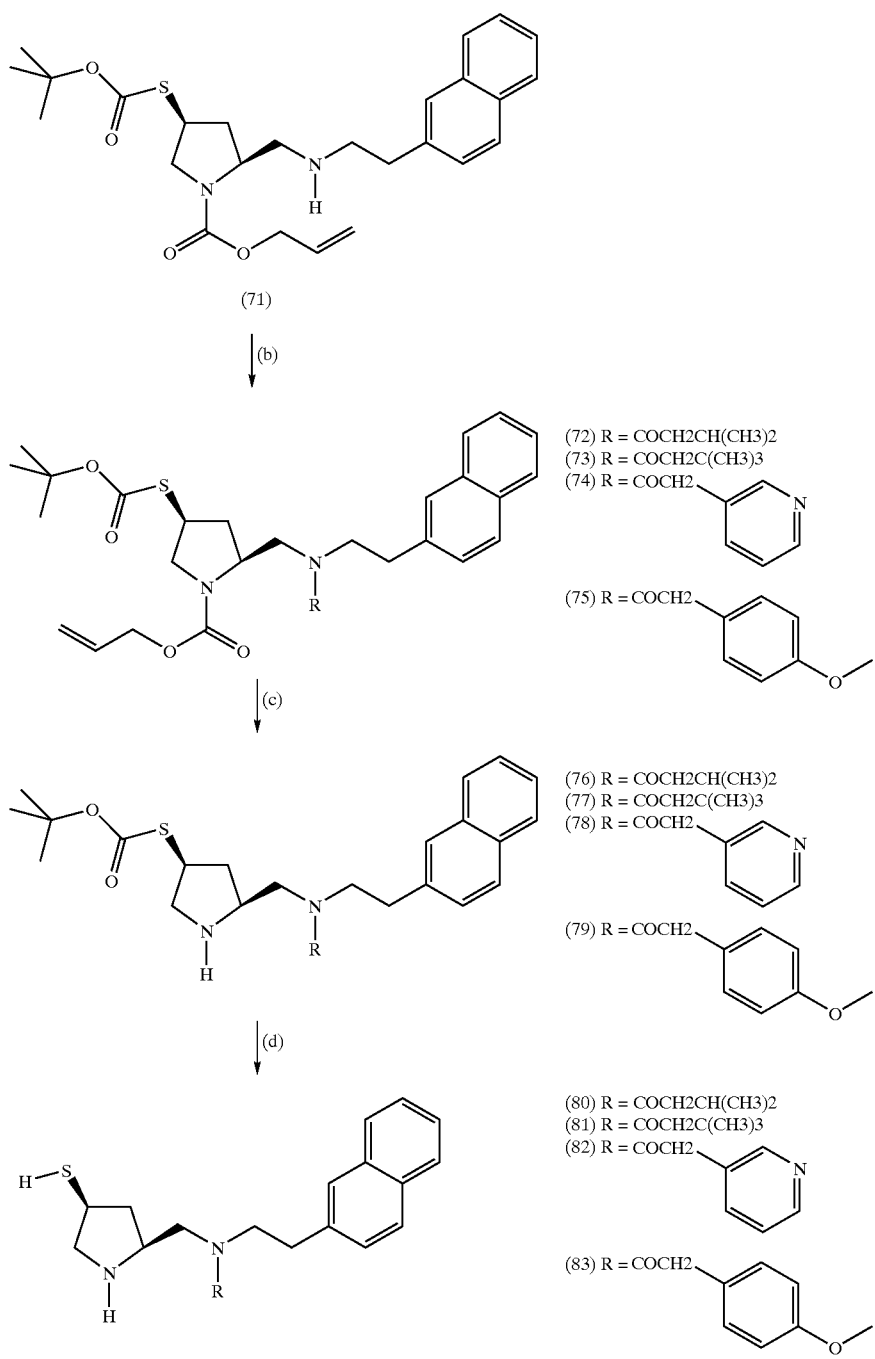

(a) 4A Molecular sieve/sodium triacetoxy borohydride/dichloromethane/- 20 deg.
(b) R = COCH2CH(CH3)2. Isovaleryl chloride/triethylamine/dichloromet hane/R.T.
    R = COCH2C(CH3)3. Tert.butylacetyl chloride/dichloromethane/trie thylamine/R.T.
    R = COCH2   3-Pyridylacetic acid/EDC/HOBT/N-methylmorpholine/dichloromethane.

R = COCH2 [4-methoxybenzyl]  4-Methoxyphenylacetic acid/EDC/HOBT/N-methylmorpholine/dichloromethane.

(c) Tributylin hydride/bis(triphenylphosphine)palladium(0) chlorid e/dichloromethane
(d) Trifluoroacetic acid/R.T.

Scheme 46
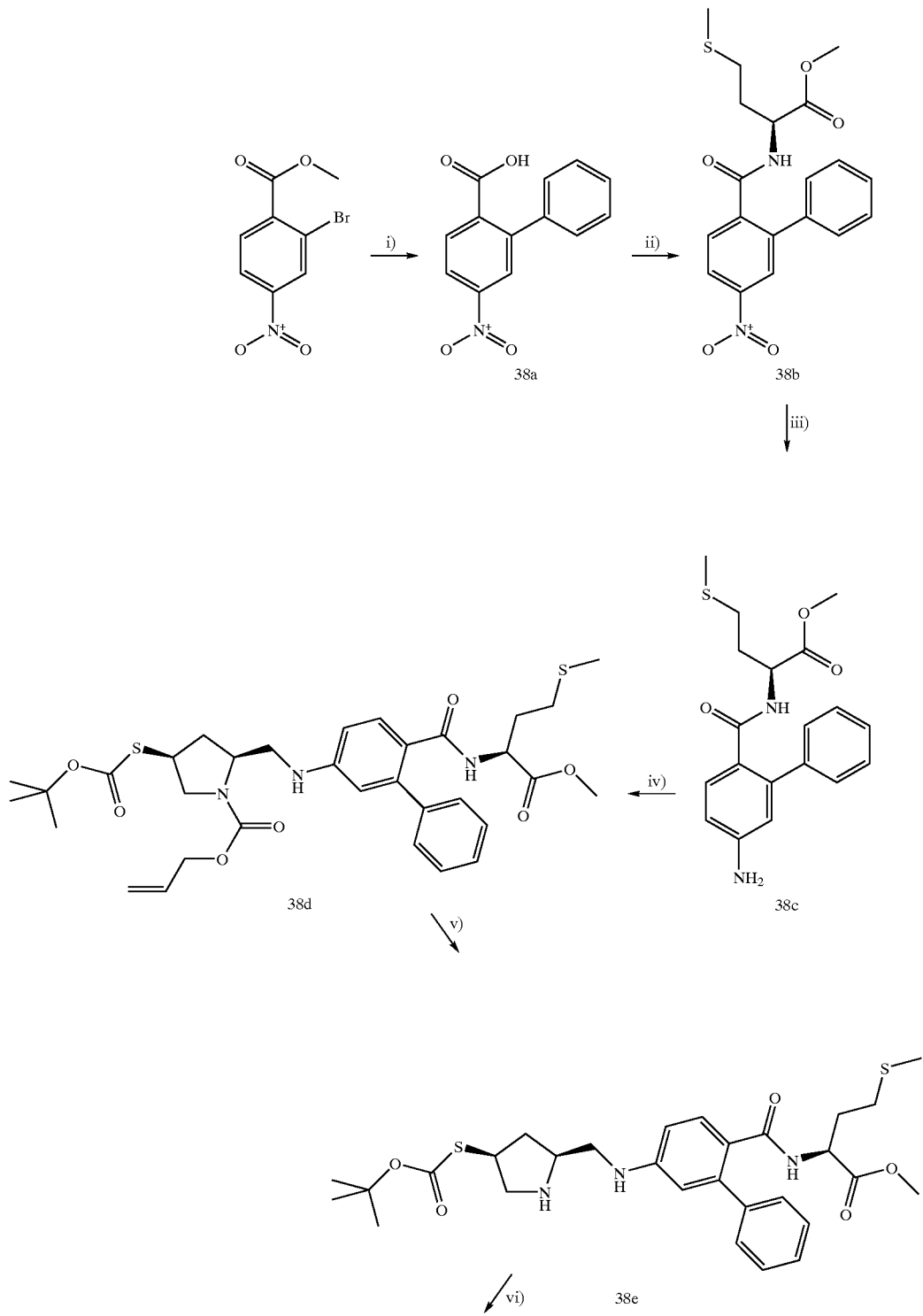

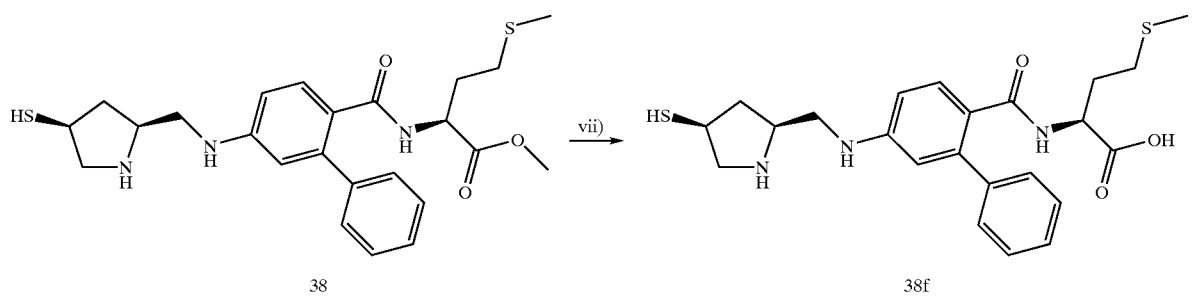
i) PhB(OH)$_2$, (PPh$_3$)$_4$ Pd$^0$/DME.NaHCO$_3$(aq) Δ Reflux
ii) EDC.HOBT/DMF 0° C.
    NMM.L-Methionine methyl ester hydrochloride 0° C.-RT
iii) SnCl$_2$.2H$_2$O/EtOAc Δ Reflux
iv) 22b/MeOH.3A° sieves
    AcOH.NaCNBH$_3$
v) PdCl$_2$(PPh$_3$)$_2$,$^n$Bu$_3$SnH/CH$_2$Cl$_2$, H$_2$O
vi) TFA
vii) 2N NaOH/MeOH
SCHEME 47
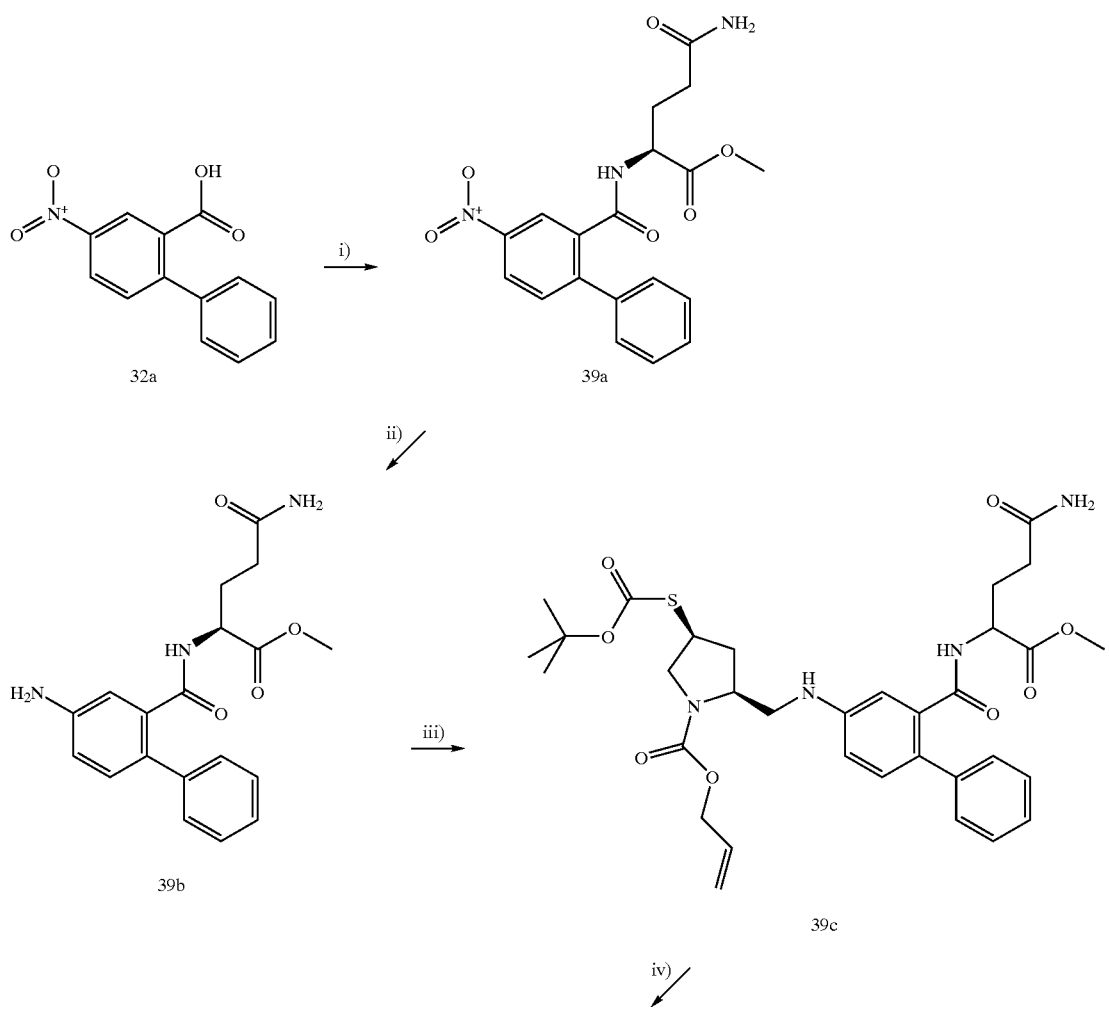

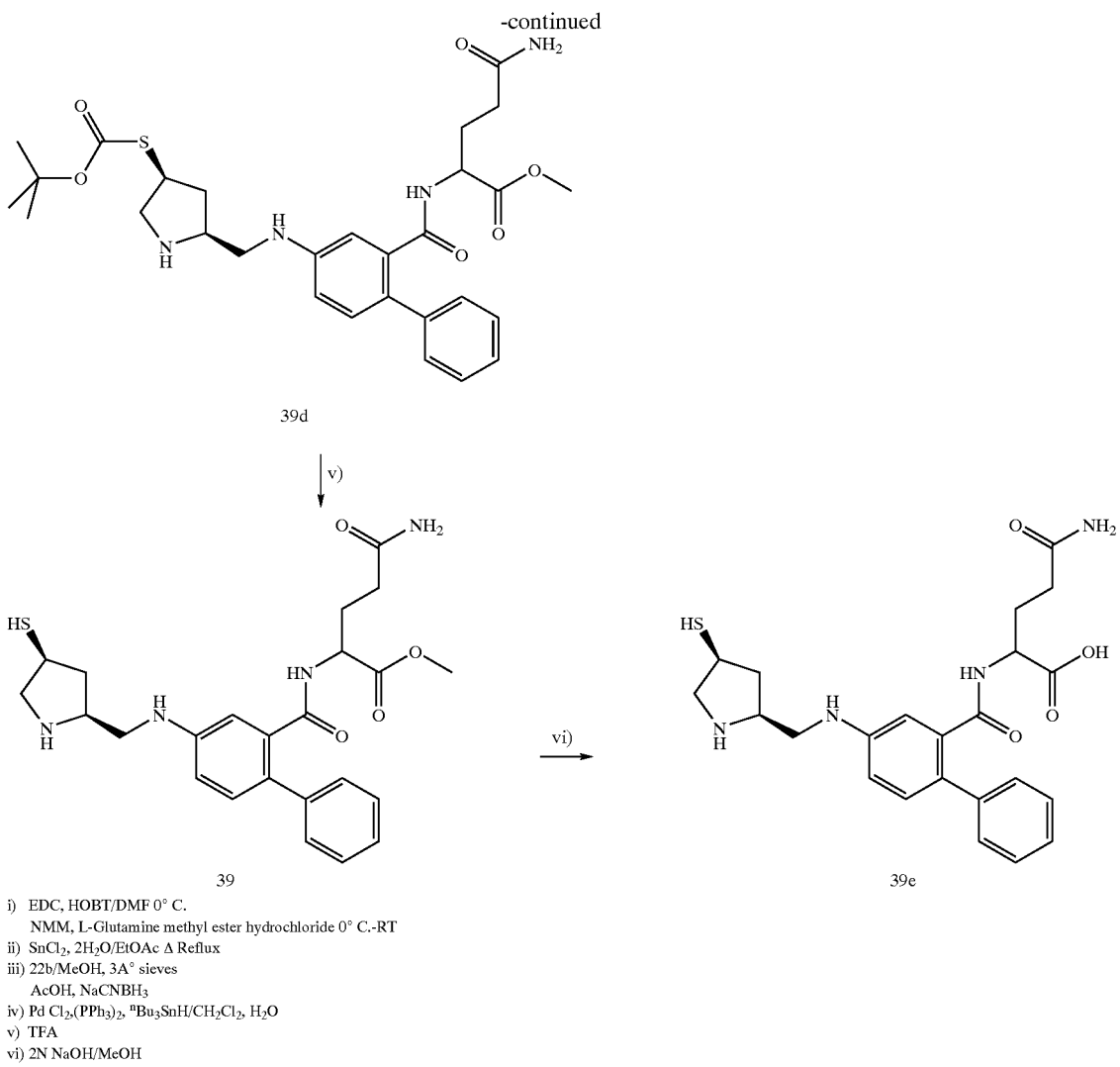

i) EDC, HOBT/DMF 0° C.
NMM, L-Glutamine methyl ester hydrochloride 0° C.-RT
ii) SnCl$_2$, 2H$_2$O/EtOAc Δ Reflux
iii) 22b/MeOH, 3A° sieves
AcOH, NaCNBH$_3$
iv) Pd Cl$_2$,(PPh$_3$)$_2$, $^n$Bu$_3$SnH/CH$_2$Cl$_2$, H$_2$O
v) TFA
vi) 2N NaOH/MeOH

What is claimed is:

1. A pharmaceutical composition comprising an inhibitor of ras farnesylation of Formula I

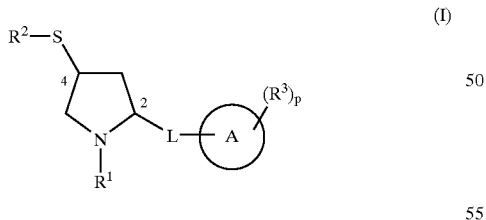

(I)

wherein:

R$^1$ is selected from H; —C$_{1-4}$alkyl; —C$_{1-3}$alkylene-Ph optionally mono or di-substituted on Ph with substituents selected from C$_{1-4}$alkyl, halogen, OH, C$_{1-4}$alkoxy, C$_{1-4}$alkanoyl, C$_{1-4}$alkanoyloxy, amino, C$_{1-4}$alkylamino, di(C$_{1-4}$alkyl)amino, C$_{1-4}$alkanoylamino, nitro, cyano, carboxy, carbamoyl, C$_{1-4}$alkoxycarbonyl, thiol, C$_{1-4}$alkylsulfanyl, C$_{1-4}$alkylsulfinyl, C$_{1-4}$alkylsulfonyl and sulfonamido; —CO—C$_{1-4}$alkyl; —CO—O—C$_{1-4}$alkyl; —CO—O—C$_{2-4}$alkenyl; —COO—(CH$_2$)$_n$Ph optionally substituted on Ph as defined for substitution on Ph in R$^1$=—C$_{1-3}$ alkylene-Ph in this claim 1 and n=0–4; —C$_{1-4}$alkylene-CONR$^4$R$^5$ where R$^4$ and R$^5$ are independently selected from H, C$_{1-4}$alkyl; and —C$_{1-4}$alkylene-COOR$^6$ where R$^6$ is selected from H, C$_{1-4}$alkyl;

R$^2$ is selected from H; —C$_{1-4}$alkyl, —C$_{1-3}$ alkylene-Ph optionally substituted on Ph as defined for substitution on Ph in R$^1$=—C$_{1-3}$ alkylene-Ph in this claim 1; —COC$_{1-4}$alkyl; and —COOC$_{1-4}$alkyl;

R$^3$ is selected from H; OH; CN; CF$_3$; NO$_2$: —C$_{1-4}$alkyl; —C$_{1-4}$alkylene-R$^7$ where R$^7$ is selected from phenyl, naphthyl, and a 5–10 membered monocyclic or bicyclic heteroaryl ring containing up to 5 heteroatoms selected from O, N and S and any aryl ring in R$^7$ is optionally substituted as defined for substitution on the Ph group in R$^1$=—C$_{1-3}$alkylene-Ph in claim 1; R$^7$; C$_{2-4}$alkenyl; halogen; —(CH$_2$)$_n$COOR$^8$ where n=0–3 and R$^8$ represents H, C$_{1-4}$alkyl, C$_{2-4}$alkenyl; —CONR$^9$ R$^{10}$ where R$^9$ and R$^{10}$ independently represent H, C$_{1-4}$alkyl, C$_{2-4}$alkenyl, —O—C$_{1-4}$alkyl, —O—C$_{2-4}$alkenyl, or —C$_{1-3}$alkylenePh optionally substituted as defined for this group for R$^1$ in this claim 1; —CON(R$^{11}$)OR$^{12}$ where R$^{11}$ and R$^{12}$ independently represent H, C$_{1-4}$alkyl and C$_{2-4}$alkenyl; a group of Formula II, —CONR$^{13}$ CHR$^{14}$ COOR$^{17}$, where R$^{13}$ is H or

141

$C_{1-4}$alkyl, $R^{17}$ is H or $C_{1-6}$alkyl, $R^{14}$ is selected from the side chain of a lipophilic amino acid, carbamoyl$C_{1-4}$ alkyl, N-(mono$C_{1-4}$alkyl)carbamoyl$C_{1-4}$alkyl and N-(di$C_{1-4}$alkyl)carbamoyl$C_{1-4}$alkyl; the group of Formula II having L or D configuration at the chiral alpha carbon in the corresponding free amino acid; a lactone of formula

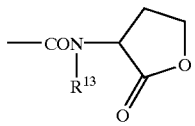

$C_{1-4}$alkyl monosubstituted on carbon with =N—OH; a group of Formula —X—$R^{15}$ where X is selected from 0, CO, $CH_2$, S, SO, $SO_2$ and $R^{15}$ is selected from $C_{1-6}$alkyl, phenyl, naphthyl, a 5–10 membered monocyclic or bicyclic heteroaryl ring containing upto 5 heteroatoms selected from O, N and S and any aryl ring in $R^{15}$ is optionally substituted as defined for the Ph group in $R^1$=—$C_{1-3}$alkylene-Ph in this claim 1;

p is 0–3 in which $R^3$ values can be the same or different;

L is a linking moiety selected from the following groups written from left to right in Formula I: —CO—$NR^{16}$- where $R^{16}$ is selected from H, $C_{1-4}$alkyl, $C_{1-4}$alkylene-Z, —CO—$C_{1-4}$alkylene-Z, —CO—$C_{1-6}$alkyl, —COZ, and Z, and Z is selected from 0-$C_{1-4}$alkyl, phenyl, naphthyl, a 5–10 membered monocyclic or bicyclic heteroaryl ring containing upto 5 heteroatoms selected from O, N and S and any aryl ring in $R^{16}$ is optionally substituted as defined for the Ph group in $R^1$=—$C_{1-3}$alkylene-Ph in this claim 1 —$CH_2$—$NR^{18}$— where $R^{18}$ represents any value defined for $R^{16}$; —$CH_2S$—; —$CH_2O$—; —$CH_2$—$CHR^{19}$— where $R^{19}$ represents any value defined for $R^{16}$; —$CH_2S$—; —$CH_2O$—; —$CH_2CHR^{19}$— where $R^{19}$ represents any value defined for $R^{16}$; —CH=$CR^{20}$— where $R^{20}$ represents any value defined for $R^{16}$; —$CH_2NR^{21}$—T— where $R^{21}$ represents any value defined for $R^{16}$, T represents —$(CH_2)_n$— where n is 1–4 and T is optionally monosubstituted with $R^{22}$ where $R^{22}$ represents any value for $R^{16}$ other than H; —$CH_2NR^{23}$—$SO_2$— where $R^{23}$ represents any value defined for $R^{16}$; where n is 0–4 and T is optionally monosubstituted with $R^{29}$ where $R^{29}$ represents any value for $R^{16}$ other than H; —CO—$NR^{25}$ —T— where $R^{25}$ represents any value defined for $R^{16}$, T represents —$(CH_2)_n$— where n is 1–4 and T is optionally monosubstituted with $R^{26}$ where $R^{26}$ represents any value for $R^{16}$ other than H; —$CH_2S$—T— where T represents —$(CH_2)_n$— where n is 1–4 and T is optionally monosubstituted with $R^{27}$ where $R^{27}$ represents any value for $R^{16}$ other than H; —$CH_2O$—T— where T represents —$(CH_2)_n$— where n is 1–4 and T is optionally monosubstituted with $R^{28}$ where $R^{28}$ represents any value for $R^{16}$ other than H;

A is selected from phenyl; naphthyl; a 5–10 membered monocyclic or bicyclic heteroaryl ring containing upto 5 heteroatoms where the heteroatoms are independently selected from O, N and S; or a —S—S— dimer thereof when $R^2$=H; or a N-oxide thereof, or an enantiomer, diastereoisomer, pharmaceutically acceptable salt, prodrug or solvate thereof together with a pharmaceutically acceptable diluent or carrier.

2. A pharmaceutical composition according to claim 1 in which $R^1$ is selected from H; —CO—O—$(CH_2)_n$Ph optionally substituted on Ph as defined for $R^1$=—$C_{1-3}$alkylene-Ph in claim 1 and n=0–4; —CO—O—$C_{2-4}$alkenyl; —CO—$C_{1-4}$ alkyl; —$C_{1-4}$alkylene-$CONR^4R^5$ where $R^4$ and $R^5$ are independently selected from H, $C_{1-4}$alkyl.

3. A pharmaceutical composition according to claim 1, in which $R^2$ is selected from H and —CO—$C_{1-4}$alkyl.

4. A pharmaceutical composition according to claim 1, in which L is selected from —$CH_2$—$NR^{18}$; —$CH_2N^{21}$—T.

5. A pharmaceutical composition according to claim 1, in which A is selected from phenyl, naphthyl, pyridyl and thienyl.

6. A pharmaceutical composition according to claim 1, in which combinations of $R^3$ and p are selected from i) $R^3$ is selected from a group of Formula II; —$C_{1-4}$ alkyl$R^7$; —O—$R^7$ and; $R^7$; and p=1–3 with the proviso that one value of $R^3$ is a group of Formula II;

ii) p=0 with the proviso that A is naphthyl and L is —$CH_2NR^{21}$—T;

iii) p=1 with the proviso that $R^3$=a group of Formula II and A is naphthyl.

7. A pharmaceutical composition according to claim 1 in which $R^1$ is selected from H; —$C_{1-4}$alkyl, —$C_{1-3}$alkylene-Ph optionally mono or di-substituted on Ph with substituents selected from $C_{1-4}$alkyl, halogen, OH, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, thiol, $C_{1-4}$alkylthio, nitro, cyano, carboxy, carbamoyl, $C_{1-4}$alkoxycarbonyl, $C_{1-4}$alkylsulfinyl, $C_{1-4}$alkylsulfonyl, sulfonamido; —CO—$C_{1-4}$alkyl; —CO—O—$C_{1-4}$alkyl; —CO—O—$C_{2-4}$alkenyl; —CO—O—$CH_2$-Ph optionally mono- or di-substituted on phenyl with substituents selected from $C_{1-4}$alkyl, halogen, OH, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, thiol, $C_{1-4}$alkylthio, nitro, cyano, carboxy, carbamoyl, $C_{1-4}$alkoxycarbonyl, $C_{1-4}$alkylthiono, $C_{1-4}$alkylsulfonyl, sulfonamido; —$C_{1-4}$ alkylene-$CONR^4R^5$ where $R^4$ & $R^5$ are independently selected from H, $C_{1-4}$alkyl; —$C_{1-4}$alkylene-$COOR^6$ where $R^6$ is selected from H, $C_{1-4}$alkyl;

$R^2$ is selected from H; —$C_{1-4}$alkyl; —$C_{1-3}$alkylene-Ph; —$COC_{1-4}$alkyl; —$COOC_{1-4}$alkyl;

$R^3$ is selected from H; OH; CN; $CF_3$; $NO_2$; —$C_{1-4}$ alkyl, —$C_{1-4}$alkylene-$R^7$ where $R^7$ is selected from phenyl, naphthyl, a 5–10 membered monocyclic or bicyclic heteroaryl ring containing upto 3 heteroatoms selected from O, N and S; $C_{2-4}$alkenyl; halogen; —$(CH_2)_n$$COOR^8$ where n=0–3 and $R^8$ represents H, $C_{1-4}$alkyl, $C_{2-4}$alkenyl; —$CONR^9R^{10}$ where $R^9$ and $R^{10}$ independently represent H, $C_{1-4}$alkyl, $C_{2-4}$alkenyl, —O—$C_{1-4}$ alkyl, —O—$C_{2-4}$alkenyl; —CON($R^{11}$)$OR^{12}$ where $R^{11}$ and $R^{12}$ independently represent H, $C_{1-4}$alkyl and $C_{2-4}$alkenyl; a group of Formula II, —$CONR^{13}$—$CHR^{14}$—$COOR^{17}$, where $R^{13}$ is H or $C_{1-4}$alkyl, $R^{17}$ is H or $C_{1-6}$alkyl, $R^{14}$ is the side chain of a lipophilic amino acid with L or D configuration at the chiral alpha carbon in the corresponding free amino acid: $C_{1-4}$alkyl monosubstituted on carbon with =N—OH; —$SO$—$C_{1-4}$alkyl: —$SO_2$—$C_{1-4}$alkyl: a group of Formula —X—$R^{15}$ where X is selected from CO, $CH_2$, S, SO, $SO_2$ and $R^{15}$ is selected from $C_{1-6}$alkyl, phenyl, naphthyl, a 5–10 membered monocyclic or bicyclic heteroaryl ring containing up to 3 heteroatoms selected from O, N and S:

p is 0–3 in which $R^3$ values can be the same or different;

L is a linking moiety selected from the following groups written from left to right in Formula I: —CO—NR$^{16}$— where R$^{16}$ is selected from H, C$_{1-4}$alkyl, C$_{1-4}$alkylene-Z and Z is selected from —O—C$_{1-4}$alkyl, phenyl, naphthyl, a 5–10 membered monocyclic or bicyclic heteroaryl ring containing upto 3 heteroatoms selected from O, N and S; —CH$_2$—NR$^{18}$— where R$^{18}$ represents any value defined for R$^{16}$; —CH$_2$S—; —CH$_2$O—; —CH$_2$—CHR$^{19}$— where R$^{19}$ represents any value defined for R$^{16}$; —CH═CR$^{20}$— where R$^{20}$ represents any value defined for R$^{16}$; —CH$_2$NR$^{21}$—T— where R$^{21}$ represents any value defined for R$^{16}$, T represents —(CH$_2$)$_n$— where n is 1–4 and T is optionally monosubstituted with R$^{22}$ where R$^{22}$ represents any value for R$^{16}$ other than H and provided at least one of R$^{21}$ and R$^{22}$ is H; —CH$_2$NR$^{23}$—SO$_2$— where R$^{23}$ represents any value defined for R$^{16}$; —CH$_2$—NR$^{24}$—CO—T— where R$^{24}$ represents any value defined for R$^{16}$, T represents —(CH$_2$)$_n$— where n is 0–4 and T is optionally monosubstituted with R$^{29}$ where R$^{29}$ represents any value for R$^{16}$ other than H, and provided at least one of R$^{24}$ and R$^{29}$ is H; —CO—NR$^{25}$—T— where R$^{25}$ represents any value defined for R$^{16}$, T represents —(CH$_2$)$_n$— where n is 1–4 and T is optionally monosubstituted with R$^{26}$ where R$^{26}$ represents any value for R$^{16}$ other than H, and provided at least one of R$^{24}$ and R$^{25}$ is H; —CH$_2$S—T— where T represents —(CH$_2$)$_n$— where n is 1–4 and T is optionally monosubstituted with R$^{27}$ where R$^{27}$ represents any value for R$^{16}$ other than H; —CH$_2$O—T— where T represents —(CH$_2$)$_n$— where n is 1–4 and T is optionally monosubstituted with R$^{28}$ where R$^{28}$ represents any value for R$^{16}$ other than H;

A is selected from phenyl; naphthyl; a 5–10 membered monocyclic or bicyclic heteroaryl ring containing upto 3 or 5 heteroatoms in the case of monocyclic and bicyclic rings respectively where the heteroatoms are independently selected from O, N & S; or a —S—S— dimer thereof when R$^2$=H.

8. A pharmaceutical composition according to any one of claims 1–7 which is in the form of a tablet.

9. A compound of any of the following classes i), ii) or iii):

class i)

Formula III

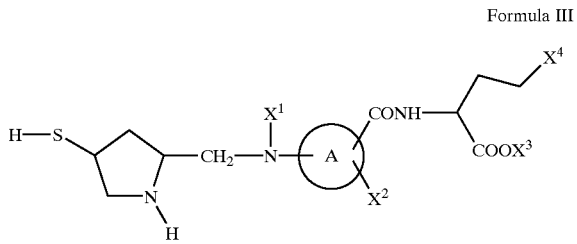

wherein:
X$^1$ is selected from H: C$_{1-6}$alkyl hydroxyC$_{1-6}$alkyl, C$_{1-6}$alkoxyC$_{1-6}$alkyl; C$_{1-6}$alkylcarbonyl; hydroxyC$_{1-6}$alkylcarbonyl; C$_{1-6}$alkoxyC$_{1-6}$alkylcarbonyl;

A is selected from phenyl, naphthyl or a 5–10 membered heterocyclic ring having upto 5 heteroatoms selected from O, N and S;

X$^2$ is selected from H; phenyl; phenylC$_{1-6}$alkyl; and a 5–6 membered heteroaryl ring containing upto 3 heteroatoms selected from O, N and S optionally linked to A by C$_{1-6}$alkyl; and X$^2$ is optionally substituted on any ring, as defined for phenyl in R$^1$=—C$_{1-3}$alkylene-Ph in claim 1;

X$^3$ is selected from H; C$_{1-6}$alkyl;

X$^4$ is selected from C$_{1-6}$alkylsulfanyl; C$_{1-6}$alkylsulfinyl; C$_{1-6}$alkylsulfonyl; carbamoyl; N-(C$_{1-6}$alkyl)carbamoyl; N-(diC$_{1-6}$alkyl)carbamoyl; and hydroxy or a C$_{1-4}$alkyl ether thereof:

class ii)

Formula IV

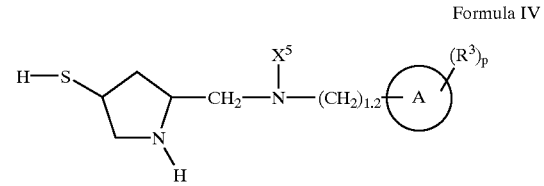

wherein:
X$^5$ is selected from —CO—C$_{1-4}$alkyl-Ph: —CO—C$_{1-6}$alkyl: —CO—C$_{1-4}$alkyl-heteroaryl where heteroaryl is a 5–10 membered heteroaryl ring containing upto 5 heteroatoms selected from O, N and S and Ph or heteroaryl are optionally substituted as defined for Ph in R$^1$=—C$_{1-3}$alkylene-Ph in claim 1; C$_{1-4}$alkyloxyC$_{1-4}$alkyl:

A is naphthyl or a 10 membered heterocyclic ring having upto 5 heteroatoms selected from O, N and S;

R$^3$ and p are as defined in claim 1;

class iii)

Formula V

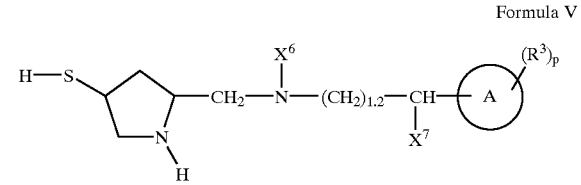

wherein
X$^6$ has any value defined for X$^5$ in ii) above;
X$^7$ is Ph optionally substituted as defined for Ph in R$^1$=—C$_{1-3}$alkylene-Ph in claim 1;
A is Ph or naphthyl or a 5–10 membered heterocyclic ring having upto 5 heteroatoms selected from O, N and S;
R$^3$ and p are as defined in claim 1;
or a N-oxide, pharmaceutically acceptable salt, prodrug or solvate thereof.

10. A process for preparing compounds of classes i), ii) or iii) as defined in claim 9 which comprises deprotecting a compound of Formula VI Formula VI

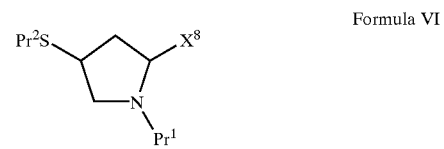

wherein X$^8$ represents the right hand side of compound classes i), ii) or iii) as defined in claim 9, Pr$^1$ is H or an amino protecting group, Pr$^2$ is H or a thio protecting group and any functional groups in X$^8$ are optionally protected with the proviso that there is at least one protecting group and optionally converting the product thus obtained into a pharmaceutically acceptable salt thereof.

11. A pharmaceutical composition comprising a compound as claimed in claim 9.

12. A method of treating ras-mediated diseases comprising administration of an effective amount of a pharmaceutical composition of claim 1 or a pharmaceutically acceptable salt or prodrug thereof to a mammal in need of such treatment.

13. A method of treating ras-mediated cancer comprising administration of an effective amount of a pharmaceutical composition of claim 1 or a pharmaceutically acceptable salt or prodrug thereof to a mammal in need of such treatment.

14. A method of treating a disease or medical condition mediated alone or in part by farnesylated ras comprising administering to a mammal requiring such treatment an effective amount of a pharmaceutical composition of claim 1 or a pharmaceutically acceptable salt or prodrug thereof.

* * * * *